United States Patent
Zhang

(10) Patent No.: US 9,512,471 B2
(45) Date of Patent: Dec. 6, 2016

(54) METHODS AND KITS FOR DETECTING HUMAN PAPILLOMAVIRUS

(75) Inventor: Lulu Zhang, Newark, CA (US)

(73) Assignee: DIACARTA Inc, Richmond, CA (US)

( * ) Notice: Subject to any disclaimer, the term of this patent is extended or adjusted under 35 U.S.C. 154(b) by 35 days.

(21) Appl. No.: 12/827,840

(22) Filed: Jun. 30, 2010

(65) Prior Publication Data
US 2012/0003625 A1 Jan. 5, 2012

(51) Int. Cl.
*C12Q 1/68* (2006.01)

(52) U.S. Cl.
CPC ............. *C12Q 1/682* (2013.01); *C12Q 1/6888* (2013.01)

(58) Field of Classification Search
None
See application file for complete search history.

(56) References Cited

U.S. PATENT DOCUMENTS

| | | | |
|---|---|---|---|
| 7,033,758 B2* | 4/2006 | Kenny et al. ................ | 435/6.11 |
| 7,709,198 B2 | 5/2010 | Luo et al. | |
| 2007/0015188 A1* | 1/2007 | Luo et al. ......................... | 435/6 |
| 2007/0161015 A1* | 7/2007 | Zheng et al. .................... | 435/6 |
| 2009/0081688 A1* | 3/2009 | Luo et al. ......................... | 435/6 |
| 2010/0124547 A1* | 5/2010 | Bramlage et al. ........... | 424/93.7 |
| 2011/0183326 A1* | 7/2011 | Zhang et al. ................ | 435/6.11 |

OTHER PUBLICATIONS

Collins et al. Nucleic Acids Research. 1997. 25(15): 2979-2984.*
Oh et al. Journal of Clinical Microbiology. 2004. 42(7): 3272-3280.*
GenBank EU869318.1.*
Buck et al. BioTechniques. 1999. 27: 528-536.*
Derchain. Gynecologic Oncology. 2004. 95: 618-623.*
Sakamoto. Journal of Biomolecular Screening. 2003. 8(6): 701-711.*
Hartley. Drug Metabolism and Disposition. 2000. 28(5): 608-616.*
Player. Journal of Histochemistry and Cytochemistry. 2001. 49(5): 603-611.*
Kenny. Journal of Histochemistry and Cytochemistry. 2002. 50(9): 1219-1227.*
Hyndman. BioTechniques. 1996. 20: 1090-1097.*
GenBank 2 (AJ388069.2, Feb. 15, 2000).*
GenBank 3 (AJ388057.1, Feb. 15, 2000).*
GenBank 4 (AF187866.1, Feb. 15, 2000).*
Ginocchio, C.C., et al, Comparison of the Third Wave Invader Human Papillomavirus (HPV) Assay and the Digene HPV Hybrid Capture 2 Assay for Detection of High Risk HPV DNA, J. of Clinical Microbiology, May 2008, vol. 46 No. 5 p. 1641-1646.
Kurtycz, Daniel F. I., et al, Comparison of Methods Trial for High-Risk HPV, Diagnostic Cytopathology, Aug. 2009, vol. 39 No. 2, p. 104-108.

(Continued)

*Primary Examiner* — Joseph G Dauner
(74) *Attorney, Agent, or Firm* — Isaac Angres

(57) ABSTRACT

The present invention provides methods and kits for determining the presence, absence, or level of an infectious agent in a sample. Specifically, the present invention provides methods and kits for detecting or quantifying certain target polynucleotides of the infectious agent. In certain embodiments, the present invention provides for such detection without the need for amplification (e.g., replication) of the target molecule and/or without the need for labor intensive purification procedures. In certain embodiments, the present invention provides positive control and housekeeping gene for normalization and quantatively detection of the copy numbers of infectious agent in a sample. In these or other embodiments, the invention allows for such detection with the desired sensitivity and/or specificity, even where the polynucleotide is present in the sample at low copy number.

12 Claims, 13 Drawing Sheets

(56) References Cited

OTHER PUBLICATIONS

Horne, et al., "Statistical thermodynamics and kinetics of DNA multiplex hybridization reactions", Biophys J., 2006, 91:4133-53.

Riccelli, et al., "DNA sequence context and multiplex hybridization reactions: melting studies of heteromorphic duplex DNA complexes", J Am Chem Soc, 2003, 125:141-50.

Shen, et al., "MPprimer: a program for reliable multiplex PCR primer design", BMC Bioinformatics, 2010, 11:143.

* cited by examiner

QuantiFungi™ system

Quantification of different species and strains of *Aspergillus* and *Candida* with QuantiFungi™

| Genus | Species | Strains | Af 18S RNA probesets Luminescent signal (10 cells/well) | Ca 18S RNA probesets Luminescent signal (10 cells/well) | Common 18S RNA probesets Luminescent signal (10 cells/well) |
|---|---|---|---|---|---|
| | Background (all reagents) | | 1537 | 1153 | 1440 |
| *Aspergillus* | *Aspergillus fumigatus* (Af) | Afc1 | 53120 | 1900 | 688533 |
| | | Afc2 | 46080 | 2883 | 57467 |
| | | Afc3 | 25453 | 817 | 44527 |
| | *Aspergillus flavus* | Afl c3 | 62120 | 2913 | 12080 |
| | | Afl c4 | 43130 | 1787 | 13297 |
| | *Aspergillus terreus* | At c5 | 36563 | 3293 | 11023 |
| *Candida* | *Candida albicans* (Ca) | SC5314 | 2337 | 2389025 | 19263 |
| | | ATCC 90028 | 1463 | 730663 | 53120 |
| | | Ca c1 | 1230 | 269597 | 75960 |
| | | Ca c4 | 1100 | 46227 | 63413 |
| | *Candida parapsilosis* | ATCC 22090 | 1510 | 120037 | 116733 |
| | | Cp c5 | 1297 | 34130 | 58130 |
| | *Candida glabrata* | Cg ATCC 2001 | 1507 | 65187 | 44817 |

SEQUENCE LISTING

<160> NUMBER OF SEQ ID NOS: 875

<210> SEQ ID NO 1
<211> LENGTH: 81
<212> TYPE: DNA
<213> ORGANISM: Unknown
<220> FEATURE:
<223> OTHER INFORMATION: Preamplifier probe

<400> SEQUENCE: 1
aggcatagga cccgtgtctt tttttttta ggcataggac ccgtgtcttt tttatgcttt     60
gactcagaaa acggtaactt c                                              81

<210> SEQ ID NO 2
<211> LENGTH: 40

```
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 2
ccagtggact ccacgacgta cttttttgaag ttaccgtttt                          40

<210> SEQ ID NO 3
<211> LENGTH: 40
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 3
ctgagtcaaa gcattttttt tctccatggt ggtgaagacg                           40

<210> SEQ ID NO 4
<211> LENGTH: 43
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 4
tcttgaggct gttgtcatac ttcttttttg aagttaccgt ttt                       43

<210> SEQ ID NO 5
<211> LENGTH: 39
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 5
ctgagtcaaa gcatttttg caggaggcat tgctgatga                            39

<210> SEQ ID NO 6
<211> LENGTH: 42
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 6
cagtagaggc agggatgatg ttcttttga agttaccgtt tt                        42

<210> SEQ ID NO 7
<211> LENGTH: 36
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 7
ctgagtcaaa gcatttttc acagccttgg cagcgc                               36

<210> SEQ ID NO 8
<211> LENGTH: 40
<212> TYPE: DNA
```

<210> SEQ ID NO 8
<211> LENGTH: 40
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 8
ccagtggact ccacgacgta cttttttgaag ttaccgtttt           40

<210> SEQ ID NO 9
<211> LENGTH: 40
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 9
ttctccatgg tggtgaagac gtttttctga gtcaaagcat           40

<210> SEQ ID NO 10
<211> LENGTH: 43
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 10
tcttgaggct gttgtcatac ttcttttttg aagttaccgt ttt        43

<210> SEQ ID NO 11
<211> LENGTH: 39
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 11
gcaggaggca ttgctgatga ttttttctgag tcaaagcat           39

<210> SEQ ID NO 12
<211> LENGTH: 42
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 12
cagtagaggc agggatgatg ttcttttttga agttaccgtt tt       42

<210> SEQ ID NO 13
<211> LENGTH: 36
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 13
cacagccttg gcagcgcttt ttctgagtca aagcat             36

<210> SEQ ID NO 14
<211> LENGTH: 43
<212> TYPE: DNA
<213> ORGANISM: Artificial Sequence

```
<220> FEATURE:
<223> OTHER INFORMATION: Human papillomavirus type 16 capture extender
      probe

<400> SEQUENCE: 14
ctcctgtggg tcctgaaaca ttttttttctc ttggaaagaa agt                    43

<210> SEQ ID NO 15
<211> LENGTH: 43
<212> TYPE: DNA
<213> ORGANISM: Artificial Sequence
<220> FEATURE:
<223> OTHER INFORMATION: Human papillomavirus type 16 capture extender
      probe

<400> SEQUENCE: 15
cacgtcgcag taactgttgc ttttttttctc ttggaaagaa agt                    43

<210> SEQ ID NO 16
<211> LENGTH: 50
<212> TYPE: DNA
<213> ORGANISM: Artificial Sequence
<220> FEATURE:
<223> OTHER INFORMATION: Human papillomavirus type 16 capture extender
      probe

<400> SEQUENCE: 16
tgttgttcca tacaaactat aacaataatt ttttctcttg gaaagaaagt              50

<210> SEQ ID NO 17
<211> LENGTH: 49
<212> TYPE: DNA
<213> ORGANISM: Artificial Sequence
<220> FEATURE:
<223> OTHER INFORMATION: Human papillomavirus type 16 capture extender
      probe

<400> SEQUENCE: 17
aatctaacat atattcatgc aatgtaggtt tttctcttgg aaagaaagt               49

<210> SEQ ID NO 18
<211> LENGTH: 43
<212> TYPE: DNA
<213> ORGANISM: Artificial Sequence
<220> FEATURE:
<223> OTHER INFORMATION: Human papillomavirus type 16 capture extender
      probe

<400> SEQUENCE: 18
atattgtaat gggctctgtc cgttttttctc ttggaaagaa agt                    43

<210> SEQ ID NO 19
<211> LENGTH: 45
<212> TYPE: DNA
<213> ORGANISM: Artificial Sequence
<220> FEATURE:
<223> OTHER INFORMATION: Human papillomavirus type 16 capture extender
      probe

<400> SEQUENCE: 19
cccattaaca ggtcttccaa agtattttttc tcttggaaag aaagt                  45

<210> SEQ ID NO 20
<211> LENGTH: 48
<212> TYPE: DNA
<213> ORGANISM: Artificial Sequence
<220> FEATURE:
```

```
<223> OTHER INFORMATION: Human papillomavirus type 16 capture extender
      probe

<400> SEQUENCE: 20
ggtagattat ggtttctgag aacagatttt ttctcttgga agaaagt                    48

<210> SEQ ID NO 21
<211> LENGTH: 41
<212> TYPE: DNA
<213> ORGANISM: Artificial Sequence
<220> FEATURE:
<223> OTHER INFORMATION: Human papillomavirus type 16 capture extender
      probe

<400> SEQUENCE: 21
cccgtaccct cttccccatt tttttctctt ggaaggaaag t                          41

<210> SEQ ID NO 22
<211> LENGTH: 44
<212> TYPE: DNA
<213> ORGANISM: Artificial Sequence
<220> FEATURE:
<223> OTHER INFORMATION: Human papillomavirus type 16 label extender
      probe

<400> SEQUENCE: 22
gtctgctttt atactaaccg gtttcttttt gaagttaccg tttt                       44

<210> SEQ ID NO 23
<211> LENGTH: 44
<212> TYPE: DNA
<213> ORGANISM: Artificial Sequence
<220> FEATURE:
<223> OTHER INFORMATION: Human papillomavirus type 16 label extender
      probe

<400> SEQUENCE: 23
gcagttctct tttggtgcat aaaatttttt ctgagtcaaa gcat                       44

<210> SEQ ID NO 24
<211> LENGTH: 42
<212> TYPE: DNA
<213> ORGANISM: Artificial Sequence
<220> FEATURE:
<223> OTHER INFORMATION: Human papillomavirus type 16 label extender
      probe

<400> SEQUENCE: 24
aactgtggta actttctggg tcgtttttga agttaccgtt tt                         42

<210> SEQ ID NO 25
<211> LENGTH: 41
<212> TYPE: DNA
<213> ORGANISM: Artificial Sequence
<220> FEATURE:
<223> OTHER INFORMATION: Human papillomavirus type 16 label extender
      probe

<400> SEQUENCE: 25
agttgtttgc agctctgtgc attttttctg agtcaaagca t                          41

<210> SEQ ID NO 26
<211> LENGTH: 47
<212> TYPE: DNA
<213> ORGANISM: Artificial Sequence
<220> FEATURE:
<223> OTHER INFORMATION: Human papillomavirus type 16 label extender
```

```
                          -continued
        probe

<400> SEQUENCE: 26
ttcccatctc tatatactat gcataaattt tttgaagtta ccgtttt          47

<210> SEQ ID NO 27
<211> LENGTH: 45
<212> TYPE: DNA
<213> ORGANISM: Artificial Sequence
<220> FEATURE:
<223> OTHER INFORMATION: Human papillomavirus type 16 label extender
      probe

<400> SEQUENCE: 27
aacatttatc acatacagca tatggatttt tctgagtcaa agcat            45

<210> SEQ ID NO 28
<211> LENGTH: 43
<212> TYPE: DNA
<213> ORGANISM: Artificial Sequence
<220> FEATURE:
<223> OTHER INFORMATION: Human papillomavirus type 16 label extender
      probe

<400> SEQUENCE: 28
cggtttgttg tattgctgtt ctaattttg aagttaccgt ttt              43

<210> SEQ ID NO 29
<211> LENGTH: 47
<212> TYPE: DNA
<213> ORGANISM: Artificial Sequence
<220> FEATURE:
<223> OTHER INFORMATION: Human papillomavirus type 16 label extender
      probe

<400> SEQUENCE: 29
taatacacct aattaacaaa tcacacaatt tttctgagtc aaagcat          47

<210> SEQ ID NO 30
<211> LENGTH: 41
<212> TYPE: DNA
<213> ORGANISM: Artificial Sequence
<220> FEATURE:
<223> OTHER INFORMATION: Human papillomavirus type 16 label extender
      probe

<400> SEQUENCE: 30
ggacacagtg gcttttgaca gttttttgaa gttaccgttt t                41

<210> SEQ ID NO 31
<211> LENGTH: 42
<212> TYPE: DNA
<213> ORGANISM: Artificial Sequence
<220> FEATURE:
<223> OTHER INFORMATION: Human papillomavirus type 16 label extender
      probe

<400> SEQUENCE: 31
ccagatgtct ttgctttct tcattttct gagtcaaagc at                42

<210> SEQ ID NO 32
<211> LENGTH: 43
<212> TYPE: DNA
<213> ORGANISM: Artificial Sequence
<220> FEATURE:
<223> OTHER INFORMATION: Human papillomavirus type 16 label extender
      probe
```

```
<400> SEQUENCE: 32
gatctgcaac aagacataca tcgattttg aagttaccgt ttt                    43

<210> SEQ ID NO 33
<211> LENGTH: 43
<212> TYPE: DNA
<213> ORGANISM: Artificial Sequence
<220> FEATURE:
<223> OTHER INFORMATION: Human papillomavirus type 16 label extender
      probe

<400> SEQUENCE: 33
tgggtttctc tacgtgttct tgatttttc tgagtcaaag cat                    43

<210> SEQ ID NO 34
<211> LENGTH: 42
<212> TYPE: DNA
<213> ORGANISM: Artificial Sequence
<220> FEATURE:
<223> OTHER INFORMATION: Human papillomavirus type 16 label extender
      probe

<400> SEQUENCE: 34
gagatcagtt gtctctggtt gcatttttga agttaccgtt tt                    42

<210> SEQ ID NO 35
<211> LENGTH: 46
<212> TYPE: DNA
<213> ORGANISM: Artificial Sequence
<220> FEATURE:
<223> OTHER INFORMATION: Human papillomavirus type 16 label extender
      probe

<400> SEQUENCE: 35
gctgtcattt aattgctcat aacagtattt ttctgagtca aagcat                46

<210> SEQ ID NO 36
<211> LENGTH: 43
<212> TYPE: DNA
<213> ORGANISM: Artificial Sequence
<220> FEATURE:
<223> OTHER INFORMATION: Human papillomavirus type 16 label extender
      probe

<400> SEQUENCE: 36
tcacacttgc aacaaaaggt tacatttttg aagttaccgt ttt                   43

<210> SEQ ID NO 37
<211> LENGTH: 39
<212> TYPE: DNA
<213> ORGANISM: Artificial Sequence
<220> FEATURE:
<223> OTHER INFORMATION: Human papillomavirus type 16 label extender
      probe

<400> SEQUENCE: 37
cgcacaaccg aagcgtagag tttttctgag tcaaagcat                        39

<210> SEQ ID NO 38
<211> LENGTH: 33
<212> TYPE: DNA
<213> ORGANISM: Artificial Sequence
<220> FEATURE:
<223> OTHER INFORMATION: Human papillomavirus type 16 blocking label
      extender probe
```

-continued

```
<400> SEQUENCE: 38
gcagtacaca cattctaata ttatatcatg tat                                    33

<210> SEQ ID NO 39
<211> LENGTH: 24
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 39
cccgaaaagc aaagtcatat acct                                              24

<210> SEQ ID NO 40
<211> LENGTH: 33
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 40
gtctatactc actaatttta gaataaaact tta                                    33

<210> SEQ ID NO 41
<211> LENGTH: 27
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 41
ttatattatg gaatctttgc tttttgt                                           27

<210> SEQ ID NO 42
<211> LENGTH: 16
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 42
ccggtccacc gacccc                                                       16

<210> SEQ ID NO 43
<211> LENGTH: 24
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 43
tgtatctcca tgcatgatta cagc                                              24

<210> SEQ ID NO 44
<211> LENGTH: 25
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 44
```
catctatttc atcctcctcc tctga                                          25

<210> SEQ ID NO 45
<211> LENGTH: 21
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 45
gttctgcttg tccagctgga c                                              21

<210> SEQ ID NO 46
<211> LENGTH: 25
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 46
cgaatgtcta cgtgtgtgct ttgta                                          25

<210> SEQ ID NO 47
<211> LENGTH: 22
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 47
ggggcacaca attcctagtg tg                                             22

<210> SEQ ID NO 48
<211> LENGTH: 21
<212> TYPE: DNA
<213> ORGANISM: Artificial Sequence
<220> FEATURE:
<223> OTHER INFORMATION: Human papillomavirus type 16 blocking label
      extender probe

<400> SEQUENCE: 48
ggtacctgca ggatcagcca t                                              21

<210> SEQ ID NO 49
<211> LENGTH: 49
<212> TYPE: DNA
<213> ORGANISM: Artificial Sequence
<220> FEATURE:
<223> OTHER INFORMATION: Human papillomavirus type 18 capture extender
      probe

<400> SEQUENCE: 49 cgttttcat taaggtgtct aagttttttt tttctcttgg aaagaaagt                 49

<210> SEQ ID NO 50
<211> LENGTH: 38
<212> TYPE: DNA
<213> ORGANISM: Artificial Sequence
<220> FEATURE:
<223> OTHER INFORMATION: Human papillomavirus type 18 capture extender
      probe

<400> SEQUENCE: 50
tgctcggttg cagcacgttt ttctcttgga aagaaagt                                38

<210> SEQ ID NO 51
<211> LENGTH: 43
<212> TYPE: DNA
<213> ORGANISM: Artificial Sequence
<220> FEATURE:
<223> OTHER INFORMATION: Human papillomavirus type 18 capture extender
      probe

<400> SEQUENCE: 51
tgttgcctta ggtccatgca tattttctc ttggaaagaa agt                           43

<210> SEQ ID NO 52
<211> LENGTH: 48
<212> TYPE: DNA
<213> ORGANISM: Artificial Sequence
<220> FEATURE:
<223> OTHER INFORMATION: Human papillomavirus type 18 capture extender
      probe

<400> SEQUENCE: 52
gctttctact actagcttaa ttctggcttt ttctcttgga aagaaagt                    48

<210> SEQ ID NO 53
<211> LENGTH: 42
<212> TYPE: DNA
<213> ORGANISM: Artificial Sequence
<220> FEATURE:
<223> OTHER INFORMATION: Human papillomavirus type 18 capture extender
      probe

<400> SEQUENCE: 53
ctggatcagc cattgttgct tttttctct tggaaagaaa gt                           42

<210> SEQ ID NO 54
<211> LENGTH: 48
<212> TYPE: DNA
<213> ORGANISM: Artificial Sequence
<220> FEATURE:
<223> OTHER INFORMATION: Human papillomavirus type 18 capture extender
      probe

<400> SEQUENCE: 54
tactacctgc taatcttcta tgagctttt ttctcttgga aagaaagt                     48

<210> SEQ ID NO 55
<211> LENGTH: 40
<212> TYPE: DNA
<213> ORGANISM: Artificial Sequence
<220> FEATURE:
<223> OTHER INFORMATION: Human papillomavirus type 18 capture extender
      probe

<400> SEQUENCE: 55
tggccaggga agatccactt ttttctcttg gaaagaaagt                             40

<210> SEQ ID NO 56
<211> LENGTH: 42
<212> TYPE: DNA
<213> ORGANISM: Artificial Sequence
<220> FEATURE:
<223> OTHER INFORMATION: Human papillomavirus type 18 capture extender
      probe

<400> SEQUENCE: 56
ttgcagctca atacaaaacg gttttctct tggaaagaaa gt                           42

<210> SEQ ID NO 57
<211> LENGTH: 41
<212> TYPE: DNA
<213> ORGANISM: Artificial Sequence
<220> FEATURE:
<223> OTHER INFORMATION: Human papillomavirus type 18 label extender
      probe

<400> SEQUENCE: 57
cccagctatg ttgtggaatc gtttttgaa gttaccgttt t                    41

<210> SEQ ID NO 58
<211> LENGTH: 41
<212> TYPE: DNA
<213> ORGANISM: Artificial Sequence
<220> FEATURE:
<223> OTHER INFORMATION: Human papillomavirus type 18 label extender
      probe

<400> SEQUENCE: 58
aatggcactg gcctctatag tgtttttctg agtcaaagca t                   41

<210> SEQ ID NO 59
<211> LENGTH: 40
<212> TYPE: DNA
<213> ORGANISM: Artificial Sequence
<220> FEATURE:
<223> OTHER INFORMATION: Human papillomavirus type 18 label extender
      probe

<400> SEQUENCE: 59
tcgttggagt ctttcctgtc gtttttgaag ttaccgtttt                     40

<210> SEQ ID NO 60
<211> LENGTH: 47
<212> TYPE: DNA
<213> ORGANISM: Artificial Sequence
<220> FEATURE:
<223> OTHER INFORMATION: Human papillomavirus type 18 label extender
      probe

<400> SEQUENCE: 60
cttaatatta tacttgtgtt tctctgcgtt tttctgagtc aaagcat             47

<210> SEQ ID NO 61
<211> LENGTH: 43
<212> TYPE: DNA
<213> ORGANISM: Artificial Sequence
<220> FEATURE:
<223> OTHER INFORMATION: Human papillomavirus type 18 label extender
      probe

<400> SEQUENCE: 61
taaatgcaat acaatgtctt gcaatttttg aagttaccgt ttt                 43

<210> SEQ ID NO 62
<211> LENGTH: 39
<212> TYPE: DNA
<213> ORGANISM: Artificial Sequence
<220> FEATURE:
<223> OTHER INFORMATION: Human papillomavirus type 18 label extender
      probe

<400> SEQUENCE: 62
ggaatttcat tttggggctc tttttctgag tcaaagcat                      39

<210> SEQ ID NO 63
<211> LENGTH: 42
<212> TYPE: DNA
<213> ORGANISM: Artificial Sequence
<220> FEATURE:
<223> OTHER INFORMATION: Human papillomavirus type 18 label extender
      probe

<400> SEQUENCE: 63
gctcgtgaca tagaaggtca accttttttga agttaccgtt tt                     42

<210> SEQ ID NO 64
<211> LENGTH: 43
<212> TYPE: DNA
<213> ORGANISM: Artificial Sequence
<220> FEATURE:
<223> OTHER INFORMATION: Human papillomavirus type 18 label extender
      probe

<400> SEQUENCE: 64
tttcttcctc tgagtcgctt aattttttc tgagtcaaag cat                      43

<210> SEQ ID NO 65
<211> LENGTH: 45
<212> TYPE: DNA
<213> ORGANISM: Artificial Sequence
<220> FEATURE:
<223> OTHER INFORMATION: Human papillomavirus type 18 label extender
      probe

<400> SEQUENCE: 65
atgattaact ccatctattt catcgttttt tgaagttacc gtttt                   45

<210> SEQ ID NO 66
<211> LENGTH: 39
<212> TYPE: DNA
<213> ORGANISM: Artificial Sequence
<220> FEATURE:
<223> OTHER INFORMATION: Human papillomavirus type 18 label extender
      probe

<400> SEQUENCE: 66
cgtcgggctg gtaaatgttg tttttctgag tcaaagcat                          39

<210> SEQ ID NO 67
<211> LENGTH: 39
<212> TYPE: DNA
<213> ORGANISM: Artificial Sequence
<220> FEATURE:
<223> OTHER INFORMATION: Human papillomavirus type 18 label extender
      probe

<400> SEQUENCE: 67
gctcgaaggt cgtctgctga tttttgaagt taccgtttt                          39

<210> SEQ ID NO 68
<211> LENGTH: 42
<212> TYPE: DNA
<213> ORGANISM: Artificial Sequence
<220> FEATURE:
<223> OTHER INFORMATION: Human papillomavirus type 18 label extender
      probe

<400> SEQUENCE: 68
tgttcagaaa cagctgctgg aattttttct gagtcaaagc at                      42

```
<210> SEQ ID NO 69
<211> LENGTH: 39
<212> TYPE: DNA
<213> ORGANISM: Artificial Sequence
<220> FEATURE:
<223> OTHER INFORMATION: Human papillomavirus type 18 label extender
      probe

<400> SEQUENCE: 69
cggacacaca aaggacaggg tttttgaagt taccgtttt                      39

<210> SEQ ID NO 70
<211> LENGTH: 38
<212> TYPE: DNA
<213> ORGANISM: Artificial Sequence
<220> FEATURE:
<223> OTHER INFORMATION: Human papillomavirus type 18 label extender
      probe

<400> SEQUENCE: 70
actgctggga tgcacaccat ttttctgagt caaagcat                       38

<210> SEQ ID NO 71
<211> LENGTH: 44
<212> TYPE: DNA
<213> ORGANISM: Artificial Sequence
<220> FEATURE:
<223> OTHER INFORMATION: Human papillomavirus type 18 label extender
      probe

<400> SEQUENCE: 71
cgtcagtttc ctcatctgaa aactttttt gaagttaccg tttt                 44

<210> SEQ ID NO 72
<211> LENGTH: 44
<212> TYPE: DNA
<213> ORGANISM: Artificial Sequence
<220> FEATURE:
<223> OTHER INFORMATION: Human papillomavirus type 18 label extender
      probe

<400> SEQUENCE: 72
cgtcaagtca tttaagcttg gtaccttttt ctgagtcaaa gcat                44

<210> SEQ ID NO 73
<211> LENGTH: 22
<212> TYPE: DNA
<213> ORGANISM: Artificial Sequence
<220> FEATURE:
<223> OTHER INFORMATION: Human papillomavirus type 18 blocking label
      extender probe

<400> SEQUENCE: 73
tgtgtgacgt tgtggttcag ct                                        22

<210> SEQ ID NO 74
<211> LENGTH: 27
<212> TYPE: DNA
<213> ORGANISM: Artificial Sequence
<220> FEATURE:
<223> OTHER INFORMATION: Human papillomavirus type 18 blocking label
      extender probe

<400> SEQUENCE: 74
ttcacactta caacacatac acaacat                                   27

<210> SEQ ID NO 75
```

```
<211> LENGTH: 26
<212> TYPE: DNA
<213> ORGANISM: Artificial Sequence
<220> FEATURE:
<223> OTHER INFORMATION: Human papillomavirus type 18 blocking label
      extender probe

<400> SEQUENCE: 75
gaattaggag tcagcagtca ttattc                                          26

<210> SEQ ID NO 76
<211> LENGTH: 44
<212> TYPE: DNA
<213> ORGANISM: Artificial Sequence
<220> FEATURE:
<223> OTHER INFORMATION: Human papillomavirus type 31 capture extender
      probe

<400> SEQUENCE: 76
gtctttctgc aggattttg aacttttct cttggaaaga aagt                        44

<210> SEQ ID NO 77
<211> LENGTH: 44
<212> TYPE: DNA
<213> ORGANISM: Artificial Sequence
<220> FEATURE:
<223> OTHER INFORMATION: Human papillomavirus type 31 capture extender
      probe

<400> SEQUENCE: 77
gcttagttca tgcaatttcc gagttttct cttggaaaga aagt                       44

<210> SEQ ID NO 78
<211> LENGTH: 47
<212> TYPE: DNA
<213> ORGANISM: Artificial Sequence
<220> FEATURE:
<223> OTHER INFORMATION: Human papillomavirus type 31 capture extender
      probe

<400> SEQUENCE: 78
cctctgtttc tgttaactga cctttgtttt tctcttggaa agaaagt                   47

<210> SEQ ID NO 79
<211> LENGTH: 50
<212> TYPE: DNA
<213> ORGANISM: Artificial Sequence
<220> FEATURE:
<223> OTHER INFORMATION: Human papillomavirus type 31 capture extender
      probe

<400> SEQUENCE: 79
atctaaattc acttactttt gaataaaatt ttttctcttg gaaagaaagt                50

<210> SEQ ID NO 80
<211> LENGTH: 48
<212> TYPE: DNA
<213> ORGANISM: Artificial Sequence
<220> FEATURE:
<223> OTHER INFORMATION: Human papillomavirus type 31 capture extender
      probe

<400> SEQUENCE: 80 catataccttt tgtttgtcaa tttttctttt ttctcttgga agaaagt                  48

<210> SEQ ID NO 81
<211> LENGTH: 43
```

```
<212> TYPE: DNA
<213> ORGANISM: Artificial Sequence
<220> FEATURE:
<223> OTHER INFORMATION: Human papillomavirus type 31 capture extender
      probe

<400> SEQUENCE: 81
acgcatgttt acacttgggt ttttttttctc ttggaaagaa agt                           43

<210> SEQ ID NO 82
<211> LENGTH: 42
<212> TYPE: DNA
<213> ORGANISM: Artificial Sequence
<220> FEATURE:
<223> OTHER INFORMATION: Human papillomavirus type 31 capture extender
      probe

<400> SEQUENCE: 82
tctgagctgt cgggtaattg cttttctct tggaaagaaa gt                              42

<210> SEQ ID NO 83
<211> LENGTH: 40
<212> TYPE: DNA
<213> ORGANISM: Artificial Sequence
<220> FEATURE:
<223> OTHER INFORMATION: Human papillomavirus type 31 label extender
      probe

<400> SEQUENCE: 83
gtagggtatt tccaatgccg atttttgaag ttaccgtttt                                40

<210> SEQ ID NO 84
<211> LENGTH: 48
<212> TYPE: DNA
<213> ORGANISM: Artificial Sequence
<220> FEATURE:
<223> OTHER INFORMATION: Human papillomavirus type 31 label extender
      probe

<400> SEQUENCE: 84
cagtagacac aattcaatct tagttcatct ttttctgagt caaagcat                       48

<210> SEQ ID NO 85
<211> LENGTH: 45
<212> TYPE: DNA
<213> ORGANISM: Artificial Sequence
<220> FEATURE:
<223> OTHER INFORMATION: Human papillomavirus type 31 label extender
      probe

<400> SEQUENCE: 85
gtggtgtgtc gtccctatat actatttttt tgaagttacc gtttt                          45

<210> SEQ ID NO 86
<211> LENGTH: 44
<212> TYPE: DNA
<213> ORGANISM: Artificial Sequence
<220> FEATURE:
<223> OTHER INFORMATION: Human papillomavirus type 31 label extender
      probe

<400> SEQUENCE: 86
cttaaacatt ttgtacacac tccgtttttt ctgagtcaaa gcat                           44

<210> SEQ ID NO 87
<211> LENGTH: 47
<212> TYPE: DNA
```

<210> SEQ ID NO 87
<211> LENGTH: 47 (implied)
<212> TYPE: DNA
<213> ORGANISM: Artificial Sequence
<220> FEATURE:
<223> OTHER INFORMATION: Human papillomavirus type 31 label extender probe

<400> SEQUENCE: 87
acacgttata cacctaatta acaaatcatt tttgaagtta ccgtttt         47

<210> SEQ ID NO 88
<211> LENGTH: 42
<212> TYPE: DNA
<213> ORGANISM: Artificial Sequence
<220> FEATURE:
<223> OTHER INFORMATION: Human papillomavirus type 31 label extender probe

<400> SEQUENCE: 88
tcttctggac acaacggtct tgttttttct gagtcaaagc at              42

<210> SEQ ID NO 89
<211> LENGTH: 45
<212> TYPE: DNA
<213> ORGANISM: Artificial Sequence
<220> FEATURE:
<223> OTHER INFORMATION: Human papillomavirus type 31 label extender probe

<400> SEQUENCE: 89 tcttttatc caaatgtctt tgttttttttt tgaagttacc gtttt           45

<210> SEQ ID NO 90
<211> LENGTH: 43
<212> TYPE: DNA
<213> ORGANISM: Artificial Sequence
<220> FEATURE:
<223> OTHER INFORMATION: Human papillomavirus type 31 label extender probe

<400> SEQUENCE: 90
ttcctcctat gttgtggaat cgttttttc tgagtcaaag cat              43

<210> SEQ ID NO 91
<211> LENGTH: 41
<212> TYPE: DNA
<213> ORGANISM: Artificial Sequence
<220> FEATURE:
<223> OTHER INFORMATION: Human papillomavirus type 31 label extender probe

<400> SEQUENCE: 91
cttgcaacgt aggtgtttct cctttttgaa gttaccgttt t               41

<210> SEQ ID NO 92
<211> LENGTH: 45
<212> TYPE: DNA
<213> ORGANISM: Artificial Sequence
<220> FEATURE:
<223> OTHER INFORMATION: Human papillomavirus type 31 label extender probe

<400> SEQUENCE: 92
ctcaggttgc aaatctaaca catagttttt tctgagtcaa agcat           45

<210> SEQ ID NO 93
<211> LENGTH: 43
<212> TYPE: DNA
<213> ORGANISM: Artificial Sequence

```
<220> FEATURE:
<223> OTHER INFORMATION: Human papillomavirus type 31 label extender
      probe

<400> SEQUENCE: 93
ggactgtcta tgacatcctc ctcattttg aagttaccgt ttt                    43

<210> SEQ ID NO 94
<211> LENGTH: 39
<212> TYPE: DNA
<213> ORGANISM: Artificial Sequence
<220> FEATURE:
<223> OTHER INFORMATION: Human papillomavirus type 31 label extender
      probe

<400> SEQUENCE: 94
ccggttctgc ttgtccagct tttttctgag tcaaagcat                        39

<210> SEQ ID NO 95
<211> LENGTH: 28
<212> TYPE: DNA
<213> ORGANISM: Artificial Sequence
<220> FEATURE:
<223> OTHER INFORMATION: Human papillomavirus type 31 blocking label
      extender probe

<400> SEQUENCE: 95
gttaaatctg taaatgcaaa atctaata                                    28

<210> SEQ ID NO 96
<211> LENGTH: 31
<212> TYPE: DNA
<213> ORGANISM: Artificial Sequence
<220> FEATURE:
<223> OTHER INFORMATION: Human papillomavirus type 31 blocking label
      extender probe

<400> SEQUENCE: 96
aatgttgttc catacacact atatctatac c                                31

<210> SEQ ID NO 97
<211> LENGTH: 21
<212> TYPE: DNA
<213> ORGANISM: Artificial Sequence
<220> FEATURE:
<223> OTHER INFORMATION: Human papillomavirus type 31 blocking label
      extender probe

<400> SEQUENCE: 97
ctatgcaacg tcctgtccac c                                           21

<210> SEQ ID NO 98
<211> LENGTH: 24
<212> TYPE: DNA
<213> ORGANISM: Artificial Sequence
<220> FEATURE:
<223> OTHER INFORMATION: Human papillomavirus type 31 blocking label
      extender probe

<400> SEQUENCE: 98
cagtacgagg tcttctccaa catg                                        24

<210> SEQ ID NO 99
<211> LENGTH: 23
<212> TYPE: DNA
<213> ORGANISM: Artificial Sequence
<220> FEATURE:
```

<223> OTHER INFORMATION: Human papillomavirus type 31 blocking label
      extender probe

<400> SEQUENCE: 99
tcataacagt ggaggtcagt tgc                                              23

<210> SEQ ID NO 100
<211> LENGTH: 45
<212> TYPE: DNA
<213> ORGANISM: Artificial Sequence
<220> FEATURE:
<223> OTHER INFORMATION: Human papillomavirus type 35 capture extender
      probe

<400> SEQUENCE: 100
caaacaaatt tcatggatgc tttctttttc tcttggaaag aaagt                      45

<210> SEQ ID NO 101
<211> LENGTH: 42
<212> TYPE: DNA
<213> ORGANISM: Artificial Sequence
<220> FEATURE:
<223> OTHER INFORMATION: Human papillomavirus type 35 capture extender
      probe

<400> SEQUENCE: 101
tactccatat ggctggcctt cttttctct tggaaagaaa gt                          42

<210> SEQ ID NO 102
<211> LENGTH: 47
<212> TYPE: DNA
<213> ORGANISM: Artificial Sequence
<220> FEATURE:
<223> OTHER INFORMATION: Human papillomavirus type 35 capture extender
      probe

<400> SEQUENCE: 102
tgtttttcta acgtttctcc atacactttt tctcttggaa agaaagt                    47

<210> SEQ ID NO 103
<211> LENGTH: 41
<212> TYPE: DNA
<213> ORGANISM: Artificial Sequence
<220> FEATURE:
<223> OTHER INFORMATION: Human papillomavirus type 35 capture extender
      probe

<400> SEQUENCE: 103
caccgtccac cgatgttatg tttttctctt ggaaagaaag t                          41

<210> SEQ ID NO 104
<211> LENGTH: 44
<212> TYPE: DNA
<213> ORGANISM: Artificial Sequence
<220> FEATURE:
<223> OTHER INFORMATION: Human papillomavirus type 35 capture extender
      probe

<400> SEQUENCE: 104
tccagctgga ccgtcaatag tattttttct cttggaaaga aagt                       44

<210> SEQ ID NO 105
<211> LENGTH: 48
<212> TYPE: DNA
<213> ORGANISM: Artificial Sequence
<220> FEATURE:
<223> OTHER INFORMATION: Human papillomavirus type 35 capture extender probe

<400> SEQUENCE: 105
ccattaataa atcttccaat ttacgtattt ttctcttgga aagaaagt                    48

<210> SEQ ID NO 106
<211> LENGTH: 42
<212> TYPE: DNA
<213> ORGANISM: Artificial Sequence
<220> FEATURE:
<223> OTHER INFORMATION: Human papillomavirus type 35 label extender
      probe

<400> SEQUENCE: 106
gcagtttgta aggtcgttca gcttttttga agttaccgtt tt                          42

<210> SEQ ID NO 107
<211> LENGTH: 42
<212> TYPE: DNA
<213> ORGANISM: Artificial Sequence
<220> FEATURE:
<223> OTHER INFORMATION: Human papillomavirus type 35 label extender
      probe

<400> SEQUENCE: 107
ttctacctcg ttgcacaaat cattttttct gagtcaaagc at                          42

<210> SEQ ID NO 108
<211> LENGTH: 46
<212> TYPE: DNA
<213> ORGANISM: Artificial Sequence
<220> FEATURE:
<223> OTHER INFORMATION: Human papillomavirus type 35 label extender
      probe

<400> SEQUENCE: 108
taattcttgt ttgcagtata cacaattttt ttgaagttac cgtttt                      46

<210> SEQ ID NO 109
<211> LENGTH: 43
<212> TYPE: DNA
<213> ORGANISM: Artificial Sequence
<220> FEATURE:
<223> OTHER INFORMATION: Human papillomavirus type 35 label extender
      probe

<400> SEQUENCE: 109
aaagtcatat acctcactcc gctgtttttc tgagtcaaag cat                         43

<210> SEQ ID NO 110
<211> LENGTH: 46
<212> TYPE: DNA
<213> ORGANISM: Artificial Sequence
<220> FEATURE:
<223> OTHER INFORMATION: Human papillomavirus type 35 label extender
      probe

<400> SEQUENCE: 110
aataaatgac ataactgttt gttgcatttt ttgaagttac cgtttt                      46

<210> SEQ ID NO 111
<211> LENGTH: 46
<212> TYPE: DNA
<213> ORGANISM: Artificial Sequence
<220> FEATURE:
<223> OTHER INFORMATION: Human papillomavirus type 35 label extender
      probe

```
<400> SEQUENCE: 111 ggttttgac atgtaataca cctaattttt ttctgagtca aagcat            46

<210> SEQ ID NO 112
<211> LENGTH: 48
<212> TYPE: DNA
<213> ORGANISM: Artificial Sequence
<220> FEATURE:
<223> OTHER INFORMATION: Human papillomavirus type 35 label extender
      probe

<400> SEQUENCE: 112
tctaaaacat agtcttgcaa tgtagttatt ttttgaagtt accgtttt         48

<210> SEQ ID NO 113
<211> LENGTH: 38
<212> TYPE: DNA
<213> ORGANISM: Artificial Sequence
<220> FEATURE:
<223> OTHER INFORMATION: Human papillomavirus type 35 label extender
      probe

<400> SEQUENCE: 113
agttgcctcg ggttccaaat ttttctgagt caaagcat                    38

<210> SEQ ID NO 114
<211> LENGTH: 46
<212> TYPE: DNA
<213> ORGANISM: Artificial Sequence
<220> FEATURE:
<223> OTHER INFORMATION: Human papillomavirus type 35 label extender
      probe

<400> SEQUENCE: 114
acacaattgc tcataacagt ataggtctttt ttgaagttac cgtttt          46

<210> SEQ ID NO 115
<211> LENGTH: 41
<212> TYPE: DNA
<213> ORGANISM: Artificial Sequence
<220> FEATURE:
<223> OTHER INFORMATION: Human papillomavirus type 35 label extender
      probe

<400> SEQUENCE: 115
cttcctcctc ctctgagctg tcttttttctg agtcaaagca t               41

<210> SEQ ID NO 116
<211> LENGTH: 40
<212> TYPE: DNA
<213> ORGANISM: Artificial Sequence
<220> FEATURE:
<223> OTHER INFORMATION: Human papillomavirus type 35 label extender
      probe

<400> SEQUENCE: 116
ggaggtgtct ggttttgctt gttttttgaag ttaccgtttt                 40

<210> SEQ ID NO 117
<211> LENGTH: 48
<212> TYPE: DNA
<213> ORGANISM: Artificial Sequence
<220> FEATURE:
<223> OTHER INFORMATION: Human papillomavirus type 35 label extender
      probe
```

<400> SEQUENCE: 117
ttacaacagg acgttacaat attataattt ttttctgagt caaagcat    48

<210> SEQ ID NO 118
<211> LENGTH: 30
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 118
tctatatact atacacaaat catagcatgc    30

<210> SEQ ID NO 119
<211> LENGTH: 26
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 119
gaataaaatt ttaaacattt catgca    26

<210> SEQ ID NO 120
<211> LENGTH: 34
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 120
actatatcta taccatctat attcacttat tttt    34

<210> SEQ ID NO 121
<211> LENGTH: 22
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 121
ttgcttttca actggacaca gc    22

<210> SEQ ID NO 122
<211> LENGTH: 27
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 122
gaatcgtttt ttttcttcta aatgtct    27

<210> SEQ ID NO 123
<211> LENGTH: 23
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 123
aacaggacat acaccgacct gtc                                           23

<210> SEQ ID NO 124
<211> LENGTH: 23
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 124
ggtttctcta cgtgttggtt tcc                                           23

<210> SEQ ID NO 125
<211> LENGTH: 23
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 125
ttctccatgc atgattacac ctc                                           23

<210> SEQ ID NO 126
<211> LENGTH: 22
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 126
cagacgtagt gtcgcctcac at                                            22

<210> SEQ ID NO 127
<211> LENGTH: 25
<212> TYPE: DNA
<213> ORGANISM: Artificial Sequence
<220> FEATURE:
<223> OTHER INFORMATION: Human papillomavirus type 35 blocking label
      extender probe

<400> SEQUENCE: 127
tgtcaatgtg tgtgctctgt acaca                                         25

<210> SEQ ID NO 128
<211> LENGTH: 42
<212> TYPE: DNA
<213> ORGANISM: Artificial Sequence
<220> FEATURE:
<223> OTHER INFORMATION: Human papillomavirus type 39 capture extender
      probe

<400> SEQUENCE: 128
tacctcggtt tgctgtagtg gtttttctct tggaaagaaa gt                      42

<210> SEQ ID NO 129
<211> LENGTH: 43
<212> TYPE: DNA
<213> ORGANISM: Artificial Sequence
<220> FEATURE:
<223> OTHER INFORMATION: Human papillomavirus type 39 capture extender
      probe

<400> SEQUENCE: 129
ggttccccgt ccctatatac tattttctc ttggaaagaa agt         43

<210> SEQ ID NO 130
<211> LENGTH: 46
<212> TYPE: DNA
<213> ORGANISM: Artificial Sequence
<220> FEATURE:
<223> OTHER INFORMATION: Human papillomavirus type 39 capture extender
      probe

<400> SEQUENCE: 130
tttatgaaat cttcgtttgc tattttttt ctcttggaaa gaaagt      46

<210> SEQ ID NO 131
<211> LENGTH: 45
<212> TYPE: DNA
<213> ORGANISM: Artificial Sequence
<220> FEATURE:
<223> OTHER INFORMATION: Human papillomavirus type 39 capture extender
      probe

<400> SEQUENCE: 131
ggtccacgca tatctgatgt tatattttc tcttggaaag aaagt        45

<210> SEQ ID NO 132
<211> LENGTH: 41
<212> TYPE: DNA
<213> ORGANISM: Artificial Sequence
<220> FEATURE:
<223> OTHER INFORMATION: Human papillomavirus type 39 capture extender
      probe

<400> SEQUENCE: 132
tttcctgcaa ggtgggcttt tttttctctt ggaaagaaag t           41

<210> SEQ ID NO 133
<211> LENGTH: 44
<212> TYPE: DNA
<213> ORGANISM: Artificial Sequence
<220> FEATURE:
<223> OTHER INFORMATION: Human papillomavirus type 39 capture extender
      probe

<400> SEQUENCE: 133
ccgtgaggct tctactacca gcttttttct cttggaaaga aagt         44

<210> SEQ ID NO 134
<211> LENGTH: 47
<212> TYPE: DNA
<213> ORGANISM: Artificial Sequence
<220> FEATURE:
<223> OTHER INFORMATION: Human papillomavirus type 39 capture extender
      probe

<400> SEQUENCE: 134
acaaatccta gtgagtccat aaacagtttt tctcttggaa agaaagt      47

<210> SEQ ID NO 135
<211> LENGTH: 45
<212> TYPE: DNA
<213> ORGANISM: Artificial Sequence
<220> FEATURE:
<223> OTHER INFORMATION: Human papillomavirus type 39 label extender
      probe

<400> SEQUENCE: 135
cccgtatttt agcataaaat tttatatttt tctgagtcaa agcat        45

<210> SEQ ID NO 136
<211> LENGTH: 43
<212> TYPE: DNA
<213> ORGANISM: Artificial Sequence
<220> FEATURE:
<223> OTHER INFORMATION: Human papillomavirus type 39 label extender
      probe

<400> SEQUENCE: 136
ccgagtccga gtaatatcgt agcttttttg aagttaccgt ttt                         43

<210> SEQ ID NO 137
<211> LENGTH: 50
<212> TYPE: DNA
<213> ORGANISM: Artificial Sequence
<220> FEATURE:
<223> OTHER INFORMATION: Human papillomavirus type 39 label extender
      probe

<400> SEQUENCE: 137
ttagttatat tttctaatgt agttgcatac attttctga gtcaaagcat                   50

<210> SEQ ID NO 138
<211> LENGTH: 41
<212> TYPE: DNA
<213> ORGANISM: Artificial Sequence
<220> FEATURE:
<223> OTHER INFORMATION: Human papillomavirus type 39 label extender
      probe

<400> SEQUENCE: 138
cacagcggtt tcagacaaca catttttgaa gttaccgttt t                           41

<210> SEQ ID NO 139
<211> LENGTH: 43
<212> TYPE: DNA
<213> ORGANISM: Artificial Sequence
<220> FEATURE:
<223> OTHER INFORMATION: Human papillomavirus type 39 label extender
      probe

<400> SEQUENCE: 139
aggtgtctta atttttctgc tggattttc tgagtcaaag cat                          43

<210> SEQ ID NO 140
<211> LENGTH: 48
<212> TYPE: DNA
<213> ORGANISM: Artificial Sequence
<220> FEATURE:
<223> OTHER INFORMATION: Human papillomavirus type 39 label extender
      probe

<400> SEQUENCE: 140
ttcattgtaa ggacataaat ctaatacaat ttttgaagtt accgtttt                    48

<210> SEQ ID NO 141
<211> LENGTH: 42
<212> TYPE: DNA
<213> ORGANISM: Artificial Sequence
<220> FEATURE:
<223> OTHER INFORMATION: Human papillomavirus type 39 label extender
      probe

<400> SEQUENCE: 141
catacaaggt caaccggctg tattttttct gagtcaaagc at                          42

<210> SEQ ID NO 142
<211> LENGTH: 42
<212> TYPE: DNA
<213> ORGANISM: Artificial Sequence
<220> FEATURE:
<223> OTHER INFORMATION: Human papillomavirus type 39 label extender
      probe

<400> SEQUENCE: 142
gtcgggttca tctatttcat ccttttttga agttaccgtt tt                         42

<210> SEQ ID NO 143
<211> LENGTH: 43
<212> TYPE: DNA
<213> ORGANISM: Artificial Sequence
<220> FEATURE:
<223> OTHER INFORMATION: Human papillomavirus type 39 label extender
      probe

<400> SEQUENCE: 143
ttgatgttgg tgattaactg catgtttttc tgagtcaaag cat                        43

<210> SEQ ID NO 144
<211> LENGTH: 42
<212> TYPE: DNA
<213> ORGANISM: Artificial Sequence
<220> FEATURE:
<223> OTHER INFORMATION: Human papillomavirus type 39 label extender
      probe

<400> SEQUENCE: 144
ggttcatccc gtctggctag tagttttttga agttaccgtt tt                        42

<210> SEQ ID NO 145
<211> LENGTH: 43
<212> TYPE: DNA
<213> ORGANISM: Artificial Sequence
<220> FEATURE:
<223> OTHER INFORMATION: Human papillomavirus type 39 label extender
      probe

<400> SEQUENCE: 145
gaacactgta ttgtgtgacg ctgttttttc tgagtcaaag cat                        43

<210> SEQ ID NO 146
<211> LENGTH: 28
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 146
catataaatc actaaatgca aattcata                                         28

<210> SEQ ID NO 147
<211> LENGTH: 32
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 147
tgcaccttat taataaatta tataactttg ta                                    32

```
<210> SEQ ID NO 148
<211> LENGTH: 25
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 148
actgtcctgt atagcttcct gctat                                         25

<210> SEQ ID NO 149
<211> LENGTH: 18
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 149
tggtccagca ccgtcgac                                                 18

<210> SEQ ID NO 150
<211> LENGTH: 18
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 150
tgcggtcctc ccgttttg                                                 18

<210> SEQ ID NO 151
<211> LENGTH: 24
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 151
cttgggtttc tcttcgtgtt agtc                                          24

<210> SEQ ID NO 152
<211> LENGTH: 23
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 152
ctgactctcc taattgctcg tga                                           23

<210> SEQ ID NO 153
<211> LENGTH: 26
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 153
gcagtgtgtt gttacactta caacac                                        26

<210> SEQ ID NO 154
```

-continued

```
<211> LENGTH: 24
<212> TYPE: DNA
<213> ORGANISM: Artificial Sequence
<220> FEATURE:
<223> OTHER INFORMATION: Human papillomavirus type 39 blocking label
      extender probe

<400> SEQUENCE: 154
ctgctgtagt tgtcgcagag tatc                                           24

<210> SEQ ID NO 155
<211> LENGTH: 44
<212> TYPE: DNA
<213> ORGANISM: Artificial Sequence
<220> FEATURE:
<223> OTHER INFORMATION: Human papillomavirus type 45 capture extender
      probe

<400> SEQUENCE: 155
tatacctctg tgcgttccaa tgttttttct cttggaaaga aagt                     44

<210> SEQ ID NO 156
<211> LENGTH: 49
<212> TYPE: DNA
<213> ORGANISM: Artificial Sequence
<220> FEATURE:
<223> OTHER INFORMATION: Human papillomavirus type 45 capture extender
      probe

<400> SEQUENCE: 156
tataaataaa tctttaaaag caaattgatt tttctcttgg aaagaaagt                49

<210> SEQ ID NO 157
<211> LENGTH: 40
<212> TYPE: DNA
<213> ORGANISM: Artificial Sequence
<220> FEATURE:
<223> OTHER INFORMATION: Human papillomavirus type 45 capture extender
      probe

<400> SEQUENCE: 157
cagtgttgct cggggtccat ttttctcttg gaaagaaagt                          40

<210> SEQ ID NO 158
<211> LENGTH: 43
<212> TYPE: DNA
<213> ORGANISM: Artificial Sequence
<220> FEATURE:
<223> OTHER INFORMATION: Human papillomavirus type 45 capture extender
      probe

<400> SEQUENCE: 158
tgactaacgc catctgcttc attttttctc ttggaaagaa agt                      43

<210> SEQ ID NO 159
<211> LENGTH: 42
<212> TYPE: DNA
<213> ORGANISM: Artificial Sequence
<220> FEATURE:
<223> OTHER INFORMATION: Human papillomavirus type 45 capture extender
      probe

<400> SEQUENCE: 159
agctcaattc tgccgtcaca cttttttctct tggaaagaaa gt                      42

<210> SEQ ID NO 160
<211> LENGTH: 44
```

```
<212> TYPE: DNA
<213> ORGANISM: Artificial Sequence
<220> FEATURE:
<223> OTHER INFORMATION: Human papillomavirus type 45 capture extender
      probe

<400> SEQUENCE: 160
catctgccga gctctctact gtattttcct cttggaaaga aagt                    44

<210> SEQ ID NO 161
<211> LENGTH: 40
<212> TYPE: DNA
<213> ORGANISM: Artificial Sequence
<220> FEATURE:
<223> OTHER INFORMATION: Human papillomavirus type 45 label extender
      probe

<400> SEQUENCE: 161
tttctgctgg gttcaatggt tttttgaag ttaccgtttt                           40

<210> SEQ ID NO 162
<211> LENGTH: 44
<212> TYPE: DNA
<213> ORGANISM: Artificial Sequence
<220> FEATURE:
<223> OTHER INFORMATION: Human papillomavirus type 45 label extender
      probe

<400> SEQUENCE: 162
cgtttgtcct taaggtgtct acgttttttt ctgagtcaaa gcat                    44

<210> SEQ ID NO 163
<211> LENGTH: 43
<212> TYPE: DNA
<213> ORGANISM: Artificial Sequence
<220> FEATURE:
<223> OTHER INFORMATION: Human papillomavirus type 45 label extender
      probe

<400> SEQUENCE: 163
tgtattacac tgccctcggt actgtttttg aagttaccgt ttt                     43

<210> SEQ ID NO 164
<211> LENGTH: 38
<212> TYPE: DNA
<213> ORGANISM: Artificial Sequence
<220> FEATURE:
<223> OTHER INFORMATION: Human papillomavirus type 45 label extender
      probe

<400> SEQUENCE: 164
gccgtgcctg gtcacaacat ttttctgagt caaagcat                           38

<210> SEQ ID NO 165
<211> LENGTH: 42
<212> TYPE: DNA
<213> ORGANISM: Artificial Sequence
<220> FEATURE:
<223> OTHER INFORMATION: Human papillomavirus type 45 label extender
      probe

<400> SEQUENCE: 165
cctacgtctg cgaagtcttt cttttttga agttaccgtt tt                       42

<210> SEQ ID NO 166
<211> LENGTH: 47
<212> TYPE: DNA
```

<210> SEQ ID NO 166
<211> LENGTH: 47
<212> TYPE: DNA
<213> ORGANISM: Artificial Sequence
<220> FEATURE:
<223> OTHER INFORMATION: Human papillomavirus type 45 label extender
      probe

<400> SEQUENCE: 166
tgcatactta ttgctatact tgtgtttctt tttctgagtc aaagcat          47

<210> SEQ ID NO 167
<211> LENGTH: 43
<212> TYPE: DNA
<213> ORGANISM: Artificial Sequence
<220> FEATURE:
<223> OTHER INFORMATION: Human papillomavirus type 45 label extender
      probe

<400> SEQUENCE: 167
ttccaaatgc aatacaattt cttgttttg aagttaccgt ttt              43

<210> SEQ ID NO 168
<211> LENGTH: 44
<212> TYPE: DNA
<213> ORGANISM: Artificial Sequence
<220> FEATURE:
<223> OTHER INFORMATION: Human papillomavirus type 45 label extender
      probe

<400> SEQUENCE: 168
caacaggatc taattcattc tgaggttttt ctgagtcaaa gcat             44

<210> SEQ ID NO 169
<211> LENGTH: 43
<212> TYPE: DNA
<213> ORGANISM: Artificial Sequence
<220> FEATURE:
<223> OTHER INFORMATION: Human papillomavirus type 45 label extender
      probe

<400> SEQUENCE: 169
ttaattgctc gtaacacaac aggttttttg aagttaccgt ttt              43

<210> SEQ ID NO 170
<211> LENGTH: 40
<212> TYPE: DNA
<213> ORGANISM: Artificial Sequence
<220> FEATURE:
<223> OTHER INFORMATION: Human papillomavirus type 45 label extender
      probe

<400> SEQUENCE: 170
cgttttcctc ctctgactcg cttttctga gtcaaagcat                   40

<210> SEQ ID NO 171
<211> LENGTH: 38
<212> TYPE: DNA
<213> ORGANISM: Artificial Sequence
<220> FEATURE:
<223> OTHER INFORMATION: Human papillomavirus type 45 label extender
      probe

<400> SEQUENCE: 171
tcgggctggt agttgtgcat ttttgaagtt accgtttt                    38

<210> SEQ ID NO 172
<211> LENGTH: 36
<212> TYPE: DNA
<213> ORGANISM: Artificial Sequence
<220> FEATURE:
<223> OTHER INFORMATION: Human papillomavirus type 45 label extender
      probe

<400> SEQUENCE: 172
cgctgtggtt cggctcgttt ttctgagtca aagcat                    36

<210> SEQ ID NO 173
<211> LENGTH: 29
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 173
gcagcatatg ctatacagtc tctatacac                            29

<210> SEQ ID NO 174
<211> LENGTH: 28
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 174
ggaataaaag tctatacatt tatggcat                             28

<210> SEQ ID NO 175
<211> LENGTH: 32
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 175
gagtttgaat aatatcttaa ttctctaatt ct                        32

<210> SEQ ID NO 176
<211> LENGTH: 26
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 176 tttttccag tgtctctcca tataca                                26

<210> SEQ ID NO 177
<211> LENGTH: 34
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 177
cttattaaca aattatacaa ctctgtatta gtta                      34

<210> SEQ ID NO 178
<211> LENGTH: 17
<212> TYPE: DNA
<213> ORGANISM: Artificial Sequence
<220> FEATURE:

```
<223> OTHER INFORMATION: Human papillomavirus type 45 blocking label
      extender probe

<400> SEQUENCE: 178
tctggcaccg caggcac                                                    17

<210> SEQ ID NO 179
<211> LENGTH: 22
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 179
tccagctatg ctgtggaatc tt                                              22

<210> SEQ ID NO 180
<211> LENGTH: 27
<212> TYPE: DNA
<213> ORGANISM: Artificial Sequence
<220> FEATURE:
<223> OTHER INFORMATION: Human papillomavirus type 45 blocking label
      extender probe

<400> SEQUENCE: 180
ttacaacata cacacaaaat tttgtga                                         27

<210> SEQ ID NO 181
<211> LENGTH: 44
<212> TYPE: DNA
<213> ORGANISM: Artificial Sequence
<220> FEATURE:
<223> OTHER INFORMATION: Human papillomavirus type 51 capture extender
      probe

<400> SEQUENCE: 181
ggtctttccc tcttgtcttc gaattttcct cttggaaaga aagt                      44

<210> SEQ ID NO 182
<211> LENGTH: 44
<212> TYPE: DNA
<213> ORGANISM: Artificial Sequence
<220> FEATURE:
<223> OTHER INFORMATION: Human papillomavirus type 51 capture extender
      probe

<400> SEQUENCE: 182
tgcatagaaa cgttcaaagc ttcttttcct cttggaaaga aagt                      44

<210> SEQ ID NO 183
<211> LENGTH: 48
<212> TYPE: DNA
<213> ORGANISM: Artificial Sequence
<220> FEATURE:
<223> OTHER INFORMATION: Human papillomavirus type 51 capture extender
      probe

<400> SEQUENCE: 183
tttgaataaa acagtaaaca ttgtttgttt ttctcttgga aagaaagt                  48

<210> SEQ ID NO 184
<211> LENGTH: 51
<212> TYPE: DNA
<213> ORGANISM: Artificial Sequence
<220> FEATURE:
<223> OTHER INFORMATION: Human papillomavirus type 51 capture extender
``` probe

<400> SEQUENCE: 184
tcgataaatc atataagctt tttttagtaa tttttctctt ggaaagaaag t         51

<210> SEQ ID NO 185
<211> LENGTH: 38
<212> TYPE: DNA
<213> ORGANISM: Artificial Sequence
<220> FEATURE:
<223> OTHER INFORMATION: Human papillomavirus type 51 capture extender
      probe

<400> SEQUENCE: 185
cgcattgccc cgtccaattt ttctcttgga aagaaagt                        38

<210> SEQ ID NO 186
<211> LENGTH: 43
<212> TYPE: DNA
<213> ORGANISM: Artificial Sequence
<220> FEATURE:
<223> OTHER INFORMATION: Human papillomavirus type 51 capture extender
      probe

<400> SEQUENCE: 186
cgtgtacgtt gccagcaatt agtttttctc ttggaaagaa agt                  43

<210> SEQ ID NO 187
<211> LENGTH: 45
<212> TYPE: DNA
<213> ORGANISM: Artificial Sequence
<220> FEATURE:
<223> OTHER INFORMATION: Human papillomavirus type 51 capture extender
      probe

<400> SEQUENCE: 187
ggagcttcaa ttctgtaaca cgtatttttc tcttggaaag aaagt                45

<210> SEQ ID NO 188
<211> LENGTH: 49
<212> TYPE: DNA
<213> ORGANISM: Artificial Sequence
<220> FEATURE:
<223> OTHER INFORMATION: Human papillomavirus type 51 label extender
      probe

<400> SEQUENCE: 188
ttacaataca cacacactac ctgtatattg tttttgaagt taccgtttt            49

<210> SEQ ID NO 189
<211> LENGTH: 49
<212> TYPE: DNA
<213> ORGANISM: Artificial Sequence
<220> FEATURE:
<223> OTHER INFORMATION: Human papillomavirus type 51 label extender
      probe

<400> SEQUENCE: 189
ttatatacat ctgctctaca taattccttt tttttctgag tcaaagcat            49

<210> SEQ ID NO 190
<211> LENGTH: 48
<212> TYPE: DNA
<213> ORGANISM: Artificial Sequence
<220> FEATURE:
<223> OTHER INFORMATION: Human papillomavirus type 51 label extender
      probe

```
<400> SEQUENCE: 190
atacaatctt aatttcagta aatgctacat ttttgaagtt accgtttt                    48

<210> SEQ ID NO 191
<211> LENGTH: 47
<212> TYPE: DNA
<213> ORGANISM: Artificial Sequence
<220> FEATURE:
<223> OTHER INFORMATION: Human papillomavirus type 51 label extender
      probe

<400> SEQUENCE: 191
catactgcat atggattatt atccctattt tttctgagtc aaagcat                     47

<210> SEQ ID NO 192
<211> LENGTH: 48
<212> TYPE: DNA
<213> ORGANISM: Artificial Sequence
<220> FEATURE:
<223> OTHER INFORMATION: Human papillomavirus type 51 label extender
      probe

<400> SEQUENCE: 192
acctgctata acgtctatac tctctaattt ttttgaagtt accgtttt                    48

<210> SEQ ID NO 193
<211> LENGTH: 46
<212> TYPE: DNA
<213> ORGANISM: Artificial Sequence
<220> FEATURE:
<223> OTHER INFORMATION: Human papillomavirus type 51 label extender
      probe

<400> SEQUENCE: 193
ttgcctctaa tgtagtacca tacacagttt ttctgagtca aagcat                      46

<210> SEQ ID NO 194
<211> LENGTH: 46
<212> TYPE: DNA
<213> ORGANISM: Artificial Sequence
<220> FEATURE:
<223> OTHER INFORMATION: Human papillomavirus type 51 label extender
      probe

<400> SEQUENCE: 194
gtggtctttg acatctatga caccttattt ttgaagttac cgtttt                      46

<210> SEQ ID NO 195
<211> LENGTH: 40
<212> TYPE: DNA
<213> ORGANISM: Artificial Sequence
<220> FEATURE:
<223> OTHER INFORMATION: Human papillomavirus type 51 label extender
      probe

<400> SEQUENCE: 195
tttgcttttc ttcaggccca atttttctga gtcaaagcat                             40

<210> SEQ ID NO 196
<211> LENGTH: 41
<212> TYPE: DNA
<213> ORGANISM: Artificial Sequence
<220> FEATURE:
<223> OTHER INFORMATION: Human papillomavirus type 51 label extender
      probe
```

<400> SEQUENCE: 196
cacttgggtt tcgttacgtt gtttttttgaa gttaccgttt t 41

<210> SEQ ID NO 197
<211> LENGTH: 42
<212> TYPE: DNA
<213> ORGANISM: Artificial Sequence
<220> FEATURE:
<223> OTHER INFORMATION: Human papillomavirus type 51 label extender
      probe

<400> SEQUENCE: 197
cattaccacg catggcttta ttatttttct gagtcaaagc at 42

<210> SEQ ID NO 198
<211> LENGTH: 47
<212> TYPE: DNA
<213> ORGANISM: Artificial Sequence
<220> FEATURE:
<223> OTHER INFORMATION: Human papillomavirus type 51 label extender
      probe

<400> SEQUENCE: 198
tgcaatacta catcttttaa ttgtggtatt tttgaagtta ccgtttt 47

<210> SEQ ID NO 199
<211> LENGTH: 45
<212> TYPE: DNA
<213> ORGANISM: Artificial Sequence
<220> FEATURE:
<223> OTHER INFORMATION: Human papillomavirus type 51 label extender
      probe

<400> SEQUENCE: 199
agtcaatttc agtctgtggt gttaaatttt tctgagtcaa agcat 45

<210> SEQ ID NO 200
<211> LENGTH: 41
<212> TYPE: DNA
<213> ORGANISM: Artificial Sequence
<220> FEATURE:
<223> OTHER INFORMATION: Human papillomavirus type 51 label extender
      probe

<400> SEQUENCE: 200
tcaaattgct cgtagcattg catttttgaa gttaccgttt t 41

<210> SEQ ID NO 201
<211> LENGTH: 44
<212> TYPE: DNA
<213> ORGANISM: Artificial Sequence
<220> FEATURE:
<223> OTHER INFORMATION: Human papillomavirus type 51 label extender
      probe

<400> SEQUENCE: 201
tacttcatcc tcctcctctg agctgttttt ctgagtcaaa gcat 44

<210> SEQ ID NO 202
<211> LENGTH: 22
<212> TYPE: DNA
<213> ORGANISM: Artificial Sequence
<220> FEATURE:
<223> OTHER INFORMATION: Human papillomavirus type 51 blocking label
      extender probe

<400> SEQUENCE: 202
acataattca tgcagcgttc gt                                        22

<210> SEQ ID NO 203
<211> LENGTH: 22
<212> TYPE: DNA
<213> ORGANISM: Artificial Sequence
<220> FEATURE:
<223> OTHER INFORMATION: Human papillomavirus type 51 blocking label
      extender probe

<400> SEQUENCE: 203
cttttttttt cgtccaccaa tt                                        22

<210> SEQ ID NO 204
<211> LENGTH: 21
<212> TYPE: DNA
<213> ORGANISM: Artificial Sequence
<220> FEATURE:
<223> OTHER INFORMATION: Human papillomavirus type 51 blocking label
      extender probe

<400> SEQUENCE: 204
cgtcccgcta tttcatggaa c                                         21

<210> SEQ ID NO 205
<211> LENGTH: 25
<212> TYPE: DNA
<213> ORGANISM: Artificial Sequence
<220> FEATURE:
<223> OTHER INFORMATION: Human papillomavirus type 51 blocking label
      extender probe

<400> SEQUENCE: 205
ctggtagctg gtcacgcata ttatc                                     25

<210> SEQ ID NO 206
<211> LENGTH: 19
<212> TYPE: DNA
<213> ORGANISM: Artificial Sequence
<220> FEATURE:
<223> OTHER INFORMATION: Human papillomavirus type 51 blocking label
      extender probe

<400> SEQUENCE: 206
gcctgtccag cccgtcttt                                            19

<210> SEQ ID NO 207
<211> LENGTH: 38
<212> TYPE: DNA
<213> ORGANISM: Artificial Sequence
<220> FEATURE:
<223> OTHER INFORMATION: Human papillomavirus type 52 capture extender
      probe

<400> SEQUENCE: 207
gtgcagggtc cggggtcttt ttctcttgga aagaaagt                       38

<210> SEQ ID NO 208
<211> LENGTH: 41
<212> TYPE: DNA
<213> ORGANISM: Artificial Sequence
<220> FEATURE:
<223> OTHER INFORMATION: Human papillomavirus type 52 capture extender
      probe

<400> SEQUENCE: 208

```
cactctgaac agcgccctgt tttttctctt ggaaagaaag t                          41
```

<210> SEQ ID NO 209
<211> LENGTH: 40
<212> TYPE: DNA
<213> ORGANISM: Artificial Sequence
<220> FEATURE:
<223> OTHER INFORMATION: Human papillomavirus type 52 capture extender
      probe

<400> SEQUENCE: 209

```
cacaggtcgg ggtctccaat ttttctcttg gaaagaaagt                             40
```

<210> SEQ ID NO 210
<211> LENGTH: 43
<212> TYPE: DNA
<213> ORGANISM: Artificial Sequence
<220> FEATURE:
<223> OTHER INFORMATION: Human papillomavirus type 52 capture extender
      probe

<400> SEQUENCE: 210

```
cagtgctatg aatgcatagc cgttttctc ttggaaagaa agt                         43
```

<210> SEQ ID NO 211
<211> LENGTH: 40
<212> TYPE: DNA
<213> ORGANISM: Artificial Sequence
<220> FEATURE:
<223> OTHER INFORMATION: Human papillomavirus type 52 capture extender
      probe

<400> SEQUENCE: 211

```
tgtgcccaac agcatttgct ttttctcttg gaaagaaagt                             40
```

<210> SEQ ID NO 212
<211> LENGTH: 41
<212> TYPE: DNA
<213> ORGANISM: Artificial Sequence
<220> FEATURE:
<223> OTHER INFORMATION: Human papillomavirus type 52 capture extender
      probe

<400> SEQUENCE: 212

```
ttcagggtcc tccattgcag tttttctctt ggaaagaaag t                          41
```

<210> SEQ ID NO 213
<211> LENGTH: 41
<212> TYPE: DNA
<213> ORGANISM: Artificial Sequence
<220> FEATURE:
<223> OTHER INFORMATION: Human papillomavirus type 52 label extender
      probe

<400> SEQUENCE: 213

```
cttccagcac ctcacacaat tcttttttgaa gttaccgttt t                         41
```

<210> SEQ ID NO 214
<211> LENGTH: 40
<212> TYPE: DNA
<213> ORGANISM: Artificial Sequence
<220> FEATURE:
<223> OTHER INFORMATION: Human papillomavirus type 52 label extender
      probe

<400> SEQUENCE: 214

```
gccttatttc atgcaccgat tttttctga gtcaaagcat                              40
```

<210> SEQ ID NO 215
<211> LENGTH: 39
<212> TYPE: DNA
<213> ORGANISM: Artificial Sequence
<220> FEATURE:
<223> OTHER INFORMATION: Human papillomavirus type 52 label extender
      probe

<400> SEQUENCE: 215
tttgcactgc acacactgca tttttgaagt taccgtttt                    39

<210> SEQ ID NO 216
<211> LENGTH: 45
<212> TYPE: DNA
<213> ORGANISM: Artificial Sequence
<220> FEATURE:
<223> OTHER INFORMATION: Human papillomavirus type 52 label extender
      probe

<400> SEQUENCE: 216
tatacctctc ttcgttgtag ctcttttttt tctgagtcaa agcat             45

<210> SEQ ID NO 217
<211> LENGTH: 44
<212> TYPE: DNA
<213> ORGANISM: Artificial Sequence
<220> FEATURE:
<223> OTHER INFORMATION: Human papillomavirus type 52 label extender
      probe

<400> SEQUENCE: 217 tttcttttc ttcaggacat aatggttttt gaagttaccg tttt               44

<210> SEQ ID NO 218
<211> LENGTH: 42
<212> TYPE: DNA
<213> ORGANISM: Artificial Sequence
<220> FEATURE:
<223> OTHER INFORMATION: Human papillomavirus type 52 label extender
      probe

<400> SEQUENCE: 218
tcgcttgttt gcattaacat gtcttttct gagtcaaagc at                 42

<210> SEQ ID NO 219
<211> LENGTH: 40
<212> TYPE: DNA
<213> ORGANISM: Artificial Sequence
<220> FEATURE:
<223> OTHER INFORMATION: Human papillomavirus type 52 label extender
      probe

<400> SEQUENCE: 219
cgcatgacgt tacacttggg tttttgaag ttaccgtttt                    40

<210> SEQ ID NO 220
<211> LENGTH: 45
<212> TYPE: DNA
<213> ORGANISM: Artificial Sequence
<220> FEATURE:
<223> OTHER INFORMATION: Human papillomavirus type 52 label extender
      probe

<400> SEQUENCE: 220 aatctttat agttgctttg tctccatttt tctgagtcaa agcat              45

<210> SEQ ID NO 221
<211> LENGTH: 40
<212> TYPE: DNA
<213> ORGANISM: Artificial Sequence
<220> FEATURE:
<223> OTHER INFORMATION: Human papillomavirus type 52 label extender
      probe

<400> SEQUENCE: 221
gccggtccac accatctgta tttttgaag ttaccgtttt                              40

<210> SEQ ID NO 222
<211> LENGTH: 41
<212> TYPE: DNA
<213> ORGANISM: Artificial Sequence
<220> FEATURE:
<223> OTHER INFORMATION: Human papillomavirus type 52 label extender
      probe

<400> SEQUENCE: 222
gcttgttctg cttgtccatc tgtttttctg agtcaaagca t                           41

<210> SEQ ID NO 223
<211> LENGTH: 45
<212> TYPE: DNA
<213> ORGANISM: Artificial Sequence
<220> FEATURE:
<223> OTHER INFORMATION: Human papillomavirus type 52 label extender
      probe

<400> SEQUENCE: 223
atgtcacaat gtagtaattg cttgtgtttt tgaagttacc gtttt                       45

<210> SEQ ID NO 224
<211> LENGTH: 45
<212> TYPE: DNA
<213> ORGANISM: Artificial Sequence
<220> FEATURE:
<223> OTHER INFORMATION: Human papillomavirus type 52 label extender
      probe

<400> SEQUENCE: 224
tagtgtgcta tcacaactgt gacaatttt tctgagtcaa agcat                        45

<210> SEQ ID NO 225
<211> LENGTH: 29
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 225
ctattcgtaa atctgtaaat agaaacttg                                         29

<210> SEQ ID NO 226
<211> LENGTH: 27
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 226
cgccatatgg attattgtct ctatata                                           27

<210> SEQ ID NO 227
<211> LENGTH: 24
<212> TYPE: DNA
<213> ORGANISM: Artificial Sequence
<220> FEATURE:
<223> OTHER INFORMATION: Human papillomavirus type 52 blocking extender probe

<400> SEQUENCE: 227
aaaagcgtag gcacataata caca                                            24

<210> SEQ ID NO 228
<211> LENGTH: 31
<212> TYPE: DNA
<213> ORGANISM: Artificial Sequence
<220> FEATURE:
<223> OTHER INFORMATION: Human papillomavirus type 52 blocking extender probe

<400> SEQUENCE: 228
tgataatgcc tatattcact tatcttagat a                                    31

<210> SEQ ID NO 229
<211> LENGTH: 27
<212> TYPE: DNA
<213> ORGANISM: Artificial Sequence
<220> FEATURE:
<223> OTHER INFORMATION: Human papillomavirus type 52 blocking extender probe

<400> SEQUENCE: 229
tctaatgttt tcccatacag tgaatat                                         27

<210> SEQ ID NO 230
<211> LENGTH: 26
<212> TYPE: DNA
<213> ORGANISM: Artificial Sequence
<220> FEATURE:
<223> OTHER INFORMATION: Human papillomavirus type 52 blocking extender probe

<400> SEQUENCE: 230
cacttaatgg tttttttacc ctctct                                          26

<210> SEQ ID NO 231
<211> LENGTH: 32
<212> TYPE: DNA
<213> ORGANISM: Artificial Sequence
<220> FEATURE:
<223> OTHER INFORMATION: Human papillomavirus type 52 blocking extender probe

<400> SEQUENCE: 231
cgtttgacaa attatacatc taatagttat tt                                   32

<210> SEQ ID NO 232
<211> LENGTH: 24
<212> TYPE: DNA
<213> ORGANISM: Artificial Sequence
<220> FEATURE:
<223> OTHER INFORMATION: Human papillomavirus type 52 blocking extender probe

<400> SEQUENCE: 232
ccaacgaccc ataatattat gaaa                                            24

<210> SEQ ID NO 233

```
<211> LENGTH: 27
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 233
ttgtttcagg ttgcagatct aatatat                                              27

<210> SEQ ID NO 234
<211> LENGTH: 25
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 234
aattgctcat agcagtgtag gtcag                                                25

<210> SEQ ID NO 235
<211> LENGTH: 23
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 235
cctcctcatc tgagctgtca cct                                                  23

<210> SEQ ID NO 236
<211> LENGTH: 22
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 236
tgtagagtac gaaggtccgt cg                                                   22

<210> SEQ ID NO 237
<211> LENGTH: 20
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 237
ccggggcaca caacttgtaa                                                      20

<210> SEQ ID NO 238
<211> LENGTH: 22
<212> TYPE: DNA
<213> ORGANISM: Artificial Sequence
<220> FEATURE:
<223> OTHER INFORMATION: Human papillomavirus type 52 blocking extender
      probe

<400> SEQUENCE: 238
ggttgtttat agccgtgcac ag                                                   22

<210> SEQ ID NO 239
<211> LENGTH: 49
```

```
<212> TYPE: DNA
<213> ORGANISM: Artificial Sequence
<220> FEATURE:
<223> OTHER INFORMATION: Human papillomavirus type 56 capture extender
      probe

<400> SEQUENCE: 239
gttagttctt ttttgcaata tacacatgtt tttctcttgg aaagaaagt                49

<210> SEQ ID NO 240
<211> LENGTH: 47
<212> TYPE: DNA
<213> ORGANISM: Artificial Sequence
<220> FEATURE:
<223> OTHER INFORMATION: Human papillomavirus type 56 capture extender
      probe

<400> SEQUENCE: 240
atgcaaaatt atatacctca gcacgttttt tctcttggaa agaaagt                  47

<210> SEQ ID NO 241
<211> LENGTH: 43
<212> TYPE: DNA
<213> ORGANISM: Artificial Sequence
<220> FEATURE:
<223> OTHER INFORMATION: Human papillomavirus type 56 capture extender
      probe

<400> SEQUENCE: 241
gcacactgca taaggaaaat cattttctc ttggaaagaa agt                       43

<210> SEQ ID NO 242
<211> LENGTH: 43
<212> TYPE: DNA
<213> ORGANISM: Artificial Sequence
<220> FEATURE:
<223> OTHER INFORMATION: Human papillomavirus type 56 capture extender
      probe

<400> SEQUENCE: 242
cacaatgcaa ttgcttttcc tcttttctc ttggaaagaa agt                       43

<210> SEQ ID NO 243
<211> LENGTH: 48
<212> TYPE: DNA
<213> ORGANISM: Artificial Sequence
<220> FEATURE:
<223> OTHER INFORMATION: Human papillomavirus type 56 capture extender
      probe

<400> SEQUENCE: 243
ctattagatg aaatcgtctt tttctgtttt ttctcttgga aagaaagt                 48

<210> SEQ ID NO 244
<211> LENGTH: 41
<212> TYPE: DNA
<213> ORGANISM: Artificial Sequence
<220> FEATURE:
<223> OTHER INFORMATION: Human papillomavirus type 56 capture extender
      probe

<400> SEQUENCE: 244
gtctccagca ccccaaacat tttttctctt ggaaagaaag t                        41

<210> SEQ ID NO 245
<211> LENGTH: 46
<212> TYPE: DNA
```

<213> ORGANISM: Artificial Sequence
<220> FEATURE:
<223> OTHER INFORMATION: Human papillomavirus type 56 capture extender
      probe

<400> SEQUENCE: 245
aggtcaattt ctgtttgagg tgttattttt ctcttggaaa gaaagt                    46

<210> SEQ ID NO 246
<211> LENGTH: 50
<212> TYPE: DNA
<213> ORGANISM: Artificial Sequence
<220> FEATURE:
<223> OTHER INFORMATION: Human papillomavirus type 56 label extender
      probe

<400> SEQUENCE: 246
catacactga atagtcataa tacctatatt tttttgaag ttaccgtttt                 50

<210> SEQ ID NO 247
<211> LENGTH: 49
<212> TYPE: DNA
<213> ORGANISM: Artificial Sequence
<220> FEATURE:
<223> OTHER INFORMATION: Human papillomavirus type 56 label extender
      probe

<400> SEQUENCE: 247 gtttttagt tatactttct agtgtagctc tttttctgag tcaaagcat                  49

<210> SEQ ID NO 248
<211> LENGTH: 48
<212> TYPE: DNA
<213> ORGANISM: Artificial Sequence
<220> FEATURE:
<223> OTHER INFORMATION: Human papillomavirus type 56 label extender
      probe

<400> SEQUENCE: 248
gtagcacctt attaataaat cacataactt ttttgaagtt accgtttt                  48

<210> SEQ ID NO 249
<211> LENGTH: 43
<212> TYPE: DNA
<213> ORGANISM: Artificial Sequence
<220> FEATURE:
<223> OTHER INFORMATION: Human papillomavirus type 56 label extender
      probe

<400> SEQUENCE: 249
cggagttaac ggactttgac atcttttttc tgagtcaaag cat                       43

<210> SEQ ID NO 250
<211> LENGTH: 48
<212> TYPE: DNA
<213> ORGANISM: Artificial Sequence
<220> FEATURE:
<223> OTHER INFORMATION: Human papillomavirus type 56 label extender
      probe

<400> SEQUENCE: 250
tgtagattct ctaggttctc tagatgtttt ttttgaagtt accgtttt                  48

<210> SEQ ID NO 251
<211> LENGTH: 46
<212> TYPE: DNA
<213> ORGANISM: Artificial Sequence

```
<220> FEATURE:
<223> OTHER INFORMATION: Human papillomavirus type 56 label extender
      probe

<400> SEQUENCE: 251
ttggtacttt accatgcatg attatacttt ttctgagtca aagcat              46

<210> SEQ ID NO 252
<211> LENGTH: 41
<212> TYPE: DNA
<213> ORGANISM: Artificial Sequence
<220> FEATURE:
<223> OTHER INFORMATION: Human papillomavirus type 56 label extender
      probe

<400> SEQUENCE: 252
cctcatcctc atcctctgag cttttttgaa gttaccgttt t                   41

<210> SEQ ID NO 253
<211> LENGTH: 43
<212> TYPE: DNA
<213> ORGANISM: Artificial Sequence
<220> FEATURE:
<223> OTHER INFORMATION: Human papillomavirus type 56 label extender
      probe

<400> SEQUENCE: 253
gctcctgcaa atggtctact tcatttttc tgagtcaaag cat                  43

<210> SEQ ID NO 254
<211> LENGTH: 40
<212> TYPE: DNA
<213> ORGANISM: Artificial Sequence
<220> FEATURE:
<223> OTHER INFORMATION: Human papillomavirus type 56 label extender
      probe

<400> SEQUENCE: 254
cttgtctagc ttgctgtggc cttttgaag ttaccgtttt                      40

<210> SEQ ID NO 255
<211> LENGTH: 48
<212> TYPE: DNA
<213> ORGANISM: Artificial Sequence
<220> FEATURE:
<223> OTHER INFORMATION: Human papillomavirus type 56 label extender
      probe

<400> SEQUENCE: 255
gtgtattagg taacacgtat gttgtttagt ttttctgagt caaagcat            48

<210> SEQ ID NO 256
<211> LENGTH: 46
<212> TYPE: DNA
<213> ORGANISM: Artificial Sequence
<220> FEATURE:
<223> OTHER INFORMATION: Human papillomavirus type 56 label extender
      probe

<400> SEQUENCE: 256
cacaaactta cactcacaac aaggtacttt ttgaagttac cgtttt              46

<210> SEQ ID NO 257
<211> LENGTH: 43
<212> TYPE: DNA
<213> ORGANISM: Artificial Sequence
<220> FEATURE:
```

<223> OTHER INFORMATION: Human papillomavirus type 56 label extender
      probe

<400> SEQUENCE: 257
ggtactgtga atgtccaact gcactttttc tgagtcaaag cat                    43

<210> SEQ ID NO 258
<211> LENGTH: 28
<212> TYPE: DNA
<213> ORGANISM: Artificial Sequence
<220> FEATURE:
<223> OTHER INFORMATION: Human papillomavirus type 56 blocker label
      extender probe

<400> SEQUENCE: 258
tccctataca ctaagtttaa ttcagtgc                                     28

<210> SEQ ID NO 259
<211> LENGTH: 33
<212> TYPE: DNA
<213> ORGANISM: Artificial Sequence
<220> FEATURE:
<223> OTHER INFORMATION: Human papillomavirus type 56 blocker label
      extender probe

<400> SEQUENCE: 259
tctaacttta ctataaaaca ataaacatac tct                               33

<210> SEQ ID NO 260
<211> LENGTH: 19
<212> TYPE: DNA
<213> ORGANISM: Artificial Sequence
<220> FEATURE:
<223> OTHER INFORMATION: Human papillomavirus type 56 blocker label
      extender probe

<400> SEQUENCE: 260
gacccggtcc aaccatgtg                                               19

<210> SEQ ID NO 261
<211> LENGTH: 24
<212> TYPE: DNA
<213> ORGANISM: Artificial Sequence
<220> FEATURE:
<223> OTHER INFORMATION: Human papillomavirus type 56 blocker label
      extender probe

<400> SEQUENCE: 261
gttctaatat aacgtcttgc agcg                                         24

<210> SEQ ID NO 262
<211> LENGTH: 22
<212> TYPE: DNA
<213> ORGANISM: Artificial Sequence
<220> FEATURE:
<223> OTHER INFORMATION: Human papillomavirus type 56 blocker label
      extender probe

<400> SEQUENCE: 262
gtccaattgc tcattgcact gt                                           22

<210> SEQ ID NO 263
<211> LENGTH: 41
<212> TYPE: DNA
<213> ORGANISM: Artificial Sequence
<220> FEATURE:
<223> OTHER INFORMATION: Human papillomavirus type 58 capture extender probe

<400> SEQUENCE: 263
ctcctctgcg tcctggaaca tttttctctt ggaaagaaag t                    41

<210> SEQ ID NO 264
<211> LENGTH: 43
<212> TYPE: DNA
<213> ORGANISM: Artificial Sequence
<220> FEATURE:
<223> OTHER INFORMATION: Human papillomavirus type 58 capture extender
      probe

<400> SEQUENCE: 264
tcaattcgat tcatgcaca gatttttctc ttggaaagaa agt                   43

<210> SEQ ID NO 265
<211> LENGTH: 43
<212> TYPE: DNA
<213> ORGANISM: Artificial Sequence
<220> FEATURE:
<223> OTHER INFORMATION: Human papillomavirus type 58 capture extender
      probe

<400> SEQUENCE: 265 gtcttttgc attcaacgca ttttttctc ttggaaagaa agt                    43

<210> SEQ ID NO 266
<211> LENGTH: 49
<212> TYPE: DNA
<213> ORGANISM: Artificial Sequence
<220> FEATURE:
<223> OTHER INFORMATION: Human papillomavirus type 58 capture extender
      probe

<400> SEQUENCE: 266
cactattctt aaatctgcaa atacaaagtt tttctcttgg aaagaaagt            49

<210> SEQ ID NO 267
<211> LENGTH: 47
<212> TYPE: DNA
<213> ORGANISM: Artificial Sequence
<220> FEATURE:
<223> OTHER INFORMATION: Human papillomavirus type 58 capture extender
      probe

<400> SEQUENCE: 267
agcaatcgta agcacacttt acatacttt tctcttggaa agaaagt               47

<210> SEQ ID NO 268
<211> LENGTH: 53
<212> TYPE: DNA
<213> ORGANISM: Artificial Sequence
<220> FEATURE:
<223> OTHER INFORMATION: Human papillomavirus type 58 capture extender
      probe

<400> SEQUENCE: 268
attaatattt catttaaaca ctttttagt gtttttctc ttggaaagaa agt         53

<210> SEQ ID NO 269
<211> LENGTH: 43
<212> TYPE: DNA
<213> ORGANISM: Artificial Sequence
<220> FEATURE:
<223> OTHER INFORMATION: Human papillomavirus type 58 capture extender
      probe

<400> SEQUENCE: 269
ccgtccaagc ctatttcatc cttttttctc ttggaaagaa agt                    43

<210> SEQ ID NO 270
<211> LENGTH: 40
<212> TYPE: DNA
<213> ORGANISM: Artificial Sequence
<220> FEATURE:
<223> OTHER INFORMATION: Human papillomavirus type 58 label extender
      probe

<400> SEQUENCE: 270
atcatgcaat gtccgtggtt tttttttgaag ttaccgtttt                        40

<210> SEQ ID NO 271
<211> LENGTH: 40
<212> TYPE: DNA
<213> ORGANISM: Artificial Sequence
<220> FEATURE:
<223> OTHER INFORMATION: Human papillomavirus type 58 label extender
      probe

<400> SEQUENCE: 271
tgtctccaac gcctgacaca atttttctga gtcaaagcat                         40

<210> SEQ ID NO 272
<211> LENGTH: 53
<212> TYPE: DNA
<213> ORGANISM: Artificial Sequence
<220> FEATURE:
<223> OTHER INFORMATION: Human papillomavirus type 58 label extender
      probe

<400> SEQUENCE: 272
ataattataa tgtctatact cacttatttt agattttttg aagttaccgt ttt          53

<210> SEQ ID NO 273
<211> LENGTH: 46
<212> TYPE: DNA
<213> ORGANISM: Artificial Sequence
<220> FEATURE:
<223> OTHER INFORMATION: Human papillomavirus type 58 label extender
      probe

<400> SEQUENCE: 273
ttgttctaat gtgtctccat atagcgattt ttctgagtca aagcat                  46

<210> SEQ ID NO 274
<211> LENGTH: 47
<212> TYPE: DNA
<213> ORGANISM: Artificial Sequence
<220> FEATURE:
<223> OTHER INFORMATION: Human papillomavirus type 58 label extender
      probe

<400> SEQUENCE: 274
caatggtctt tgacaaataa tacatctatt tttgaagtta ccgtttt                 47

<210> SEQ ID NO 275
<211> LENGTH: 42
<212> TYPE: DNA
<213> ORGANISM: Artificial Sequence
<220> FEATURE:
<223> OTHER INFORMATION: Human papillomavirus type 58 label extender
      probe

<400> SEQUENCE: 275 tgccttttt tttcttgtgg acattttct gagtcaaagc at                              42

<210> SEQ ID NO 276
<211> LENGTH: 41
<212> TYPE: DNA
<213> ORGANISM: Artificial Sequence
<220> FEATURE:
<223> OTHER INFORMATION: Human papillomavirus type 58 label extender
      probe

<400> SEQUENCE: 276
cctgtccaac gacccgaaat atttttgaa gttaccgttt t                              41

<210> SEQ ID NO 277
<211> LENGTH: 39
<212> TYPE: DNA
<213> ORGANISM: Artificial Sequence
<220> FEATURE:
<223> OTHER INFORMATION: Human papillomavirus type 58 label extender
      probe

<400> SEQUENCE: 277
tccaacacac tgcacagcgc ttttctgag tcaaagcat                                 39

<210> SEQ ID NO 278
<211> LENGTH: 41
<212> TYPE: DNA
<213> ORGANISM: Artificial Sequence
<220> FEATURE:
<223> OTHER INFORMATION: Human papillomavirus type 58 label extender
      probe

<400> SEQUENCE: 278
tgtgtttgtc tacgtcgggg tcttttgaa gttaccgttt t                              41

<210> SEQ ID NO 279
<211> LENGTH: 42
<212> TYPE: DNA
<213> ORGANISM: Artificial Sequence
<220> FEATURE:
<223> OTHER INFORMATION: Human papillomavirus type 58 label extender
      probe

<400> SEQUENCE: 279
atggcgttgt tacaggttac actttttct gagtcaaagc at                             42

<210> SEQ ID NO 280
<211> LENGTH: 43
<212> TYPE: DNA
<213> ORGANISM: Artificial Sequence
<220> FEATURE:
<223> OTHER INFORMATION: Human papillomavirus type 58 label extender
      probe

<400> SEQUENCE: 280
tcatagcaga ataggtcagt tggtttttg aagttaccgt ttt                            43

<210> SEQ ID NO 281
<211> LENGTH: 42
<212> TYPE: DNA
<213> ORGANISM: Artificial Sequence
<220> FEATURE:
<223> OTHER INFORMATION: Human papillomavirus type 58 label extender
      probe

<400> SEQUENCE: 281
cgtctgagct gtcacataat tgcttttct gagtcaaagc at 42

<210> SEQ ID NO 282
<211> LENGTH: 24
<212> TYPE: DNA
<213> ORGANISM: Artificial Sequence
<220> FEATURE:
<223> OTHER INFORMATION: Human papillomavirus type 58 blocking label
      extender probe

<400> SEQUENCE: 282
tcatatacct cagatcgctg caaa 24

<210> SEQ ID NO 283
<211> LENGTH: 24
<212> TYPE: DNA
<213> ORGANISM: Artificial Sequence
<220> FEATURE:
<223> OTHER INFORMATION: Human papillomavirus type 58 blocking label
      extender probe

<400> SEQUENCE: 283
tgcaaatgga tttccatctc tata 24

<210> SEQ ID NO 284
<211> LENGTH: 26
<212> TYPE: DNA
<213> ORGANISM: Artificial Sequence
<220> FEATURE:
<223> OTHER INFORMATION: Human papillomavirus type 58 blocking label
      extender probe

<400> SEQUENCE: 284
tatgaaacct tttgtttaaa tccaca 26

<210> SEQ ID NO 285
<211> LENGTH: 20
<212> TYPE: DNA
<213> ORGANISM: Artificial Sequence
<220> FEATURE:
<223> OTHER INFORMATION: Human papillomavirus type 58 blocking label
      extender probe

<400> SEQUENCE: 285
gcgttgggtt gtttcctctc 20

<210> SEQ ID NO 286
<211> LENGTH: 31
<212> TYPE: DNA
<213> ORGANISM: Artificial Sequence
<220> FEATURE:
<223> OTHER INFORMATION: Human papillomavirus type 58 blocking label
      extender probe

<400> SEQUENCE: 286
tcaggatgta aatctaaaat atattctctt a 31

<210> SEQ ID NO 287
<211> LENGTH: 40
<212> TYPE: DNA
<213> ORGANISM: Artificial Sequence
<220> FEATURE:
<223> OTHER INFORMATION: Human papillomavirus type 59 capture extender
      probe

<400> SEQUENCE: 287
ggatcctcaa agcgtgccat ttttctcttg gaaagaaagt    40

<210> SEQ ID NO 288
<211> LENGTH: 43
<212> TYPE: DNA
<213> ORGANISM: Artificial Sequence
<220> FEATURE:
<223> OTHER INFORMATION: Human papillomavirus type 59 capture extender
      probe

<400> SEQUENCE: 288
tgatgcgaat atcatgcaga ggttttctc ttggaaagaa agt    43

<210> SEQ ID NO 289
<211> LENGTH: 45
<212> TYPE: DNA
<213> ORGANISM: Artificial Sequence
<220> FEATURE:
<223> OTHER INFORMATION: Human papillomavirus type 59 capture extender
      probe

<400> SEQUENCE: 289
tctataacag cgtatcagca gctcttttc tcttggaaag aaagt    45

<210> SEQ ID NO 290
<211> LENGTH: 45
<212> TYPE: DNA
<213> ORGANISM: Artificial Sequence
<220> FEATURE:
<223> OTHER INFORMATION: Human papillomavirus type 59 capture extender
      probe

<400> SEQUENCE: 290
tgttggacat agaggtttta ggcatttttc tcttggaaag aaagt    45

<210> SEQ ID NO 291
<211> LENGTH: 41
<212> TYPE: DNA
<213> ORGANISM: Artificial Sequence
<220> FEATURE:
<223> OTHER INFORMATION: Human papillomavirus type 59 capture extender
      probe

<400> SEQUENCE: 291
taggtgtctt gctcgggtcc tttttctctt ggaaagaaag t    41

<210> SEQ ID NO 292
<211> LENGTH: 43
<212> TYPE: DNA
<213> ORGANISM: Artificial Sequence
<220> FEATURE:
<223> OTHER INFORMATION: Human papillomavirus type 59 capture extender
      probe

<400> SEQUENCE: 292
aaagtgttgc ttttggtcca tgttttctc ttggaaagaa agt    43

<210> SEQ ID NO 293
<211> LENGTH: 40
<212> TYPE: DNA
<213> ORGANISM: Artificial Sequence
<220> FEATURE:
<223> OTHER INFORMATION: Human papillomavirus type 59 label extender
      probe

<400> SEQUENCE: 293
cccctttgca aaacacacaa ttttttgaag ttaccgtttt    40

<210> SEQ ID NO 294
<211> LENGTH: 44
<212> TYPE: DNA
<213> ORGANISM: Artificial Sequence
<220> FEATURE:
<223> OTHER INFORMATION: Human papillomavirus type 59 label extender
      probe

<400> SEQUENCE: 294 tcaaataccct ctctttcttg cagttttttt ctgagtcaaa gcat                    44

<210> SEQ ID NO 295
<211> LENGTH: 43
<212> TYPE: DNA
<213> ORGANISM: Artificial Sequence
<220> FEATURE:
<223> OTHER INFORMATION: Human papillomavirus type 59 label extender
      probe

<400> SEQUENCE: 295
cctctaatgt ttctccatac acggtttttg aagttaccgt ttt                      43

<210> SEQ ID NO 296
<211> LENGTH: 42
<212> TYPE: DNA
<213> ORGANISM: Artificial Sequence
<220> FEATURE:
<223> OTHER INFORMATION: Human papillomavirus type 59 label extender
      probe

<400> SEQUENCE: 296
atgtaacggt gtcttggttt cagttttcct gagtcaaagc at                       42

<210> SEQ ID NO 297
<211> LENGTH: 38
<212> TYPE: DNA
<213> ORGANISM: Artificial Sequence
<220> FEATURE:
<223> OTHER INFORMATION: Human papillomavirus type 59 label extender
      probe

<400> SEQUENCE: 297
gcgcttgtcg ttgctgtctt ttttgaagtt accgtttt                            38

<210> SEQ ID NO 298
<211> LENGTH: 46
<212> TYPE: DNA
<213> ORGANISM: Artificial Sequence
<220> FEATURE:
<223> OTHER INFORMATION: Human papillomavirus type 59 label extender
      probe

<400> SEQUENCE: 298
cattgtttta caccagtgtt tcactacttt ttctgagtca aagcat                   46

<210> SEQ ID NO 299
<211> LENGTH: 44
<212> TYPE: DNA
<213> ORGANISM: Artificial Sequence
<220> FEATURE:
<223> OTHER INFORMATION: Human papillomavirus type 59 label extender
      probe

<400> SEQUENCE: 299
ggttccaaat ctaaaacaat gtcacttttt gaagttaccg tttt                     44

<210> SEQ ID NO 300
<211> LENGTH: 44
<212> TYPE: DNA
<213> ORGANISM: Artificial Sequence
<220> FEATURE:
<223> OTHER INFORMATION: Human papillomavirus type 59 label extender
      probe

<400> SEQUENCE: 300
aaggtcaact tcctcataat tttgtttttt ctgagtcaaa gcat                          44

<210> SEQ ID NO 301
<211> LENGTH: 42
<212> TYPE: DNA
<213> ORGANISM: Artificial Sequence
<220> FEATURE:
<223> OTHER INFORMATION: Human papillomavirus type 59 label extender
      probe

<400> SEQUENCE: 301
tcaggtaatt gctcgtagca cacttttga agttaccgtt tt                             42

<210> SEQ ID NO 302
<211> LENGTH: 40
<212> TYPE: DNA
<213> ORGANISM: Artificial Sequence
<220> FEATURE:
<223> OTHER INFORMATION: Human papillomavirus type 59 label extender
      probe

<400> SEQUENCE: 302
ttttcattct cggagtcgga gttttctga gtcaaagcat                                40

<210> SEQ ID NO 303
<211> LENGTH: 44
<212> TYPE: DNA
<213> ORGANISM: Artificial Sequence
<220> FEATURE:
<223> OTHER INFORMATION: Human papillomavirus type 59 label extender
      probe

<400> SEQUENCE: 303
gcgaggtttc tactactagc tgaagttttt gaagttaccg tttt                          44

<210> SEQ ID NO 304
<211> LENGTH: 38
<212> TYPE: DNA
<213> ORGANISM: Artificial Sequence
<220> FEATURE:
<223> OTHER INFORMATION: Human papillomavirus type 59 label extender
      probe

<400> SEQUENCE: 304
aaggctcgca atccgtcttt ttttctgagt caaagcat                                 38

<210> SEQ ID NO 305
<211> LENGTH: 24
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 305
ggcagtttgt atggtcgttg tgta                                                24

```
<210> SEQ ID NO 306
<211> LENGTH: 25
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 306
aatattcaat gttgtgctca aatca                                           25

<210> SEQ ID NO 307
<211> LENGTH: 30
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 307
tacactataa ataagtcatt aaaagcaaat                                      30

<210> SEQ ID NO 308
<211> LENGTH: 24
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 308
gctgcatacg gtgtacagtc tcta                                            24

<210> SEQ ID NO 309
<211> LENGTH: 26
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 309
cataaaatga aatgcatttc agacac                                          26

<210> SEQ ID NO 310
<211> LENGTH: 33
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 310
aatctctata atatcttaat tctcttactc ttg                                  33

<210> SEQ ID NO 311
<211> LENGTH: 29
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 311
cttttttcag ttatatgctt taatttatc                                       29

<210> SEQ ID NO 312
```

```
<211> LENGTH: 29
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 312
tatatattcc agctatatta tggaatctt                                          29

<210> SEQ ID NO 313
<211> LENGTH: 21
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 313
gacacccacg acactgtcct g                                                  21

<210> SEQ ID NO 314
<211> LENGTH: 26
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 314
gatgattaac tccatctggt tcatct                                             26

<210> SEQ ID NO 315
<211> LENGTH: 24
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 315
cagctcgtct agctagtagc aaag                                               24

<210> SEQ ID NO 316
<211> LENGTH: 22
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 316
acaatgttgt gacgctgtgg tt                                                 22

<210> SEQ ID NO 317
<211> LENGTH: 28
<212> TYPE: DNA
<213> ORGANISM: Artificial Sequence
<220> FEATURE:
<223> OTHER INFORMATION: Human papillomavirus type 59 blocking label
      extender probe

<400> SEQUENCE: 317
ttgattatta cacttacaac acacacac                                           28

<210> SEQ ID NO 318
<211> LENGTH: 45
```

```
<212> TYPE: DNA
<213> ORGANISM: Artificial Sequence
<220> FEATURE:
<223> OTHER INFORMATION: Human papillomavirus type 68 capture extender
      probe

<400> SEQUENCE: 318
gtcatgcaat gtagtgtcca atgttttttc tcttggaaag aaagt            45

<210> SEQ ID NO 319
<211> LENGTH: 45
<212> TYPE: DNA
<213> ORGANISM: Artificial Sequence
<220> FEATURE:
<223> OTHER INFORMATION: Human papillomavirus type 68 capture extender
      probe

<400> SEQUENCE: 319
tgttaggtgc cttagttttt ctgcttttc tcttggaaag aaagt             45

<210> SEQ ID NO 320
<211> LENGTH: 42
<212> TYPE: DNA
<213> ORGANISM: Artificial Sequence
<220> FEATURE:
<223> OTHER INFORMATION: Human papillomavirus type 68 capture extender
      probe

<400> SEQUENCE: 320
cgcttactgg tccagcagtg ctttttctct tggaaagaaa gt               42

<210> SEQ ID NO 321
<211> LENGTH: 40
<212> TYPE: DNA
<213> ORGANISM: Artificial Sequence
<220> FEATURE:
<223> OTHER INFORMATION: Human papillomavirus type 68 capture extender
      probe

<400> SEQUENCE: 321
cggtgggctt tggtccatgt ttttctcttg gaaagaaagt                  40

<210> SEQ ID NO 322
<211> LENGTH: 45
<212> TYPE: DNA
<213> ORGANISM: Artificial Sequence
<220> FEATURE:
<223> OTHER INFORMATION: Human papillomavirus type 68 capture extender
      probe

<400> SEQUENCE: 322
atagctctaa cacaatttcc tgcattttc tcttggaaag aaagt             45

<210> SEQ ID NO 323
<211> LENGTH: 41
<212> TYPE: DNA
<213> ORGANISM: Artificial Sequence
<220> FEATURE:
<223> OTHER INFORMATION: Human papillomavirus type 68 capture extender
      probe

<400> SEQUENCE: 323
cccgcgacgc ttctactact tttttctctt ggaaagaaag t                41

<210> SEQ ID NO 324
<211> LENGTH: 47
<212> TYPE: DNA
```

<213> ORGANISM: Artificial Sequence
<220> FEATURE:
<223> OTHER INFORMATION: Human papillomavirus type 68 capture extender
      probe

<400> SEQUENCE: 324
caaaatttag tgagtccata aacagctttt tctcttggaa agaaagt             47

<210> SEQ ID NO 325
<211> LENGTH: 48
<212> TYPE: DNA
<213> ORGANISM: Artificial Sequence
<220> FEATURE:
<223> OTHER INFORMATION: Human papillomavirus type 68 label extender
      probe

<400> SEQUENCE: 325
cttctgcaat agacacagtc tattgtaact ttttgaagtt accgtttt            48

<210> SEQ ID NO 326
<211> LENGTH: 45
<212> TYPE: DNA
<213> ORGANISM: Artificial Sequence
<220> FEATURE:
<223> OTHER INFORMATION: Human papillomavirus type 68 label extender
      probe

<400> SEQUENCE: 326
catatacctc tgtccgttgt agttgctttt tctgagtcaa agcat               45

<210> SEQ ID NO 327
<211> LENGTH: 43
<212> TYPE: DNA
<213> ORGANISM: Artificial Sequence
<220> FEATURE:
<223> OTHER INFORMATION: Human papillomavirus type 68 label extender
      probe

<400> SEQUENCE: 327
atttaataca tgattggcat gcagtttttg aagttaccgt ttt                 43

<210> SEQ ID NO 328
<211> LENGTH: 44
<212> TYPE: DNA
<213> ORGANISM: Artificial Sequence
<220> FEATURE:
<223> OTHER INFORMATION: Human papillomavirus type 68 label extender
      probe

<400> SEQUENCE: 328
cgtagttccc gtattttagc ataaattttt ctgagtcaaa gcat                44

<210> SEQ ID NO 329
<211> LENGTH: 43
<212> TYPE: DNA
<213> ORGANISM: Artificial Sequence
<220> FEATURE:
<223> OTHER INFORMATION: Human papillomavirus type 68 label extender
      probe

<400> SEQUENCE: 329
gcatacaccg attccgagta atattttttg aagttaccgt ttt                 43

<210> SEQ ID NO 330
<211> LENGTH: 50
<212> TYPE: DNA
<213> ORGANISM: Artificial Sequence

```
<220> FEATURE:
<223> OTHER INFORMATION: Human papillomavirus type 68 label extender
      probe

<400> SEQUENCE: 330
ctttgtatta gttatggttt ctaatgtagt tttttctga gtcaaagcat            50

<210> SEQ ID NO 331
<211> LENGTH: 49
<212> TYPE: DNA
<213> ORGANISM: Artificial Sequence
<220> FEATURE:
<223> OTHER INFORMATION: Human papillomavirus type 68 label extender
      probe

<400> SEQUENCE: 331
actcatgcac cttatcaata aattatataa tttttgaagt taccgtttt            49

<210> SEQ ID NO 332
<211> LENGTH: 40
<212> TYPE: DNA
<213> ORGANISM: Artificial Sequence
<220> FEATURE:
<223> OTHER INFORMATION: Human papillomavirus type 68 label extender
      probe

<400> SEQUENCE: 332
tggacacaat ggtttcaggc atttttctga gtcaaagcat                      40

<210> SEQ ID NO 333
<211> LENGTH: 42
<212> TYPE: DNA
<213> ORGANISM: Artificial Sequence
<220> FEATURE:
<223> OTHER INFORMATION: Human papillomavirus type 68 label extender
      probe

<400> SEQUENCE: 333
cggctgtatt tcattgtatg gacttttga agttaccgtt tt                    42

<210> SEQ ID NO 334
<211> LENGTH: 42
<212> TYPE: DNA
<213> ORGANISM: Artificial Sequence
<220> FEATURE:
<223> OTHER INFORMATION: Human papillomavirus type 68 label extender
      probe

<400> SEQUENCE: 334
tgctcgtgac atacaaggtc aacttttct gagtcaaagc at                    42

<210> SEQ ID NO 335
<211> LENGTH: 45
<212> TYPE: DNA
<213> ORGANISM: Artificial Sequence
<220> FEATURE:
<223> OTHER INFORMATION: Human papillomavirus type 68 label extender
      probe

<400> SEQUENCE: 335
ctatttcatc gtctgaatct cctaatttt tgaagttacc gtttt                 45

<210> SEQ ID NO 336
<211> LENGTH: 39
<212> TYPE: DNA
<213> ORGANISM: Artificial Sequence
<220> FEATURE:
```

<223> OTHER INFORMATION: Human papillomavirus type 68 label extender
      probe

<400> SEQUENCE: 336
aactgcatgg tcgggttcat tttttctgag tcaaagcat                    39

<210> SEQ ID NO 337
<211> LENGTH: 39
<212> TYPE: DNA
<213> ORGANISM: Artificial Sequence
<220> FEATURE:
<223> OTHER INFORMATION: Human papillomavirus type 68 label extender
      probe

<400> SEQUENCE: 337
gctgttgttc gtcccgtctg tttttgaagt taccgtttt                    39

<210> SEQ ID NO 338
<211> LENGTH: 44
<212> TYPE: DNA
<213> ORGANISM: Artificial Sequence
<220> FEATURE:
<223> OTHER INFORMATION: Human papillomavirus type 68 label extender
      probe

<400> SEQUENCE: 338
caacacagac actgaattct gtgacttttt ctgagtcaaa gcat              44

<210> SEQ ID NO 339
<211> LENGTH: 27
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 339
ctacacatag gtcactaaag gcaaatt                                 27

<210> SEQ ID NO 340
<211> LENGTH: 24
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 340
caaatggtac cccgtctcta taca                                    24

<210> SEQ ID NO 341
<211> LENGTH: 26
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 341
gctattttat gtaatcttcg ttttgt                                  26

<210> SEQ ID NO 342
<211> LENGTH: 24
<212> TYPE: DNA
<213> ORGANISM: Artificial Sequence
<220> FEATURE:
<223> OTHER INFORMATION: Human papillomavirus type 68 blocking label extender probe

<400> SEQUENCE: 342
cgacactgtc ctgtaaagtt tcct                                            24

<210> SEQ ID NO 343
<211> LENGTH: 20
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 343
gtatgcgtct gcggtcctct                                                 20

<210> SEQ ID NO 344
<211> LENGTH: 29
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 344
catagttact taaacttgtg tttcttgac                                       29

<210> SEQ ID NO 345
<211> LENGTH: 26
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 345
gctagtagta gatgttggtg gtgatt                                          26

<210> SEQ ID NO 346
<211> LENGTH: 24
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 346
agttgcagtg ccttgttaca ctta                                            24

<210> SEQ ID NO 347
<211> LENGTH: 22
<212> TYPE: DNA
<213> ORGANISM: Artificial Sequence
<220> FEATURE:
<223> OTHER INFORMATION: Human papillomavirus type 68 blocking label
      extender probe

<400> SEQUENCE: 347
tgttgtagtg tccgcaggtt gt                                              22

<210> SEQ ID NO 348
<211> LENGTH: 39
<212> TYPE: DNA
<213> ORGANISM: Artificial Sequence
<220> FEATURE:
<223> OTHER INFORMATION: Human papillomavirus type 6 capture extender
      probe

<400> SEQUENCE: 348
tggatagccg cctcgaaatt tttctcttgg aaagaaagt                                39

<210> SEQ ID NO 349
<211> LENGTH: 38
<212> TYPE: DNA
<213> ORGANISM: Artificial Sequence
<220> FEATURE:
<223> OTHER INFORMATION: Human papillomavirus type 6 capture extender
      probe

<400> SEQUENCE: 349
cacgcgcagg ctgcatattt ttctcttgga aagaaagt                                 38

<210> SEQ ID NO 350
<211> LENGTH: 44
<212> TYPE: DNA
<213> ORGANISM: Artificial Sequence
<220> FEATURE:
<223> OTHER INFORMATION: Human papillomavirus type 6 capture extender
      probe

<400> SEQUENCE: 350
tttttccatg aaattctagg cagttttttct cttggaaaga aagt                         44

<210> SEQ ID NO 351
<211> LENGTH: 39
<212> TYPE: DNA
<213> ORGANISM: Artificial Sequence
<220> FEATURE:
<223> OTHER INFORMATION: Human papillomavirus type 6 capture extender
      probe

<400> SEQUENCE: 351
taggcagcga cccttccatt tttctcttgg aaagaaagt                                39

<210> SEQ ID NO 352
<211> LENGTH: 48
<212> TYPE: DNA
<213> ORGANISM: Artificial Sequence
<220> FEATURE:
<223> OTHER INFORMATION: Human papillomavirus type 6 capture extender
      probe

<400> SEQUENCE: 352
caatatcctt tagggtaaca tgtcttcttt ttctcttgga aagaaagt                      48

<210> SEQ ID NO 353
<211> LENGTH: 44
<212> TYPE: DNA
<213> ORGANISM: Artificial Sequence
<220> FEATURE:
<223> OTHER INFORMATION: Human papillomavirus type 6 capture extender
      probe

<400> SEQUENCE: 353
cagaagctgt tgcacttctc tgatttttct cttggaaaga aagt                          44

<210> SEQ ID NO 354
<211> LENGTH: 40
<212> TYPE: DNA
<213> ORGANISM: Artificial Sequence
<220> FEATURE:
<223> OTHER INFORMATION: Human papillomavirus type 6 capture extender
      probe

<400> SEQUENCE: 354
ggtcttcggt gcgcagatgt ttttctcttg gaaagaaagt         40

<210> SEQ ID NO 355
<211> LENGTH: 45
<212> TYPE: DNA
<213> ORGANISM: Artificial Sequence
<220> FEATURE:
<223> OTHER INFORMATION: Human papillomavirus type 6 label extender
      probe

<400> SEQUENCE: 355
attaatttgc aacgtatgca tagatatttt tgaagttacc gtttt    45

<210> SEQ ID NO 356
<211> LENGTH: 41
<212> TYPE: DNA
<213> ORGANISM: Artificial Sequence
<220> FEATURE:
<223> OTHER INFORMATION: Human papillomavirus type 6 label extender
      probe

<400> SEQUENCE: 356
gtgcattctt gcaaaacaca catttttctg agtcaaagca t        41

<210> SEQ ID NO 357
<211> LENGTH: 44
<212> TYPE: DNA
<213> ORGANISM: Artificial Sequence
<220> FEATURE:
<223> OTHER INFORMATION: Human papillomavirus type 6 label extender
      probe

<400> SEQUENCE: 357
tatgaataaa tctctgctgt ggtcattttt gaagttaccg tttt     44

<210> SEQ ID NO 358
<211> LENGTH: 44
<212> TYPE: DNA
<213> ORGANISM: Artificial Sequence
<220> FEATURE:
<223> OTHER INFORMATION: Human papillomavirus type 6 label extender
      probe

<400> SEQUENCE: 358
caggaccttt aggtgtttat atgcattttt ctgagtcaaa gcat     44

<210> SEQ ID NO 359
<211> LENGTH: 43
<212> TYPE: DNA
<213> ORGANISM: Artificial Sequence
<220> FEATURE:
<223> OTHER INFORMATION: Human papillomavirus type 6 label extender
      probe

<400> SEQUENCE: 359
tcttcaactg ttgttgcata tccattttg aagttaccgt ttt       43

<210> SEQ ID NO 360
<211> LENGTH: 47
<212> TYPE: DNA
<213> ORGANISM: Artificial Sequence
<220> FEATURE:
<223> OTHER INFORMATION: Human papillomavirus type 6 label extender
      probe

<400> SEQUENCE: 360

```
cacgtctaag atgtcttgtt tagtttcttt tttctgagtc aaagcat          47
```

<210> SEQ ID NO 361
<211> LENGTH: 45
<212> TYPE: DNA
<213> ORGANISM: Artificial Sequence
<220> FEATURE:
<223> OTHER INFORMATION: Human papillomavirus type 6 label extender
      probe

<400> SEQUENCE: 361

```
cgccttggtt agtatatgtt ttaccttttt tgaagttacc gtttt            45
```

<210> SEQ ID NO 362
<211> LENGTH: 43
<212> TYPE: DNA
<213> ORGANISM: Artificial Sequence
<220> FEATURE:
<223> OTHER INFORMATION: Human papillomavirus type 6 label extender
      probe

<400> SEQUENCE: 362

```
cgtacaattt agctttatga accgtttttc tgagtcaaag cat              43
```

<210> SEQ ID NO 363
<211> LENGTH: 43
<212> TYPE: DNA
<213> ORGANISM: Artificial Sequence
<220> FEATURE:
<223> OTHER INFORMATION: Human papillomavirus type 6 label extender
      probe

<400> SEQUENCE: 363

```
ggtctggagg ttgcaggtct aatattttg aagttaccgt ttt               43
```

<210> SEQ ID NO 364
<211> LENGTH: 44
<212> TYPE: DNA
<213> ORGANISM: Artificial Sequence
<220> FEATURE:
<223> OTHER INFORMATION: Human papillomavirus type 6 label extender
      probe

<400> SEQUENCE: 364

```
tgctcatagc aatgtaaccc tacagttttt ctgagtcaaa gcat             44
```

<210> SEQ ID NO 365
<211> LENGTH: 46
<212> TYPE: DNA
<213> ORGANISM: Artificial Sequence
<220> FEATURE:
<223> OTHER INFORMATION: Human papillomavirus type 6 label extender
      probe

<400> SEQUENCE: 365

```
acctcatctt ctgagctgtc tactaatttt ttgaagttac cgtttt           46
```

<210> SEQ ID NO 366
<211> LENGTH: 39
<212> TYPE: DNA
<213> ORGANISM: Artificial Sequence
<220> FEATURE:
<223> OTHER INFORMATION: Human papillomavirus type 6 label extender
      probe

<400> SEQUENCE: 366

```
cttgtccgtc cacttcgtcc tttttctgag tcaaagcat                           39
```

<210> SEQ ID NO 367
<211> LENGTH: 41
<212> TYPE: DNA
<213> ORGANISM: Artificial Sequence
<220> FEATURE:
<223> OTHER INFORMATION: Human papillomavirus type 6 label extender
      probe

<400> SEQUENCE: 367

```
cagtcgaacg ttgctgtcac attttttgaa gttaccgttt t                        41
```

<210> SEQ ID NO 368
<211> LENGTH: 44
<212> TYPE: DNA
<213> ORGANISM: Artificial Sequence
<220> FEATURE:
<223> OTHER INFORMATION: Human papillomavirus type 6 label extender
      probe

<400> SEQUENCE: 368

```
tgtctgtttc tgtacactgc acaacttttt ctgagtcaaa gcat                     44
```

<210> SEQ ID NO 369
<211> LENGTH: 28
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 369

```
gcataatcaa agtgtctata ttggttta                                       28
```

<210> SEQ ID NO 370
<211> LENGTH: 23
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 370

```
tgacacaggt agcaccgaat tag                                            23
```

<210> SEQ ID NO 371
<211> LENGTH: 23
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 371

```
tttctacttc acacagcggt ttg                                            23
```

<210> SEQ ID NO 372
<211> LENGTH: 21
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 372

```
catgcatgtt gtccagcagt g                                              21
```

<210> SEQ ID NO 373
<211> LENGTH: 26
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 373
gaaatgttgt tttaaaggtt gtgaat                                    26

<210> SEQ ID NO 374
<211> LENGTH: 23
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 374
ccacagcaac aggtcactat ttg                                       23

<210> SEQ ID NO 375
<211> LENGTH: 26
<212> TYPE: DNA
<213> ORGANISM: Artificial Sequence
<220> FEATURE:
<223> OTHER INFORMATION: Human papillomavirus type 6 blocking label
      extender probe

<400> SEQUENCE: 375
ggacacacta tgtttagtgt tcccaa                                    26

<210> SEQ ID NO 376
<211> LENGTH: 46
<212> TYPE: DNA
<213> ORGANISM: Artificial Sequence
<220> FEATURE:
<223> OTHER INFORMATION: Human papillomavirus type 11 capture extender
      probe

<400> SEQUENCE: 376
caaagaaaga ttaaacgtct tgcactttttt ctcttggaaa gaaagt             46

<210> SEQ ID NO 377
<211> LENGTH: 43
<212> TYPE: DNA
<213> ORGANISM: Artificial Sequence
<220> FEATURE:
<223> OTHER INFORMATION: Human papillomavirus type 11 capture extender
      probe

<400> SEQUENCE: 377
cgcactgaat ttgcagagtg tgttttttctc ttggaaagaa agt                43

<210> SEQ ID NO 378
<211> LENGTH: 46
<212> TYPE: DNA
<213> ORGANISM: Artificial Sequence
<220> FEATURE:
<223> OTHER INFORMATION: Human papillomavirus type 11 capture extender
      probe

<400> SEQUENCE: 378
tggtttcttc ttctactgta ggtgcttttt ctcttggaaa gaaagt              46

<210> SEQ ID NO 379
<211> LENGTH: 49
<212> TYPE: DNA
<213> ORGANISM: Artificial Sequence
<220> FEATURE:
<223> OTHER INFORMATION: Human papillomavirus type 11 capture extender
      probe

<400> SEQUENCE: 379
cgaattaaca cttttaaaat atcttcattt tttctcttgg aaagaaagt                49

<210> SEQ ID NO 380
<211> LENGTH: 41
<212> TYPE: DNA
<213> ORGANISM: Artificial Sequence
<220> FEATURE:
<223> OTHER INFORMATION: Human papillomavirus type 11 capture extender
      probe

<400> SEQUENCE: 380
agcgtgcctt tcccaatatg tttttctctt ggaaagaaag t                        41

<210> SEQ ID NO 381
<211> LENGTH: 42
<212> TYPE: DNA
<213> ORGANISM: Artificial Sequence
<220> FEATURE:
<223> OTHER INFORMATION: Human papillomavirus type 11 capture extender
      probe

<400> SEQUENCE: 381
accctacagg gtcaggaggc ttttttctct tggaaagaaa gt                       42

<210> SEQ ID NO 382
<211> LENGTH: 42
<212> TYPE: DNA
<213> ORGANISM: Artificial Sequence
<220> FEATURE:
<223> OTHER INFORMATION: Human papillomavirus type 11 capture extender
      probe

<400> SEQUENCE: 382
gtgcgtcttg tttgtccacc ttttttctct tggaaagaaa gt                       42

<210> SEQ ID NO 383
<211> LENGTH: 43
<212> TYPE: DNA
<213> ORGANISM: Artificial Sequence
<220> FEATURE:
<223> OTHER INFORMATION: Human papillomavirus type 11 label extender
      probe

<400> SEQUENCE: 383
tggaggcatc tttactttcc ataattttg aagttaccgt ttt                       43

<210> SEQ ID NO 384
<211> LENGTH: 44
<212> TYPE: DNA
<213> ORGANISM: Artificial Sequence
<220> FEATURE:
<223> OTHER INFORMATION: Human papillomavirus type 11 label extender
      probe

<400> SEQUENCE: 384
aactggtcta tagatgttgc agacgttttt ctgagtcaaa gcat                     44

```
<210> SEQ ID NO 385
<211> LENGTH: 42
<212> TYPE: DNA
<213> ORGANISM: Artificial Sequence
<220> FEATURE:
<223> OTHER INFORMATION: Human papillomavirus type 11 label extender
      probe

<400> SEQUENCE: 385
atatgcatat atctctgcgg tggtttttga agttaccgtt tt                          42

<210> SEQ ID NO 386
<211> LENGTH: 44
<212> TYPE: DNA
<213> ORGANISM: Artificial Sequence
<220> FEATURE:
<223> OTHER INFORMATION: Human papillomavirus type 11 label extender
      probe

<400> SEQUENCE: 386
acacaacctt taggttctta taggctttt ctgagtcaaa gcat                         44

<210> SEQ ID NO 387
<211> LENGTH: 38
<212> TYPE: DNA
<213> ORGANISM: Artificial Sequence
<220> FEATURE:
<223> OTHER INFORMATION: Human papillomavirus type 11 label extender
      probe

<400> SEQUENCE: 387
aagcaacagg cacacgctgt ttttgaagtt accgtttt                               38

<210> SEQ ID NO 388
<211> LENGTH: 42
<212> TYPE: DNA
<213> ORGANISM: Artificial Sequence
<220> FEATURE:
<223> OTHER INFORMATION: Human papillomavirus type 11 label extender
      probe

<400> SEQUENCE: 388
ggttaatttt cccttgcagt tctttttcct gagtcaaagc at                          42

<210> SEQ ID NO 389
<211> LENGTH: 41
<212> TYPE: DNA
<213> ORGANISM: Artificial Sequence
<220> FEATURE:
<223> OTHER INFORMATION: Human papillomavirus type 11 label extender
      probe

<400> SEQUENCE: 389
cggcttgtga cacaggtaac aattttgaa gttaccgttt t                            41

<210> SEQ ID NO 390
<211> LENGTH: 45
<212> TYPE: DNA
<213> ORGANISM: Artificial Sequence
<220> FEATURE:
<223> OTHER INFORMATION: Human papillomavirus type 11 label extender
      probe

<400> SEQUENCE: 390
tgctttagtt tttctatttc acacaatttt tctgagtcaa agcat                       45

<210> SEQ ID NO 391
```

<210> SEQ ID NO 391
<211> LENGTH: 45
<212> TYPE: DNA
<213> ORGANISM: Artificial Sequence
<220> FEATURE:
<223> OTHER INFORMATION: Human papillomavirus type 11 label extender probe

<400> SEQUENCE: 391
cttccactgg ttatttagtt ttatgatttt tgaagttacc gtttt        45

<210> SEQ ID NO 392
<211> LENGTH: 40
<212> TYPE: DNA
<213> ORGANISM: Artificial Sequence
<220> FEATURE:
<223> OTHER INFORMATION: Human papillomavirus type 11 label extender probe

<400> SEQUENCE: 392
ccagcagtgt aagcaacgac cttttttctga gtcaaagcat        40

<210> SEQ ID NO 393
<211> LENGTH: 45
<212> TYPE: DNA
<213> ORGANISM: Artificial Sequence
<220> FEATURE:
<223> OTHER INFORMATION: Human papillomavirus type 11 label extender probe

<400> SEQUENCE: 393
gtcttctaat tgctcatagc aatgtatttt tgaagttacc gtttt        45

<210> SEQ ID NO 394
<211> LENGTH: 41
<212> TYPE: DNA
<213> ORGANISM: Artificial Sequence
<220> FEATURE:
<223> OTHER INFORMATION: Human papillomavirus type 11 label extender probe

<400> SEQUENCE: 394
tgtccacctc atcttctgag ctttttctg agtcaaagca t        41

<210> SEQ ID NO 395
<211> LENGTH: 46
<212> TYPE: DNA
<213> ORGANISM: Artificial Sequence
<220> FEATURE:
<223> OTHER INFORMATION: Human papillomavirus type 11 label extender probe

<400> SEQUENCE: 395
gtatttggta atgttgtgtt aaaggttttt ttgaagttac cgtttt        46

<210> SEQ ID NO 396
<211> LENGTH: 40
<212> TYPE: DNA
<213> ORGANISM: Artificial Sequence
<220> FEATURE:
<223> OTHER INFORMATION: Human papillomavirus type 11 label extender probe

<400> SEQUENCE: 396
cacatccaca gcaacaggtc atttttctga gtcaaagcat        40

<210> SEQ ID NO 397
<211> LENGTH: 40

```
<212> TYPE: DNA
<213> ORGANISM: Artificial Sequence
<220> FEATURE:
<223> OTHER INFORMATION: Human papillomavirus type 11 label extender
      probe

<400> SEQUENCE: 397
caaccagtcg gacgttgctg tttttttgaag ttaccgtttt                          40

<210> SEQ ID NO 398
<211> LENGTH: 41
<212> TYPE: DNA
<213> ORGANISM: Artificial Sequence
<220> FEATURE:
<223> OTHER INFORMATION: Human papillomavirus type 11 label extender
      probe

<400> SEQUENCE: 398
atgtctccgt ctgtgcactc catttttctg agtcaaagca t                        41

<210> SEQ ID NO 399
<211> LENGTH: 21
<212> TYPE: DNA
<213> ORGANISM: Artificial Sequence
<220> FEATURE:
<223> OTHER INFORMATION: Human papillomavirus type 11 blocking label
      extender probe

<400> SEQUENCE: 399
tcagtgcatt cctgcaaaac a                                              21

<210> SEQ ID NO 400
<211> LENGTH: 21
<212> TYPE: DNA
<213> ORGANISM: Artificial Sequence
<220> FEATURE:
<223> OTHER INFORMATION: Human papillomavirus type 11 blocking label
      extender probe

<400> SEQUENCE: 400
caaagggaaa gttgtctcgc c                                              21

<210> SEQ ID NO 401
<211> LENGTH: 29
<212> TYPE: DNA
<213> ORGANISM: Artificial Sequence
<220> FEATURE:
<223> OTHER INFORMATION: Human papillomavirus type 11 blocking label
      extender probe

<400> SEQUENCE: 401
atatgcagca taattaaagt gtctatatt                                      29

<210> SEQ ID NO 402
<211> LENGTH: 24
<212> TYPE: DNA
<213> ORGANISM: Artificial Sequence
<220> FEATURE:
<223> OTHER INFORMATION: Human papillomavirus type 11 blocking label
      extender probe

<400> SEQUENCE: 402
taacaagtct tccatgcatg ttgt                                           24

<210> SEQ ID NO 403
<211> LENGTH: 27
<212> TYPE: DNA
```

<213> ORGANISM: Artificial Sequence
<220> FEATURE:
<223> OTHER INFORMATION: Human papillomavirus type 11 blocking label
      extender probe

<400> SEQUENCE: 403
gcaggtctag tactatatcc tttaggg                                          27

<210> SEQ ID NO 404
<211> LENGTH: 41
<212> TYPE: DNA
<213> ORGANISM: Artificial Sequence
<220> FEATURE:
<223> OTHER INFORMATION: Human papillomavirus type 40 capture extender
      probe

<400> SEQUENCE: 404
tcatacaggg tcctggcctg ttttctctt ggaaagaaag t                           41

<210> SEQ ID NO 405
<211> LENGTH: 42
<212> TYPE: DNA
<213> ORGANISM: Artificial Sequence
<220> FEATURE:
<223> OTHER INFORMATION: Human papillomavirus type 40 capture extender
      probe

<400> SEQUENCE: 405
ggaccgtctt gcaaaacaca ctttttctct tggaaagaaa gt                         42

<210> SEQ ID NO 406
<211> LENGTH: 39
<212> TYPE: DNA
<213> ORGANISM: Artificial Sequence
<220> FEATURE:
<223> OTHER INFORMATION: Human papillomavirus type 40 capture extender
      probe

<400> SEQUENCE: 406
cgtggacatg cggcgtgttt tttctcttgg aaagaaagt                             39

<210> SEQ ID NO 407
<211> LENGTH: 47
<212> TYPE: DNA
<213> ORGANISM: Artificial Sequence
<220> FEATURE:
<223> OTHER INFORMATION: Human papillomavirus type 40 capture extender
      probe

<400> SEQUENCE: 407
aaagaattgc gtcttcttta caatattttt tctcttggaa agaaagt                    47

<210> SEQ ID NO 408
<211> LENGTH: 46
<212> TYPE: DNA
<213> ORGANISM: Artificial Sequence
<220> FEATURE:
<223> OTHER INFORMATION: Human papillomavirus type 40 capture extender
      probe

<400> SEQUENCE: 408
agtttagaca tacaggttca gggtgttttt ctcttggaaa gaaagt                     46

<210> SEQ ID NO 409
<211> LENGTH: 48
<212> TYPE: DNA
<213> ORGANISM: Artificial Sequence

```
<220> FEATURE:
<223> OTHER INFORMATION: Human papillomavirus type 40 capture extender
      probe

<400> SEQUENCE: 409
acaccgagtt actactttaa atgattgttt ttctcttgga aagaaagt                  48

<210> SEQ ID NO 410
<211> LENGTH: 44
<212> TYPE: DNA
<213> ORGANISM: Artificial Sequence
<220> FEATURE:
<223> OTHER INFORMATION: Human papillomavirus type 40 capture extender
      probe

<400> SEQUENCE: 410
tgatggaaca atgcactgct aagttttct cttggaaaga aagt                       44

<210> SEQ ID NO 411
<211> LENGTH: 44
<212> TYPE: DNA
<213> ORGANISM: Artificial Sequence
<220> FEATURE:
<223> OTHER INFORMATION: Human papillomavirus type 40 label extender
      probe

<400> SEQUENCE: 411
tgtaatattg cactggtcac acagtttttt gaagttaccg tttt                      44

<210> SEQ ID NO 412
<211> LENGTH: 41
<212> TYPE: DNA
<213> ORGANISM: Artificial Sequence
<220> FEATURE:
<223> OTHER INFORMATION: Human papillomavirus type 40 label extender
      probe

<400> SEQUENCE: 412
aatcaatttg caacgtaggc aatttttctg agtcaaagca t                         41

<210> SEQ ID NO 413
<211> LENGTH: 42
<212> TYPE: DNA
<213> ORGANISM: Artificial Sequence
<220> FEATURE:
<223> OTHER INFORMATION: Human papillomavirus type 40 label extender
      probe

<400> SEQUENCE: 413
ggccagtacc tcagctgttt ttattttga agttaccgtt tt                         42

<210> SEQ ID NO 414
<211> LENGTH: 46
<212> TYPE: DNA
<213> ORGANISM: Artificial Sequence
<220> FEATURE:
<223> OTHER INFORMATION: Human papillomavirus type 40 label extender
      probe

<400> SEQUENCE: 414
cacaacatat aactctctaa aggcaaattt ttctgagtca aagcat                    46

<210> SEQ ID NO 415
<211> LENGTH: 37
<212> TYPE: DNA
<213> ORGANISM: Artificial Sequence
<220> FEATURE:
```

<223> OTHER INFORMATION: Human papillomavirus type 40 label extender
      probe

<400> SEQUENCE: 415
ccgtgcaggt ccaggcactt tttgaagtta ccgtttt                                    37

<210> SEQ ID NO 416
<211> LENGTH: 48
<212> TYPE: DNA
<213> ORGANISM: Artificial Sequence
<220> FEATURE:
<223> OTHER INFORMATION: Human papillomavirus type 40 label extender
      probe

<400> SEQUENCE: 416
atctaaagtt tctgtattgg tttacttttt ttttctgagt caaagcat                        48

<210> SEQ ID NO 417
<211> LENGTH: 43
<212> TYPE: DNA
<213> ORGANISM: Artificial Sequence
<220> FEATURE:
<223> OTHER INFORMATION: Human papillomavirus type 40 label extender
      probe

<400> SEQUENCE: 417
gttaatcctg tctcttcttc cacgttttg aagttaccgt ttt                              43

<210> SEQ ID NO 418
<211> LENGTH: 46
<212> TYPE: DNA
<213> ORGANISM: Artificial Sequence
<220> FEATURE:
<223> OTHER INFORMATION: Human papillomavirus type 40 label extender
      probe

<400> SEQUENCE: 418
cagcatctaa tccttacttg taaaatgttt ttctgagtca aagcat                          46

<210> SEQ ID NO 419
<211> LENGTH: 43
<212> TYPE: DNA
<213> ORGANISM: Artificial Sequence
<220> FEATURE:
<223> OTHER INFORMATION: Human papillomavirus type 40 label extender
      probe

<400> SEQUENCE: 419
ccctgtccac gaatctttta atttttttg aagttaccgt ttt                              43

<210> SEQ ID NO 420
<211> LENGTH: 45
<212> TYPE: DNA
<213> ORGANISM: Artificial Sequence
<220> FEATURE:
<223> OTHER INFORMATION: Human papillomavirus type 40 label extender
      probe

<400> SEQUENCE: 420
catttcttcc agcaatgtag acagtatttt tctgagtcaa agcat                           45

<210> SEQ ID NO 421
<211> LENGTH: 41
<212> TYPE: DNA
<213> ORGANISM: Artificial Sequence
<220> FEATURE:
<223> OTHER INFORMATION: Human papillomavirus type 40 label extender

```
    probe

<400> SEQUENCE: 421
gagctgtcta attgctcgtt gcttttgaa gttaccgttt t                    41

<210> SEQ ID NO 422
<211> LENGTH: 44
<212> TYPE: DNA
<213> ORGANISM: Artificial Sequence
<220> FEATURE:
<223> OTHER INFORMATION: Human papillomavirus type 40 label extender
      probe

<400> SEQUENCE: 422
ctgttcatgg tcatcttctg agtctttttt ctgagtcaaa gcat                44

<210> SEQ ID NO 423
<211> LENGTH: 46
<212> TYPE: DNA
<213> ORGANISM: Artificial Sequence
<220> FEATURE:
<223> OTHER INFORMATION: Human papillomavirus type 40 label extender
      probe

<400> SEQUENCE: 423
tctactgtgt aagctgtcta gttggtcttt ttgaagttac cgtttt             46

<210> SEQ ID NO 424
<211> LENGTH: 37
<212> TYPE: DNA
<213> ORGANISM: Artificial Sequence
<220> FEATURE:
<223> OTHER INFORMATION: Human papillomavirus type 40 label extender
      probe

<400> SEQUENCE: 424
cgtgggttgc tcacgctctt tttctgagtc aaagcat                       37

<210> SEQ ID NO 425
<211> LENGTH: 17
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 425
ggaaagtcgt cgcgcca                                             17

<210> SEQ ID NO 426
<211> LENGTH: 19
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 426
gttggtgcat aggctgcgt                                           19

<210> SEQ ID NO 427
<211> LENGTH: 21
<212> TYPE: DNA
<213> ORGANISM: Artificial Sequence
<220> FEATURE:
<223> OTHER INFORMATION: Human papillomavirus type 40 blocking label
      extender probe
```

<400> SEQUENCE: 427
gacaaaggct tgtggcactt g                                              21

<210> SEQ ID NO 428
<211> LENGTH: 20
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 428
ggttggtttt ttccacggga                                                20

<210> SEQ ID NO 429
<211> LENGTH: 19
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 429
gcgttggcct ttctccatg                                                 19

<210> SEQ ID NO 430
<211> LENGTH: 23
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 430
caggtttaac acaatgtctc cga                                            23

<210> SEQ ID NO 431
<211> LENGTH: 24
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 431
caaatttact tgcaggtcct gttg                                           24

<210> SEQ ID NO 432
<211> LENGTH: 23
<212> TYPE: DNA
<213> ORGANISM: Artificial Sequence
<220> FEATURE:
<223> OTHER INFORMATION: Human papillomavirus type 40 blocking label
      extender probe

<400> SEQUENCE: 432
cgcaccaaac actgacaaaa tac                                            23

<210> SEQ ID NO 433
<211> LENGTH: 43
<212> TYPE: DNA
<213> ORGANISM: Artificial Sequence
<220> FEATURE:
<223> OTHER INFORMATION: Human papillomavirus type 42 capture extender
      probe

```
<400> SEQUENCE: 433
acattctgcc ttaactggga cctttttctc ttggaaagaa agt                    43

<210> SEQ ID NO 434
<211> LENGTH: 43
<212> TYPE: DNA
<213> ORGANISM: Artificial Sequence
<220> FEATURE:
<223> OTHER INFORMATION: Human papillomavirus type 42 capture extender
      probe

<400> SEQUENCE: 434
cctgttaagt gcttttttgca cctttttctc ttggaaagaa agt                   43

<210> SEQ ID NO 435
<211> LENGTH: 38
<212> TYPE: DNA
<213> ORGANISM: Artificial Sequence
<220> FEATURE:
<223> OTHER INFORMATION: Human papillomavirus type 42 capture extender
      probe

<400> SEQUENCE: 435
acgcgagcac ctctgcgttt ttctcttgga aagaaagt                          38

<210> SEQ ID NO 436
<211> LENGTH: 51
<212> TYPE: DNA
<213> ORGANISM: Artificial Sequence
<220> FEATURE:
<223> OTHER INFORMATION: Human papillomavirus type 42 capture extender
      probe

<400> SEQUENCE: 436
caatataaat tgaaatcttg tacctgtatc tttttctctt ggaaagaaag t            51

<210> SEQ ID NO 437
<211> LENGTH: 42
<212> TYPE: DNA
<213> ORGANISM: Artificial Sequence
<220> FEATURE:
<223> OTHER INFORMATION: Human papillomavirus type 42 capture extender
      probe

<400> SEQUENCE: 437
cattgtcctc tgcaatgcgt atttttctct tggaaagaaa gt                     42

<210> SEQ ID NO 438
<211> LENGTH: 42
<212> TYPE: DNA
<213> ORGANISM: Artificial Sequence
<220> FEATURE:
<223> OTHER INFORMATION: Human papillomavirus type 42 capture extender
      probe

<400> SEQUENCE: 438
cgctgtatgt cctgtttggc tttttctct tggaaagaaa gt                      42

<210> SEQ ID NO 439
<211> LENGTH: 44
<212> TYPE: DNA
<213> ORGANISM: Artificial Sequence
<220> FEATURE:
<223> OTHER INFORMATION: Human papillomavirus type 42 capture extender
      probe

<400> SEQUENCE: 439
```
cttatgtccg cctctgtaca ctgttttct cttggaaaga aagt        44

<210> SEQ ID NO 440
<211> LENGTH: 42
<212> TYPE: DNA
<213> ORGANISM: Artificial Sequence
<220> FEATURE:
<223> OTHER INFORMATION: Human papillomavirus type 42 label extender
      probe

<400> SEQUENCE: 440
ctgtgatgag gcagatgtac ctgtttttga agttaccgtt tt        42

<210> SEQ ID NO 441
<211> LENGTH: 44
<212> TYPE: DNA
<213> ORGANISM: Artificial Sequence
<220> FEATURE:
<223> OTHER INFORMATION: Human papillomavirus type 42 label extender
      probe

<400> SEQUENCE: 441
tacacaattg gtataatgtg cgtggttttt ctgagtcaaa gcat       44

<210> SEQ ID NO 442
<211> LENGTH: 40
<212> TYPE: DNA
<213> ORGANISM: Artificial Sequence
<220> FEATURE:
<223> OTHER INFORMATION: Human papillomavirus type 42 label extender
      probe

<400> SEQUENCE: 442
gcaatgtcag cccaaattcc ttttttgaag ttaccgtttt            40

<210> SEQ ID NO 443
<211> LENGTH: 43
<212> TYPE: DNA
<213> ORGANISM: Artificial Sequence
<220> FEATURE:
<223> OTHER INFORMATION: Human papillomavirus type 42 label extender
      probe

<400> SEQUENCE: 443
aaatgcagga aatctgtaaa ttccttttc tgagtcaaag cat         43

<210> SEQ ID NO 444
<211> LENGTH: 43
<212> TYPE: DNA
<213> ORGANISM: Artificial Sequence
<220> FEATURE:
<223> OTHER INFORMATION: Human papillomavirus type 42 label extender
      probe

<400> SEQUENCE: 444
caaaatgctg atctttcgta gtgttttttg aagttaccgt ttt        43

<210> SEQ ID NO 445
<211> LENGTH: 46
<212> TYPE: DNA
<213> ORGANISM: Artificial Sequence
<220> FEATURE:
<223> OTHER INFORMATION: Human papillomavirus type 42 label extender
      probe

<400> SEQUENCE: 445

```
agtccagttt ctttctccac tgtatacttt ttctgagtca aagcat        46
```

<210> SEQ ID NO 446
<211> LENGTH: 41
<212> TYPE: DNA
<213> ORGANISM: Artificial Sequence
<220> FEATURE:
<223> OTHER INFORMATION: Human papillomavirus type 42 label extender
      probe

<400> SEQUENCE: 446

```
gataacggct tttgacacaa ggttttttgaa gttaccgttt t            41
```

<210> SEQ ID NO 447
<211> LENGTH: 44
<212> TYPE: DNA
<213> ORGANISM: Artificial Sequence
<220> FEATURE:
<223> OTHER INFORMATION: Human papillomavirus type 42 label extender
      probe

<400> SEQUENCE: 447

```
aatatgatgg ttttttttcgc tctgttttttt ctgagtcaaa gcat        44
```

<210> SEQ ID NO 448
<211> LENGTH: 44
<212> TYPE: DNA
<213> ORGANISM: Artificial Sequence
<220> FEATURE:
<223> OTHER INFORMATION: Human papillomavirus type 42 label extender
      probe

<400> SEQUENCE: 448

```
atgtcaaaca aaacaatgtc ctttattttt gaagttaccg tttt          44
```

<210> SEQ ID NO 449
<211> LENGTH: 40
<212> TYPE: DNA
<213> ORGANISM: Artificial Sequence
<220> FEATURE:
<223> OTHER INFORMATION: Human papillomavirus type 42 label extender
      probe

<400> SEQUENCE: 449

```
atgggtgtct cacacgttgg ttttttctga gtcaaagcat               40
```

<210> SEQ ID NO 450
<211> LENGTH: 41
<212> TYPE: DNA
<213> ORGANISM: Artificial Sequence
<220> FEATURE:
<223> OTHER INFORMATION: Human papillomavirus type 42 label extender
      probe

<400> SEQUENCE: 450

```
caaaagcatc tgttgcaggt ttttttttgaa gttaccgttt t            41
```

<210> SEQ ID NO 451
<211> LENGTH: 42
<212> TYPE: DNA
<213> ORGANISM: Artificial Sequence
<220> FEATURE:
<223> OTHER INFORMATION: Human papillomavirus type 42 label extender
      probe

<400> SEQUENCE: 451

```
ggacacacaa tatccagtgt gccttttttct gagtcaaagc at           42
```

<210> SEQ ID NO 452
<211> LENGTH: 26
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 452
caccactacc aaatctttaa aatggt                                    26

<210> SEQ ID NO 453
<211> LENGTH: 23
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 453
gcatatggaa agtccttcct cca                                       23

<210> SEQ ID NO 454
<211> LENGTH: 23
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 454
attctaaaca aaatgcacat gca                                       23

<210> SEQ ID NO 455
<211> LENGTH: 25
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 455
cgcagtgcac aaattttaga attaa                                     25

<210> SEQ ID NO 456
<211> LENGTH: 29
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 456
cacatctaat ttgttgttct tctaaaagt                                 29

<210> SEQ ID NO 457
<211> LENGTH: 20
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 457
caccgacccg tccactgaca                                           20

<210> SEQ ID NO 458
<211> LENGTH: 19
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 458
gggtaggcgt ctctccacg                                                   19

<210> SEQ ID NO 459
<211> LENGTH: 25
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 459
caattgttca tagcaataca ggtca                                            25

<210> SEQ ID NO 460
<211> LENGTH: 23
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 460
tggtcatctt catctgagct gtc                                              23

<210> SEQ ID NO 461
<211> LENGTH: 28
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 461
ctgtgtacac acacacagta ttctgtaa                                         28

<210> SEQ ID NO 462
<211> LENGTH: 27
<212> TYPE: DNA
<213> ORGANISM: Artificial Sequence
<220> FEATURE:
<223> OTHER INFORMATION: Human papillomavirus type 42 blocking label
      extender probe

<400> SEQUENCE: 462
cacaacgagt ttaacagact tgtaaca                                          27

<210> SEQ ID NO 463
<211> LENGTH: 42
<212> TYPE: DNA
<213> ORGANISM: Artificial Sequence
<220> FEATURE:
<223> OTHER INFORMATION: Human papillomavirus type 43 capture extender
      probe

<400> SEQUENCE: 463
agcatgcagc aaacggatat cttttctct tggaaagaaa gt                          42

```
<210> SEQ ID NO 464
<211> LENGTH: 43
<212> TYPE: DNA
<213> ORGANISM: Artificial Sequence
<220> FEATURE:
<223> OTHER INFORMATION: Human papillomavirus type 43 capture extender
      probe

<400> SEQUENCE: 464
ccatgaaact gtagacaggc cattttttctc ttggaaagaa agt                    43

<210> SEQ ID NO 465
<211> LENGTH: 48
<212> TYPE: DNA
<213> ORGANISM: Artificial Sequence
<220> FEATURE:
<223> OTHER INFORMATION: Human papillomavirus type 43 capture extender
      probe

<400> SEQUENCE: 465
tcaaagtgcc tatattgact tatttttttt ttctcttgga aagaaagt                48

<210> SEQ ID NO 466
<211> LENGTH: 45
<212> TYPE: DNA
<213> ORGANISM: Artificial Sequence
<220> FEATURE:
<223> OTHER INFORMATION: Human papillomavirus type 43 capture extender
      probe

<400> SEQUENCE: 466
acagtatctg catatgctgc gtagtttttc tcttggaaag aaagt                   45

<210> SEQ ID NO 467
<211> LENGTH: 44
<212> TYPE: DNA
<213> ORGANISM: Artificial Sequence
<220> FEATURE:
<223> OTHER INFORMATION: Human papillomavirus type 43 capture extender
      probe

<400> SEQUENCE: 467
atgcatgatt tccagcaatg tagttttttct cttggaaaga aagt                   44

<210> SEQ ID NO 468
<211> LENGTH: 41
<212> TYPE: DNA
<213> ORGANISM: Artificial Sequence
<220> FEATURE:
<223> OTHER INFORMATION: Human papillomavirus type 43 capture extender
      probe

<400> SEQUENCE: 468
ttaatgtgcc caacagcagg tttttctctt ggaaagaaag t                       41

<210> SEQ ID NO 469
<211> LENGTH: 44
<212> TYPE: DNA
<213> ORGANISM: Artificial Sequence
<220> FEATURE:
<223> OTHER INFORMATION: Human papillomavirus type 43 label extender
      probe

<400> SEQUENCE: 469
catcacacaa ctcaaatata gtccgttttt gaagttaccg tttt                    44

<210> SEQ ID NO 470
```

```
<211> LENGTH: 46
<212> TYPE: DNA
<213> ORGANISM: Artificial Sequence
<220> FEATURE:
<223> OTHER INFORMATION: Human papillomavirus type 43 label extender
      probe

<400> SEQUENCE: 470
gcagagtagg caaagttatg ttacactttt ttctgagtca aagcat              46

<210> SEQ ID NO 471
<211> LENGTH: 43
<212> TYPE: DNA
<213> ORGANISM: Artificial Sequence
<220> FEATURE:
<223> OTHER INFORMATION: Human papillomavirus type 43 label extender
      probe

<400> SEQUENCE: 471
acttccgtgg taagtaacca cttcttttg aagttaccgt ttt                 43

<210> SEQ ID NO 472
<211> LENGTH: 46
<212> TYPE: DNA
<213> ORGANISM: Artificial Sequence
<220> FEATURE:
<223> OTHER INFORMATION: Human papillomavirus type 43 label extender
      probe

<400> SEQUENCE: 472
tttaaatctc taaatgcaaa cgataatttt ttctgagtca aagcat              46

<210> SEQ ID NO 473
<211> LENGTH: 46
<212> TYPE: DNA
<213> ORGANISM: Artificial Sequence
<220> FEATURE:
<223> OTHER INFORMATION: Human papillomavirus type 43 label extender
      probe

<400> SEQUENCE: 473
aacactgttt gcttagtttc ttcttctttt ttgaagttac cgtttt             46

<210> SEQ ID NO 474
<211> LENGTH: 44
<212> TYPE: DNA
<213> ORGANISM: Artificial Sequence
<220> FEATURE:
<223> OTHER INFORMATION: Human papillomavirus type 43 label extender
      probe

<400> SEQUENCE: 474
cttacagcat ctaatgcaca aatcattttt ctgagtcaaa gcat                44

<210> SEQ ID NO 475
<211> LENGTH: 40
<212> TYPE: DNA
<213> ORGANISM: Artificial Sequence
<220> FEATURE:
<223> OTHER INFORMATION: Human papillomavirus type 43 label extender
      probe

<400> SEQUENCE: 475
tggtgataat ggcttgtggc attttgaag ttaccgtttt                     40

<210> SEQ ID NO 476
<211> LENGTH: 44
```

```
<212> TYPE: DNA
<213> ORGANISM: Artificial Sequence
<220> FEATURE:
<223> OTHER INFORMATION: Human papillomavirus type 43 label extender
      probe

<400> SEQUENCE: 476
gcacaatatg ctgtactttt tccacttttt ctgagtcaaa gcat                    44

<210> SEQ ID NO 477
<211> LENGTH: 45
<212> TYPE: DNA
<213> ORGANISM: Artificial Sequence
<220> FEATURE:
<223> OTHER INFORMATION: Human papillomavirus type 43 label extender
      probe

<400> SEQUENCE: 477
atgtatttta aagaattgtg ccttttttt tgaagttacc gtttt                    45

<210> SEQ ID NO 478
<211> LENGTH: 40
<212> TYPE: DNA
<213> ORGANISM: Artificial Sequence
<220> FEATURE:
<223> OTHER INFORMATION: Human papillomavirus type 43 label extender
      probe

<400> SEQUENCE: 478
gcagtatcct ttccacacgc ttttttctga gtcaaagcat                         40

<210> SEQ ID NO 479
<211> LENGTH: 44
<212> TYPE: DNA
<213> ORGANISM: Artificial Sequence
<220> FEATURE:
<223> OTHER INFORMATION: Human papillomavirus type 43 label extender
      probe

<400> SEQUENCE: 479
tggttgcata gttagcacat agtctttttt gaagttaccg tttt                    44

<210> SEQ ID NO 480
<211> LENGTH: 44
<212> TYPE: DNA
<213> ORGANISM: Artificial Sequence
<220> FEATURE:
<223> OTHER INFORMATION: Human papillomavirus type 43 label extender
      probe

<400> SEQUENCE: 480
cgttacaggt taagcttcta ggttcttttt ctgagtcaaa gcat                    44

<210> SEQ ID NO 481
<211> LENGTH: 43
<212> TYPE: DNA
<213> ORGANISM: Artificial Sequence
<220> FEATURE:
<223> OTHER INFORMATION: Human papillomavirus type 43 label extender
      probe

<400> SEQUENCE: 481
attacacaca gacaggatgt gcactttttg aagttaccgt ttt                     43

<210> SEQ ID NO 482
<211> LENGTH: 41
<212> TYPE: DNA
```

```
<213> ORGANISM: Artificial Sequence
<220> FEATURE:
<223> OTHER INFORMATION: Human papillomavirus type 43 label extender
      probe

<400> SEQUENCE: 482
agagcactgc acaacaagtc gatttttctg agtcaaagca t                    41

<210> SEQ ID NO 483
<211> LENGTH: 20
<212> TYPE: DNA
<213> ORGANISM: Artificial Sequence
<220> FEATURE:
<223> OTHER INFORMATION: Human papillomavirus type 43 blocking label
      extender probe

<400> SEQUENCE: 483
ctgatcgtcg gcttttttcc                                            20

<210> SEQ ID NO 484
<211> LENGTH: 25
<212> TYPE: DNA
<213> ORGANISM: Artificial Sequence
<220> FEATURE:
<223> OTHER INFORMATION: Human papillomavirus type 43 blocking label
      extender probe

<400> SEQUENCE: 484
tctgagtctg agctgtctaa ttgct                                      25

<210> SEQ ID NO 485
<211> LENGTH: 19
<212> TYPE: DNA
<213> ORGANISM: Artificial Sequence
<220> FEATURE:
<223> OTHER INFORMATION: Human papillomavirus type 43 blocking label
      extender probe

<400> SEQUENCE: 485
gggttgctca cgctcatcc                                             19

<210> SEQ ID NO 486
<211> LENGTH: 20
<212> TYPE: DNA
<213> ORGANISM: Artificial Sequence
<220> FEATURE:
<223> OTHER INFORMATION: Human papillomavirus type 43 blocking label
      extender probe

<400> SEQUENCE: 486
acttgctggt cctgttgcgt                                            20

<210> SEQ ID NO 487
<211> LENGTH: 30
<212> TYPE: DNA
<213> ORGANISM: Artificial Sequence
<220> FEATURE:
<223> OTHER INFORMATION: Human papillomavirus type 43 blocking label
      extender probe

<400> SEQUENCE: 487
tctgttacaa ctctgtaaac ttgtagattc                                 30

<210> SEQ ID NO 488
<211> LENGTH: 26
<212> TYPE: DNA
<213> ORGANISM: Artificial Sequence
```

```
<220> FEATURE:
<223> OTHER INFORMATION: Human papillomavirus type 43 blocking label
      extender probe

<400> SEQUENCE: 488
tcttctagct tcttgatgtc actgtc                                          26

<210> SEQ ID NO 489
<211> LENGTH: 47
<212> TYPE: DNA
<213> ORGANISM: Artificial Sequence
<220> FEATURE:
<223> OTHER INFORMATION: Human papillomavirus type 44 capture extender
      probe

<400> SEQUENCE: 489
cctctgcagt acttaacgtt tttctgtttt tctcttggaa agaaagt                   47

<210> SEQ ID NO 490
<211> LENGTH: 46
<212> TYPE: DNA
<213> ORGANISM: Artificial Sequence
<220> FEATURE:
<223> OTHER INFORMATION: Human papillomavirus type 44 capture extender
      probe

<400> SEQUENCE: 490
gcacgtccag aattgactta tttgtttttt ctcttggaaa gaaagt                    46

<210> SEQ ID NO 491
<211> LENGTH: 42
<212> TYPE: DNA
<213> ORGANISM: Artificial Sequence
<220> FEATURE:
<223> OTHER INFORMATION: Human papillomavirus type 44 capture extender
      probe

<400> SEQUENCE: 491
tttaatgaat cgcgccttgt cttttttctct tggaaagaaa gt                       42

<210> SEQ ID NO 492
<211> LENGTH: 44
<212> TYPE: DNA
<213> ORGANISM: Artificial Sequence
<220> FEATURE:
<223> OTHER INFORMATION: Human papillomavirus type 44 capture extender
      probe

<400> SEQUENCE: 492
cgacccttcc aggtatcttg taattttttct cttggaaaga aagt                     44

<210> SEQ ID NO 493
<211> LENGTH: 48
<212> TYPE: DNA
<213> ORGANISM: Artificial Sequence
<220> FEATURE:
<223> OTHER INFORMATION: Human papillomavirus type 44 capture extender
      probe

<400> SEQUENCE: 493
cctttaaggt agtatagttt ccatgcattt ttctcttgga agaaagt                   48

<210> SEQ ID NO 494
<211> LENGTH: 45
<212> TYPE: DNA
<213> ORGANISM: Artificial Sequence
<220> FEATURE:
```

<223> OTHER INFORMATION: Human papillomavirus type 44 capture extender
      probe

<400> SEQUENCE: 494
gaggttccag ctgtaaaaca atttttttc tcttggaaag aaagt                    45

<210> SEQ ID NO 495
<211> LENGTH: 39
<212> TYPE: DNA
<213> ORGANISM: Artificial Sequence
<220> FEATURE:
<223> OTHER INFORMATION: Human papillomavirus type 44 label extender
      probe

<400> SEQUENCE: 495
gcagacgtgg aggcatttgc tttttgaagt taccgtttt                          39

<210> SEQ ID NO 496
<211> LENGTH: 45
<212> TYPE: DNA
<213> ORGANISM: Artificial Sequence
<220> FEATURE:
<223> OTHER INFORMATION: Human papillomavirus type 44 label extender
      probe

<400> SEQUENCE: 496
ccttgcacaa ctggtctata ctttgttttt tctgagtcaa agcat                   45

<210> SEQ ID NO 497
<211> LENGTH: 42
<212> TYPE: DNA
<213> ORGANISM: Artificial Sequence
<220> FEATURE:
<223> OTHER INFORMATION: Human papillomavirus type 44 label extender
      probe

<400> SEQUENCE: 497
attgtgcata ggaatgttgc actttttga agttaccgtt tt                       42

<210> SEQ ID NO 498
<211> LENGTH: 42
<212> TYPE: DNA
<213> ORGANISM: Artificial Sequence
<220> FEATURE:
<223> OTHER INFORMATION: Human papillomavirus type 44 label extender
      probe

<400> SEQUENCE: 498
caaaacacgc ataaaatttg cagttttct gagtcaaagc at                       42

<210> SEQ ID NO 499
<211> LENGTH: 38
<212> TYPE: DNA
<213> ORGANISM: Artificial Sequence
<220> FEATURE:
<223> OTHER INFORMATION: Human papillomavirus type 44 label extender
      probe

<400> SEQUENCE: 499
acaaatggca caggctgcat ttttgaagtt accgtttt                           38

<210> SEQ ID NO 500
<211> LENGTH: 45
<212> TYPE: DNA
<213> ORGANISM: Artificial Sequence
<220> FEATURE:
<223> OTHER INFORMATION: Human papillomavirus type 44 label extender

```
               probe

<400> SEQUENCE: 500
tgattgacct taccttgtag ttctaatttt tctgagtcaa agcat            45

<210> SEQ ID NO 501
<211> LENGTH: 42
<212> TYPE: DNA
<213> ORGANISM: Artificial Sequence
<220> FEATURE:
<223> OTHER INFORMATION: Human papillomavirus type 44 label extender
      probe

<400> SEQUENCE: 501
ccgcgtagtt aaaatgccta aatttttga agttaccgtt tt                42

<210> SEQ ID NO 502
<211> LENGTH: 45
<212> TYPE: DNA
<213> ORGANISM: Artificial Sequence
<220> FEATURE:
<223> OTHER INFORMATION: Human papillomavirus type 44 label extender
      probe

<400> SEQUENCE: 502
ttcttcttcc actgttactg catatctttt tctgagtcaa agcat            45

<210> SEQ ID NO 503
<211> LENGTH: 40
<212> TYPE: DNA
<213> ORGANISM: Artificial Sequence
<220> FEATURE:
<223> OTHER INFORMATION: Human papillomavirus type 44 label extender
      probe

<400> SEQUENCE: 503
ggcacaaata gcagcgtatc atttttgaag ttaccgtttt                  40

<210> SEQ ID NO 504
<211> LENGTH: 39
<212> TYPE: DNA
<213> ORGANISM: Artificial Sequence
<220> FEATURE:
<223> OTHER INFORMATION: Human papillomavirus type 44 label extender
      probe

<400> SEQUENCE: 504
cacgtggcac aatggtttgt tttttctgag tcaaagcat                   39

<210> SEQ ID NO 505
<211> LENGTH: 41
<212> TYPE: DNA
<213> ORGANISM: Artificial Sequence
<220> FEATURE:
<223> OTHER INFORMATION: Human papillomavirus type 44 label extender
      probe

<400> SEQUENCE: 505
caatgtaggc ctacagggtc agtttttgaa gttaccgttt t                41

<210> SEQ ID NO 506
<211> LENGTH: 43
<212> TYPE: DNA
<213> ORGANISM: Artificial Sequence
<220> FEATURE:
<223> OTHER INFORMATION: Human papillomavirus type 44 label extender
      probe
```

<400> SEQUENCE: 506
tctgagctgt ctaattgctc attgtttttc tgagtcaaag cat        43

<210> SEQ ID NO 507
<211> LENGTH: 33
<212> TYPE: DNA
<213> ORGANISM: Artificial Sequence
<220> FEATURE:
<223> OTHER INFORMATION: Human papillomavirus type 44 blocking label
      extender probe

<400> SEQUENCE: 507
ctacatataa ctgtttatat gcgaatgaat aaa        33

<210> SEQ ID NO 508
<211> LENGTH: 22
<212> TYPE: DNA
<213> ORGANISM: Artificial Sequence
<220> FEATURE:
<223> OTHER INFORMATION: Human papillomavirus type 44 blocking label
      extender probe

<400> SEQUENCE: 508
aatggaaagt ttcctcggta ca        22

<210> SEQ ID NO 509
<211> LENGTH: 21
<212> TYPE: DNA
<213> ORGANISM: Artificial Sequence
<220> FEATURE:
<223> OTHER INFORMATION: Human papillomavirus type 44 blocking label
      extender probe

<400> SEQUENCE: 509
caatatgtgg cgcaccttttt c        21

<210> SEQ ID NO 510
<211> LENGTH: 22
<212> TYPE: DNA
<213> ORGANISM: Artificial Sequence
<220> FEATURE:
<223> OTHER INFORMATION: Human papillomavirus type 44 blocking label
      extender probe

<400> SEQUENCE: 510
tgatgtccaa caatggaagc ag        22

<210> SEQ ID NO 511
<211> LENGTH: 41
<212> TYPE: DNA
<213> ORGANISM: Artificial Sequence
<220> FEATURE:
<223> OTHER INFORMATION: Hepatitis B virus capture extender probe

<400> SEQUENCE: 511
ggggagwccg cgtaaagaga tttttctctt ggaaagaaag t        41

<210> SEQ ID NO 512
<211> LENGTH: 40
<212> TYPE: DNA
<213> ORGANISM: Artificial Sequence
<220> FEATURE:
<223> OTHER INFORMATION: Hepatitis B virus capture extender probe

<400> SEQUENCE: 512

-continued

```
tgcracgtgc agaggtgaat ttttctcttg gaaagaaagt                    40
```

<210> SEQ ID NO 513
<211> LENGTH: 48
<212> TYPE: DNA
<213> ORGANISM: Artificial Sequence
<220> FEATURE:
<223> OTHER INFORMATION: Hepatitis B virus capture extender probe

<400> SEQUENCE: 513

```
ragtccaaga gtcctcttat gyaagacttt ttctcttgga aagaaagt          48
```

<210> SEQ ID NO 514
<211> LENGTH: 43
<212> TYPE: DNA
<213> ORGANISM: Artificial Sequence
<220> FEATURE:
<223> OTHER INFORMATION: Hepatitis B virus capture extender probe

<400> SEQUENCE: 514

```
cagaggtgaa aagttgcat grttttctc ttggaaagaa agt                  43
```

<210> SEQ ID NO 515
<211> LENGTH: 40
<212> TYPE: DNA
<213> ORGANISM: Artificial Sequence
<220> FEATURE:
<223> OTHER INFORMATION: Hepatitis B virus capture extender probe

<400> SEQUENCE: 515

```
amggrtcaat gtccatgcct ttttctcttg gaaagaaagt                    40
```

<210> SEQ ID NO 516
<211> LENGTH: 46
<212> TYPE: DNA
<213> ORGANISM: Artificial Sequence
<220> FEATURE:
<223> OTHER INFORMATION: Hepatitis B virus capture extender probe

<400> SEQUENCE: 516

```
tcagaaggca aaaamgagag taactttttt ctcttggaaa gaaagt             46
```

<210> SEQ ID NO 517
<211> LENGTH: 44
<212> TYPE: DNA
<213> ORGANISM: Artificial Sequence
<220> FEATURE:
<223> OTHER INFORMATION: Hepatitis B virus capture extender probe

<400> SEQUENCE: 517

```
atdgcttgcc tkagtgchgt atgttttttct cttggaaaga aagt              44
```

<210> SEQ ID NO 518
<211> LENGTH: 44
<212> TYPE: DNA
<213> ORGANISM: Artificial Sequence
<220> FEATURE:
<223> OTHER INFORMATION: Hepatitis B virus capture extender probe

<400> SEQUENCE: 518

```
cggaagtgtt gataagatag gggttttct cttggaaaga aagt                44
```

<210> SEQ ID NO 519
<211> LENGTH: 39
<212> TYPE: DNA
<213> ORGANISM: Artificial Sequence -continued

```
<220> FEATURE:
<223> OTHER INFORMATION: Hepatitis B virus capture extender probe

<400> SEQUENCE: 519
ctkcgtctgc gaggcgagtt tttctcttgg aaagaaagt                                39

<210> SEQ ID NO 520
<211> LENGTH: 40
<212> TYPE: DNA
<213> ORGANISM: Artificial Sequence
<220> FEATURE:
<223> OTHER INFORMATION: Hepatitis B virus label extender probe

<400> SEQUENCE: 520
ggcagatgag aaggcacaga ctttttgaag ttaccgtttt                               40

<210> SEQ ID NO 521
<211> LENGTH: 37
<212> TYPE: DNA
<213> ORGANISM: Artificial Sequence
<220> FEATURE:
<223> OTHER INFORMATION: Hepatitis B virus label extender probe

<400> SEQUENCE: 521
gcgaagtgca cacggwcctt tttctgagtc aaagcat                                 37

<210> SEQ ID NO 522
<211> LENGTH: 39
<212> TYPE: DNA
<213> ORGANISM: Artificial Sequence
<220> FEATURE:
<223> OTHER INFORMATION: Hepatitis B virus label extender probe

<400> SEQUENCE: 522
tcggtcgttg acattrcwgr tttttgaagt taccgtttt                               39

<210> SEQ ID NO 523
<211> LENGTH: 43
<212> TYPE: DNA
<213> ORGANISM: Artificial Sequence
<220> FEATURE:
<223> OTHER INFORMATION: Hepatitis B virus label extender probe

<400> SEQUENCE: 523
cagtctttga agtakgcctc aaggtttttc tgagtcaaag cat                          43

<210> SEQ ID NO 524
<211> LENGTH: 44
<212> TYPE: DNA
<213> ORGANISM: Artificial Sequence
<220> FEATURE:
<223> OTHER INFORMATION: Hepatitis B virus label extender probe

<400> SEQUENCE: 524
gcctacagcc tccyartaca aagacttttt gaagttaccg tttt                         44

<210> SEQ ID NO 525
<211> LENGTH: 42
<212> TYPE: DNA
<213> ORGANISM: Artificial Sequence
<220> FEATURE:
<223> OTHER INFORMATION: Hepatitis B virus label extender probe

<400> SEQUENCE: 525
tgmtggtgmr casaccaatt tatttttct gagtcaaagc at                            42
```

<210> SEQ ID NO 526
<211> LENGTH: 43
<212> TYPE: DNA
<213> ORGANISM: Artificial Sequence
<220> FEATURE:
<223> OTHER INFORMATION: Hepatitis B virus label extender probe

<400> SEQUENCE: 526
ggacatgwac awgagatgat yaggttttg aagttaccgt ttt                43

<210> SEQ ID NO 527
<211> LENGTH: 41
<212> TYPE: DNA
<213> ORGANISM: Artificial Sequence
<220> FEATURE:
<223> OTHER INFORMATION: Hepatitis B virus label extender probe

<400> SEQUENCE: 527
cagcttggag gcttgaacag trtttttctg agtcaaagca t                41

<210> SEQ ID NO 528
<211> LENGTH: 41
<212> TYPE: DNA
<213> ORGANISM: Artificial Sequence
<220> FEATURE:
<223> OTHER INFORMATION: Hepatitis B virus label extender probe

<400> SEQUENCE: 528
agactctaag gcytcycgat acttttgaa gttaccgttt t                  41

<210> SEQ ID NO 529
<211> LENGTH: 40
<212> TYPE: DNA
<213> ORGANISM: Artificial Sequence
<220> FEATURE:
<223> OTHER INFORMATION: Hepatitis B virus label extender probe

<400> SEQUENCE: 529
rtgaggtgar caatgytcmg gtttttctga gtcaaagcat                   40

<210> SEQ ID NO 530
<211> LENGTH: 45
<212> TYPE: DNA
<213> ORGANISM: Artificial Sequence
<220> FEATURE:
<223> OTHER INFORMATION: Hepatitis B virus label extender probe

<400> SEQUENCE: 530
cctcktcgtc taacaacagt agtytctttt tgaagttacc gtttt             45

<210> SEQ ID NO 531
<211> LENGTH: 41
<212> TYPE: DNA
<213> ORGANISM: Artificial Sequence
<220> FEATURE:
<223> OTHER INFORMATION: Hepatitis B virus label extender probe

<400> SEQUENCE: 531
cagcttggag gcttgaacag trtttttctg agtcaaagca t                 41

<210> SEQ ID NO 532
<211> LENGTH: 37
<212> TYPE: DNA
<213> ORGANISM: Artificial Sequence
<220> FEATURE:
<223> OTHER INFORMATION: Hepatitis B virus label extender probe

```
<400> SEQUENCE: 532
cgacgcggcg attgagaytt tttgaagtta ccgtttt                              37

<210> SEQ ID NO 533
<211> LENGTH: 42
<212> TYPE: DNA
<213> ORGANISM: Artificial Sequence
<220> FEATURE:
<223> OTHER INFORMATION: Hepatitis B virus label extender probe

<400> SEQUENCE: 533
attcccgaga ttgagatcty ctgtttttct gagtcaaagc at                        42

<210> SEQ ID NO 534
<211> LENGTH: 44
<212> TYPE: DNA
<213> ORGANISM: Artificial Sequence
<220> FEATURE:
<223> OTHER INFORMATION: Hepatitis B virus label extender probe

<400> SEQUENCE: 534
gwgtccaagg ratactaaca ttgagttttt gaagttaccg tttt                      44

<210> SEQ ID NO 535
<211> LENGTH: 42
<212> TYPE: DNA
<213> ORGANISM: Artificial Sequence
<220> FEATURE:
<223> OTHER INFORMATION: Hepatitis B virus label extender probe

<400> SEQUENCE: 535
cccmgtaaar tttcccacct tatttttct gagtcaaagc at                         42

<210> SEQ ID NO 536
<211> LENGTH: 19
<212> TYPE: DNA
<213> ORGANISM: Artificial Sequence
<220> FEATURE:
<223> OTHER INFORMATION: Hepatitis B virus blocking label extender probe

<400> SEQUENCE: 536
gcgttcacgg tggtctcca                                                  19

<210> SEQ ID NO 537
<211> LENGTH: 19
<212> TYPE: DNA
<213> ORGANISM: Artificial Sequence
<220> FEATURE:
<223> OTHER INFORMATION: Hepatitis B virus blocking label extender probe

<400> SEQUENCE: 537
cttgggcarg whbysdygg                                                  19

<210> SEQ ID NO 538
<211> LENGTH: 24
<212> TYPE: DNA
<213> ORGANISM: Artificial Sequence
<220> FEATURE:
<223> OTHER INFORMATION: Hepatitis B virus blocking label extender probe

<400> SEQUENCE: 538
arctcctccc astchktaaa yama                                            24

<210> SEQ ID NO 539
```

```
<211> LENGTH: 22
<212> TYPE: DNA
<213> ORGANISM: Artificial Sequence
<220> FEATURE:
<223> OTHER INFORMATION: Hepatitis B virus blocking label extender probe

<400> SEQUENCE: 539
ctttaaycta rtctcctccc cc                                              22

<210> SEQ ID NO 540
<211> LENGTH: 18
<212> TYPE: DNA
<213> ORGANISM: Artificial Sequence
<220> FEATURE:
<223> OTHER INFORMATION: Hepatitis B virus blocking label extender probe

<400> SEQUENCE: 540
cyaaagccay ccaaggca                                                   18

<210> SEQ ID NO 541
<211> LENGTH: 24
<212> TYPE: DNA
<213> ORGANISM: Artificial Sequence
<220> FEATURE:
<223> OTHER INFORMATION: Hepatitis B virus blocking label extender probe

<400> SEQUENCE: 541
ccacagwagc tccaaattct ttat                                            24

<210> SEQ ID NO 542
<211> LENGTH: 26
<212> TYPE: DNA
<213> ORGANISM: Artificial Sequence
<220> FEATURE:
<223> OTHER INFORMATION: Hepatitis B virus blocking label extender probe

<400> SEQUENCE: 542
gdagatchck daydgaagga aagaag                                          26

<210> SEQ ID NO 543
<211> LENGTH: 19
<212> TYPE: DNA
<213> ORGANISM: Artificial Sequence
<220> FEATURE:
<223> OTHER INFORMATION: Hepatitis B virus blocking label extender probe

<400> SEQUENCE: 543
agagcwgagg ckgtrtcda                                                  19

<210> SEQ ID NO 544
<211> LENGTH: 22
<212> TYPE: DNA
<213> ORGANISM: Artificial Sequence
<220> FEATURE:
<223> OTHER INFORMATION: Hepatitis B virus blocking label extender probe

<400> SEQUENCE: 544
yatyarbtcm ccccarcava gr                                              22

<210> SEQ ID NO 545
<211> LENGTH: 19
<212> TYPE: DNA
<213> ORGANISM: Artificial Sequence
<220> FEATURE:
<223> OTHER INFORMATION: Hepatitis B virus blocking label extender probe

<400> SEQUENCE: 545
```

```
ccacccaggt rgmyarakt                                                    19

<210> SEQ ID NO 546
<211> LENGTH: 23
<212> TYPE: DNA
<213> ORGANISM: Artificial Sequence
<220> FEATURE:
<223> OTHER INFORMATION: Hepatitis B virus blocking label extender probe

<400> SEQUENCE: 546
tgywggrtct tccaaattah ywc                                               23

<210> SEQ ID NO 547
<211> LENGTH: 25
<212> TYPE: DNA
<213> ORGANISM: Artificial Sequence
<220> FEATURE:
<223> OTHER INFORMATION: Hepatitis B virus blocking label extender probe

<400> SEQUENCE: 547
catarytkac tactardtcc ctrga                                             25

<210> SEQ ID NO 548
<211> LENGTH: 24
<212> TYPE: DNA
<213> ORGANISM: Artificial Sequence
<220> FEATURE:
<223> OTHER INFORMATION: Hepatitis B virus blocking label extender probe

<400> SEQUENCE: 548
wytttarrcc catrttaryr ttra                                              24

<210> SEQ ID NO 549
<211> LENGTH: 27
<212> TYPE: DNA
<213> ORGANISM: Artificial Sequence
<220> FEATURE:
<223> OTHER INFORMATION: Hepatitis B virus blocking label extender probe

<400> SEQUENCE: 549
awatrtgaaa ccacaatagt tgyctra                                           27

<210> SEQ ID NO 550
<211> LENGTH: 25
<212> TYPE: DNA
<213> ORGANISM: Artificial Sequence
<220> FEATURE:
<223> OTHER INFORMATION: Hepatitis B virus blocking label extender probe

<400> SEQUENCE: 550
gtytctctyc caaaagtrag rcarg                                             25

<210> SEQ ID NO 551
<211> LENGTH: 26
<212> TYPE: DNA
<213> ORGANISM: Artificial Sequence
<220> FEATURE:
<223> OTHER INFORMATION: Hepatitis B virus blocking label extender probe

<400> SEQUENCE: 551
craaagasac caaataytcw akdach                                            26

<210> SEQ ID NO 552
<211> LENGTH: 21
<212> TYPE: DNA
```

```
<213> ORGANISM: Artificial Sequence
<220> FEATURE:
<223> OTHER INFORMATION: Hepatitis B virus blocking label extender probe

<400> SEQUENCE: 552
gwggagtgcg aatccacact c                                              21

<210> SEQ ID NO 553
<211> LENGTH: 21
<212> TYPE: DNA
<213> ORGANISM: Artificial Sequence
<220> FEATURE:
<223> OTHER INFORMATION: Hepatitis B virus blocking label extender probe

<400> SEQUENCE: 553
cattwggtgg tctrtadgcd g                                              21

<210> SEQ ID NO 554
<211> LENGTH: 47
<212> TYPE: DNA
<213> ORGANISM: Artificial Sequence
<220> FEATURE:
<223> OTHER INFORMATION: Human immunodeficiency virus A capture extender
      probe

<400> SEQUENCE: 554
ttcatttcct ccaatccccct tatgtgtttt tctcttggaa agaaagt                 47

<210> SEQ ID NO 555
<211> LENGTH: 52
<212> TYPE: DNA
<213> ORGANISM: Artificial Sequence
<220> FEATURE:
<223> OTHER INFORMATION: Human immunodeficiency virus A capture extender
      probe

<400> SEQUENCE: 555
attgctgtga tatctttcat gttcttcttg atttttctct tggaaagaaa gt            52

<210> SEQ ID NO 556
<211> LENGTH: 53
<212> TYPE: DNA
<213> ORGANISM: Artificial Sequence
<220> FEATURE:
<223> OTHER INFORMATION: Human immunodeficiency virus A capture extender
      probe

<400> SEQUENCE: 556
actgctacca gaattacttt cccttctaaa tgttttctc ttggaaagaa agt            53

<210> SEQ ID NO 557
<211> LENGTH: 47
<212> TYPE: DNA
<213> ORGANISM: Artificial Sequence
<220> FEATURE:
<223> OTHER INFORMATION: Human immunodeficiency virus A capture extender
      probe

<400> SEQUENCE: 557
cgctggtaaa attgctgcca ttgtcttttt tctcttggaa agaaagt                  47

<210> SEQ ID NO 558
<211> LENGTH: 47
<212> TYPE: DNA
<213> ORGANISM: Artificial Sequence
<220> FEATURE:
<223> OTHER INFORMATION: Human immunodeficiency virus A capture extender
``` probe

<400> SEQUENCE: 558
ctccttgact ttggggattg tagggatttt tctcttggaa agaaagt                47

<210> SEQ ID NO 559
<211> LENGTH: 59
<212> TYPE: DNA
<213> ORGANISM: Artificial Sequence
<220> FEATURE:
<223> OTHER INFORMATION: Human immunodeficiency virus A label extender
      probe

<400> SEQUENCE: 559
ctgattccag agctgactaa tttatctact tgtttttctg agtcaaagca tgaagttac    59

<210> SEQ ID NO 560
<211> LENGTH: 60
<212> TYPE: DNA
<213> ORGANISM: Artificial Sequence
<220> FEATURE:
<223> OTHER INFORMATION: Human immunodeficiency virus A label extender
      probe

<400> SEQUENCE: 560
gccttatcta tcccatctaa aaatagtatc ttcttttct gagtcaaagc atgaagttac    60

<210> SEQ ID NO 561
<211> LENGTH: 56
<212> TYPE: DNA
<213> ORGANISM: Artificial Sequence
<220> FEATURE:
<223> OTHER INFORMATION: Human immunodeficiency virus A label extender
      probe

<400> SEQUENCE: 561
agattaaaat cactagccat tgctctccat ttttctgagt caaagcatga agttac       56

<210> SEQ ID NO 562
<211> LENGTH: 58
<212> TYPE: DNA
<213> ORGANISM: Artificial Sequence
<220> FEATURE:
<223> OTHER INFORMATION: Human immunodeficiency virus A label extender
      probe

<400> SEQUENCE: 562
ggctactatt tcctttgcta ctataggtgg ctttttctga gtcaaagcat gaagttac     58

<210> SEQ ID NO 563
<211> LENGTH: 55
<212> TYPE: DNA
<213> ORGANISM: Artificial Sequence
<220> FEATURE:
<223> OTHER INFORMATION: Human immunodeficiency virus A label extender
      probe

<400> SEQUENCE: 563
gactacagtc tacctgtcca tgcatggctt tttctgagtc aaagcatgaa gttac        55

<210> SEQ ID NO 564
<211> LENGTH: 56
<212> TYPE: DNA
<213> ORGANISM: Artificial Sequence
<220> FEATURE:
<223> OTHER INFORMATION: Human immunodeficiency virus A label extender
      probe

<400> SEQUENCE: 564
ctgcttctat atagccactg gctacatggt ttttctgagt caaagcatga agttac         56

<210> SEQ ID NO 565
<211> LENGTH: 54
<212> TYPE: DNA
<213> ORGANISM: Artificial Sequence
<220> FEATURE:
<223> OTHER INFORMATION: Human immunodeficiency virus A label extender
      probe

<400> SEQUENCE: 565
cctgccctgt ttctgctggg ataactttt ttctgagtca aagcatgaag ttac            54

<210> SEQ ID NO 566
<211> LENGTH: 56
<212> TYPE: DNA
<213> ORGANISM: Artificial Sequence
<220> FEATURE:
<223> OTHER INFORMATION: Human immunodeficiency virus A label extender
      probe

<400> SEQUENCE: 566
gtgtgtacta cttttactgg ccatcctcct ttttctgagt caaagcatga agttac         56

<210> SEQ ID NO 567
<211> LENGTH: 53
<212> TYPE: DNA
<213> ORGANISM: Artificial Sequence
<220> FEATURE:
<223> OTHER INFORMATION: Human immunodeficiency virus A label extender
      probe

<400> SEQUENCE: 567
ccaccaacag gctgctttaa atgcagtttt tctgagtcaa agcatgaagt tac            53

<210> SEQ ID NO 568
<211> LENGTH: 30
<212> TYPE: DNA
<213> ORGANISM: Artificial Sequence
<220> FEATURE:
<223> OTHER INFORMATION: Human immunodeficiency virus A blocking label
      extender probe

<400> SEQUENCE: 568 ttccccttt agttgacatt tatcacagct                                       30

<210> SEQ ID NO 569
<211> LENGTH: 26
<212> TYPE: DNA
<213> ORGANISM: Artificial Sequence
<220> FEATURE:
<223> OTHER INFORMATION: Human immunodeficiency virus A blocking label
      extender probe

<400> SEQUENCE: 569
tgtgcaatct aattgccaca tccctg                                          26

<210> SEQ ID NO 570
<211> LENGTH: 29
<212> TYPE: DNA
<213> ORGANISM: Artificial Sequence
<220> FEATURE:
<223> OTHER INFORMATION: Human immunodeficiency virus A blocking label
      extender probe

<400> SEQUENCE: 570
tgctaatttt agcaaaaagt atgctgcct					29

<210> SEQ ID NO 571
<211> LENGTH: 26
<212> TYPE: DNA
<213> ORGANISM: Artificial Sequence
<220> FEATURE:
<223> OTHER INFORMATION: Human immunodeficiency virus A blocking label
      extender probe

<400> SEQUENCE: 571
atcccaaatt cctgttggat gtttgc					26

<210> SEQ ID NO 572
<211> LENGTH: 52
<212> TYPE: DNA
<213> ORGANISM: Artificial Sequence
<220> FEATURE:
<223> OTHER INFORMATION: Human immunodeficiency virus B capture extender
      probe

<400> SEQUENCE: 572
tgcttctata tacccactgg ctacatgaac tttttctct tggaaagaaa gt					52

<210> SEQ ID NO 573
<211> LENGTH: 41
<212> TYPE: DNA
<213> ORGANISM: Artificial Sequence
<220> FEATURE:
<223> OTHER INFORMATION: Human immunodeficiency virus B capture extender
      probe

<400> SEQUENCE: 573
caacaggcgg ccttgaccgc tttttctctt ggaaagaaag t					41

<210> SEQ ID NO 574
<211> LENGTH: 42
<212> TYPE: DNA
<213> ORGANISM: Artificial Sequence
<220> FEATURE:
<223> OTHER INFORMATION: Human immunodeficiency virus B capture extender
      probe

<400> SEQUENCE: 574
tcctgcttga cccccgccca cttttttctct tggaaagaaa gt					42

<210> SEQ ID NO 575
<211> LENGTH: 46
<212> TYPE: DNA
<213> ORGANISM: Artificial Sequence
<220> FEATURE:
<223> OTHER INFORMATION: Human immunodeficiency virus B capture extender
      probe

<400> SEQUENCE: 575
gcactatagt ccccaatccc ccctcttttt ctcttggaaa gaaagt					46

<210> SEQ ID NO 576
<211> LENGTH: 46
<212> TYPE: DNA
<213> ORGANISM: Artificial Sequence
<220> FEATURE:
<223> OTHER INFORMATION: Human immunodeficiency virus B capture extender
      probe

<400> SEQUENCE: 576

```
ctttccagag gagctttgct ggtcctttt ctcttggaaa gaaagt         46
```

<210> SEQ ID NO 577
<211> LENGTH: 53
<212> TYPE: DNA
<213> ORGANISM: Artificial Sequence
<220> FEATURE:
<223> OTHER INFORMATION: Human immunodeficiency virus B capture extender
      probe

<400> SEQUENCE: 577

```
actcttatct tgtattacta ctgccccttc acttttctc ttggaaagaa agt    53
```

<210> SEQ ID NO 578
<211> LENGTH: 58
<212> TYPE: DNA
<213> ORGANISM: Artificial Sequence
<220> FEATURE:
<223> OTHER INFORMATION: Human immunodeficiency virus B label extender
      probe

<400> SEQUENCE: 578

```
caatctagtt gccatattcc tggactacag ttttttctga gtcaaagcat gaagttac    58
```

<210> SEQ ID NO 579
<211> LENGTH: 60
<212> TYPE: DNA
<213> ORGANISM: Artificial Sequence
<220> FEATURE:
<223> OTHER INFORMATION: Human immunodeficiency virus B label extender
      probe

<400> SEQUENCE: 579

```
gctaccagga taactcttcc ttctaaatgt gtatttttct gagtcaaagc atgaagttac    60
```

<210> SEQ ID NO 580
<211> LENGTH: 52
<212> TYPE: DNA
<213> ORGANISM: Artificial Sequence
<220> FEATURE:
<223> OTHER INFORMATION: Human immunodeficiency virus B label extender
      probe

<400> SEQUENCE: 580

```
gccctgtctc tgctgggatc acttcttttt ctgagtcaaa gcatgaagtt ac    52
```

<210> SEQ ID NO 581
<211> LENGTH: 57
<212> TYPE: DNA
<213> ORGANISM: Artificial Sequence
<220> FEATURE:
<223> OTHER INFORMATION: Human immunodeficiency virus B label extender
      probe

<400> SEQUENCE: 581

```
tgtatgtatt gtctttactg gccatcttcc tttttctgag tcaaagcatg aagttac    57
```

<210> SEQ ID NO 582
<211> LENGTH: 60
<212> TYPE: DNA
<213> ORGANISM: Artificial Sequence
<220> FEATURE:
<223> OTHER INFORMATION: Human immunodeficiency virus B label extender
      probe

<400> SEQUENCE: 582

```
ttctttattc atagattcta ctactccttg acttttttct gagtcaaagc atgaagttac      60
```

<210> SEQ ID NO 583
<211> LENGTH: 58
<212> TYPE: DNA
<213> ORGANISM: Artificial Sequence
<220> FEATURE:
<223> OTHER INFORMATION: Human immunodeficiency virus B label extender
      probe

<400> SEQUENCE: 583

```
gatctcttac ctgtcctata attttcttta attttctga gtcaaagcat gaagttac         58
```

<210> SEQ ID NO 584
<211> LENGTH: 57
<212> TYPE: DNA
<213> ORGANISM: Artificial Sequence
<220> FEATURE:
<223> OTHER INFORMATION: Human immunodeficiency virus B label extender
      probe

<400> SEQUENCE: 584

```
tttgtactgc tgtcttaaga tgttcagcct tttttctgag tcaaagcatg aagttac          57
```

<210> SEQ ID NO 585
<211> LENGTH: 57
<212> TYPE: DNA
<213> ORGANISM: Artificial Sequence
<220> FEATURE:
<223> OTHER INFORMATION: Human immunodeficiency virus B label extender
      probe

<400> SEQUENCE: 585

```
ttcttttaaa attgtggatg aatactgcca tttttctgag tcaaagcatg aagttac          57
```

<210> SEQ ID NO 586
<211> LENGTH: 59
<212> TYPE: DNA
<213> ORGANISM: Artificial Sequence
<220> FEATURE:
<223> OTHER INFORMATION: Human immunodeficiency virus B label extender
      probe

<400> SEQUENCE: 586

```
ctgttgctat tatgtctatt attctctccc ctttttctg agtcaaagca tgaagttac         59
```

<210> SEQ ID NO 587
<211> LENGTH: 59
<212> TYPE: DNA
<213> ORGANISM: Artificial Sequence
<220> FEATURE:
<223> OTHER INFORMATION: Human immunodeficiency virus B label extender
      probe

<400> SEQUENCE: 587

```
aatttgtttt tgtaattctt tggtttgtat gttttttctg agtcaaagca tgaagttac        59
```

<210> SEQ ID NO 588
<211> LENGTH: 58
<212> TYPE: DNA
<213> ORGANISM: Artificial Sequence
<220> FEATURE:
<223> OTHER INFORMATION: Human immunodeficiency virus B label extender
      probe

<400> SEQUENCE: 588

```
tgtaatagac ccgaaaattt tgaatttttg tttttctga gtcaaagcat gaagttac          58
```

<210> SEQ ID NO 589
<211> LENGTH: 56
<212> TYPE: DNA
<213> ORGANISM: Artificial Sequence
<220> FEATURE:
<223> OTHER INFORMATION: Human immunodeficiency virus B label extender
      probe

<400> SEQUENCE: 589
gccatctgtt ttccataatc cctaatgatt ttttctgagt caaagcatga agttac        56

<210> SEQ ID NO 590
<211> LENGTH: 56
<212> TYPE: DNA
<213> ORGANISM: Artificial Sequence
<220> FEATURE:
<223> OTHER INFORMATION: Human immunodeficiency virus B label extender
      probe

<400> SEQUENCE: 590
cctgtctact tgccatacaa tcatcacctt ttttctgagt caaagcatga agttac        56

<210> SEQ ID NO 591
<211> LENGTH: 32
<212> TYPE: DNA
<213> ORGANISM: Artificial Sequence
<220> FEATURE:
<223> OTHER INFORMATION: Human immunodeficiency virus B blocking label
      extender probe

<400> SEQUENCE: 591
tgctaatttt aagagaaagt atgctgtttc ct                                  32

<210> SEQ ID NO 592
<211> LENGTH: 27
<212> TYPE: DNA
<213> ORGANISM: Artificial Sequence
<220> FEATURE:
<223> OTHER INFORMATION: Human immunodeficiency virus B blocking label
      extender probe

<400> SEQUENCE: 592
actactggtg aagttgctgc cattgtc                                        27

<210> SEQ ID NO 593
<211> LENGTH: 25
<212> TYPE: DNA
<213> ORGANISM: Artificial Sequence
<220> FEATURE:
<223> OTHER INFORMATION: Human immunodeficiency virus B blocking label
      extender probe

<400> SEQUENCE: 593
ttggggattg tagggaatgc caaat                                          25

<210> SEQ ID NO 594
<211> LENGTH: 26
<212> TYPE: DNA
<213> ORGANISM: Artificial Sequence
<220> FEATURE:
<223> OTHER INFORMATION: Human immunodeficiency virus B blocking label
      extender probe

<400> SEQUENCE: 594
tttccaaagt ggatctctgc tgtccc                                         26

<210> SEQ ID NO 595
<211> LENGTH: 33
<212> TYPE: DNA
<213> ORGANISM: Artificial Sequence
<220> FEATURE:
<223> OTHER INFORMATION: Human immunodeficiency virus B blocking label extender probe

<400> SEQUENCE: 595
ctttactttt cttcttggta ctacttttat gtc    33

<210> SEQ ID NO 596
<211> LENGTH: 56
<212> TYPE: DNA
<213> ORGANISM: Artificial Sequence
<220> FEATURE:
<223> OTHER INFORMATION: Human immunodeficiency virus F capture extender probe

<400> SEQUENCE: 596
ttctttagct ctttattcat tgattctact actccttttt ctcttggaaa gaaagt    56

<210> SEQ ID NO 597
<211> LENGTH: 46
<212> TYPE: DNA
<213> ORGANISM: Artificial Sequence
<220> FEATURE:
<223> OTHER INFORMATION: Human immunodeficiency virus F capture extender probe

<400> SEQUENCE: 597 ttccctgca ctgtaccccc caatcttttt ctcttggaaa gaaagt    46

<210> SEQ ID NO 598
<211> LENGTH: 50
<212> TYPE: DNA
<213> ORGANISM: Artificial Sequence
<220> FEATURE:
<223> OTHER INFORMATION: Human immunodeficiency virus F capture extender probe

<400> SEQUENCE: 598
gctgtccctg taataaaccc ggaaattttt ttttctcttg gaaagaaagt    50

<210> SEQ ID NO 599
<211> LENGTH: 47
<212> TYPE: DNA
<213> ORGANISM: Artificial Sequence
<220> FEATURE:
<223> OTHER INFORMATION: Human immunodeficiency virus F capture extender probe

<400> SEQUENCE: 599
tgccccttca cctttccaga gtagctttt tctcttggaa agaaagt    47

<210> SEQ ID NO 600
<211> LENGTH: 49
<212> TYPE: DNA
<213> ORGANISM: Artificial Sequence
<220> FEATURE:
<223> OTHER INFORMATION: Human immunodeficiency virus F capture extender probe

<400> SEQUENCE: 600
cgtcacctgc catctgtttt ccataatctt tttctcttgg aaagaaagt    49

```
<210> SEQ ID NO 601
<211> LENGTH: 58
<212> TYPE: DNA
<213> ORGANISM: Artificial Sequence
<220> FEATURE:
<223> OTHER INFORMATION: Human immunodeficiency virus F label extender
      probe

<400> SEQUENCE: 601
ttcagcttga tctcttacct gtcctatgat cttttctga gtcaaagcat gaagttac      58

<210> SEQ ID NO 602
<211> LENGTH: 58
<212> TYPE: DNA
<213> ORGANISM: Artificial Sequence
<220> FEATURE:
<223> OTHER INFORMATION: Human immunodeficiency virus F label extender
      probe

<400> SEQUENCE: 602
atactgccat ttgtactgct gtcttaagat gttttctga gtcaaagcat gaagttac      58

<210> SEQ ID NO 603
<211> LENGTH: 55
<212> TYPE: DNA
<213> ORGANISM: Artificial Sequence
<220> FEATURE:
<223> OTHER INFORMATION: Human immunodeficiency virus F label extender
      probe

<400> SEQUENCE: 603
cccccttttc ttttaaaatt gtggatgatt tttctgagtc aaagcatgaa gttac         55

<210> SEQ ID NO 604
<211> LENGTH: 60
<212> TYPE: DNA
<213> ORGANISM: Artificial Sequence
<220> FEATURE:
<223> OTHER INFORMATION: Human immunodeficiency virus F label extender
      probe

<400> SEQUENCE: 604
ttgtatgtct gttgctatta tgtctattat tctttttct gagtcaaagc atgaagttac    60

<210> SEQ ID NO 605
<211> LENGTH: 60
<212> TYPE: DNA
<213> ORGANISM: Artificial Sequence
<220> FEATURE:
<223> OTHER INFORMATION: Human immunodeficiency virus F label extender
      probe

<400> SEQUENCE: 605 gaattttgt aacttgtttt tgtaattctt tagttttttc tgagtcaaag catgaagtta    60

<210> SEQ ID NO 606
<211> LENGTH: 55
<212> TYPE: DNA
<213> ORGANISM: Artificial Sequence
<220> FEATURE:
<223> OTHER INFORMATION: Human immunodeficiency virus F label extender
      probe

<400> SEQUENCE: 606
ttgctggtcc tttccaaact gggtctcttt tttctgagtc aaagcatgaa gttac         55

<210> SEQ ID NO 607
```

```
<210> SEQ ID NO 607
<211> LENGTH: 60
<212> TYPE: DNA
<213> ORGANISM: Artificial Sequence
<220> FEATURE:
<223> OTHER INFORMATION: Human immunodeficiency virus F label extender
      probe

<400> SEQUENCE: 607
ctacttttat ttcactattg tcttgtatga ctactttttc tgagtcaaag catgaagtta    60

<210> SEQ ID NO 608
<211> LENGTH: 52
<212> TYPE: DNA
<213> ORGANISM: Artificial Sequence
<220> FEATURE:
<223> OTHER INFORMATION: Human immunodeficiency virus F label extender
      probe

<400> SEQUENCE: 608
tcatcctgtc tacctgccac acaattttttt ctgagtcaaa gcatgaagtt ac            52

<210> SEQ ID NO 609
<211> LENGTH: 29
<212> TYPE: DNA
<213> ORGANISM: Artificial Sequence
<220> FEATURE:
<223> OTHER INFORMATION: Human immunodeficiency virus F blocking label
      extender probe

<400> SEQUENCE: 609
cctaatgatc tttgcttttc ttcttggca                                       29

<210> SEQ ID NO 610
<211> LENGTH: 48
<212> TYPE: DNA
<213> ORGANISM: Artificial Sequence
<220> FEATURE:
<223> OTHER INFORMATION: Influenza A virus subtype H1N1 capture extender
      probe

<400> SEQUENCE: 610
ggttctattg gaaaatgaaa gaactttttt ttctcttgga aagaaagt                  48

<210> SEQ ID NO 611
<211> LENGTH: 41
<212> TYPE: DNA
<213> ORGANISM: Artificial Sequence
<220> FEATURE:
<223> OTHER INFORMATION: Influenza A virus subtype H1N1 capture extender
      probe

<400> SEQUENCE: 611
caaaatgagc aggggtcagg tttttctctt ggaaagaaag t                         41

<210> SEQ ID NO 612
<211> LENGTH: 40
<212> TYPE: DNA
<213> ORGANISM: Artificial Sequence
<220> FEATURE:
<223> OTHER INFORMATION: Influenza A virus subtype H1N1 capture extender
      probe

<400> SEQUENCE: 612
tgccggtttc attgaagggt ttttctcttg gaaagaaagt                           40

<210> SEQ ID NO 613
<211> LENGTH: 45
```

<212> TYPE: DNA
<213> ORGANISM: Artificial Sequence
<220> FEATURE:
<223> OTHER INFORMATION: Influenza A virus subtype H1N1 capture extender probe

<400> SEQUENCE: 613
ccagcctccc atttcagaat atactttttc tcttggaaag aaagt 45

<210> SEQ ID NO 614
<211> LENGTH: 43
<212> TYPE: DNA
<213> ORGANISM: Artificial Sequence
<220> FEATURE:
<223> OTHER INFORMATION: Influenza A virus subtype H1N1 capture extender probe

<400> SEQUENCE: 614
acacccaagg gtgctataaa catttttctc ttggaaagaa agt 43

<210> SEQ ID NO 615
<211> LENGTH: 43
<212> TYPE: DNA
<213> ORGANISM: Artificial Sequence
<220> FEATURE:
<223> OTHER INFORMATION: Influenza A virus subtype H1N1 capture extender probe

<400> SEQUENCE: 615
caagccggaa atagcaataa gatttttctc ttggaaagaa agt 43

<210> SEQ ID NO 616
<211> LENGTH: 44
<212> TYPE: DNA
<213> ORGANISM: Artificial Sequence
<220> FEATURE:
<223> OTHER INFORMATION: Influenza A virus subtype H1N1 capture extender probe

<400> SEQUENCE: 616
aaaaggaaat tcatacccaa agctttttct cttggaaaga aagt 44

<210> SEQ ID NO 617
<211> LENGTH: 42
<212> TYPE: DNA
<213> ORGANISM: Artificial Sequence
<220> FEATURE:
<223> OTHER INFORMATION: Influenza A virus subtype H1N1 capture extender probe

<400> SEQUENCE: 617
aaaggtgtaa cggcagcatg ttttttctct tggaaagaaa gt 42

<210> SEQ ID NO 618
<211> LENGTH: 46
<212> TYPE: DNA
<213> ORGANISM: Artificial Sequence
<220> FEATURE:
<223> OTHER INFORMATION: Influenza A virus subtype H1N1 capture extender probe

<400> SEQUENCE: 618
ctcagtgtca tcatttgaaa ggtttttttt ctcttggaaa gaaagt 46

<210> SEQ ID NO 619
<211> LENGTH: 44
<212> TYPE: DNA

<213> ORGANISM: Artificial Sequence
<220> FEATURE:
<223> OTHER INFORMATION: Influenza A virus subtype H1N1 capture extender prob
<220> FEATURE:
<223> OTHER INFORMATION: Influenza A virus subtype H1N1 capture extender
      probe

<400

<223> OTHER INFORMATION: Influenza A virus subtype H1N1 label extender
      probe

<400> SEQUENCE: 631
tgatgatggt ttcctggaca tttttttctg agtcaaagca t                              41

<210> SEQ ID NO 632
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 632
ggtaaagagt tcaaccacct ggattttga agttaccgtt tt                              42

<210> SEQ ID NO 633
<211> LENGTH: 46
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 633
aagatgaata cacagttcac agcagtattt ttctgagtca aagcat                         46

<210> SEQ ID NO 634
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 634
cacacagaat gccattgacg agtttttgaa gttaccgttt t                              41

<210> SEQ ID NO 635
<211> LENGTH: 40
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 635
atatgcagcc gacctgaaga gttttctga gtcaaagcat                                 40

<210> SEQ ID NO 636
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 636
tggatggtac ggttatcacc atttttgaa gttaccgttt t                               41

<210> SEQ ID NO 637
<211> LENGTH: 39
<212> TYPE: DNA
<213> ORGANISM: Artificial Sequence
<220> FEATURE:
<223> OTHER INFORMATION: Influenza A virus subtype H1N1 label extender

```
              probe

<400> SEQUENCE: 637
gggtggacag ggatggtaga tttttctgag tcaaagcat                              39

<210> SEQ ID NO 638
<211> LENGTH: 37
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 638
aggcctattt ggggccattt tttgaagtta ccgtttt                                37

<210> SEQ ID NO 639
<211> LENGTH: 44
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 639
ggaatatccc gtctattcaa tctagttttt ctgagtcaaa gcat                        44

<210> SEQ ID NO 640
<211> LENGTH: 40
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 640
tgagactggc cacaggattg atttttgaag ttaccgtttt                             40

<210> SEQ ID NO 641
<211> LENGTH: 45
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 641
tccaaaatat gtaaaaagca caaaatttt tctgagtcaa agcat                        45

<210> SEQ ID NO 642
<211> LENGTH: 43
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 642
cacgattgca atacaacttg tcaattttg aagttaccgt ttt                          43

<210> SEQ ID NO 643
<211> LENGTH: 46
<212> TYPE: DNA
<213> ORGANISM: Artificial Sequence
<220> FEATURE:
<223> OTHER INFORMATION: Influenza A virus subtype H1N1 label extender
      probe
```

<400> SEQUENCE: 643
ggtattatca tttcagatac accagtcttt ttctgagtca aagcat        46

<210> SEQ ID NO 644
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 644
gtggtaccga gatatgcatt cgttttttgaa gttaccgttt t        41

<210> SEQ ID NO 645
<211> LENGTH: 42
<212> TYPE: DNA
<213> ORGANISM: Artificial Sequence
<220> FEATURE:
<223> OTHER INFORMATION: Influenza A virus subtype H1N1 label extender probe

<400> SEQUENCE: 645
cattcgaagc aactggaaat ctatttttct gagtcaaagc at 42

<210> SEQ ID NO 646
<211> LENGTH: 42
<212> TYPE: DNA
<213> ORGANISM: Artificial Sequence
<220> FEATURE:
<223> OTHER INFORMATION: Influenza A virus subtype H1N1 label extender probe

<400> SEQUENCE: 646
agtagagccg ggagacaaaa taatttttga agttaccgtt tt 42

<210> SEQ ID NO 647
<211> LENGTH: 45
<212> TYPE: DNA
<213> ORGANISM: Artificial Sequence
<220> FEATURE:
<223> OTHER INFORMATION: Influenza A virus subtype H1N1 label extender probe

<400> SEQUENCE: 647
gggagaatga actattactg gacacttttt tctgagtcaa agcat 45

<210> SEQ ID NO 648
<211> LENGTH: 44
<212> TYPE: DNA
<213> ORGANISM: Artificial Sequence
<220> FEATURE:
<223> OTHER INFORMATION: Influenza A virus subtype H1N1 label extender probe

<400> SEQUENCE: 648
aatgcagata catatgtttt tgtggttttt gaagttaccg tttt 44

<210> SEQ ID NO 649
<211> LENGTH: 44
<212> TYPE: DNA
<213> ORGANISM: Artificial Sequence
<220> FEATURE:
<223> OTHER INFORMATION: Influenza A virus subtype H1N1 label extender probe

```
<400> SEQUENCE: 649
tgctgaccaa caaagtctct atcagttttt ctgagtcaaa gcat 44

<210> SEQ ID NO 650
<211> LENGTH: 48
<212> TYPE: DNA
<213> ORGANISM: Artificial Sequence
<220> FEATURE:
<223> OTHER INFORMATION: Influenza A virus subtype H1N1 label extender probe
<400> SEQUENCE: 650
ttctacaaaa atttaatatg gctagttaat ttttgaagtt accgtttt 48

<210> SEQ ID NO 651
<211> LENGTH: 40
<212> TYPE: DNA
<213> ORGANISM: Artificial Sequence
<220> FEATURE:
<223> OTHER INFORMATION: Influenza A virus subtype H1N1 label extender probe
<400> SEQUENCE: 651
cctcatgctg gagcaaaaag ctttttctga gtcaaagcat 40

<210> SEQ ID NO 652
<211> LENGTH: 39
<212> TYPE: DNA
<213> ORGANISM: Artificial Sequence
<220> FEATURE:
<223> OTHER INFORMATION: Influenza A virus subtype H1N1 label extender probe
<400> SEQUENCE: 652
ggcccaatca tgactcgaac tttttgaagt taccgtttt 39

<210> SEQ ID NO 653
<211> LENGTH: 44
<212> TYPE: DNA
<213> ORGANISM: Artificial Sequence
<220> FEATURE:
<223> OTHER INFORMATION: Influenza A virus subtype H1N1 label extender probe
<400> SEQUENCE: 653
gagatattcc ccaagacaag ttcatttttt ctgagtcaaa gcat 44

<210> SEQ ID NO 654
<211> LENGTH: 43
<212> TYPE: DNA
<213> ORGANISM: Artificial Sequence
<220> FEATURE:
<223> OTHER INFORMATION: Influenza A virus subtype H1N1 label extender probe
<400> SEQUENCE: 654
tgaggagcta agagagcaat tgagtttttg aagttaccgt ttt 43

<210> SEQ ID NO 655
<211> LENGTH: 42
<212> TYPE: DNA
<213> ORGANISM: Artificial Sequence
<220> FEATURE:
<223> OTHER INFORMATION: Influenza A virus subtype H1N1 label extender probe

<400> SEQUENCE: 655
 tacccaggag atttcatcga ttattttct gagtcaaagc at         42

<210> SEQ ID NO 656
<211> LENGTH: 43
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 656
cctagttcag acaatggaac gtgttttttg aagttaccgt ttt        43

<210> SEQ ID NO 657
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 657
catggtccta cattgtggaa acatttttct gagtcaaagc at         42

<210> SEQ ID NO 658
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 658
tgaatcactc tccacagcaa gcttttttga agttaccgtt tt         42

<210> SEQ ID NO 659
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 659
ggatcctggg aaatccagag tgttttttctg agtcaaagca t         41

<210> SEQ ID NO 660
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 660
tggacttaca atgccgaact gttttttga agttaccgtt tt         42

<210> SEQ ID NO 661
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 661
tgatgatggt ttcctggaca ttttttttctg agtcaaagca t                    41

<210> SEQ ID NO 662
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 662
ggtaaagagt tcaaccacct ggattttttga agttaccgtt tt                   42

<210> SEQ ID NO 663
<211> LENGTH: 46
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 663
aagatgaata cacagttcac agcagtattt ttctgagtca aagcat                46

<210> SEQ ID NO 664
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 664
cacacagaat gccattgacg agtttttgaa gttaccgttt t                     41

<210> SEQ ID NO 665
<211> LENGTH: 40
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 665
atatgcagcc gacctgaaga gtttttctga gtcaaagcat                       40

<210> SEQ ID NO 666
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 666
tggatggtac ggttatcacc attttttgaa gttaccgttt t                     41

<210> SEQ ID NO 667
<211> LENGTH: 39
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 667
gggtggacag ggatggtaga ttttttctgag tcaaagcat                       39

<210> SEQ ID NO 668
<211> LENGTH: 37
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 668
aggcctattt ggggccattt tttgaagtta ccgtttt                              37

<210> SEQ ID NO 669
<211> LENGTH: 44
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 669
ggaatatccc gtctattcaa tctagttttt ctgagtcaaa gcat                      44

<210> SEQ ID NO 670
<211> LENGTH: 40
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 670
tgagactggc cacaggattg atttttgaag ttaccgtttt                           40

<210> SEQ ID NO 671
<211> LENGTH: 45
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 671
tccaaaatat gtaaaaagca caaaattttt tctgagtcaa agcat                     45

<210> SEQ ID NO 672
<211> LENGTH: 43
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 672
cacgattgca atacaacttg tcaatttttg aagttaccgt ttt                       43

<210> SEQ ID NO 673
<211> LENGTH: 46
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 673
ggtattatca tttcagatac accagtcttt ttctgagtca aagcat                    46

<210> SEQ ID NO 674
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 674
gtggtaccga gatatgcatt cgttttgaa gttaccgttt t                         41

<210> SEQ ID NO 675
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 675
cattcgaagc aactggaaat ctattttct gagtcaaagc at                        42

<210> SEQ ID NO 676
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 676
agtagagccg ggagacaaaa taatttttga agttaccgtt tt                       42

<210> SEQ ID NO 677
<211> LENGTH: 45
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 677
gggagaatga actattactg gacactttt tctgagtcaa agcat                     45

<210> SEQ ID NO 678
<211> LENGTH: 44
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 678
aatgcagata catatgtttt tgtggttttt gaagttaccg tttt                     44

<210> SEQ ID NO 679
<211> LENGTH: 44
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 679
tgctgaccaa caaagtctct atcagttttt ctgagtcaaa gcat                     44

```
<210> SEQ ID NO 680
<211> LENGTH: 48
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 680
ttctacaaaa atttaatatg gctagttaat ttttgaagtt accgtttt                48

<210> SEQ ID NO 681
<211> LENGTH: 40
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 681
cctcatgctg gagcaaaaag ctttttctga gtcaaagcat                         40

<210> SEQ ID NO 682
<211> LENGTH: 39
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 682
ggcccaatca tgactcgaac tttttgaagt

```
<211> LENGTH: 43
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 686
cctagttcag acaatggaac gtgttttttg aagttaccgt ttt                           43

<210> SEQ ID NO 687
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 687
catggtccta cattgtggaa acatttttct gagtcaaagc at                            42

<210> SEQ ID NO 688
<211> LENGTH: 42
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 688
tgaatcactc tccacagcaa gctttttga agttaccgtt tt                             42

<210> SEQ ID NO 689
<211> LENGTH: 41
<212> TYPE: DNA
<213> ORGANISM: Artificial Sequence
<220> FEATURE:
<223> OTHER INFORMATION: Influenza A virus subtype H1N1 label extender
      probe

<400> SEQUENCE: 689
ggatcctggg aaatccagag tgtttttctg agtcaaagca t                             41

<210> SEQ ID NO 690
<211> LENGTH: 30
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 690
aaaaagaata gagaatttaa ataaaaaagt                                          30

<210> SEQ ID NO 691
<211> LENGTH: 30
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 691
attactaaca aagtaaattc tgttattgaa                                          30

<210> SEQ ID NO 692
<211> LENGTH: 22
```

<212> TYPE: DNA
<213> ORGANISM: Artificial Sequence
<220> FEATURE:
<223> OTHER INFORMATION: Influenza A virus subtype H1N1 blocking label
extender probe

<400> SEQUENCE: 692
atccgatcac aattggaaaa tg 22

<210> SEQ ID NO 693
<211> LENGTH: 23
<212> TYPE: DNA
<213> ORGANISM: Artificial Sequence
<220> FEATURE:
<223> OTHER INFORMATION: Influenza A virus subtype H1N1 blocking label
extender probe

<400> SEQUENCE: 693
caatggaaag aaatgctgga tct 23

<210> SEQ ID NO 694
<211> LENGTH: 21
<212> TYPE: DNA
<213> ORGANISM: Artificial Sequence
<220> FEATURE:
<223> OTHER INFORMATION: Influenza A virus subtype H1N1 blocking label
extender probe

<400> SEQUENCE: 694
cccaaagtga gggatcaaga a 21

<210> SEQ ID NO 695
<211> LENGTH: 25
<212> TYPE: DNA
<213> ORGANISM: Artificial Sequence
<220> FEATURE:
<223> OTHER INFORMATION: Influenza A virus subtype H1N1 blocking label
extender probe

<400> SEQUENCE: 695
ggtcatcaag atacagcaag aagtt 25

<210> SEQ ID NO 696
<211> LENGTH: 24
<212> TYPE: DNA
<213> ORGANISM: Artificial Sequence
<220> FEATURE:
<223> OTHER INFORMATION: Influenza A virus subtype H1N1 blocking label
extender probe

<400> SEQUENCE: 696
gggcattcac catccatcta ctag 24

<210> SEQ ID NO 697
<211> LENGTH: 23
<212> TYPE: DNA
<213> ORGANISM: Artificial Sequence
<220> FEATURE:
<223> OTHER INFORMATION: Influenza A virus subtype H1N1 blocking label
extender probe

<400> SEQUENCE: 697
gggaaagaag tcctcgtgct atg 23

<210> SEQ ID NO 698
<211> LENGTH: 26
<212> TYPE: DNA

<213> ORGANISM: Artificial Sequence
<220> FEATURE:
<223> OTHER INFORMATION: Influenza A virus subtype H1N1 blocking label
      extender probe

<400> SEQUENCE: 698
tcagcaaatc ctacattaat gataaa                                       26

<210> SEQ ID NO 699
<211> LENGTH: 30
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 699
aaaaagaata gagaatttaa ataaaaaagt                                   30

<210> SEQ ID NO 700
<211> LENGTH: 30
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 700
attactaaca aagtaaattc tgttattgaa                                   30

<210> SEQ ID NO 701
<211> LENGTH: 22
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 701
atccgatcac aattggaaaa tg                                           22

<210> SEQ ID NO 702
<211> LENGTH: 23
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 702
caatggaaag aaatgctgga tct                                          23

<210> SEQ ID NO 703
<211> LENGTH: 21
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 703
cccaaagtga gggatcaaga a                                            21

<210> SEQ ID NO 704
<211> LENGTH: 25
<212> TYPE: DNA
<213> ORGANISM: Artificial Sequence -continued
<220> FEATURE:
<223> OTHER INFORMATION: Influenza A virus subtype H1N1 blocking label
      extender probe

<400> SEQUENCE: 704
ggtcatcaag atacagcaag aagtt 25

<210> SEQ ID NO 705
<211> LENGTH: 24
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 705
gggcattcac catccatcta ctag 24

<210> SEQ ID NO 706
<211> LENGTH: 23
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 706
gggaaagaag tcctcgtgct atg 23

<210> SEQ ID NO 707
<211> LENGTH: 26
<212> TYPE: DNA
<213> ORGANISM: Artificial Sequence
<220> FEATURE:
<223> OTHER INFORMATION: Influenza A virus subtype H1N1 blocking label
      extender probe

<400> SEQUENCE: 707
tcagcaaatc ctacattaat gataaa 26

<210> SEQ ID NO 708
<211> LENGTH: 51
<212> TYPE: DNA
<213> ORGANISM: Artificial Sequence
<220> FEATURE:
<223> OTHER INFORMATION: Hepatitis C virus capture extender probe

<400> SEQUENCE: 708
taacgccatg gctagacgct ttctgcgtga tttttctctt ggaaagaaag t 51

<210> SEQ ID NO 709
<211> LENGTH: 49
<212> TYPE: DNA
<213> ORGANISM: Artificial Sequence
<220> FEATURE:
<223> OTHER INFORMATION: Hepatitis C virus capture extender probe

<400> SEQUENCE: 709
gcgggttgat ccaagaaagg acccggtctt tttctcttgg aaagaaagt 49

<210> SEQ ID NO 710
<211> LENGTH: 47
<212> TYPE: DNA
<213> ORGANISM: Artificial Sequence
<220> FEATURE:
<223> OTHER INFORMATION: Hepatitis C virus capture extender probe -continued

<400> SEQUENCE: 710
ggcacgccca aatctccagg cattgatttt tctcttggaa agaaagt     47

<210> SEQ ID NO 711
<211> LENGTH: 43
<212> TYPE: DNA
<213> ORGANISM: Artificial Sequence
<220> FEATURE:
<223> OTHER INFORMATION: Hepatitis C virus capture extender probe

<400> SEQUENCE: 711
agacctcccg gggcactcgc aattttttctc ttggaaagaa agt     43

<210> SEQ ID NO 712
<211> LENGTH: 43
<212> TYPE: DNA
<213> ORGANISM: Artificial Sequence
<220> FEATURE:
<223> OTHER INFORMATION: Hepatitis C virus capture extender probe

<400> SEQUENCE: 712
cctaccctcg ggctggcgag ccttttttctc ttggaaagaa agt     43

<210> SEQ ID NO 713
<211> LENGTH: 47
<212> TYPE: DNA
<213> ORGANISM: Artificial Sequence
<220> FEATURE:
<223> OTHER INFORMATION: Hepatitis C virus capture extender probe

<400> SEQUENCE: 713
caccccaagc cctcattgcc atagagtttt tctcttggaa agaaagt     47

<210> SEQ ID NO 714
<211> LENGTH: 48
<212> TYPE: DNA
<213> ORGANISM: Artificial Sequence
<220> FEATURE:
<223> OTHER INFORMATION: Hepatitis C virus capture extender probe

<400> SEQUENCE: 714
cgagcggaat gtaccccatg agatcggttt ttctcttgga aagaaagt     48

<210> SEQ ID NO 715
<211> LENGTH: 55
<212> TYPE: DNA
<213> ORGANISM: Artificial Sequence
<220> FEATURE:
<223> OTHER INFORMATION: Hepatitis C virus label extender probe

<400> SEQUENCE: 715
ggtcctggag gctgcacgac actcatactt tttctgagtc aaagcatgaa gttac     55

<210> SEQ ID NO 716
<211> LENGTH: 51
<212> TYPE: DNA
<213> ORGANISM: Artificial Sequence
<220> FEATURE:
<223> OTHER INFORMATION: Hepatitis C virus label extender probe

<400> SEQUENCE: 716
ccgcagacca ctatggctct cccgtttttc tgagtcaaag catgaagtta c     51

<210> SEQ ID NO 717
<211> LENGTH: 54

```
<212> TYPE: DNA
<213> ORGANISM: Artificial Sequence
<220> FEATURE:
<223> OTHER INFORMATION: Hepatitis C virus label extender probe

<400> SEQUENCE: 717
gtcctggcaa ttccggtgta ctcaccgttt ttctgagtca aagcatgaag ttac        54

<210> SEQ ID NO 718
<211> LENGTH: 56
<212> TYPE: DNA
<213> ORGANISM: Artificial Sequence
<220> FEATURE:
<223> OTHER INFORMATION: Hepatitis C virus label extender probe

<400> SEQUENCE: 718
caacactact cggctagcag tctcgcgggt ttttctgagt caaagcatga agttac      56

<210> SEQ ID NO 719
<211> LENGTH: 56
<212> TYPE: DNA
<213> ORGANISM: Artificial Sequence
<220> FEATURE:
<223> OTHER INFORMATION: Hepatitis C virus label extender probe

<400> SEQUENCE: 719
caccctatca ggcagtacca caaggccttt ttttctgagt caaagcatga agttac      56

<210> SEQ ID NO 720
<211> LENGTH: 53
<212> TYPE: DNA
<213> ORGANISM: Artificial Sequence
<220> FEATURE:
<223> OTHER INFORMATION: Hepatitis C virus label extender probe

<400> SEQUENCE: 720
ttcgtgctca tggtgcacgg tctacgtttt tctgagtcaa agcatgaagt tac         53

<210> SEQ ID NO 721
<211> LENGTH: 59
<212> TYPE: DNA
<213> ORGANISM: Artificial Sequence
<220> FEATURE:
<223> OTHER INFORMATION: Hepatitis C virus label extender probe

<400> SEQUENCE: 721
ggtgttacgt ttggtttttc tttgaggttt agtttttctg agtcaaagca tgaagttac   59

<210> SEQ ID NO 722
<211> LENGTH: 55
<212> TYPE: DNA
<213> ORGANISM: Artificial Sequence
<220> FEATURE:
<223> OTHER INFORMATION: Hepatitis C virus label extender probe

<400> SEQUENCE: 722
cccctgcgcg gcaacaggta aactccactt tttctgagtc aaagcatgaa gttac       55

<210> SEQ ID NO 723
<211> LENGTH: 49
<212> TYPE: DNA
<213> ORGANISM: Artificial Sequence
<220> FEATURE:
<223> OTHER INFORMATION: Hepatitis C virus label extender probe

<400> SEQUENCE: 723
```

```
gtcgcgcgca cacccaacct ggtttttctg agtcaaagca tgaagttac         49
```

<210> SEQ ID NO 724
<211> LENGTH: 54
<212> TYPE: DNA
<213> ORGANISM: Artificial Sequence
<220> FEATURE:
<223> OTHER INFORMATION: Hepatitis C virus label extender probe

<400> SEQUENCE: 724

```
ttggggatag gttgtcgcct tccacgattt ttctgagtca aagcatgaag ttac    54
```

<210> SEQ ID NO 725
<211> LENGTH: 52
<212> TYPE: DNA
<213> ORGANISM: Artificial Sequence
<220> FEATURE:
<223> OTHER INFORMATION: Hepatitis C virus label extender probe

<400> SEQUENCE: 725

```
acggggtgac aggagccatc ctgccttttt ctgagtcaaa gcatgaagtt ac      52
```

<210> SEQ ID NO 726
<211> LENGTH: 52
<212> TYPE: DNA
<213> ORGANISM: Artificial Sequence
<220> FEATURE:
<223> OTHER INFORMATION: Hepatitis C virus label extender probe

<400> SEQUENCE: 726

```
ccaaattgcg cgacctacgc cggggttttt ctgagtcaaa gcatgaagtt ac      52
```

<210> SEQ ID NO 727
<211> LENGTH: 58
<212> TYPE: DNA
<213> ORGANISM: Artificial Sequence
<220> FEATURE:
<223> OTHER INFORMATION: Hepatitis C virus label extender probe

<400> SEQUENCE: 727

```
aagccgcacg tgagggtatc gatgacctta cttttctga gtcaaagcat gaagttac   58
```

<210> SEQ ID NO 728
<211> LENGTH: 23
<212> TYPE: DNA
<213> ORGANISM: Artificial Sequence
<220> FEATURE:
<223> OTHER INFORMATION: Hepatitis C virus blocking label extender probe

<400> SEQUENCE: 728

```
acttgacgtc ctgtgggcgg cgg                                     23
```

<210> SEQ ID NO 729
<211> LENGTH: 24
<212> TYPE: DNA
<213> ORGANISM: Artificial Sequence
<220> FEATURE:
<223> OTHER INFORMATION: Hepatitis C virus blocking label extender probe

<400> SEQUENCE: 729

```
cgacgatctg accaccgccc ggga                                    24
```

<210> SEQ ID NO 730
<211> LENGTH: 27
<212> TYPE: DNA
<213> ORGANISM: Artificial Sequence
<220> FEATURE:
<223> OTHER INFORMATION: Hepatitis C virus blocking label extender probe

<400> SEQUENCE: 730
ggttgcgacc gctcggaagt cttccta 27

<210> SEQ ID NO 731
<211> LENGTH: 24
<212> TYPE: DNA
<213> ORGANISM: Artificial Sequence
<220> FEATURE:
<223> OTHER INFORMATION: Hepatitis C virus blocking label extender probe

<400> SEQUENCE: 731
ccaggggtac ccgggctgag ccca 24

<210> SEQ ID NO 732
<211> LENGTH: 25
<212> TYPE: DNA
<213> ORGANISM: Artificial Sequence
<220> FEATURE:
<223> OTHER INFORMATION: Hepatitis C virus blocking label extender probe

<400> SEQUENCE: 732
tggggcccca actaggccga gagcc 25

<210> SEQ ID NO 733
<211> LENGTH: 48
<212> TYPE: DNA
<213> ORGANISM: Artificial Sequence
<220> FEATURE:
<223> OTHER INFORMATION: SARS coronavirus capture extender probe

<400> SEQUENCE: 733
ccagtaaact gattaactgg ttcttcattt ttctcttgga aagaaagt 48

<210> SEQ ID NO 734
<211> LENGTH: 47
<212> TYPE: DNA
<213> ORGANISM: Artificial Sequence
<220> FEATURE:
<223> OTHER INFORMATION: SARS coronavirus capture extender probe

<400> SEQUENCE: 734
gtgtatgtta gcagcattta caatcatttt tctcttggaa agaaagt 47

<210> SEQ ID NO 735
<211> LENGTH: 41
<212> TYPE: DNA
<213> ORGANISM: Artificial Sequence
<220> FEATURE:
<223> OTHER INFORMATION: SARS coronavirus capture extender probe

<400> SEQUENCE: 735
ccttttgcat ggcaccattg tttttctctt ggaaagaaag t 41

<210> SEQ ID NO 736
<211> LENGTH: 45
<212> TYPE: DNA
<213> ORGANISM: Artificial Sequence
<220> FEATURE:
<223> OTHER INFORMATION: SARS coronavirus capture extender probe

<400> SEQUENCE: 736
gcaagattat gtccagaaag caaatttttc tcttggaaag aaagt 45

-continued

<210> SEQ ID NO 737
<211> LENGTH: 43
<212> TYPE: DNA
<213> ORGANISM: Artificial Sequence
<220> FEATURE:
<223> OTHER INFORMATION: SARS coronavirus capture extender probe

<400> SEQUENCE: 737
gctgccttaa gaagctggat gttttttctc ttggaaagaa agt       43

<210> SEQ ID NO 738
<211> LENGTH: 43
<212> TYPE: DNA
<213> ORGANISM: Artificial Sequence
<220> FEATURE:
<223> OTHER INFORMATION: SARS coronavirus capture extender probe

<400> SEQUENCE: 738
ggtttagcac caaatatgcc tgttttctc ttggaaagaa agt        43

<210> SEQ ID NO 739
<211> LENGTH: 46
<212> TYPE: DNA
<213> ORGANISM: Artificial Sequence
<220> FEATURE:
<223> OTHER INFORMATION: SARS coronavirus label extender probe

<400> SEQUENCE: 739
caatctctga ttgctcagta gtatcatttt ttgaagttac cgtttt    46

<210> SEQ ID NO 740
<211> LENGTH: 41
<212> TYPE: DNA
<213> ORGANISM: Artificial Sequence
<220> FEATURE:
<223> OTHER INFORMATION: SARS coronavirus label extender probe

<400> SEQUENCE: 740
ggtgtaggtt ctggttctgg cttttttctg agtcaaagca t         41

<210> SEQ ID NO 741
<211> LENGTH: 47
<212> TYPE: DNA
<213> ORGANISM: Artificial Sequence
<220> FEATURE:
<223> OTHER INFORMATION: SARS coronavirus label extender probe

<400> SEQUENCE: 741
ggcaacattg tcagtaagtt ttaaataatt tttgaagtta ccgtttt   47

<210> SEQ ID NO 742
<211> LENGTH: 45
<212> TYPE: DNA
<213> ORGANISM: Artificial Sequence
<220> FEATURE:
<223> OTHER INFORMATION: SARS coronavirus label extender probe

<400> SEQUENCE: 742
tccttaacga tgtcaacaca tttaatttt tctgagtcaa agcat      45

<210> SEQ ID NO 743
<211> LENGTH: 42
<212> TYPE: DNA
<213> ORGANISM: Artificial Sequence
<220> FEATURE:
<223> OTHER INFORMATION: SARS coronavirus label extender probe -continued

<400> SEQUENCE: 743
gctacaccac caccatgttt cagtttttga agttaccgtt tt                42

<210> SEQ ID NO 744
<211> LENGTH: 40
<212> TYPE: DNA
<213> ORGANISM: Artificial Sequence
<220> FEATURE:
<223> OTHER INFORMATION: SARS coronavirus label extender probe

<400> SEQUENCE: 744
gttgccttgt tgagtgcacc tttttctga gtcaaagcat                    40

<210> SEQ ID NO 745
<211> LENGTH: 47
<212> TYPE: DNA
<213> ORGANISM: Artificial Sequence
<220> FEATURE:
<223> OTHER INFORMATION: SARS coronavirus label extender probe

<400> SEQUENCE: 745
ccatttagct taatgtaatc atcactcttt tttgaagtta ccgtttt           47

<210> SEQ ID NO 746
<211> LENGTH: 43
<212> TYPE: DNA
<213> ORGANISM: Artificial Sequence
<220> FEATURE:
<223> OTHER INFORMATION: SARS coronavirus label extender probe

<400> SEQUENCE: 746
caagaccctc ctactgtaag agggtttttc tgagtcaaag cat               43

<210> SEQ ID NO 747
<211> LENGTH: 43
<212> TYPE: DNA
<213> ORGANISM: Artificial Sequence
<220> FEATURE:
<223> OTHER INFORMATION: SARS coronavirus label extender probe

<400> SEQUENCE: 747
ccaacaacat gcagacactt cttattttg aagttaccgt ttt                43

<210> SEQ ID NO 748
<211> LENGTH: 42
<212> TYPE: DNA
<213> ORGANISM: Artificial Sequence
<220> FEATURE:
<223> OTHER INFORMATION: SARS coronavirus label extender probe

<400> SEQUENCE: 748
cctcacctgc atttaggtta ggttttttct gagtcaaagc at                42

<210> SEQ ID NO 749
<211> LENGTH: 45
<212> TYPE: DNA
<213> ORGANISM: Artificial Sequence
<220> FEATURE:
<223> OTHER INFORMATION: SARS coronavirus label extender probe

<400> SEQUENCE: 749
tgtcctgtga attgaaattt tcatattttt tgaagttacc gtttt             45

<210> SEQ ID NO 750

<211> LENGTH: 43
<212> TYPE: DNA
<213> ORGANISM: Artificial Sequence
<220> FEATURE:
<223> OTHER INFORMATION: SARS coronavirus label extender probe

<400> SEQUENCE: 750
ctgacaacaa tggtgcaagt aagattttc tgagtcaaag cat    43

<210> S

```
<220> FEATURE:
<223> OTHER INFORMATION: Mycobacterium tuberculosis capture extender
      probe

<400> SEQUENCE: 756
tcgcccgcac gctcactttt tctcttggaa agaaagt                              37

<210> SEQ ID NO 757
<211> LENGTH: 37
<212> TYPE: DNA
<213> ORGANISM: Artificial Sequence
<220> FEATURE:
<223> OTHER INFORMATION: Mycobacterium tuberculosis label extender
      probe

<400> SEQUENCE: 757
cgccttggta ggccgtcatt tttgaagtta ccgtttt                              37

<210> SEQ ID NO 758
<211> LENGTH: 36
<212> TYPE: DNA
<213> ORGANISM: Artificial Sequence
<220> FEATURE:
<223> OTHER INFORMATION: Mycobacterium tuberculosis label extender probe

<400> SEQUENCE: 758
ggccggctac ccgtcgtttt ttctgagtca aagcat                               36

<210> SEQ ID NO 759
<211> LENGTH: 40
<212> TYPE: DNA
<213> ORGANISM: Artificial Sequence
<220> FEATURE:
<223> OTHER INFORMATION: Mycobacterium tuberculosis label extender probe

<400> SEQUENCE: 759
ggccgtatct cagtcccagt gtttttgaag ttaccgtttt                           40

<210> SEQ ID NO 760
<211> LENGTH: 40
<212> TYPE: DNA
<213> ORGANISM: Artificial Sequence
<220> FEATURE:
<223> OTHER INFORMATION: Mycobacterium tuberculosis label extender probe

<400> SEQUENCE: 760
gctgcctccc gtaggagtct gtttttctga gtcaaagcat                           40

<210> SEQ ID NO 761
<211> LENGTH: 41
<212> TYPE: DNA
<213> ORGANISM: Artificial Sequence
<220> FEATURE:
<223> OTHER INFORMATION: Mycobacterium tuberculosis label extender probe

<400> SEQUENCE: 761
ccattgtgca atattcccca cttttttgaa gttaccgttt t                         41

<210> SEQ ID NO 762
<211> LENGTH: 37
<212> TYPE: DNA
<213> ORGANISM: Artificial Sequence
<220> FEATURE:
<223> OTHER INFORMATION: Mycobacterium tuberculosis label extender probe

<400> SEQUENCE: 762
```

```
gctgcatcag gcttgcgctt tttctgagtc aaagcat                                37
```

<210> SEQ ID NO 763
<211> LENGTH: 35
<212> TYPE: DNA
<213> ORGANISM: Artificial Sequence
<220> FEATURE:
<223> OTHER INFORMATION: Mycobacterium tuberculosis label extender probe

<400> SEQUENCE: 763

```
tcccccacgc ggcgtctttt tgaagttacc gtttt                                  35
```

<210> SEQ ID NO 764
<211> LENGTH: 38
<212> TYPE: DNA
<213> ORGANISM: Artificial Sequence
<220> FEATURE:
<223> OTHER INFORMATION: Mycobacterium tuberculosis label extender probe

<400> SEQUENCE: 764

```
tacaacccga aggccgtcat ttttctgagt caaagcat                               38
```

<210> SEQ ID NO 765
<211> LENGTH: 41
<212> TYPE: DNA
<213> ORGANISM: Artificial Sequence
<220> FEATURE:
<223> OTHER INFORMATION: Mycobacterium tuberculosis label extender probe

<400> SEQUENCE: 765

```
tgcttcttct ccacctaccg tcttttttgaa gttaccgttt t                          41
```

<210> SEQ ID NO 766
<211> LENGTH: 37
<212> TYPE: DNA
<213> ORGANISM: Artificial Sequence
<220> FEATURE:
<223> OTHER INFORMATION: Mycobacterium tuberculosis label extender probe

<400> SEQUENCE: 766

```
tggcacgtag ttggccggtt tttctgagtc aaagcat                               37
```

<210> SEQ ID NO 767
<211> LENGTH: 39
<212> TYPE: DNA
<213> ORGANISM: Artificial Sequence
<220> FEATURE:
<223> OTHER INFORMATION: Mycobacterium tuberculosis label extender probe

<400> SEQUENCE: 767

```
ctacgtatta ccgcggctgc tttttgaagt taccgtttt                              39
```

<210> SEQ ID NO 768
<211> LENGTH: 37
<212> TYPE: DNA
<213> ORGANISM: Artificial Sequence
<220> FEATURE:
<223> OTHER INFORMATION: Mycobacterium tuberculosis label extender probe

<400> SEQUENCE: 768

```
ccggacaacg ctcgcacctt tttctgagtc aaagcat                               37
```

<210> SEQ ID NO 769
<211> LENGTH: 42
<212> TYPE: DNA
<213> ORGANISM: Artificial Sequence

```
<220> FEATURE:
<223> OTHER INFORMATION: Mycobacterium tuberculosis label extender probe

<400> SEQUENCE: 769
cgagctcttt acgcccagta atttttttga agttaccgtt tt                          42

<210> SEQ ID NO 770
<211> LENGTH: 40
<212> TYPE: DNA
<213> ORGANISM: Artificial Sequence
<220> FEATURE:
<223> OTHER INFORMATION: Mycobacterium tuberculosis label extender probe

<400> SEQUENCE: 770
aacaacgcga caaaccacct atttttctga gtcaaagcat                             40

<210> SEQ ID NO 771
<211> LENGTH: 21
<212> TYPE: DNA
<213> ORGANISM: Artificial Sequence
<220> FEATURE:
<223> OTHER INFORMATION: Mycobacterium tuberculosis blocking label
      extender probe

<400> SEQUENCE: 771
ccccaccaac aagctgatag g                                                 21

<210> SEQ ID NO 772
<211> LENGTH: 22
<212> TYPE: DNA
<213> ORGANISM: Artificial Sequence
<220> FEATURE:
<223> OTHER INFORMATION: Mycobacterium tuberculosis blocking label
      extender probe

<400> SEQUENCE: 772
ttcgtcgatg gtgaaagagg tt                                                22

<210> SEQ ID NO 773
<211> LENGTH: 20
<212> TYPE: DNA
<213> ORGANISM: Artificial Sequence
<220> FEATURE:
<223> OTHER INFORMATION: Mycobacterium tuberculosis blocking label
      extender probe

<400> SEQUENCE: 773
aatccgagag aacccggacc                                                   20

<210> SEQ ID NO 774
<211> LENGTH: 40
<212> TYPE: DNA
<213> ORGANISM: Artificial Sequence
<220> FEATURE:
<223> OTHER INFORMATION: Treponema pallidum capture extender probe

<400> SEQUENCE: 774
ccccttacgt gttaccgcgt ttttctcttg gaaagaaagt                             40

<210> SEQ ID NO 775
<211> LENGTH: 40
<212> TYPE: DNA
<213> ORGANISM: Artificial Sequence
<220> FEATURE:
<223> OTHER INFORMATION: Treponema pallidum capture extender probe

<400> SEQUENCE: 775
```

```
ccaggcttac cagtccgcct ttttctcttg gaaagaaagt                              40
```

<210> SEQ ID NO 776
<211> LENGTH: 43
<212> TYPE: DNA
<213> ORGANISM: Artificial Sequence
<220> FEATURE:
<223> OTHER INFORMATION: Treponema pallidum capture extender probe

<400> SEQUENCE: 776

```
cctccgtgat tctagaccag cattttctc ttggaaagaa agt                           43
```

<210> SEQ ID NO 777
<211> LENGTH: 40
<212> TYPE: DNA
<213> ORGANISM: Artificial Sequence
<220> FEATURE:
<223> OTHER INFORMATION: Treponema pallidum capture extender probe

<400> SEQUENCE: 777

```
ttcgccaccg gtgttcttct ttttctcttg gaaagaaagt                              40
```

<210> SEQ ID NO 778
<211> LENGTH: 41
<212> TYPE: DNA
<213> ORGANISM: Artificial Sequence
<220> FEATURE:
<223> OTHER INFORMATION: Treponema pallidum capture extender probe

<400> SEQUENCE: 778

```
cgcacctcag cgtcaatcat tttttctctt ggaaagaaag t                            41
```

<210> SEQ ID NO 779
<211> LENGTH: 38
<212> TYPE: DNA
<213> ORGANISM: Artificial Sequence
<220> FEATURE:
<223> OTHER INFORMATION: Treponema pallidum capture extender probe

<400> SEQUENCE: 779

```
taatgcgttc gcgtcggttt ttctcttgga aagaaagt                                38
```

<210> SEQ ID NO 780
<211> LENGTH: 38
<212> TYPE: DNA
<213> ORGANISM: Artificial Sequence
<220> FEATURE:
<223> OTHER INFORMATION: Treponema pallidum label extender probe

<400> SEQUENCE: 780

```
ggggcttatt cgcacgactt ttttgaagtt accgtttt                                38
```

<210> SEQ ID NO 781
<211> LENGTH: 40
<212> TYPE: DNA
<213> ORGANISM: Artificial Sequence
<220> FEATURE:
<223> OTHER INFORMATION: Treponema pallidum label extender probe

<400> SEQUENCE: 781

```
gctgctggca cgtaattagc ctttttctga gtcaaagcat                              40
```

<210> SEQ ID NO 782
<211> LENGTH: 40
<212> TYPE: DNA

<213> ORGANISM: Artificial Sequence
<220> FEATURE:
<223> OTHER INFORMATION: Treponema pallidum label extender probe

<400> SEQUENCE: 782
aataattccg aacaacgctc gtttttgaag ttaccgtttt                                40

<210> SEQ ID NO 783
<211> LENGTH: 37
<212> TYPE: DNA
<213> ORGANISM: Artificial Sequence
<220> FEATURE:
<223> OTHER INFORMATION: Treponema pallidum label extender probe

<400> SEQUENCE: 783
tgcatgccct ttacgccctt tttctgagtc aaagcat                                 37

<210> SEQ ID NO 784
<211> LENGTH: 39
<212> TYPE: DNA
<213> ORGANISM: Artificial Sequence
<220> FEATURE:
<223> OTHER INFORMATION: Treponema pallidum label extender probe

<400> SEQUENCE: 784
ttgagctcgg ggatttcaca tttttgaagt taccgtttt                               39

<210> SEQ ID NO 785
<211> LENGTH: 40
<212> TYPE: DNA
<213> ORGANISM: Artificial Sequence
<220> FEATURE:
<223> OTHER INFORMATION: Treponema pallidum label extender probe

<400> SEQUENCE: 785
gtacccagtg cagttcccaa gtttttctga gtcaaagcat                              40

<210> SEQ ID NO 786
<211> LENGTH: 39
<212> TYPE: DNA
<213> ORGANISM: Artificial Sequence
<220> FEATURE:
<223> OTHER INFORMATION: Treponema pallidum label extender probe

<400> SEQUENCE: 786
cacttggaat tccggtttcc tttttgaagt taccgtttt                               39

<210> SEQ ID NO 787
<211> LENGTH: 44
<212> TYPE: DNA
<213> ORGANISM: Artificial Sequence
<220> FEATURE:
<223> OTHER INFORMATION: Treponema pallidum label extender probe

<400> SEQUENCE: 787
caaatatcta cagattccac ccctattttt ctgagtcaaa gcat                         44

<210> SEQ ID NO 788
<211> LENGTH: 38
<212> TYPE: DNA
<213> ORGANISM: Artificial Sequence
<220> FEATURE:
<223> OTHER INFORMATION: Treponema pallidum label extender probe

<400> SEQUENCE: 788
tgttcgctcc ccacaccttt ttttgaagtt accgtttt                                38

<210> SEQ ID NO 789
<211> LENGTH: 44
<212> TYPE: DNA
<213> ORGANISM: Artificial Sequence
<220> FEATURE:
<223> OTHER INFORMATION: Treponema pallidum label extender probe

<400> SEQUENCE: 789
tgtggactac cagggtatct aatccttttt ctgagtcaaa gcat            44

<210> SEQ ID NO 790
<211> LENGTH: 45
<212> TYPE: DNA
<213> ORGANISM: Artificial Sequence
<220> FEATURE:
<223> OTHER INFORMATION: Treponema pallidum label extender probe

<400> SEQUENCE: 790
caacacctag tgtacatcgt ttactgtttt tgaagttacc gtttt           45

<210> SEQ ID NO 791
<211> LENGTH: 36
<212> TYPE: DNA
<213> ORGANISM: Artificial Sequence
<220> FEATURE:
<223> OTHER INFORMATION: Treponema pallidum label extender probe

<400> SEQUENCE: 791
cgccgagact catgcccttt ttctgagtca aagcat                     36

<210> SEQ ID NO 792
<211> LENGTH: 16
<212> TYPE: DNA
<213> ORGANISM: Artificial Sequence
<220> FEATURE:
<223> OTHER INFORMATION: Treponema pallidum blocking label extender
      probe

<400> SEQUENCE: 792
cggccagaaa cccgcc                                           16

<210> SEQ ID NO 793
<211> LENGTH: 38
<212> TYPE: DNA
<213> ORGANISM: Artificial Sequence
<220> FEATURE:
<223> OTHER INFORMATION: Aspergillus fumigatus capture extender probe

<400> SEQUENCE: 793
actcgcggtg aggcggattt ttctcttgga aagaaagt                   38

<210> SEQ ID NO 794
<211> LENGTH: 40
<212> TYPE: DNA
<213> ORGANISM: Artificial Sequence
<220> FEATURE:
<223> OTHER INFORMATION: Aspergillus fumigatus capture extender probe

<400> SEQUENCE: 794
aaggtccagc cggaccagtt ttttctcttg gaaagaaagt                 40

<210> SEQ ID NO 795
<211> LENGTH: 41
<212> TYPE: DNA
<213> ORGANISM: Artificial Sequence
<220> FEATURE:
<223> OTHER INFORMATION: Aspergillus fumigatus capture extender probe

<400> SEQUENCE: 795
catgaggttc cccagaagga tttttctctt ggaaagaaag t        41

<210> SEQ ID NO 796
<211> LENGTH: 41
<212> TYPE: DNA
<213> ORGANISM: Artificial Sequence
<220> FEATURE:
<223> OTHER INFORMATION: Aspergillus fumigatus capture extender probe

<400> SEQUENCE: 796
cagctgaata ctgacgcccc tttttctctt ggaaagaaag t        41

<210> SEQ ID NO 797
<211> LENGTH: 41
<212> TYPE: DNA
<213> ORGANISM: Artificial Sequence
<220> FEATURE:
<223> OTHER INFORMATION: Aspergillus fumigatus capture extender probe

<400> SEQUENCE: 797
gaaaacatcc ttggcgaatg tttttctctt ggaaagaaag t        41

<210> SEQ ID NO 798
<211> LENGTH: 42
<212> TYPE: DNA
<213> ORGANISM: Artificial Sequence
<220> FEATURE:
<223> OTHER INFORMATION: Aspergillus fumigatus capture extender probe

<400> SEQUENCE: 798
cgagcgggtc atcatagaaa cttttctct tggaaagaaa gt        42

<210> SEQ ID NO 799
<211> LENGTH: 45
<212> TYPE: DNA
<213> ORGANISM: Artificial Sequence
<220> FEATURE:
<223> OTHER INFORMATION: Aspergillus fumigatus label extender probe

<400> SEQUENCE: 799
aggttcaact acgagctttt taactgtttt tgaagttacc gtttt        45

<210> SEQ ID NO 800
<211> LENGTH: 36
<212> TYPE: DNA
<213> ORGANISM: Artificial Sequence
<220> FEATURE:
<223> OTHER INFORMATION: Aspergillus fumigatus label extender probe

<400> SEQUENCE: 800
ccggccagcc agacccattt ttctgagtca aagcat        36

<210> SEQ ID NO 801
<211> LENGTH: 43
<212> TYPE: DNA
<213> ORGANISM: Artificial Sequence
<220> FEATURE:
<223> OTHER INFORMATION: Aspergillus fumigatus label extender probe

<400> SEQUENCE: 801
gcctgctttg aacactctaa ttttttttg aagttaccgt ttt        43

<210> SEQ ID NO 802
<211> LENGTH: 42
<212> TYPE: DNA
<213> ORGANISM: Artificial Sequence
<220> FEATURE:
<223> OTHER INFORMATION: Aspergillus fumigatus label extender probe

<400> SEQUENCE: 802
catgctaatg tattcgagca aagtttttct gagtcaaagc at                    42

<210> SEQ ID NO 803
<211> LENGTH: 44
<212> TYPE: DNA
<213> ORGANISM: Artificial Sequence
<220> FEATURE:
<223> OTHER INFORMATION: Aspergillus fumigatus label extender probe

<400> SEQUENCE: 803
cggtcctaga aaccaacaaa atagattttt gaagttaccg tttt                  44

<210> SEQ ID NO 804
<211> LENGTH: 44
<212> TYPE: DNA
<213> ORGANISM: Artificial Sequence
<220> FEATURE:
<223> OTHER INFORMATION: Aspergillus fumigatus label extender probe

<400> SEQUENCE: 804
cgactatccc tattaatcat tacggttttt ctgagtcaaa gcat                  44

<210> SEQ ID NO 805
<211> LENGTH: 42
<212> TYPE: DNA
<213> ORGANISM: Artificial Sequence
<220> FEATURE:
<223> OTHER INFORMATION: Aspergillus fumigatus label extender probe

<400> SEQUENCE: 805
aaatccaaga atttcacctc tgattttga agttaccgtt tt                     42

<210> SEQ ID NO 806
<211> LENGTH: 43
<212> TYPE: DNA
<213> ORGANISM: Artificial Sequence
<220> FEATURE:
<223> OTHER INFORMATION: Aspergillus fumigatus label extender probe

<400> SEQUENCE: 806
ctttcgcagt agttagtctt cagctttttc tgagtcaaag cat                   43

<210> SEQ ID NO 807
<211> LENGTH: 43
<212> TYPE: DNA
<213> ORGANISM: Artificial Sequence
<220> FEATURE:
<223> OTHER INFORMATION: Aspergillus fumigatus label extender probe

<400> SEQUENCE: 807
cctaactttc gttccctgat taatttttg aagttaccgt ttt                    43

<210> SEQ ID NO 808
<211> LENGTH: 42
<212> TYPE: DNA
<213> ORGANISM: Artificial Sequence
<220> FEATURE:
<223> OTHER INFORMATION: Aspergillus fumigatus label extender probe

<400> SEQUENCE: 808
cggtatctga tcgtcttcga tccttttct gagtcaaagc at                    42

<210> SEQ ID NO 809
<211> LENGTH: 45
<212> TYPE: DNA
<213> ORGANISM: Artificial Sequence
<220> FEATURE:
<223> OTHER INFORMATION: Aspergillus fumigatus label extender probe

<400> SEQUENCE: 809
ggcatagttt atggttaaga ctacgatttt tgaagttacc gtttt               45

<210> SEQ ID NO 810
<211> LENGTH: 37
<212> TYPE: DNA
<213> ORGANISM: Artificial Sequence
<220> FEATURE:
<223> OTHER INFORMATION: Aspergillus fumigatus label extender probe

<400> SEQUENCE: 810
accgcccgat ccctagtctt tttctgagtc aaagcat                        37

<210> SEQ ID NO 811
<211> LENGTH: 19
<212> TYPE: DNA
<213> ORGANISM: Artificial Sequence
<220> FEATURE:
<223> OTHER INFORMATION: Aspergillus fumigatus blocking label extender
      probe

<400> SEQUENCE: 811
ccccacagcc agtgaaggc                                            19

<210> SEQ ID NO 812
<211> LENGTH: 23
<212> TYPE: DNA
<213> ORGANISM: Artificial Sequence
<220> FEATURE:
<223> OTHER INFORMATION: Aspergillus fumigatus blocking label extender
      probe

<400> SEQUENCE: 812
ttcacagtaa aagtcctggt tcc                                       23

<210> SEQ ID NO 813
<211> LENGTH: 24
<212> TYPE: DNA
<213> ORGANISM: Artificial Sequence
<220> FEATURE:
<223> OTHER INFORMATION: Aspergillus fumigatus blocking label extender
      probe

<400> SEQUENCE: 813
accgcacgtc ctattctatt attc                                      24

<210> SEQ ID NO 814
<211> LENGTH: 40
<212> TYPE: DNA
<213> ORGANISM: Artificial Sequence
<220> FEATURE:
<223> OTHER INFORMATION: Candida albicans capture extender probe

<400> SEQUENCE: 814
aaaaagatgg accggccagt ttttctcttg gaaagaaagt                     40

<210> SEQ ID NO 815
<211> LENGTH: 40
<212> TYPE: DNA
<213> ORGANISM: Artificial Sequence
<220> FEATURE:
<223> OTHER INFORMATION: Candida albicans capture extender probe

<400> SEQUENCE: 815
acccagaagg aaaggctcgt ttttctcttg gaaagaaagt                                40

<210> SEQ ID NO 816
<211> LENGTH: 40
<212> TYPE: DNA
<213> ORGANISM: Artificial Sequence
<220> FEATURE:
<223> OTHER INFORMATION: Candida albicans capture extender probe

<400> SEQUENCE: 816
tggttcgcca taaatggctt ttttctcttg gaaagaaagt                                40

<210> SEQ ID NO 817
<211> LENGTH: 40
<212> TYPE: DNA
<213> ORGANISM: Artificial Sequence
<220> FEATURE:
<223> OTHER INFORMATION: Candida albicans capture extender probe

<400> SEQUENCE: 817
actgataccc ccgaccgtct ttttctcttg gaaagaaagt                                40

<210> SEQ ID NO 818
<211> LENGTH: 44
<212> TYPE: DNA
<213> ORGANISM: Artificial Sequence
<220> FEATURE:
<223> OTHER INFORMATION: Candida albicans capture extender probe

<400> SEQUENCE: 818
aaacgtcctt ggtaaatgct ttcttttttct cttggaaaga aagt                          44

<210> SEQ ID NO 819
<211> LENGTH: 42
<212> TYPE: DNA
<213> ORGANISM: Artificial Sequence
<220> FEATURE:
<223> OTHER INFORMATION: Candida albicans capture extender probe

<400> SEQUENCE: 819
gtgccgattg cgtcaataaa atttttctct tggaaagaaa gt                             42

<210> SEQ ID NO 820
<211> LENGTH: 47
<212> TYPE: DNA
<213> ORGANISM: Artificial Sequence
<220> FEATURE:
<223> OTHER INFORMATION: Candida albicans label extender probe

<400> SEQUENCE: 820
gagcttttta actgcaacaa ctttaatatt tttgaagtta ccgtttt                        47

<210> SEQ ID NO 821
<211> LENGTH: 40
<212> TYPE: DNA
<213> ORGANISM: Artificial Sequence
<220> FEATURE:

<223> OTHER INFORMATION: Candida albicans label extender probe

<400> SEQUENCE: 821
ccaagcccaa ggttcaacta cttttctga gtcaaagcat                    40

<210> SEQ ID NO 822
<211> LENGTH: 39
<212> TYPE: DNA
<213> ORGANISM: Artificial Sequence
<220> FEATURE:
<223> OTHER INFORMATION: Candida albicans label extender probe

<400> SEQUENCE: 822
gagcaaaggc ctgctttgaa tttttgaagt taccgtttt                    39

<210> SEQ ID NO 823
<211> LENGTH: 49
<212> TYPE: DNA
<213> ORGANISM: Artificial Sequence
<220> FEATURE:
<223> OTHER INFORMATION: Candida albicans label extender probe

<400> SEQUENCE: 823
cctattctat tattccatgc taatatattc tttttctgag tcaaagcat          49

<210> SEQ ID NO 824
<211> LENGTH: 44
<212> TYPE: DNA
<213> ORGANISM: Artificial Sequence
<220> FEATURE:
<223> OTHER INFORMATION: Candida albicans label extender probe

<400> SEQUENCE: 824
aaccaacaaa atagaaccat aacgtttttt gaagttaccg tttt              44

<210> SEQ ID NO 825
<211> LENGTH: 46
<212> TYPE: DNA
<213> ORGANISM: Artificial Sequence
<220> FEATURE:
<223> OTHER INFORMATION: Candida albicans label extender probe

<400> SEQUENCE: 825
cctattaatc attacgatgg tcctagattt ttctgagtca aagcat            46

<210> SEQ ID NO 826
<211> LENGTH: 44
<212> TYPE: DNA
<213> ORGANISM: Artificial Sequence
<220> FEATURE:
<223> OTHER INFORMATION: Candida albicans label extender probe

<400> SEQUENCE: 826
agaatttcac ctctgacaac tgaatttttt gaagttaccg tttt              44

<210> SEQ ID NO 827
<211> LENGTH: 45
<212> TYPE: DNA
<213> ORGANISM: Artificial Sequence
<220> FEATURE:
<223> OTHER INFORMATION: Candida albicans label extender probe

<400> SEQUENCE: 827
gcagtagtta gtcttcagta aatccatttt tctgagtcaa agcat             45

```
<210> SEQ ID NO 828
<211> LENGTH: 44
<212> TYPE: DNA
<213> ORGANISM: Artificial Sequence
<220> FEATURE:
<223> OTHER INFORMATION: Candida albicans label extender probe

<400> SEQUENCE: 828
cctaactttc gttcttgatt aatgattttt gaagttaccg tttt            44

<210> SEQ ID NO 829
<211> LENGTH: 42
<212> TYPE: DNA
<213> ORGANISM: Artificial Sequence
<220> FEATURE:
<223> OTHER INFORMATION: Candida albicans label extender probe

<400> SEQUENCE: 829
cggtatctga tcatcttcga tccttttct gagtcaaagc at               42

<210> SEQ ID NO 830
<211> LENGTH: 45
<212> TYPE: DNA
<213> ORGANISM: Artificial Sequence
<220> FEATURE:
<223> OTHER INFORMATION: Candida albicans label extender probe

<400> SEQUENCE: 830
ggcatagttt atggttaaga ctacgatttt tgaagttacc gtttt           45

<210> SEQ ID NO 831
<211> LENGTH: 41
<212> TYPE: DNA
<213> ORGANISM: Artificial Sequence
<220> FEATURE:
<223> OTHER INFORMATION: Candida albicans label extender probe

<400> SEQUENCE: 831
gaacaacaac cgatccctag tctttttctg agtcaaagca t               41

<210> SEQ ID NO 832
<211> LENGTH: 19
<212> TYPE: DNA
<213> ORGANISM: Artificial Sequence
<220> FEATURE:
<223> OTHER INFORMATION: Candida albicans blocking label extender probe

<400> SEQUENCE: 832
gctgggtcca gtacgcatc                                        19

<210> SEQ ID NO 833
<211> LENGTH: 28
<212> TYPE: DNA
<213> ORGANISM: Artificial Sequence
<220> FEATURE:
<223> OTHER INFORMATION: Candida albicans blocking label extender probe

<400> SEQUENCE: 833
cactctaatt ttttcaaagt aaaagtcc                              28

<210> SEQ ID NO 834
<211> LENGTH: 41
<212> TYPE: DNA
<213> ORGANISM: Artificial Sequence
<220> FEATURE:
<223> OTHER INFORMATION: Crytococcus neoformans capture extender probe
```

<400> SEQUENCE: 834
gcctcgccag acctgaagtt tttttctctt ggaaagaaag t                   41

<210> SEQ ID NO 835
<211> LENGTH: 40
<212> TYPE: DNA
<213> ORGANISM: Artificial Sequence
<220> FEATURE:
<223> OTHER INFORMATION: Crytococcus neoformans capture extender probe

<400> SEQUENCE: 835
gcactccgtg aggaggacct ttttctcttg gaaagaaagt                     40

<210> SEQ ID NO 836
<211> LENGTH: 40
<212> TYPE: DNA
<213> ORGANISM: Artificial Sequence
<220> FEATURE:
<223> OTHER INFORMATION: Crytococcus neoformans capture extender probe

<400> SEQUENCE: 836
ggttcccctg cacacccagt ttttctcttg gaaagaaagt                     40

<210> SEQ ID NO 837
<211> LENGTH: 42
<212> TYPE: DNA
<213> ORGANISM: Artificial Sequence
<220> FEATURE:
<223> OTHER INFORMATION: Crytococcus neoformans capture extender probe

<400> SEQUENCE: 837
gcgattgcct gctttgaaca cttttctct tggaaagaaa gt                   42

<210> SEQ ID NO 838
<211> LENGTH: 45
<212> TYPE: DNA
<213> ORGANISM: Artificial Sequence
<220> FEATURE:
<223> OTHER INFORMATION: Crytococcus neoformans capture extender probe

<400> SEQUENCE: 838
cggcatcgtt tactgttaag actattttc tcttggaaag aaagt                45

<210> SEQ ID NO 839
<211> LENGTH: 39
<212> TYPE: DNA
<213> ORGANISM: Artificial Sequence
<220> FEATURE:
<223> OTHER INFORMATION: Crytococcus neoformans capture extender probe

<400> SEQUENCE: 839
cgtgggccga tccctagttt tttctcttgg aaagaaagt                      39

<210> SEQ ID NO 840
<211> LENGTH: 42
<212> TYPE: DNA
<213> ORGANISM: Artificial Sequence
<220> FEATURE:
<223> OTHER INFORMATION: Crytococcus neoformans label extender probe

<400> SEQUENCE: 840
gaggtaaggt ccagcaagac agtttttga agttaccgtt tt                   42

<210> SEQ ID NO 841
<211> LENGTH: 42

```
<212> TYPE: DNA
<213> ORGANISM: Artificial Sequence
<220> FEATURE:
<223> OTHER INFORMATION: Crytococcus neoformans label extender probe

<400> SEQUENCE: 841
taaagagcat acaggaccac cagttttcct gagtcaaagc at                          42

<210> SEQ ID NO 842
<211> LENGTH: 44
<212> TYPE: DNA
<213> ORGANISM: Artificial Sequence
<220> FEATURE:
<223> OTHER INFORMATION: Crytococcus neoformans label extender probe

<400> SEQUENCE: 842
tattattcca tgctaatgta ttcggttttt gaagttaccg tttt                        44

<210> SEQ ID NO 843
<211> LENGTH: 42
<212> TYPE: DNA
<213> ORGANISM: Artificial Sequence
<220> FEATURE:
<223> OTHER INFORMATION: Crytococcus neoformans label extender probe

<400> SEQUENCE: 843
aaatagaacc gcacgtccta ttcttttct gagtcaaagc at                           42

<210> SEQ ID NO 844
<211> LENGTH: 40
<212> TYPE: DNA
<213> ORGANISM: Artificial Sequence
<220> FEATURE:
<223> OTHER INFORMATION: Crytococcus neoformans label extender probe

<400> SEQUENCE: 844
cggcgatcct agaaaccaac attttgaag ttaccgtttt                              40

<210> SEQ ID NO 845
<211> LENGTH: 42
<212> TYPE: DNA
<213> ORGANISM: Artificial Sequence
<220> FEATURE:
<223> OTHER INFORMATION: Crytococcus neoformans label extender probe

<400> SEQUENCE: 845
ccgaccgtcc ctattaatca ttatttttct gagtcaaagc at                          42

<210> SEQ ID NO 846
<211> LENGTH: 45
<212> TYPE: DNA
<213> ORGANISM: Artificial Sequence
<220> FEATURE:
<223> OTHER INFORMATION: Crytococcus neoformans label extender probe

<400> SEQUENCE: 846
ccgtcaatct aagaatttca cctctatttt tgaagttacc gtttt                       45

<210> SEQ ID NO 847
<211> LENGTH: 40
<212> TYPE: DNA
<213> ORGANISM: Artificial Sequence
<220> FEATURE:
<223> OTHER INFORMATION: Crytococcus neoformans label extender probe

<400> SEQUENCE: 847
```

```
gctttcgcag ttgttggtct ttttttctga gtcaaagcat                          40

<210> SEQ ID NO 848
<211> LENGTH: 41
<212> TYPE: DNA
<213> ORGANISM: Artificial Sequence
<220> FEATURE:
<223> OTHER INFORMATION: Crytococcus neoformans label extender probe

<400> SEQUENCE: 848
ccctaacctt cgttcttgat cattttttgaa gttaccgttt t                       41

<210> SEQ ID NO 849
<211> LENGTH: 44
<212> TYPE: DNA
<213> ORGANISM: Artificial Sequence
<220> FEATURE:
<223> OTHER INFORMATION: Crytococcus neoformans label extender probe

<400> SEQUENCE: 849
caacggtatc taatcgtttt tgatctttttt ctgagtcaaa gcat                    44

<210> SEQ ID NO 850
<211> LENGTH: 40
<212> TYPE: DNA
<213> ORGANISM: Artificial Sequence
<220> FEATURE:
<223> OTHER INFORMATION: Crytococcus neoformans label extender probe

<400> SEQUENCE: 850
gccgacccag tcagagattg atttttgaag ttaccgtttt                          40

<210> SEQ ID NO 851
<211> LENGTH: 44
<212> TYPE: DNA
<213> ORGANISM: Artificial Sequence
<220> FEATURE:
<223> OTHER INFORMATION: Crytococcus neoformans label extender probe

<400> SEQUENCE: 851
caaagacttt gatttctcgt aaggtttttt ctgagtcaaa gcat                     44

<210> SEQ ID NO 852
<211> LENGTH: 26
<212> TYPE: DNA
<213> ORGANISM: Artificial Sequence
<220> FEATURE:
<223> OTHER INFORMATION: Crytococcus neoformans blocking label extender
      probe

<400> SEQUENCE: 852
tctaattttt tcaaggtaaa attcct                                         26

<210> SEQ ID NO 853
<211> LENGTH: 20
<212> TYPE: DNA
<213> ORGANISM: Artificial Sequence
<220> FEATURE:
<223> OTHER INFORMATION: Crytococcus neoformans blocking label extender
      probe

<400> SEQUENCE: 853
gcaacggaat accaatgccc                                                20

<210> SEQ ID NO 854
<211> LENGTH: 21
```

```
<212> TYPE: DNA
<213> ORGANISM: Artificial Sequence
<220> FEATURE:
<223> OTHER INFORMATION: Crytococcus neoformans blocking label extender
      probe

<400> SEQUENCE: 854
atgaaaacgt ccttggcaaa t                                              21

<210> SEQ ID NO 855
<211> LENGTH: 43
<212> TYPE: DNA
<213> ORGANISM: Unknown
<220> FEATURE:
<223> OTHER INFORMATION: Glyceraldehyde 3-phosphate dehydrogenase
      capture extender probe

<400> SEQUENCE: 855
ggtcaatgaa ggggtcattg atttttctc ttggaaagaa agt                       43

<210> SEQ ID NO 856
<211> LENGTH: 41
<212> TYPE: DNA
<213> ORGANISM: Unknown
<220> FEATURE:
<223> OTHER INFORMATION: Glyceraldehyde 3-phosphate dehydrogenase
      capture extender probe

<400> SEQUENCE: 856
ccttgacggt gccatggaat tttttctctt ggaaagaaag t                        41

<210> SEQ ID NO 857
<211> LENGTH: 40
<212> TYPE: DNA
<213> ORGANISM: Unknown
<220> FEATURE:
<223> OTHER INFORMATION: Glyceraldehyde 3-phosphate dehydrogenase
      capture extender probe

<400> SEQUENCE: 857
cgccccactt gattttggat ttttctcttg gaaagaaagt                          40

<210> SEQ ID NO 858
<211> LENGTH: 43
<212> TYPE: DNA
<213> ORGANISM: Unknown
<220> FEATURE:
<223> OTHER INFORMATION: Glyceraldehyde 3-phosphate dehydrogenase
      capture extender probe

<400> SEQUENCE: 858
gagatgatga ccctttggc tctttttctc ttggaaagaa agt                       43

<210> SEQ ID NO 859
<211> LENGTH: 38
<212> TYPE: DNA
<213> ORGANISM: Unknown
<220> FEATURE:
<223> OTHER INFORMATION: Glyceraldehyde 3-phosphate dehydrogenase
      label extender probe

<400> SEQUENCE: 859
ggagcagaga gcgaagcggt ttttgaagtt accgtttt                            38

<210> SEQ ID NO 860
<211> LENGTH: 39
<212> TYPE: DNA
```

```
<213> ORGANISM: Unknown
<220> FEATURE:
<223> OTHER INFORMATION: Glyceraldehyde 3-phosphate dehydrogenase
      label extender probe

<400> SEQUENCE: 860
cggctgactg tcgaacagga tttttctgag tcaaagcat                              39

<210> SEQ ID NO 861
<211> LENGTH: 36
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 861
gagcgatgtg gctcggcttt ttgaagttac cgtttt                                 36

<210> SEQ ID NO 862
<211> LENGTH: 39
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 862
tcaccttccc catggtgtct tttttctgag tcaaagcat                              39

<210> SEQ ID NO 863
<211> LENGTH: 37
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 863
ccaggcgccc aatacgactt tttgaagtta ccgtttt                                37

<210> SEQ ID NO 864
<211> LENGTH: 40
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 864
agttaaaagc agccctggtg atttttctga gtcaaagcat                             40

<210> SEQ ID NO 865
<211> LENGTH: 44
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 865
tggaacatgt aaaccatgta gttgattttt gaagttaccg tttt                        44

<210> SEQ ID NO 866
<211> LENGTH: 40
<212> TYPE: DNA
<213> ORGANISM: Unknown
```

```
<220> FEATURE:
<223> OTHER INFORMATION: Glyceraldehyde 3-phosphate dehydrogenase label
      extender probe

<400> SEQUENCE: 866
ttgccatggg tggaatcata tttttttctga gtcaaagcat                              40

<210> SEQ ID NO 867
<211> LENGTH: 40
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 867
tgacaagctt cccgttctca gtttttgaag ttaccgtttt                               40

<210> SEQ ID NO 868
<211> LENGTH: 40
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 868
tggtgatggg atttccattg attttttctga gtcaaagcat                              40

<210> SEQ ID NO 869
<211> LENGTH: 39
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 869
gacgtactca gcgccagcat tttttgaagt taccgtttt                                39

<210> SEQ ID NO 870
<211> LENGTH: 39
<212> TYPE: DNA
<213> ORGANISM: Unknown
<220> FEATURE:
<223> OTHER INFORMATION: Glyceraldehyde 3-phosphate dehydrogenase label
      extender probe

<400> SEQUENCE: 870
aagacgccag tggactccac tttttctgag tcaaagcat                                39

<210> SEQ ID NO 871
<211> LENGTH: 21
<212> TYPE: DNA
<213> ORGANISM: Unknown
<220> FEATURE:
<223> OTHER INFORMATION: Glyceraldehyde 3-phosphate dehydrogenase
      blocking label extender probe

<400> SEQUENCE: 871
caaatccgtt gactccgacc t                                                   21

<210> SEQ ID NO 872
<211> LENGTH: 23
<212> TYPE: DNA
<213> ORGANISM: Unknown
<220> FEATURE:
```

```
<223> OTHER INFORMATION: Glyceraldehyde 3-phosphate dehydrogenase
      blocking label extender probe

<400> SEQUENCE: 872
ggcaacaata tccactttac cag                                           23

<210> SEQ ID NO 873
<211> LENGTH: 20
<212> TYPE: DNA
<213> ORGANISM: Unknown
<220> FEATURE:
<223> OTHER INFORMATION: Glyceraldehyde 3-phosphate dehydrogenase
      blocking label extender probe

<400> SEQUENCE: 873
gggatctcgc tcctggaaga                                               20

<210> SEQ ID NO 874
<211> LENGTH: 20
<212> TYPE: DNA
<213> ORGANISM: Unknown
<220> FEATURE:
<223> OTHER INFORMATION: Glyceraldehyde 3-phosphate dehydrogenase
      blocking label extender probe

<400> SEQUENCE: 874
cagccttctc catggtggtg                                               20

<210> SEQ ID NO 875
<211> LENGTH: 18
<212> TYPE: DNA
<213> ORGANISM: Unknown
<220> FEATURE:
<223> OTHER INFORMATION: Glyceraldehyde 3-phosphate dehydrogenase
      blocking label extender probe

<400> SEQUENCE: 875
ccccctgcaa atgagccc                                                 18
```

METHODS AND KITS FOR DETECTING HUMAN PAPILLOMAVIRUS

The Sequence Listing for this application is labeled "Sept2010-SeqList_ST25.txt" which was created on Sept. 20, 2010 and is 193 KB. The entire content of the sequence listing is incorporated herein by reference in its entirety.

FIELD OF THE INVENTION

This invention relates to detecting the presence, absence, or level of an infectious agent in a sample.

BACKGROUND OF THE INVENTION

Although many tests have been developed to diagnose infection, many of these tests are only specific and/or sensitive when there is a high load of the infectious agent present, i.e. in the case of late or advanced stages of infection. In addition, some of these tests require highly technical personnel or specialized knowledge to carry out the tests.

For example, to date, there is no robust test available for detecting high risk strains of HPV in pap smears, and which is both clinically sensitive and specific, as well as convenient, easy and inexpensive, without the need for highly trained personnel. (Kurtycz et al., *Comparison of Methods Trial for High-Risk HPV Diagnostic Cytopathology* 38:104-108 (2009); Ginocchio et al., *Comparison of the Third Wave Invader Human Papilloma (HPV) Assay and the Digene HPV Hybrid Capture 2 Assay for Detection of High-Risk HPV DNA J. Clin. Microbiol.* 46:1641-1646 (2008)). The Pap or Papanicolau test is currently the test of choice for the initial screening of pre-malignant or malignant cervical cancers caused by HPV. The Pap test is a cytology test which requires highly trained personnel to discriminate between normal cells and cells undergoing malignant lesions under a light microscope. The Diagene-HC2 DNA test, which is the only FDA-market approved HPV test, relies on the capture of DNA/RNA hybrids on a solid phase. The captured DNA/RNA hybrids are detected using an enzyme-linked antibody upon amplification. Although the test can detect up to thirteen HPV types, it has poor sensitivity (5000 copies/mL) and specificity. Furthermore, the test requires purification of DNA from the sample and it cross-hybridizes with low-risk and high-risk HPV types when the viral load in the sample is high.

Other tests for HPV include GenProbe's Aptima HPV test, Third Wave's Invader HPV DNA test, Ventana's Inform1 HPV in-situ hybridization test, and other PCR-based tests, including Roche's Amplicor or Linear Array HPV DNA tests. These tests require purification of the nucleic acid from the samples and/or amplification of the target nucleic acids prior to detection, which can result in poor sensitivity or specificity. In addition, these tests can be expensive and time-consuming. Furthermore, since most of these tests require amplification of the target polynucleotides, a highly clean and dedicated environment is required to ensure that there is no carry over or cross contamination between samples.

Accordingly, there is a need for an efficient, rapid, reliable, and inexpensive method and/or assay for detecting an infectious agent, such as HPV, and which has the desired level of sensitivity and specificity for screening and/or evaluating samples for the presence or level of the infectious agent.

SUMMARY OF THE INVENTION

The present invention provides methods and kits for determining the presence, absence, or level of an infectious agent in a sample. Specifically, the present invention provides methods and kits for detecting or quantifying certain target polynucleotides of the infectious agent. In certain embodiments, the present invention provides for such detection without the need for amplification (e.g., replication) of the target molecule and/or without the need for labor and/or time intensive procedures. In these or other embodiments, the invention allows for such detection with the desired sensitivity and/or specificity, even where the polynucleotide is present in the sample at low copy number.

In one aspect, the invention provides a method for detecting the presence, absence, or level of an infectious agent in a sample, such as a biological sample. The method comprises capturing a target polynucleotide, if present, from the sample, where the target polynucleotide is indicative of the presence of the infectious agent. The target polynucleotide is then detected directly or indirectly by hybridization with one or a series of signal-amplifying polynucleotide probes (e.g., branched DNA). The method allows detection of the target polynucleotide, with the desired specificity and/or sensitivity, and at low copy number, to thereby allow for detection of even early stage infection.

The target polynucleotide may be captured from the sample by hybridization to a Capture Extender probe having at least a first sequence and a second sequence, the first sequence hybridizing to the target polynucleotide and the second sequence hybridizing to an immobilized capture probe. The capture probe may be immobilized via any solid support (e.g., chip, bead, or well).

The captured target polynucleotide is then detected by hybridizing one or a series of signal-amplifying polynucleotide probe(s) directly or indirectly to the target. The series of signal-amplifying probes may comprise branched DNA. For example, the series of signal-amplifying probes may comprise a pre-Amplifier probe, an Amplifier probe, and a Label probe. Specifically, the pre-Amplifier probe hybridizes to the target through a Label Extender probe. The Label Extender probe generally has a first sequence and a second sequence, the first sequence hybridizing to the target polynucleotide and the second sequence hybridizing to the pre-Amplifier probe. Consecutive hybridizations of Amplifier probes and Label probes may then be conducted to amplify the signal. The signal-amplifying probes may allow for amplification of the signal 40 times or more, and in some embodiments, 200 times or more (e.g., relative to the number of hybridized Label Extender probes).

In various embodiments, the target polynucleotide or biomarker is a polynucleotide involved in the replication machinery of the infectious agent (e.g., cis- or trans-acting factor), a polynucleotide encoding a protein involved in replication or transcription, or a polynucleotide encoding a cell surface protein, integral membrane protein, etc. For example, in the case of HPV the target polynucleotides may be independently selected from E6 and E7 sequences. Exemplary Capture Extender and Label Extender probes for various infectious agent targets, including HPV, HBV, HIV, influenza H1N1, HCV, SARS, *Mycobacterium*, Syphilis, *Aspergillus, Candida*, and *Cryptococcus* are described herein.

In another aspect, the present invention provides a kit for detecting target polynucleotides. The kit provides one or more Capture Extender probes and one or more Label Extender probes for the detection of particular target polynucleotide(s), and exemplary pairs or "sets" of Capture Extender probes and Label Extender probes are disclosed herein. In some embodiments, the kit may further comprise one or more capture probes, a solid support, and/or a signal amplifying probe set (e.g., the set comprising a pre-Amplifier probe, an Amplifier probe, and a Label probe). The kit may comprise (in addition to the Capture Extender and Label Extender probes for detecting the target polynucleotide), Capture Extender and Label Extender probes for detecting one or more positive and/or negative control sequences. The positive control probes may be used to normalize between samples and/or to calculate the copy number of polynucleotides present. Exemplary positive control probes may comprise sequences from housekeeping genes, such as but not limited to glyceraldehyde 3-phosphate dehydrogenase (GAPDH/GAPD).

Other aspects and embodiments of the invention will be apparent to the skilled artisan in view of the following detailed description.

BRIEF DESCRIPTION OF THE DRAWINGS

FIG. 9 shows quantifying different species and strains of *Aspergillus* and *Candida*.

DETAILED DESCRIPTION OF THE INVENTION

Figure 1A:
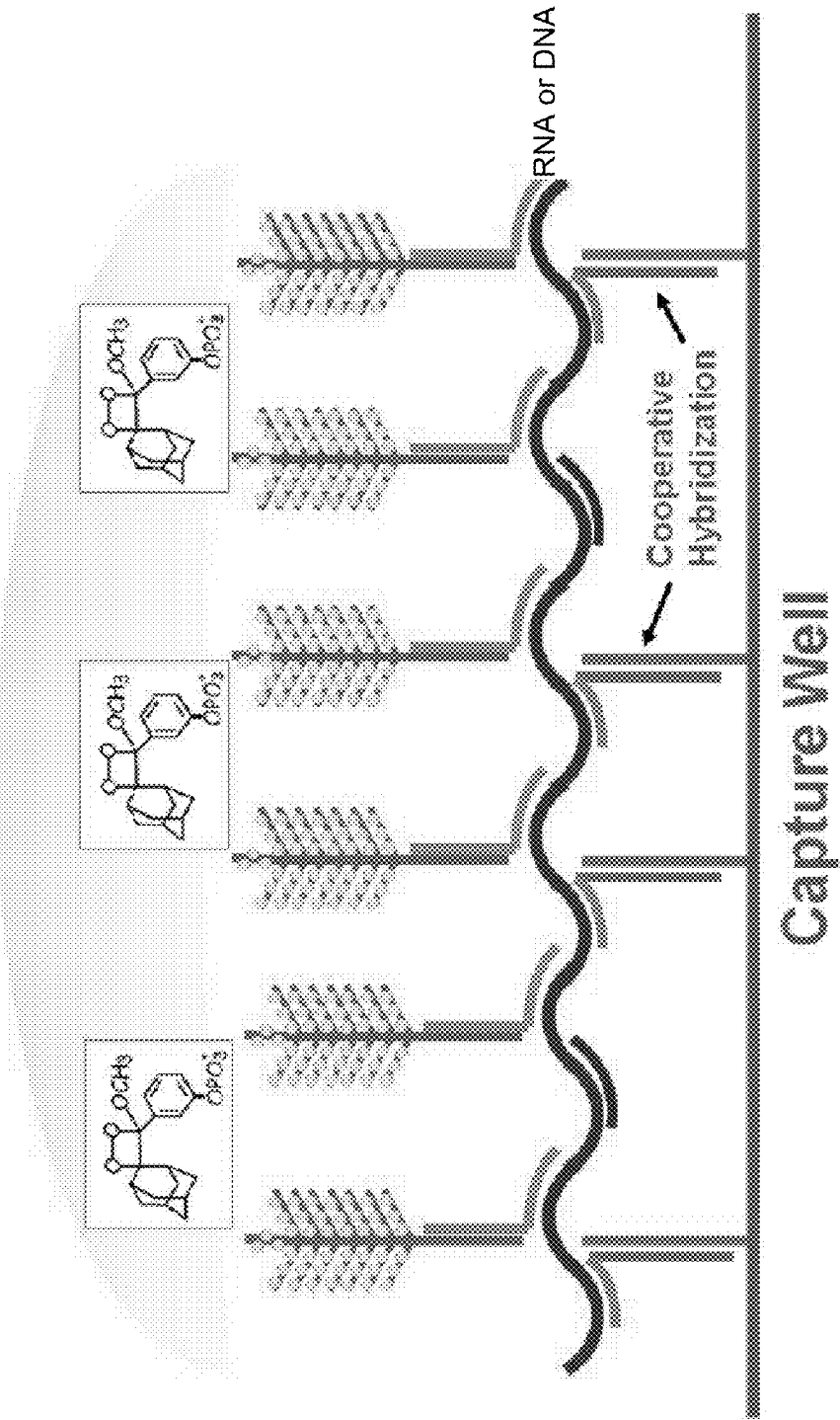
FIG. 1(A, B, and C) illustrates the components of the test system for detecting target polynucleotides in connection with the invention.

The present invention provides methods and kits for determining the presence, absence, or level of an infectious agent in a sample. Specifically, the present invention provides methods and kits for detecting or quantifying certain target polynucleotides of the infectious agent. In certain embodiments, the present invention provides for such detection without the need for amplification (e.g., replication) of the target molecule and/or without the need for labor and/or time intensive procedures, such as nucleic acid purification steps. In these or other embodiments, the invention allows for rapid detection of the target, with the desired sensitivity and/or specificity, even where the polynucleotide is present in the sample at low copy number.

In one aspect, the invention provides a method for detecting the presence, absence, or level of an infectious agent, such as a biological sample. The method comprises capturing one or more target polynucleotide(s), if present, from the sample, wherein the target polynucleotide is indicative of the presence of the infectious agent. In one embodiment, a single polynucleotide of interest is detected (single plex detection). In another embodiment, two polynucleotides of interest are detected (two-plex detection), or more than two polynucleotides of interest are detected (multiplex detection). The target polynucleotide is then detected directly or indirectly by hybridization with one or a series of signal-amplifying polynucleotide probes. The method may further comprise detecting the level of one or more control polynucleotides, for example, to normalize signals across samples.

For example, the target polynucleotide may be captured by hybridization to a Capture Extender probe having at least a first sequence and a second sequence, the first sequence hybridizing to the target polynucleotide and the second sequence hybridizing to an immobilized capture probe. The capture probe may be immobilized via any solid support, including but not limited to a chip (e.g., an array), well, bead, or other solid support or matrix.

The captured target polynucleotide is then detected by hybridizing one or a series of signal-amplifying polynucleotide probes, either directly to the target polynucleotide, or indirectly through a Label Extender probe. A Label Extender probe generally has a first sequence and a second sequence, the first sequence hybridizing to the target polynucleotide and the second sequence hybridizing to a signal-amplifying polynucleotide probe. The signal-amplifying probe may comprise branched DNA, e.g., may include a pre-Amplifier probe, an Amplifier probe, and a Label probe.

The sample may be a liquid sample, or a biological sample, such as, for example, a body fluid. In various embodiments, the sample is blood, plasma, serum, urine, vaginal secretion, pap smear, semen, nasal swabbing, lung lavage, pleural effusion, sputum, and throat swab. In other embodiments liquid samples can be obtained from swabs of objects such as toilet seats, pond water, tree sap, and insect or plant extracts. Other types of samples for which detection of infectious agents is desired may be employed in connection with the invention. In certain embodiments, a nucleic acid purification step may be performed prior to detection, such as the use of any commercially available filter-based method or kit for purification of nucleic acids. In other embodiments, no such purification step is required.

The method of detection may be carried out using the principles set forth in U.S. Pat. No. 7,709,198, which is hereby incorporated by reference. For example, detection generally takes place with the use of a series of signal amplifying polynucleotide probes (e.g., branched DNA), which is hybridized directly to the target polynucleotide, or indirectly through a series of hybridization reactions. The signal-amplifying probes obviate the need for thermal cycling or amplification of the target sequences prior to detection. Thus, in such embodiments, the method intensifies the signal of hybridization by multiple layers of probe hybridization, instead of any actual nucleotide sequence amplification of the target polynucleotide.

In various embodiments, the target polynucleotide (which may be linear or circular) is captured on a solid support by hybridizing to one or more sets of probes. The set of probes generally comprises a Capture Extender and a Label Extender, and optionally a Blocking Label Extender (or blocking probe).

The Capture Extender indirectly captures the target polynucleotide by hybridizing, simultaneously, to the target polynucleotide and a Capture Probe attached to a solid support, e.g., bead, chip, etc. The Capture Extender generally has a first sequence that hybridizes to the target polynucleotide and a second sequence that hybridizes to the Capture Probe. The Capture Extender optionally comprises a linking sequence between the first sequence and the second sequence. The first sequence of the Capture Extender, which hybridizes to the target polynucleotide, is generally from about 15 to about 30 nucleotides in length, or about 20 to about 27 nucleotides in length. The sequence and length is generally selected to hybridize under the hybridization conditions selected or described herein. The second sequence of the Capture Extender, which may hybridize to the capture probe, may be any capturable sequence, but is generally selected to hybridize under the selected hybridization conditions. The capture sequence is generally about 10 to about 30 nucleotides in length, and exemplary capture sequences are disclosed herein. The linking sequence is selected to provide for the physical independence of the first and second sequences, and is selected to avoid significant structural constraints. The linking sequence may be short, for example, from about 2 to about 10 nucleotides. The linking sequence may be poly(T) or poly(A) in certain embodiments.

Various Capture Extender sequences (and sets of Label Extender probes) are disclosed herein for the detection of numerous infectious agents. See Tables 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, and 93. It is understood that various modifications of these sequences may be made within the spirit of the invention, such as the addition or deletion of from 1 to 4 nucleotides to any or each of the target-hybridizing sequence, capture sequence, and/or linking sequence, or the addition of from 1 to 5 degenerate nucleotides.

A Blocking Label Extender may optionally be employed to block certain sequences. Such optional blocking probes (and sets of Blocking probes) for use with the invention are described in Tables 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, and 95. It is understood that various modifications of these sequences may be made within the spirit of the invention, such as the addition or deletion of from 1 to 4 nucleotides, or the addition of from 1 to 5 degenerate nucleotides.

The Label Extender hybridizes to the target polynucleotide and a signal-amplifying polynucleotide simultaneously. For example, the Label Extender generally comprises a first sequence that hybridizes to the target sequence, and a second sequence that hybridizes to a signal amplifying probe. The Label Extender may optionally have a linking sequence. The first sequence which hybridizes to the target sequence may generally be from about 15 to about 30 nucleotides in length, or about 20 to about 27 nucleotides in length. The sequence and length of the first sequence is generally selected to hybridize under the hybridization conditions selected or described herein. The second sequence of the Label Extender, which may hybridize to the signal amplifying probe, is generally selected to hybridize under the selected hybridization conditions. The second sequence is generally about 10 to about 30 nucleotides in length, and exemplary sequences are disclosed herein. The linking sequence is selected to provide for the physical independence of the first and second sequences, and is selected to avoid significant structural constraints. The linking sequence may be short, for example, from about 2 to about 10 nucleotides. The linking sequence may be poly(T) or poly (A) in certain embodiments.

Various Label Extender sequences (including Label Extender probe sets) for the detection of certain infectious agents are disclosed herein. See Tables 1, 2, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, and 94. It is understood that various modifications of these sequences may be made within the spirit of the invention, such as the addition or deletion of from 1 to 4 nucleotides to any or each of the target-hybridizing sequence, capture sequence, and/or linking sequence, or the addition of from 1 to 5 degenerate nucleotides.

The hybridization conditions for the assay include selected temperature, time, and reagents so as to allow for rapid, sensitive, and/or specific detection. For example, the hybridization temperatures may be independently selected in the range of about 45° C. to about 65° C., or about 50° C. to about 60° C., such as about 55° C. The hybridization buffer is generally 3×SSC, or comparable hybridization buffer.

The length of time for hybridization of the Capture Extender and the Label Extender probes may be selected based on the type of virus suspected, the stage of infection, the copy number of virus present in the sample, etc. In some embodiments, the Capture Extender and Label Extender probes are allowed to hybridize to the target for at least about 5 minutes, such as within the range of about 10 minutes to about 120 minutes, such as about 20 to about 90 minutes, or about 30 or 60 minutes. In certain embodiments, the Capture Extender and Label Extender probes are allowed to hybridize to the target for about 60 minutes to about 4 hours, 8 hours, 12 hours or overnight (e.g., from 18 to 24 hours). With samples suspected of representing early stages of an infection (or where the copy number of target polynucleotides is expected to be low), the Capture Extender and the Label Extender probes are allow to hybridize to the target for a longer period of time, than for samples suspected of representing advanced stages of infection (or where a high copy number of the target polynucleotides is expected). For example, the hybridization time may be from about 1 hour to about 4 hours, from about 3 hours to 8 hours, from about 7 hours to about 12 hours, or from about 12 hours to about 24 hours or longer for samples obtained from the early stages of infection or where the copy number of infectious agents are low. Where the copy number of infectious agents are high or during the late or advance stages of infection, the length of time needed for the probes to hybridize to the target polynucleotide may be from about 5 minutes to about one hour.

A robust detection of the hybridization reactions is obtained by either directly detecting the multiple hybridizations of Label Extenders to the target polynucleotide, or by further hybridization of one or a series of signal-amplifying probes. For example, detection may occur by hybridizing a pre-Amplifier probe to the label extender probe, and hybridizing Amplifier probes to the pre-Amplifier probe, which complex may be detected with Label probes. Such reactions may take place in consecutive hybridizations, e.g., at conditions in the range of 40 to 60° C., in 3×SSC (or comparable hybridization buffer), and for about 30 to about 60 minutes each. Exact conditions may be selected based upon the sequences and melting temperature of each probe. Exemplary sequences/structures for the pre-Amplifier probe, Amplifier probe, and label probes are known. For illustration, an exemplary sequence of the preamplifier is 5' AGGCATAGGACCCGTGTCTttttttttttAGGCATAGGAC-CCGTGTCTttttt<u>ATGCTTTGACTCAG AAAACGGTAACTTC</u> 3' (SEQ ID NO:1). The underlined sequences are complementary to sequences in the GAPD Label Extenders (used as a positive control as described herein).

The configuration and hybridization of test components, such as Label Extenders, may be as described in U.S. Pat. No 7,709,198, which is hereby incorporated by reference. For example, Label Extenders may be described with reference to the "cruciform" configuration or the "double Z" configuration. See FIG. 1C. Generally, one end of the Label Extender hybridizes to the preamplifier probe, and the other end hybridizes to the target polynucleotide. The pre-amplifier probe may hybridize to a single Label Extender probe as described herein (e.g., cruciform configuration). In some embodiments using the double Z-configuration, the preamplifier probe hybridizes to two Label Extender probes.

An exemplary Label Extender probe set in the cruciform configuration is set-forth in Table 1 and Table 94, for glyceraldehyde 3-phosphate dehydrogenase (GAPD), which may be used as a control for normalizing across samples, and for quantifying polynucleotide copy number.

The sequences complementary to the preamplifier sequence of SEQ ID NO: 1 is underlined for each of the Label Extenders shown in Table 1.

Figure 1B:
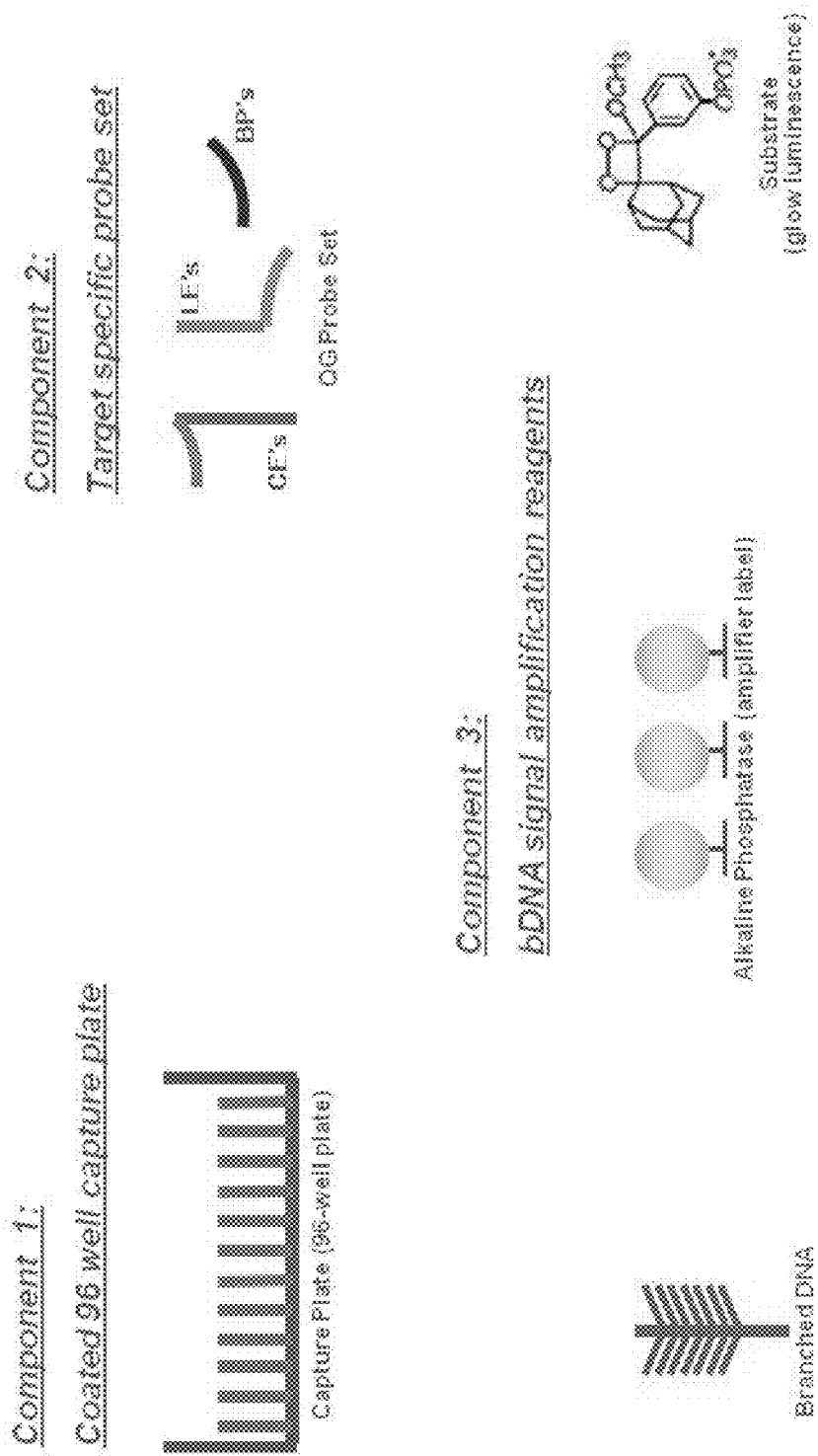
Figure 1C:
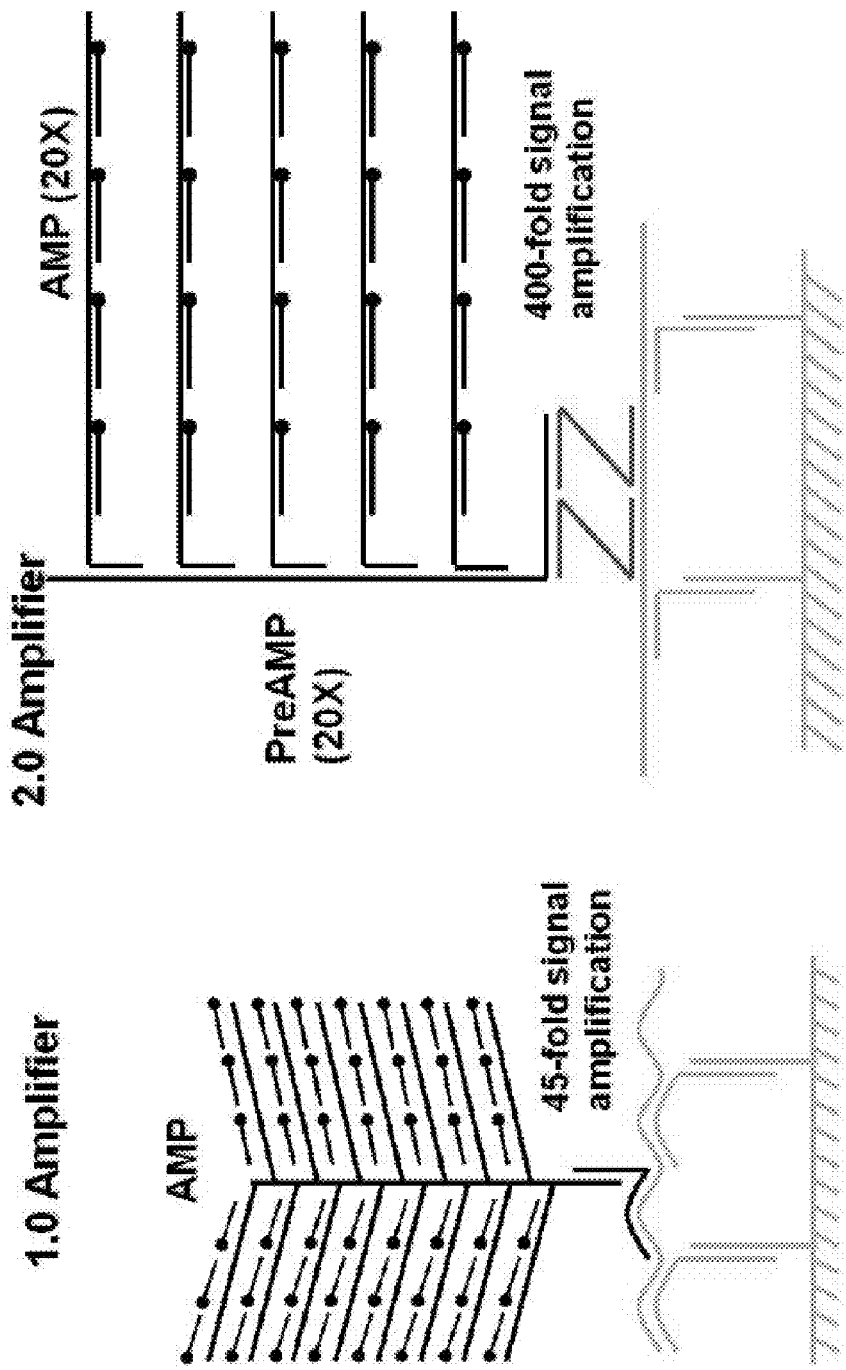

The Amplifier probe or Label probe, in particular embodiments, is conjugated with Alkaline Phosphatase, allowing its detection with glow luminescence. Alternatively, an Amplifier probe or label probe may have a chromogenic or fluorescent generating moiety (e.g., enzyme) to provide an intensified signal in the presence of the appropriate substrate. An exemplary format is shown in FIG. 1, illustrating an Alkaline Phosphatase Label probe and corresponding luminescent substrate.

The number of Amplifier probes that hybridize to the growing complex, per the number of hybridized pre-Amplifier probes, may be within the range of 5:1 to 20:1. The number of Label probes that hybridize to the growing complex, per the number of hybridized Amplifier probes, may be within the range of 2:1 to about 5:1.

The Capture Extender and the Label Extender are designed to comprise at least one sequence that recognizes (hybridizes) to the target polynucleotide. The level of complementarity is appropriately selected based upon the desired hybridization conditions and selectivity, and in some embodiments, the complementary sequence is fully complementary to its intended target. In certain embodiments, the

TABLE 1

GADP Label Extenders with Cruciform Configuration

| SEQ ID NO: | PROBE IDENTIFIER | LABEL EXTENDER NUCLEOTIDE SEQ OF GLYCERALDEHYDE 3-PHOSPHATE DEHYDROGENASE | |
|---|---|---|---|
| SEQ ID NO: 2 | GAPD127 | ccagtggactccacgacgtacTTTTTgaagttaccgtttt | CP1 tail |
| SEQ ID NO: 3 | GAPD128 | ctgagtcaaagcatTTTTTttctccatggtggtgaagacg | CP2 head |
| SEQ ID NO: 4 | GAPD129 | tcttgaggctgttgtcatacttctTTTTTgaagttaccgtttt | CP1 tail |
| SEQ ID NO: 5 | GAPD130 | ctgagtcaaagcatTTTTTgcaggaggcattgctgatga | CP2 head |
| SEQ ID NO: 6 | GAPD131 | cagtagaggcagggatgatgttcTTTTTgaagttaccgtttt | CP1 tail |
| SEQ ID NO: 7 | GAPD132 | ctgagtcaaagcatTTTTTcacagccttggcagcgc | CP2 head |

Table 2 shows an exemplary Label Extender probe set for GAPD in the double Z configuration. The sequences complementary to the preamplifier sequence is underlined for each of the Label Extenders shown in Table 2.

Capture Extender and/or Label Extender includes from 1 to about 5 degenerate nucleotides in the target-hybridizing sequence, so as to provide for the desired selectivity or cross-reactivity.

TABLE 2

GAPD Label Extenders with Double Z configuration

| SEQ ID NO: | PROBE IDENTIFIER | LABEL EXTENDER NUCLEOTIDE SEQ OF GLYCERALDEHYDE 3-PHOSPHATE DEHYDROGENASE | |
|---|---|---|---|
| SEQ ID NO: 8 | GAPD217 | ccagtggactccacgacgtacTTTTTgaagttaccgtttt | CP1 tail |
| SEQ ID NO: 9 | GAPD218 | ttctccatggtggtgaagacgTTTTTctgagtcaaagcat | CP2 tail |
| SEQ ID NO: 10 | GAPD219 | tcttgaggctgttgtcatacttaTTTTTgaagttaccgtttt | CP1 tail |
| SEQ ID NO: 11 | GAPD220 | gcaggaggcattgctgatgaTTTTTctgagtcaaagcat | CP2 tail |
| SEQ ID NO: 12 | GAPD221 | cagtagaggcagggatgatgttcTTTTTgaagttaccgtttt | CP1 tail |
| SEQ ID NO: 13 | GAPD222 | cacagccttggcagcgcTTTTTctgagtcaaagcat | CP2 tail |

The Capture Extender and Label Extender may be designed to recognize and bind to such target sequences as inverted terminal repeats (e.g., of a virus genome); bacterial 5S, 16S, or 23S ribosomal RNA sequences, terminal inverted repeat sequences (TIR), miniature inverted repeat transposable elements (MITE), CpG sequences in prokaryotic cells such as bacteria; or 18S or 28S ribosomal RNA sequences in eukaryotic cells, such as fungi or parasites.

In various embodiments, the sensitivity of the detection is less than about 1000 copies, less than about 500 copies, less than about 250 copies, or less than about 100 copies (e.g., about 25 copies) of the target sequence. The full test may take less than about 7 hours, and in some embodiments, may take less than about 6 hours, or less than about 5 hours.

Detection moeities for the target polynucleotide and controls may be the same or different, and may be independently selected from a luminescence-generating moiety, such as but not limited to alkaline phosphatase having a luminescent substrate, and a chromogenic generating moiety, such as but not limited to a horseradish peroxidase (HRP). In some embodiments, detection of the one or more target polynucleotides may be carried out simultaneously or sequentially with the detection of the positive control or normalization control (e.g., GAPDH), that is, in the same or parallel reaction. In some embodiments, detection signals for the target polynucleotide and the normalization control may be read sequentially from a patient sample in the same reaction. In such embodiments, after detection of a luminescent or chromogenic reaction, the sample is washed, and a different luminescent or chromogenic reagent is added.

In various embodiments, the target polynucleotide is indicative of the presence of a virus of the family Paramyxoviridae (e.g., parainfluenza, mumps, measles); Orthomyxoviridae (e.g., influenza); Hepadnaviridae (e.g., hepatitis); Adenoviridae (e.g., acute respiratory disease); Poxviridae (e.g., small pox); Herpesviridae (e.g., HSV, Varicella Zoster, Karposi sarcoma); Papillomaviridae (e.g., HPV); Polyomaviridae (e.g., cystitis or mild or acute respiratory diseases); Parvoviridae; Rhabdoviridae (e.g., rabies); Filoviridae (e.g., hemorrhagic fever caused by Ebola virus and Marburg virus); Bunyaviridae (e.g., encephalitis, Hantavirus respiratory syndrome, Rift Valley fever); Arenaviridae (e.g., aseptic meningitis, encephalitis, meningoencephalitis, Lassa fever); Coronaviridae (e.g., severe acute respiratory syndrome or SARS); Flaviviradae (e.g., Dengue hemorrhagic fever); Togaviridae; Picornaviridae; Caliciviridae (e.g., winter vomiting disease); Astroviridae (e.g., gastroenteritis); Retroviridae (e.g., HIV, HTLV) and Reoviridae (e.g., Colorado Tick fever).

In certain embodiments, the target polynucleotide is an HPV target polynucleotide, and may be a high risk type HPV, such as type 16, 18, 31, 33, 35, 39, 45, 51, 52, 56, 58, 59, or 68; or may be a low risk type HPV, such as type 6, 11, 40, 42, 43, or 44. High risk sexually transmitted HPV may lead to development of cervical intraepithelial neoplasia (CIN), vulvar intraepithelial neoplasia (VIN), penile intraepithelial neoplasia (PIN), and/or anal intraepithelial neoplasia (AIN), whereas low risk sexually transmitted HPV may lead to genital warts and are not life-threatening since they do not lead to cervical cancer. Of the high risk type HPV, types 16 and 18 are the most dangerous since they cause about 70% of cervical cancer. For example, in a NIH study, it was found that 10% of women infected with type 16 or 18 HPV developed advance precancerous cervical disease (CIN3) within 3 years while 20% did so in 10 years.

The invention in certain embodiments allows for the determination of a specific type of HPV present in a sample, and/or distinguishes between early course of the infection, and late or latent stage of HPV infection.

In various embodiments, the target polynucleotide sequence is a portion of an HPV late viral gene (e.g., L1 and/or L2), or an early viral gene (e.g., E1 and/or E2), which encode proteins responsible for replicating and maintaining the viral DNA as a circular episome. In one exemplary embodiment, the target polynucleotide is a portion of the gene encoding the E6 and/or E7 proteins of the HPV. In particular, the target polynucleotides are derived from the mRNA regions encoding the E6 and/or E7 proteins that mediate degradation of the tumor suppressors, p53 and retinoblastoma (RB), by interfering with the regulation of the cell cycle.

In certain embodiments, the target polynucleotide is an E6 and/or E7 sequence of HPV type 16. In such embodiments, at least one Capture Extender (e.g., at least two, three, four, or five) comprise a target-hybridizing sequence selected from Table 3 (underlined). At least one Capture Extender may comprise, consist essentially of, or consist of a sequence independently selected from SEQ ID NOS: 14 to 21 (Tables 3). In these or other embodiments, at least one Label Extender (e.g., at least two, three, four, or five) comprises a target-hybridizing sequence selected from Table 4 (underlined). At least one Label Extender may comprise, consist essentially of, or consist of a sequence selected from SEQ ID NOS: 22 to 37 (Table 4). The method may further employ a Blocking Label Extender (BL), e.g., at least one, two, or three BLs each comprising, consisting essentially of, or consisting of a sequence selected from SEQ ID NOS: 38 to 48 (Table 5).

TABLE 3

Capture Extender of HPV type 16

| SEQ ID NO | CAPTURE EXTENDER NUCLEOTIDE SEQUENCE OF HPV TYPE-16 |
|---|---|
| 14. | ctcctgtgggtcctgaaacattTTTTTctcttggaaagaaagt |
| 15. | cacgtcgcagtaactgttgcttTTTTTctcttggaaagaaagt |
| 16. | tgttgttccatacaaactataacaataatTTTTTctcttggaaagaaagt |
| 17. | aatctaacatatattcatgcaatgtaggTTTTTctcttggaaagaaagt |
| 18. | atattgtaatgggctctgtccgTTTTTctcttggaaagaaagt |
| 19. | cccattaacaggtcttccaaagtaTTTTTctcttggaaagaaagt |
| 20. | ggtagattatggtttctgagaacagatTTTTTctcttggaaagaaagt |
| 21. | cccgtaccctcttccccattTTTTTctcttggaaggaaagt |

TABLE 4

Label Extender of HPV type 16

| SEQ ID NO | LABEL EXTENDER NUCLEOTIDE SEQUENCE OF HPV TYPE-16 |
|---|---|
| 22. | gtctgcttttatactaaccggtttcTTTTTgaagttaccgtttt |
| 23. | gcagttctcttttggtgcataaaatTTTTTctgagtcaaagcat |

TABLE 4-continued

Label Extender of HPV type 16

| SEQ ID NO | LABEL EXTENDER NUCLEOTIDE SEQUENCE OF HPV TYPE-16 |
|---|---|
| 24. | aactgtggtaactttctgggtcgTTTTTgaagttaccgtttt |
| 25. | agttgtttgcagctctgtgcatTTTTTctgagtcaaagcat |
| 26. | ttcccatctctatatactatgcataaatTTTTTgaagttaccgtttt |
| 27. | aacatttatcacatacagcatatggaTTTTTctgagtcaaagcat |
| 28. | cggtttgttgtattgctgttctaaTTTTTgaagttaccgtttt |
| 29. | taatacacctaattaacaaatcacacaaTTTTTctgagtcaaagcat |
| 30. | ggacacagtggcttttgacagtTTTTTgaagttaccgtttt |
| 31. | ccagatgtctttgcttttcttcaTTTTTctgagtcaaagcat |
| 32. | gatctgcaacaagacatacatcgaTTTTTgaagttaccgtttt |
| 33. | tgggtttctctacgtgttcttgatTTTTTctgagtcaaagcat |
| 34. | gagatcagttgtctctggttgcaTTTTTgaagttaccgtttt |
| 35. | gctgtcatttaattgctcataacagtaTTTTTctgagtcaaagcat |
| 36. | tcacacttgcaacaaaaggttacaTTTTTgaagttaccgtttt |
| 37. | cgcacaaccgaagcgtagagTTTTTctgagtcaaagcat |

TABLE 5

Blocking Label Extender of HPV type 16

| SEQ ID NO | BLOCKING LABEL EXTENDER NUCLEOTIDE SEQUENCE OF HPV TYPE-16 |
|---|---|
| 38. | gcagtacacacattctaatattatatcatgtat |
| 39. | cccgaaaagcaaagtcatatacct |
| 40. | gtctatactcactaattttagaataaaacttta |
| 41. | ttatattatggaatctttgcttttgt |
| 42. | ccggtccaccgacccc |
| 43. | tgtatctccatgcatgattacagc |
| 44. | catctatttcatcctcctcctctga |
| 45. | gttctgcttgtccagctggac |
| 46. | cgaatgtctacgtgtgtgctttgta |
| 47. | ggggcacacaattcctagtgtg |
| 48. | ggtacctgcaggatcagccat |

In certain embodiments, the target polynucleotide is an E6 or E7 sequence from HPV type 18. In such embodiments, at least one Capture Extender probe (e.g., at least two, three, four, or five) comprises a target-hybridizing sequence selected from Table 6 (underlined). Thus, at least one Capture Extender may comprise, consist essentially of, or consist of a sequence selected from SEQ ID NOS: 49 to 56 (Tables 6). At least one Label Extender probe (e.g., at least two, three, four, or five) may comprise a target-hybridizing sequence selected from Table 7 (underlined). At least one Label Extender may comprise, consist essentially of, or consist of a sequence selected from SEQ ID NOS: 57 to 72. (Table 7). The test may further employ Blocking Label (BL), e.g., at least one, two, or three BLs each containing a sequence selected from SEQ ID NOS: 73 to 75 (Table 8).

TABLE 6

Capture Extender of HPV type 18

| SEQ ID NO | CAPTURE EXTENDER NUCLEOTIDE SEQUENCE OF HPV TYPE-18 |
|---|---|
| 49. | cgtttttcattaaggtgtctaagtttttTTTTTctcttggaaagaaagt |
| 50. | tgctcggttgcagcacgTTTTTctcttggaaagaaagt |
| 51. | tgttgccttaggtccatgcataTTTTTctcttggaaagaaagt |
| 52. | gctttctactactagcttaattctggcTTTTTctcttggaaagaaagt |
| 53. | ctggatcagccattgttgcttTTTTTctcttggaaagaaagt |
| 54. | tactacctgctaatcttctatgagcttTTTTTctcttggaaagaaagt |
| 55. | tggccagggaagatccactTTTTTctcttggaaagaaagt |
| 56. | ttgcagctcaatacaaaacggTTTTTctcttggaaagaaagt |

TABLE 7

Label Extender of HPV type 18

| SEQ ID NO | LABEL EXTENDER NUCLEOTIDE SEQUENCE OF HPV TYPE-18 |
|---|---|
| 57. | cccagctatgttgtggaatcgtTTTTTgaagttaccgtttt |
| 58. | aatggcactggcctctatagtgTTTTTctgagtcaaagcat |
| 59. | tcgttggagtctttcctgtcgTTTTTgaagttaccgtttt |
| 60. | cttaatattatacttgtgtttctctgcgTTTTTctgagtcaaagcat |
| 61. | taaatgcaatacaatgtcttgcaaTTTTTgaagttaccgtttt |
| 62. | ggaatttcattttggggctcTTTTTctgagtcaaagcat |
| 63. | gctcgtgacatagaaggtcaaccTTTTTgaagttaccgtttt |
| 64. | tttcttcctctgagtcgcttaattTTTTTctgagtcaaagcat |
| 65. | atgattaactccatctatttcatcgtTTTTTgaagttaccgtt tt |
| 66. | cgtcgggctggtaaatgttgTTTTTctgagtcaaagcat |
| 67. | gctcgaaggtcgtctgctgaTTTTTgaagttaccgtttt |
| 68. | tgttcagaaacagctgctggaatTTTTTctgagtcaaagcat |
| 69. | cggacacacaaaggacagggTTTTTgaagttaccgtttt |
| 70. | actgctgggatgcacaccaTTTTTctgagtcaaagcat |
| 71. | cgtcagtttcctcatctgaaaacttTTTTTgaagttaccgtttt |
| 72. | cgtcaagtcatttaagcttggtaccTTTTTctgagtcaaagcat |

TABLE 8

Blocking Label Extender of HPV type 18

| SEQ ID NO | BLOCKING LABEL EXTENDER NUCLEOTIDE SEQUENCE OF HPV TYPE-18 |
|---|---|
| 73. | tgtgtgacgttgtggttcagct |
| 74. | ttcacacttacaacacatacacaacat |
| 75. | gaattaggagtcagcagtcattattc |

In certain embodiments, the target polynucleotide is an E6 or E7 sequence from HPV type 31. In such embodiments, at least one Capture Extender probe (e.g., at least two, three, four, or five) comprises a target-hybridizing sequence selected from Table 9 (underlined). Thus, at least one Capture Extender may comprise, consist essentially of, or consist of a sequence selected from SEQ ID NOS: 76 to 82 (Tables 9). At least one Label Extender probe (e.g., at least two, three, four, or five) may comprise a target-hybridizing sequence selected from Table 10 (underlined). At least one Label Extender may comprise, consist essentially of, or consist of a sequence selected from SEQ ID NOS: 83 to 94 (Table 10). The test may further employ Blocking Label (BL), e.g., at least one, two, or three BLs each containing a sequence selected from SEQ ID NOS: 95 to 99 (Table 11).

TABLE 9

Capture Extender of HPV type 31

| SEQ ID NO | CAPTURE EXTENDER OF HPV TYPE 31 |
|---|---|
| 76. | gtctttctgcaggattttttgaacTTTTTctcttggaaagaaagt |
| 77. | gcttagttcatgcaatttccgagTTTTTctcttggaaagaaagt |
| 78. | cctctgtttctgttaactgacctttgTTTTTctcttggaaagaaagt |
| 79. | atctaaattcacttacttttgaataaaatTTTTTctcttggaaagaaagt |
| 80. | catataccttttgtttgtcaatttttctTTTTTctcttggaaagaaagt |
| 81. | acgcatgtttacacttgggtttTTTTTctcttggaaagaaagt |
| 82. | tctgagctgtcgggtaattgcTTTTTctcttggaaagaaagt |

TABLE 10

Label Extender of HPV type 31

| SEQ ID NO | LABEL EXTENDER OF HPV TYPE 31 |
|---|---|
| 83. | gtagggtatttccaatgccgaTTTTTgaagttaccgtttt |
| 84. | cagtagacacaattcaatcttagttcatcTTTTTctgagtcaaagcat |
| 85. | gtggtgtgtcgtccctatatactattTTTTTgaagttaccgttt |
| 86. | cttaaacattttgtacacactccgtTTTTTctgagtcaaagcat |

TABLE 10-continued

Label Extender of HPV type 31

| SEQ ID NO | LABEL EXTENDER OF HPV TYPE 31 |
|---|---|
| 87. | acacgttatacacctaattaacaaatcaTTTTTgaagttaccgtttt |
| 88. | tcttctggacacaacggtctttgTTTTTctgagtcaaagcat |
| 89. | tcttttttatccaaatgtctttgttttTTTTTgaagttaccgttt |
| 90. | ttcctcctatgttgtggaatcgttTTTTTctgagtcaaagcat |
| 91. | cttgcaacgtaggtgtttctccTTTTTgaagttaccgtttt |
| 92. | ctcaggttgcaaatctaacacatagtTTTTTctgagtcaaagcat |
| 93. | ggactgtctatgacatcctcctcaTTTTTgaagttaccgtttt |
| 94. | ccggttctgcttgtccagctTTTTTctgagtcaaagcat |

TABLE 11

Blocking Label Extender of HPV type 31

| SEQ ID NO | BLOCKING EXTENDER OF HPV TYPE 31 |
|---|---|
| 95. | gttaaatctgtaaatgcaaaatctaata |
| 96. | aatgttgttccatacacactatatctatacc |
| 97. | ctatgcaacgtcctgtccacc |
| 98. | cagtacgaggtcttctccaacatg |
| 99. | tcataacagtggaggtcagttgc |

In certain embodiments, the target polynucleotide is an E6 and/or E7 sequence from HPV type 35. In such embodiments, at least one Capture Extender probe (e.g., at least two, three, four, or five) comprises a target hybridizing sequence selected from Table 12 (underlined). At least one Capture Extender probe may comprise, consist essentially of, or consist of a sequence selected from SEQ ID NOS: 100 to 105 (Tables 12). In such embodiments, at least one Label Extender (e.g., at least two, three, four, or five) may comprise a target-hybridizing sequence shown in Table 13 (underlined). At least one Label Extender probe may comprise, consist essentially of, or consist of a sequence selected from SEQ ID NOS: 106 to 117 (Table 13). The test may further employ a Blocking Label (BL), e.g., at least one, two, or three BLs each containing a sequence selected from SEQ ID NOS: 118 to 127 (Table 14).

TABLE 12

Capture Extender of HPV type 35

| SEQ ID NO | CAPTURE EXTENDER NUCLEOTIDE SEQUENCE OF HPV TYPE-35 |
|---|---|
| 100. | caaacaaatttcatggatgctttcTTTTTctcttggaaagaaagt |

TABLE 12-continued

Capture Extender of HPV type 35

| SEQ ID NO | CAPTURE EXTENDER NUCLEOTIDE SEQUENCE OF HPV TYPE-35 |
|---|---|
| 101. | tactccatatggctggccttcTTTTTctcttggaaagaaagt |
| 102. | tgtttttctaacgtttctccatacacTTTTTctcttggaaagaaagt |
| 103. | caccgtccaccgatgttatgTTTTTctcttggaaagaaagt |
| 104. | tccagctggaccgtcaatagtatTTTTTctcttggaaagaaagt |
| 105. | ccattaataaatcttccaatttacgtaTTTTTctcttggaaagaaagt |

TABLE 13

Label Extender of HPV type 35

| SEQ ID NO | LABEL EXTENDER NUCLEOTIDE SEQUENCE OF HPV TYPE-35 |
|---|---|
| 106. | gcagtttgtaaggtcgttcagctTTTTTgaagttaccgtttt |
| 107. | ttctacctcgttgcacaaatcatTTTTTctgagtcaaagcat |
| 108. | taattcttgtttgcagtatacacaattTTTTTgaagttaccgttt |
| 109. | aaagtcatataccctcactccgctgTTTTTctgagtcaaagcat |
| 110. | aataaatgacataactgtttgttgcatTTTTTgaagttaccgttt |
| 111. | ggtttttgacatgtaatacacctaattTTTTTctgagtcaaagcat |
| 112. | tctaaaacatagtcttgcaatgtagttatTTTTTgaagttaccgtttt |
| 113. | agttgcctcgggttccaaaTTTTTctgagtcaaagcat |
| 114. | acacaattgctcataacagtataggtcTTTTTgaagttaccgttt |
| 115. | cttcctcctcctctgagctgtcTTTTTctgagtcaaagcat |
| 116. | ggaggtgtctggttttgcttgTTTTTgaagttaccgtttt |
| 117. | ttacaacaggacgttacaatattataattTTTTTctgagtcaaagcat |

TABLE 14

Blocking Label Extender of HPV type 35

| SEQ ID NO | BLOCKING LABEL EXTENDER NUCLEOTIDE SEQUENCE OF HPV TYPE-35 |
|---|---|
| 118. | tctatatactatacacaaatcatagcatgc |
| 119. | gaataaaattttaaacatttcatgca |
| 120. | actatatctataccatctatattcacttatttt |
| 121. | ttgcttttcaactggacacagc |
| 122. | gaatcgttttttttcttctaaatgtct |
| 123. | aacaggacatacaccgacctgtc |

TABLE 14-continued

Blocking Label Extender of HPV type 35

| SEQ ID NO | BLOCKING LABEL EXTENDER NUCLEOTIDE SEQUENCE OF HPV TYPE-35 |
|---|---|
| 124. | ggtttctctacgtgttggtttcc |
| 125. | ttctccatgcatgattacacctc |
| 126. | cagacgtagtgtcgcctcacat |
| 127. | tgtcaatgtgtgtgctctgtacaca |

In certain embodiments, the target polynucleotide is an E6 or E7 sequence from HPV type 39. In such embodiments, at least one Capture Extender probe (e.g., at least two, three, four, or five) comprises a target-hybridizing sequence selected from Table 15 (underlined). Thus, at least one Capture Extender may comprise, consist essentially of, or consist of a sequence selected from SEQ ID NOS: 128 to 134 (Tables 15). At least one Label Extender probe (e.g., at least two, three, four, or five) may comprise a target-hybridizing sequence selected from Table 7 (underlined). At least one Label Extender may comprise, consist essentially of, or consist of a sequence selected from SEQ ID NOS: 135 to 145 (Table 16). The test may further employ Blocking Label (BL), e.g., at least one, two, or three BLs each containing a sequence selected from SEQ ID NOS: 146 to 154 (Table 17).

TABLE 15

Capture Extender of HPV type 39

| SEQ ID NO | CAPTURE EXTENDER OF HPV TYPE 39 |
|---|---|
| 128. | tacctcggtttgctgtagtggTTTTTctcttggaaagaaagt |
| 129. | ggttccccgtccctatatactaTTTTTctcttggaaagaaagt |
| 130. | tttatgaaatcttcgtttgctatttTTTTTctcttggaaagaaagt |
| 131. | ggtccacgcatatctgatgttataTTTTTctcttggaaagaaagt |
| 132. | tttcctgcaaggtgggctttTTTTTctcttggaaagaaagt |
| 133. | ccgtgaggcttctactaccagctTTTTTctcttggaaagaaagt |
| 134. | acaaatcctagtgagtccataaacagTTTTTctcttggaaagaaagt |

TABLE 16

Label Extender of HPV type 39

| SEQ ID NO | LABEL EXTENDER OF HPV TYPE 39 |
|---|---|
| 135. | cccgtatttagcataaaattttataTTTTTctgagtcaaagcat |
| 136. | ccgagtccgagtaatatcgtagctTTTTTgaagttaccgtttt |
| 137. | ttagttatattttctaatgtagttgcatacaTTTTTctgagtcaaagcat |

TABLE 16-continued

Label Extender of HPV type 39

| SEQ ID NO | LABEL EXTENDER OF HPV TYPE 39 |
|---|---|
| 138. | cacagcggtttcagacaacacaTTTTTgaagttaccgtttt |
| 139. | aggtgtcttaatttttctgctggaTTTTTctgagtcaaagcat |
| 140. | ttcattgtaaggacataaatctaatacaaTTTTTgaagttaccgtttt |
| 141. | catacaaggtcaaccggctgtatTTTTTctgagtcaaagcat |
| 142. | gtcgggttcatctatttcatcctTTTTTgaagttaccgtttt |
| 143. | ttgatgttggtgattaactgcatgTTTTTctgagtcaaagcat |
| 144. | ggttcatcccgtctggctagtagTTTTTgaagttaccgtttt |
| 145. | gaacactgtattgtgtgacgctgtTTTTTctgagtcaaagcat |

TABLE 17

Blocking Label Extender of HPV type 39

| SEQ ID NO | BLOCKING LABEL EXTENDER OF HPV TYPE 39 |
|---|---|
| 146. | catataaatcactaaatgcaaattcata |
| 147. | tgcaccttattaataaattatataactttgta |
| 148. | actgtcctgtatagcttcctgctat |
| 149. | tggtccagcaccgtcgac |
| 150. | tgcggtcctcccgttttg |
| 151. | cttgggtttctcttcgtgttagtc |
| 152. | ctgactctcctaattgctcgtga |
| 153. | gcagtgtgttgttacacttacaacac |
| 154. | ctgctgtagttgtcgcagagtatc |

TABLE 18

Capture Extender of HPV type 45

| SEQ ID NO | CAPTURE EXTENDER OF HPV TYPE 45 |
|---|---|
| 155. | tatacctctgtgcgttccaatgtTTTTTctcttggaaagaaagt |
| 156. | tataaataaatctttaaaagcaaattgaTTTTTctcttggaaagaaagt |
| 157. | cagtgttgctcggggtccaTTTTTctcttggaaagaaagt |
| 158. | tgactaacgccatctgcttcatTTTTTctcttggaaagaaagt |
| 159. | agctcaattctgccgtcacacTTTTTctcttggaaagaaagt |
| 160. | catctgccgagctctctactgtaTTTTTctcttggaaagaaagt |

TABLE 19

Label Extender of HPV type 45

| SEQ ID NO | LABEL EXTENDER OF HPV TYPE 45 |
|---|---|
| 161. | tttctgctgggttcaatgattTTTTTgaagttaccgtttt |
| 162. | cgtttgtccttaaggtgtctacgttTTTTTctgagtcaaagcat |
| 163. | tgtattacactgccctcggtactgTTTTTgaagttaccgtttt |
| 164. | gccgtgcctggtcacaacaTTTTTctgagtcaaagcat |
| 165. | cctacgtctgcgaagtctttcttTTTTTgaagttaccgtttt |
| 166. | tgcatacttattgctatacttgtgtttcTTTTTctgagtcaaagcat |
| 167. | ttccaaatgcaatacaatttcttgTTTTTgaagttaccgtttt |
| 168. | caacaggatctaattcattctgaggTTTTTctgagtcaaagcat |
| 169. | ttaattgctcgtaacacaacaggtTTTTTgaagttaccgtttt |
| 170. | cgttttcctcctctgactcgcTTTTTctgagtcaaagcat |
| 171. | tcgggctggtagttgtgcaTTTTTgaagttaccgtttt |
| 172. | cgctgtggttcggctcgTTTTTctgagtcaaagcat |

TABLE 20

Blocking Label Extender of HPV type 45

| SEQ ID NO | BLOCKING LABEL EXTENDER OF HPV TYPE 45 |
|---|---|
| 173. | gcagcatatgctatacagtctctatacac |
| 174. | ggaataaaagtctatacatttatggcat |
| 175. | gagtttgaataatatcttaattctctaattct |
| 176. | ttttttccagtgtctctccatataca |
| 177. | cttattaacaaattatacaactctgtattagtta |
| 178. | tctggcaccgcaggcac |
| 179. | tccagctatgctgtggaatctt |
| 180. | ttacaacatacacacaaaattttgtga |

In certain embodiments, the target polynucleotide is an E6 and/or E7 sequence from HPV type 45. In such embodiments, at least one Capture Extender probe (e.g., at least two, three, four, or five) comprises a target hybridizing sequence selected from Table 18 (underlined). At least one Capture Extender probe may comprise, consist essentially of, or consist of a sequence selected from SEQ ID NOS: 155 to 160 (Tables 18). In such embodiments, at least one Label Extender (e.g., at least two, three, four, or five) may comprise a target-hybridizing sequence shown in Table 19 (underlined). At least one Label Extender probe may comprise, consist essentially of, or consist of a sequence selected from SEQ ID NOS: 161 to 172 (Table 19). The test may further employ a Blocking Label (BL), e.g., at least one, two, or three BLs each containing a sequence selected from SEQ ID NOS: 173 to 180 (Table 20).

In certain embodiments, the target polynucleotide is an E6 and/or E7 sequence from HPV type 51. In such embodiments, at least one Capture Extender probe (e.g., at least two, three, four, or five) comprises a target hybridizing sequence selected from Table 21 (underlined). At least one Capture Extender probe may comprise, consist essentially of, or consist of a sequence selected from SEQ ID NOS: 181 to 187 (Tables 21). In such embodiments, at least one Label Extender (e.g., at least two, three, four, or five) may comprise a target-hybridizing sequence shown in Table 22 (underlined). At least one Label Extender probe may comprise, consist essentially of, or consist of a sequence selected from SEQ ID NOS: 188 to 201 (Table 22). The test may further employ a Blocking Label (BL), e.g., at least one, two, or three BLs each containing a sequence selected from SEQ ID NOS: 202 to 206 (Table 23).

TABLE 21

Capture Extender of HPV type 51

| SEQ ID NO | CAPTURE EXTENDER OF HPV TYPE 51 |
|---|---|
| 181. | ggtctttccctcttgtcttcgaaTTTTTctcttggaaagaaagt |
| 182. | tgcatagaaacgttcaaagcttcTTTTTctcttggaaagaaagt |
| 183. | tttgaataaaacagtaaacattgtttgTTTTTctcttggaaagaaagt |
| 184. | tcgataaatcatataagcttttttagtaaTTTTTctcttggaaagaaagt |
| 185. | cgcattgccccgtccaaTTTTTctcttggaaagaaagt |
| 186. | cgtgtacgttgccagcaattagTTTTTctcttggaaagaaagt |
| 187. | ggagcttcaattctgtaacacgtaTTTTTctcttggaaagaaagt |

TABLE 22

Label Extender of HPV type 51

| SEQ ID NO | LABEL EXTENDER OF HPV TYPE 51 |
|---|---|
| 188. | ttacaatacacacacactacctgtatattgTTTTTgaagttaccgtttt |
| 189. | ttatatacatctgctctacataattcctttTTTTTctgagtcaaagcat |
| 190. | atacaatcttaatttcagtaaatgctacaTTTTTgaagttaccgtttt |
| 191. | catactgcatatggattattatccctatTTTTTctgagtcaaagcat |
| 192. | acctgctataacgtctatactctctaattTTTTTgaagttaccgtttt |
| 193. | ttgcctctaatgtagtaccatacacagTTTTTctgagtcaaagcat |
| 194. | gtggtctttgacatctatgacaccttaTTTTTgaagttaccgtttt |
| 195. | tttgcttttcttcaggcccaaTTTTTctgagtcaaagcat |
| 196. | cacttgggtttcgttacgttgtTTTTTgaagttaccgttttt |

TABLE 22-continued

Label Extender of HPV type 51

| SEQ ID NO | LABEL EXTENDER OF HPV TYPE 51 |
|---|---|
| 197. | cattaccacgcatggctttattaTTTTTctgagtcaaagcat |
| 198. | tgcaatactacatcttttaattgtggtaTTTTTgaagttaccgtttt |
| 199. | agtcaatttcagtctgtggttgttaaaTTTTTctgagtcaaagcat |
| 200. | tcaaattgctcgtagcattgcaTTTTTgaagttaccgtttt |
| 201. | tacttcatcctcctcctctgagctgTTTTTctgagtcaaagcat |

TABLE 23

Blocking Label Extender of HPV type 51

| SEQ ID NO | BLOCKING EXTENDER OF HPV TYPE 51 |
|---|---|
| 202. | acataattcatgcagcgttcgt |
| 203. | cttttttttttcgtccaccaatt |
| 204. | cgtcccgctatttcatggaac |
| 205. | ctggtagctggtcacgcatattatc |
| 206. | gcctgtccagcccgtcttt |

In certain embodiments, the target polynucleotide is an E6 and/or E7 sequence from HPV type 52. In such embodiments, at least one Capture Extender probe (e.g., at least two, three, four, or five) comprises a target hybridizing sequence selected from Table 24 (underlined). At least one Capture Extender probe may comprise, consist essentially of, or consist of a sequence selected from SEQ ID NOS: 207 to 212 (Tables 24). In such embodiments, at least one Label Extender (e.g., at least two, three, four, or five) may comprise a target-hybridizing sequence shown in Table 25 (underlined). At least one Label Extender probe may comprise, consist essentially of, or consist of a sequence selected from SEQ ID NOS: 213 to 224 (Table 25). The test may further employ a Blocking Label (BL), e.g., at least one, two, or three BLs each containing a sequence selected from SEQ ID NOS: 225 to 238 (Table 26).

TABLE 24

Capture Extender of HPV type 52

| SEQ ID NO | CAPTURE EXTENDER OF HPV TYPE 52 |
|---|---|
| 207. | gtgcagggtccgggtcTTTTTctcttggaaagaaagt |
| 208. | cactctgaacagcgccctgtTTTTTctcttggaaagaaagt |
| 209. | cacaggtcggggtctccaaTTTTTctcttggaaagaaagt |
| 210. | cagtgctatgaatgcatagccgTTTTTctcttggaaagaaagt |
| 211. | tgtcccaacagcatttgcTTTTTctcttggaaagaaagt |
| 212. | ttcagggtcctccattgcagTTTTTctcttggaaagaaagt |

TABLE 25

Label Extender of HPV type 52

| SEQ ID NO | LABEL EXTENDER OF HPV TYPE 52 |
|---|---|
| 213. | cttccagcacctcacacaattcTTTTTgaagttaccgtttt |
| 214. | gccttatttcatgcaccgattTTTTTctgagtcaaagcat |
| 215. | tttgcactgcacacactgcaTTTTTgaagttaccgtttt |
| 216. | tatacctctcttcgttgtagctctttTTTTTctgagtcaaagcat |
| 217. | tttctttttcttcaggacataatggTTTTTgaagttaccgtttt |
| 218. | tcgcttgtttgcattaacatgtcTTTTTctgagtcaaagcat |
| 219. | cgcatgacgttacacttgggtTTTTTgaagttaccgtttt |
| 220. | aatcttttatagttgctttgtctccaTTTTTctgagtcaaagcat |
| 221. | gccggtccacaccatctgtatTTTTTgaagttaccgtttt |
| 222. | gcttgttctgcttgtccatctgTTTTTctgagtcaaagcat |
| 223. | atgtcacaatgtagtaattgcttgtgTTTTTgaagttaccgtttt |
| 224. | tagtgtgctatcacaactgtgacaatTTTTTctgagtcaaagcat |

TABLE 26

Blocking Label Extender of HPV type 52

| SEQ ID NO | BLOCKING LABEL EXTENDER OF HPV TYPE 52 |
|---|---|
| 225. | ctattcgtaaatctgtaaatagaaacttg |
| 226. | cgccatatggattattgtctctatata |
| 227. | aaaagcgtaggcacataatacaca |
| 228. | tgataatgcctatattcacttatcttagata |
| 229. | tctaatgttttcccatacagtgaatat |
| 230. | cacttaatggttttttttaccctctct |
| 231. | cgtttgacaaattatacatctaatagttattt |
| 232. | ccaacgacccataatattatgaaa |
| 233. | ttgtttcaggttgcagatctaatatat |
| 234. | aattgctcatagcagtgtaggtcag |
| 235. | cctcctcatctgagctgtcacct |
| 236. | tgtagagtacgaaggtccgtcg |
| 237. | ccggggcacacaacttgtaa |
| 238. | ggttgtttatagccgtgcacag |

In certain embodiments, the target polynucleotide is an E6 and/or E7 sequence from HPV type 56. In such embodiments, at least one Capture Extender probe (e.g., at least two, three, four, or five) comprises a target hybridizing sequence selected from Table 27 (underlined). At least one Capture Extender probe may comprise, consist essentially of, or consist of a sequence selected from SEQ ID NOS: 239 to 245 (Tables 27). In such embodiments, at least one Label Extender (e.g., at least two, three, four, or five) may comprise a target-hybridizing sequence shown in Table 28 (underlined). At least one Label Extender probe may comprise, consist essentially of, or consist of a sequence selected from SEQ ID NOS: 246 to 257 (Table 28). The test may further employ a Blocking Label (BL), e.g., at least one, two, or three BLs each containing a sequence selected from SEQ ID NOS: 258 to 262 (Table 29).

TABLE 27

Capture Extender of HPV type 56

| SEQ ID NO | CAPTURE EXTENDER OF HPV TYPE 56 |
|---|---|
| 239. | gttagttctttttttgcaatatacacatgTTTTTctcttggaaagaaagt |
| 240. | atgcaaaattatatacctcagcacgtTTTTTctcttggaaagaaagt |
| 241. | gcacactgcataaggaaaatcaTTTTTctcttggaaagaaagt |
| 242. | cacaatgcaattgcttttcctcTTTTTctcttggaaagaaagt |
| 243. | ctattagatgaaatcgtcttttctgtTTTTTctcttggaaagaaagt |
| 244. | gtctccagcaccccaaacatTTTTTctcttggaaagaaagt |
| 245. | aggtcaatttctgtttgaggtgttaTTTTTctcttggaaagaaagt |

TABLE 28

Label Extender of HPV type 56

| SEQ ID NO | LABEL EXTENDER OF HPV TYPE 56 |
|---|---|
| 246. | catacactgaatagtcataatacctatatttTTTTTgaagttaccgtttt |
| 247. | gttttttagttatactttctagtgtagctcTTTTTctgagtcaaagcat |
| 248. | gtagcaccttattaataaatcacataactTTTTTgaagttaccgtttt |
| 249. | cggagttaacggactttgacatctTTTTTctgagtcaaagcat |
| 250. | tgtagattctctaggttctctagatgtttTTTTTgaagttaccgtttt |
| 251. | ttggtactttaccatgcatgattatacTTTTTctgagtcaaagcat |
| 252. | cctcatcctcatcctctgagctTTTTTgaagttaccgtttt |
| 253. | gctcctgcaaatggtctacttcatTTTTTctgagtcaaagcat |
| 254. | cttgtctagcttgctgtggccTTTTTgaagttaccgtttt |
| 255. | gtgtattaggtaacacgtatgttgtttagTTTTTctgagtcaaagcat |
| 256. | cacaaacttacactcacaacaaggtacTTTTTgaagttaccgtttt |
| 257. | ggtactgtgaatgtccaactgcacTTTTTctgagtcaaagcat |

TABLE 29

Blocking Label Extender of HPV type 56

| SEQ ID NO | BLOCKING LABEL EXTENDER OF HPV TYPE 56 |
|---|---|
| 258. | tccctatacactaagtttaattcagtgc |
| 259. | tctaactttactataaaacaataaacatactct |
| 260. | gacccggtccaaccatgtg |
| 261. | gttctaatataacgtcttgcagcg |
| 262. | gtccaattgctcattgcactgt |

In certain embodiments, the target polynucleotide is an E6 and/or E7 sequence from HPV type 58. In such embodiments, at least one Capture Extender probe (e.g., at least two, three, four, or five) comprises a target hybridizing sequence selected from Table 30 (underlined). At least one Capture Extender probe may comprise, consist essentially of, or consist of a sequence selected from SEQ ID NOS: 263 to 269 (Tables 30). In such embodiments, at least one Label Extender (e.g., at least two, three, four, or five) may comprise a target-hybridizing sequence shown in Table 31 (underlined). At least one Label Extender probe may comprise, consist essentially of, or consist of a sequence selected from SEQ ID NOS: 270 to 281 (Table 31). The test may further employ a Blocking Label (BL), e.g., at least one, two, or three BLs each containing a sequence selected from SEQ ID NOS: 282 to 286 (Table 32).

TABLE 30

Capture Extender of HPV type 58

| SEQ ID NO | CAPTURE EXTENDER OF HPV TYPE 58 |
|---|---|
| 263. | <u>ctcctctgcgtcctggaaca</u>TTTTTctcttggaaagaaagt |
| 264. | <u>tcaattcgatttcatgcacaga</u>TTTTTctcttggaaagaaagt |
| 265. | <u>gtcttttgcattcaacgcatt</u>TTTTTctcttggaaagaaagt |
| 266. | <u>cactattcttaaatctgcaaatacaaag</u>TTTTTctcttggaaagaaagt |
| 267. | <u>agcaatcgtaagcacactttacatac</u>TTTTTctcttggaaagaaagt |
| 268. | <u>attaatatttcatttaaacactttttagtgt</u>TTTTTctcttggaaagaaagt |
| 269. | <u>ccgtccaagcctatttcatcct</u>TTTTTctcttggaaagaaagt |

TABLE 31

Label Extender of HPV type 58

| SEQ ID NO | LABEL EXTENDER OF HPV TYPE 58 |
|---|---|
| 270. | <u>atcatgcaatgtccgtggttt</u>TTTTTgaagttaccgtttt |
| 271. | <u>tgtctccaacgcctgacacaa</u>TTTTTctgagtcaaagcat |
| 272. | <u>ataattataatgtctatactcacttattttagat</u>TTTTTgaagttaccgtttt |

TABLE 31-continued

Label Extender of HPV type 58

| SEQ ID NO | LABEL EXTENDER OF HPV TYPE 58 |
|---|---|
| 273. | <u>ttgttctaatgtgtctccatatagcga</u>TTTTTctgagtcaaagcat |
| 274. | <u>caatggtctttgacaaataatacatcta</u>TTTTTgaagttaccgtttt |
| 275. | <u>tgccttttttttttcttgtggaca</u>TTTTTctgagtcaaagcat |
| 276. | <u>cctgtccaacgacccgaaatat</u>TTTTTgaagttaccgtttt |
| 277. | <u>tccaacacactgcacagcgc</u>TTTTTctgagtcaaagcat |
| 278. | <u>tgtgtttgtctacgtcggggtc</u>TTTTTgaagttaccgtttt |
| 279. | <u>atggcgttgttacaggttacact</u>TTTTTctgagtcaaagcat |
| 280. | <u>tcatagcagaataggtcagttggt</u>TTTTTgaagttaccgtttt |
| 281. | <u>cgtctgagctgtcacataattgc</u>TTTTTctgagtcaaagcat |

TABLE 32

Blocking Label Extender of HPV type 58

| SEQ ID NO | BLOCKING LABEL EXTENDER OF HPV TYPE 58 |
|---|---|
| 282. | tcatatacctcagatcgctgcaaa |
| 283. | tgcaaatggatttccatctctata |
| 284. | tatgaaaccttttgtttaaatccaca |
| 285. | gcgttgggttgtttcctctc |
| 286. | tcaggatgtaaatctaaatatattctctta |

In certain embodiments, the target polynucleotide is an E6 and/or E7 sequence from HPV type 59. In such embodiments, at least one Capture Extender probe (e.g., at least two, three, four, or five) comprises a target hybridizing sequence selected from Table 33 (underlined). At least one Capture Extender probe may comprise, consist essentially of, or consist of a sequence selected from SEQ ID NOS: 287 to 292 (Tables 33). In such embodiments, at least one Label Extender (e.g., at least two, three, four, or five) may comprise a target-hybridizing sequence shown in Table 34 (underlined). At least one Label Extender probe may comprise, consist essentially of, or consist of a sequence selected from SEQ ID NOS: 293 to 304 (Table 34). The test may further employ a Blocking Label (BL), e.g., at least one, two, or three BLs each containing a sequence selected from SEQ ID NOS: 305 to 317 (Table 35).

TABLE 33

Capture Extender of HPV type 59

| SEQ ID NO | CAPTURE EXTENDER OF HPV TYPE 59 |
|---|---|
| 287. | <u>ggatcctcaaagcgtgcca</u>TTTTTctcttggaaagaaagt |
| 288. | <u>tgatacgaatatcatgcagagg</u>TTTTTctcttggaaagaaagt |

TABLE 33-continued

Capture Extender of HPV type 59

| SEQ ID NO | CAPTURE EXTENDER OF HPV TYPE 59 |
|---|---|
| 289. | tctataacagcgtatcagcagctcTTTTTctcttggaaagaaagt |
| 290. | tgttggacatagaggttttaggcaTTTTTctcttggaaagaaagt |
| 291. | taggtgtcttgctcgggtccTTTTTctcttggaaagaaagt |
| 292. | aaagtgttgcttttggtccatgTTTTTctcttggaaagaaagt |

TABLE 34

Label Extender of HPV type 59

| SEQ ID NO | LABEL EXTENDER OF HPV TYPE 59 |
|---|---|
| 293. | cccctttgcaaaacacacaatTTTTTgaagttaccgtttt |
| 294. | tcaaatacctctctttcttgcagttTTTTTctgagtcaaagcat |
| 295. | cctctaatgtttctccatacacggTTTTTgaagttaccgtttt |
| 296. | atgtaacggtgtcttggtttcagTTTTTctgagtcaaagcat |
| 297. | gcgcttgtcgttgctgtctTTTTTgaagttaccgtttt |
| 298. | cattgttttacaccagtgtttcactacTTTTTctgagtcaaagcat |
| 299. | ggttccaaatctaaaacaatgtcacTTTTTgaagttaccgtttt |
| 300. | aaggtcaacttcctcataattttgtTTTTTctgagtcaaagcat |
| 301. | tcaggtaattgctcgtagcacacTTTTTgaagttaccgtttt |
| 302. | ttttcattctcggagtcggagTTTTTctgagtcaaagcat |
| 303. | gcgaggtttctactactagctgaagTTTTTgaagttaccgtttt |
| 304. | aaggctcgcaatccgtcttTTTTTctgagtcaaagcat |

TABLE 35

Blocking Label Extender of HPV type 59

| SEQ ID NO | BLOCKING LABEL EXTENDER OF HPV TYPE 59 |
|---|---|
| 305. | ggcagtttgtatggtcgttgtga |
| 306. | aatattcaatgttgtgctcaaatca |
| 307. | tacactataaataagtcattaaaagcaaat |
| 308. | gctgcatacggtgtacagtctcta |
| 309. | cataaaatgaaatgcatttcagacac |
| 310. | aatctctataatatcttaattctcttactcttg |
| 311. | cttttttcagttatatgctttaatttatc |
| 312. | tatatattccagctatattatggaatctt |

TABLE 35-continued

Blocking Label Extender of HPV type 59

| SEQ ID NO | BLOCKING LABEL EXTENDER OF HPV TYPE 59 |
|---|---|
| 313. | gacacccacgacactgtcctg |
| 314. | gatgattaactccatctggttcatct |
| 315. | cagctcgtctagctagtagcaaag |
| 316. | acaatgttgtgacgctgtggtt |
| 317. | ttgattattacacttacaacacacac |

In certain embodiments, the target polynucleotide is an E6 and/or E7 sequence from HPV type 68. In such embodiments, at least one Capture Extender probe (e.g., at least two, three, four, or five) comprises a target hybridizing sequence selected from Table 36 (underlined). At least one Capture Extender probe may comprise, consist essentially of, or consist of a sequence selected from SEQ ID NOS: 318 to 324 (Tables 36). In such embodiments, at least one Label Extender (e.g., at least two, three, four, or five) may comprise a target-hybridizing sequence shown in Table 37 (underlined). At least one Label Extender probe may comprise, consist essentially of, or consist of a sequence selected from SEQ ID NOS: 325 to 338 (Table 37). The test may further employ a Blocking Label (BL), e.g., at least one, two, or three BLs each containing a sequence selected from SEQ ID NOS: 339 to 347 (Table 38).

TABLE 36

Capture Extender of HPV type 68

| SEQ ID NO | CAPTURE EXTENDER OF HPV TYPE 68 |
|---|---|
| 318. | gtcatgcaatgtagtgtccaatgtTTTTTctcttggaaagaaagt |
| 319. | tgttaggtgccttagtattctgcTTTTTctcttggaaagaaagt |
| 320. | cgcttactggtccagcagtgcTTTTTctcttggaaagaaagt |
| 321. | cggtgggctttggtccatgTTTTTctcttggaaagaaagt |
| 322. | atagctctaacacaatttcctgcaTTTTTctcttggaaagaaagt |
| 323. | cccgcgacgcttctactactTTTTTctcttggaaagaaagt |
| 324. | caaaatttagtgagtccataaacagcTTTTTctcttggaaagaaagt |

TABLE 37

Label Extender of HPV type 68

| SEQ ID NO | LABEL EXTENDER OF HPV TYPE 68 |
|---|---|
| 325. | cttctgcaatagacacagtctattgtaacTTTTTgaagttaccgtttt |
| 326. | catatacctctgtccgttgtagttgcTTTTTctgagtcaaagcat |
| 327. | atttaatacatgattggcatgcagTTTTTgaagttaccgtttt |
| 328. | cgtagttcccgtattttagcataaaTTTTTctgagtcaaagcat |
| 329. | gcatacaccgattccgagtaatatTTTTTgaagttaccgtttt |
| 330. | ctttgtattagttatggtttctaatgtagttTTTTTctgagtcaaagcat |
| 331. | actcatgcaccttatcaataaattatataaTTTTTgaagttaccgtttt |
| 332. | tggacacaatggtttcaggcaTTTTTctgagtcaaagcat |
| 333. | cggctgtatttcattgtatggacTTTTTgaagttaccgtttt |
| 334. | tgctcgtgacatacaaggtcaacTTTTTctgagtcaaagcat |
| 335. | ctatttcatcgtctgaatctcctaatTTTTTgaagttaccgtttt |
| 336. | aactgcatggtcgggttcatTTTTTctgagtcaaagcat |
| 337. | gctgttgttcgtcccgtctgTTTTTgaagttaccgtttt |
| 338. | caacacagacactgaattctgtgacTTTTTctgagtcaaagcat |

TABLE 38

Blocking Label Extender of HPV type 68

| SEQ ID NO | BLOCKING LABEL EXTENDER OF HPV TYPE 68 |
|---|---|
| 339. | ctacacataggtcactaaaggcaaatt |
| 340. | caaatggtaccccgtctctataca |
| 341. | gctattttatgtaatcttcgttttgt |
| 342. | cgacactgtcctgtaaagtttcct |
| 343. | gtatgcgtctgcggtcctct |
| 344. | catagttacttaaacttgtgtttcttgac |
| 345. | gctagtagtagatgttggtggtgatt |
| 346. | agttgcagtgccttgttacactta |
| 347. | tgttgtagtgtccgcaggttgt |

In certain embodiments, the target polynucleotide is an E6 and/or E7 sequence from low risk-HPV type 6. In such embodiments, at least one Capture Extender probe (e.g., at least two, three, four, or five) comprises a target hybridizing sequence selected from Table 39 (underlined). At least one Capture Extender probe may comprise, consist essentially of, or consist of a sequence selected from SEQ ID NOS: 348 to 354 (Tables 39). In such embodiments, at least one Label Extender (e.g., at least two, three, four, or five) may comprise a target-hybridizing sequence shown in Table 40 (underlined). At least one Label Extender probe may comprise, consist essentially of, or consist of a sequence selected from SEQ ID NOS: 355 to 368 (Table 40). The test may further employ a Blocking Label (BL), e.g., at least one, two, or three BLs each containing a sequence selected from SEQ ID NOS: 369 to 375 (Table 41).

TABLE 39

Capture Extender of HPV type 6

| SEQ ID NO | CAPTURE EXTENDER OF HPV TYPE 6 |
|---|---|
| 348. | tggatagccgcctcgaaaTTTTTctcttggaaagaaagt |
| 349. | cacgcgcaggctgcataTTTTTctcttggaaagaaagt |
| 350. | tttttccatgaaattctaggcagTTTTTctcttggaaagaaagt |
| 351. | taggcagcgacccttccaTTTTTctcttggaaagaaagt |
| 352. | caatatcctttaggqtaacatgtcttcTTTTTctcttggaaagaaagt |
| 353. | cagaagctgttgcacttctctgaTTTTTctcttggaaagaaagt |
| 354. | ggtcttcggtgcgcagatgTTTTTctcttggaaagaaagt |

TABLE 40

Label Extender of HPV type 6

| SEQ ID NO | LABEL EXTENDER OF HPV TYPE 6 |
|---|---|
| 355. | attaatttgcaacgtatgcatagataTTTTTgaagttaccgtttt |
| 356. | gtgcattcttgcaaaacacacaTTTTTctgagtcaaagcat |
| 357. | tatgaataaatctctgctgtggtcaTTTTTgaagttaccgtttt |
| 358. | caggacctttaggtgtttatatgcaTTTTTctgagtcaaagcat |
| 359. | tcttcaactgttgttgcatatccaTTTTTgaagttaccgtttt |
| 360. | cacgtctaagatgtcttgtttagtttctTTTTTctgagtcaaagcat |
| 361. | cgccttggttagtatatgttttacctTTTTTgaagttaccgtttt |

TABLE 40-continued

Label Extender of HPV type 6

| SEQ ID NO | LABEL EXTENDER OF HPV TYPE 6 |
|---|---|
| 362. | cgtacaatttagctttatgaaccgTTTTTctgagtcaaagcat |
| 363. | ggtctggaggttgcaggtctaataTTTTTgaagttaccgtttt |

TABLE 40-continued

Label Extender of HPV type 6

| SEQ ID NO | LABEL EXTENDER OF HPV TYPE 6 |
|---|---|
| 364. | tgctcatagcaatgtaaccctacagTTTTTctgagtcaaagcat |
| 365. | acctcatcttctgagctgtctactaatTTTTTgaagttaccgtttt |
| 366. | cttgtccgtccacttcgtccTTTTTctgagtcaaagcat |
| 367. | cagtcgaacgttgctgtcacatTTTTTgaagttaccgtttt |
| 368. | tgtctgtttctgtacactgcacaacTTTTTctgagtcaaagcat |

TABLE 41

Blocking Label Extender of HPV type 6

| SEQ ID NO | BLOCKING LABEL EXTENDER OF HPV TYPE 6 |
|---|---|
| 369. | gcataatcaaagtgtctatattggttta |
| 370. | tgacacaggtagcaccgaattag |
| 371. | tttctacttcacacagcggtttg |
| 372. | catgcatgttgtccagcagtg |
| 373. | gaaatgttgttttaaaggttgtgaat |
| 374. | ccacagcaacaggtcactatttg |
| 375. | ggacacactatgtttagtgttcccaa | least two, three, four, or five) comprises a target hybridizing sequence selected from Table 42 (underlined). At least one Capture Extender probe may comprise, consist essentially of, or consist of a sequence selected from SEQ ID NOS: 376 to 382 (Tables 42). In such embodiments, at least one Label Extender (e.g., at least two, three, four, or five) may comprise a target-hybridizing sequence shown in Table 43 (underlined). At least one Label Extender probe may comprise, consist essentially of, or consist of a sequence selected from SEQ ID NOS: 383 to 398 (Table 43). The test may further employ a Blocking Label (BL), e.g., at least one, two, or three BLs each containing a sequence selected from SEQ ID NOS: 399 to 403 (Table 44).

TABLE 42

Capture Extender of HPV type 11

| SEQ ID NO | CAPTURE EXTENDER OF HPV TYPE 11 |
|---|---|
| 376. | caaagaaagattaaacgtcttgcacTTTTTctcttggaaagaaagt |
| 377. | cgcactgaatttgcagagtgtgTTTTTctcttggaaagaaagt |
| 378. | tggttttctcttctactgtaggtgcTTTTTctcttggaaagaaagt |
| 379. | cgaattaacacttttaaaatatcttcatTTTTTctcttggaaagaaagt |
| 380. | agcgtgcctttcccaatatgTTTTTctcttggaaagaaagt |
| 381. | accctacagggtcaggaggctTTTTTctcttggaaagaaagt |
| 382. | gtgcgtcttgtttgtccacctTTTTTctcttggaaagaaagt |

TABLE 43

Label Extender of HPV type 11

| SEQ ID NO | LABEL EXTENDER OF HPV TYPE 11 |
|---|---|
| 383. | tggaggcatctttactttccataaTTTTTgaagttaccgtttt |
| 384. | aactggtctatagatgttgcagacgTTTTTctgagtcaaagcat |
| 385. | atatgcatatatctctgcggtggTTTTTgaagttaccgtttt |
| 386. | acacaacctttaggttcttataggcTTTTTctgagtcaaagcat |
| 387. | aagcaacaggcacacgctgTTTTTgaagttaccgtttt |
| 388. | ggttaattttcccttgcagttctTTTTTctgagtcaaagcat |
| 389. | cggcttgtgacacaggtaacaaTTTTTgaagttaccgtttt |
| 390. | tgctttagttttctatttcacacaaTTTTTctgagtcaaagcat |
| 391. | cttccactggttatttagttttatgaTTTTTgaagttaccgtttt |
| 392. | ccagcagtgtaagcaacgaccTTTTTctgagtcaaagcat |
| 393. | gtcttctaattgctcatagcaatgtaTTTTTgaagttaccgtttt |
| 394. | tgtccacctcatcttctgagctTTTTTctgagtcaaagcat |
| 395. | gtatttggtaatgttgtgttaaaggttTTTTTgaagttaccgtttt |
| 396. | cacatccacagcaacaggtcaTTTTTctgagtcaaagcat |
| 397. | caaccagtcggacgttgctgtTTTTTgaagttaccgtttt |
| 398. | atgtctccgtctgtgcactccaTTTTTctgagtcaaagcat |

In certain embodiments, the target polynucleotide is an E6 and/or E7 sequence from low risk-HPV type 11. In such embodiments, at least one Capture Extender probe (e.g., at

TABLE 44

Blocking Label Extender of HPV type 11

| SEQ ID NO | BLOCKING LABEL EXTENDER OF HPV TYPE 11 |
|---|---|
| 399. | tcagtgcattcctgcaaaaca |
| 400. | caaagggaaagttgtctcgcc |
| 401. | atatgcagcataattaaagtgtctatatt |
| 402. | taacaagtcttccatgcatgttgt |
| 403. | gcaggtctagtactatatcctttaggg |

In certain embodiments, the target polynucleotide is an E6 and/or E7 sequence from low risk-HPV type 40. In such embodiments, at least one Capture Extender probe (e.g., at least two, three, four, or five) comprises a target hybridizing sequence selected from Table 45 (underlined). At least one Capture Extender probe may comprise, consist essentially of, or consist of a sequence selected from SEQ ID NOS: 404 to 410 (Tables 45). In such embodiments, at least one Label Extender (e.g., at least two, three, four, or five) may comprise a target-hybridizing sequence shown in Table 46 (underlined). At least one Label Extender probe may comprise, consist essentially of, or consist of a sequence selected from SEQ ID NOS: 411 to 424 (Table 46). The test may further employ a Blocking Label (BL), e.g., at least one, two, or three BLs each containing a sequence selected from SEQ ID NOS: 425 to 432 (Table 47).

TABLE 45

Capture Extender of HPV type 40

| SEQ ID NO | CAPTURE EXTENDER OF HPV TYPE 40 |
|---|---|
| 404. | tcatacagggtcctggcctgTTTTTctcttggaaagaaagt |
| 405. | ggaccgtcttgcaaaacacacTTTTTctcttggaaagaaagt |
| 406. | cgtggacatgcggcgtgtTTTTTctcttggaaagaaagt |
| 407. | aaagaattgcgtcttctttacaatatTTTTTctcttggaaagaaagt |
| 408. | agtttagacatacaggttcagggtgTTTTTctcttggaaagaaagt |
| 409. | acaccgagttactactttaaatgattgTTTTTctcttggaaagaaagt |
| 410. | tgatggaacaatgcactgctaagTTTTTctcttggaaagaaagt |

TABLE 46

Label Extender of HPV type 40

| SEQ ID NO | LABEL EXTENDER OF HPV TYPE 40 |
|---|---|
| 411. | tgtaatattgcactggtcacacagtTTTTTgaagttaccgtttt |
| 412. | aatcaatttgcaacgtaggcaaTTTTTctgagtcaaagcat |
| 413. | ggccagtacctcagctgttttaTTTTTgaagttaccgtttt |
| 414. | cacaacatataactctctaaaggcaaaTTTTTctgagtcaaagcat |
| 415. | ccgtgcaggtccaggcacTTTTTgaagttaccgtttt |
| 416. | atctaaagtttctgtattggtttacttttTTTTTctgagtcaaagcat |

TABLE 46-continued

Label Extender of HPV type 40

| SEQ ID NO | LABEL EXTENDER OF HPV TYPE 40 |
|---|---|
| 417. | gttaatcctgtctcttcttccacgTTTTTgaagttaccgtttt |
| 418. | cagcatctaatccttacttgtaaaatgTTTTTctgagtcaaagcat |
| 419. | ccctgtccacgaatcttttaatttTTTTTgaagttaccgtttt |
| 420. | catttcttccagcaatgtagacagtaTTTTTctgagtcaaagcat |
| 421. | gagctgtctaattgctcgttgcTTTTTgaagttaccgtttt |
| 422. | ctgttcatggtcatcttctgagtctTTTTTctgagtcaaagcat |
| 423. | tctactgtgtaagctgtctagttggtcTTTTTgaagttaccgtttt |
| 424. | cgtgggttgctcacgctcTTTTTctgagtcaaagcat |

TABLE 47

Blocking Label Extender of HPV type 40

| SEQ ID NO | BLOCKING LABEL EXTENDER OF HPV TYPE 40 |
|---|---|
| 425. | ggaaagtcgtcgcgcca |
| 426. | gttggtgcataggctgcgt |
| 427. | gacaaaggcttgtggcacttg |
| 428. | ggttggttttttccacggga |
| 429. | gcgttggcctttctccatg |
| 430. | caggtttaacacaatgtctccga |
| 431. | caaatttacttgcaggtcctgttg |
| 432. | cgcaccaaacactgacaaaatac |

In certain embodiments, the target polynucleotide is an E6 and/or E7 sequence from low risk-HPV type 42. In such embodiments, at least one Capture Extender probe (e.g., at least two, three, four, or five) comprises a target hybridizing sequence selected from Table 48 (underlined). At least one Capture Extender probe may comprise, consist essentially of, or consist of a sequence selected from SEQ ID NOS: 433 to 439 (Tables 48). In such embodiments, at least one Label Extender (e.g., at least two, three, four, or five) may comprise a target-hybridizing sequence shown in Table 49 (underlined). At least one Label Extender probe may comprise, consist essentially of, or consist of a sequence selected from SEQ ID NOS: 440 to 451 (Table 49). The test may further employ a Blocking Label (BL), e.g., at least one, two, or three BLs each containing a sequence selected from SEQ ID NOS: 452 to 462 (Table 50).

TABLE 48

Capture Extender of HPV type 42

| SEQ ID NO | CAPTURE EXTENDER OF HPV TYPE 42 |
|---|---|
| 433. | acattctgccttaactgggaccTTTTTctcttggaaagaaagt |
| 434. | cctgttaagtgcttttttgcaccTTTTTctcttggaaagaaagt |
| 435. | acgcgagcacctctgcgTTTTTctcttggaaagaaagt |
| 436. | caatataaattgaaatcttgtacctgtatcTTTTTctcttggaaagaaagt |
| 437. | cattgtcctctgcaatgcgtaTTTTTctcttggaaagaaagt |
| 438. | cgctgtatgtcctgtttggctTTTTTctcttggaaagaaagt |
| 439. | cttatgtccgcctctgtacactgTTTTTctcttggaaagaaagt |

TABLE 49

Label Extender of HPV type 42

| SEQ ID NO | LABEL EXTENDER OF HPV TYPE 42 |
|---|---|
| 440. | ctgtgatgaggcagatgtacctgTTTTTgaagttaccgtttt |
| 441. | tacacaattggtataatgtgcgtggTTTTTctgagtcaaagcat |
| 442. | gcaatgtcagcccaaattcctTTTTTgaagttaccgtttt |
| 443. | aaatgcaggaaatctgtaaattccTTTTTctgagtcaaagcat |
| 444. | caaaatgctgatctttcgtagtgtTTTTTgaagttaccgtttt |
| 445. | agtccagtttctttctccactgtatacTTTTTctgagtcaaagcat |
| 446. | gataacggcttttgacacaaggTTTTTgaagttaccgtttt |
| 447. | aatatgatggttttttcgctctgtTTTTTctgagtcaaagcat |
| 448. | atgtcaaacaaaacaatgtcctttaTTTTTgaagttaccgtttt |
| 449. | atgggtgtctcacacgttggtTTTTTctgagtcaaagcat |
| 450. | caaaagcatctgttgcaggtttTTTTTgaagttaccgtttt |
| 451. | ggacacacaatatccagtgtgccTTTTTctgagtcaaagcat |

TABLE 50

Blocking Label Extender of HPV type 42

| SEQ ID NO | BLOCKING LABEL EXTENDER OF HPV TYPE 42 |
|---|---|
| 452. | caccactaccaaatcttaaaatggt |
| 453. | gcatatggaaagtccttcctcca |
| 454. | attctaaacaaaatgcacatgca |
| 455. | cgcagtgcacaaattttagaattaa |
| 456. | cacatctaatttgttgttcttctaaaagt |
| 457. | caccgacccgtccactgaca |
| 458. | gggtaggcgtctctccacg |
| 459. | caattgttcatagcaatacaggtca |
| 460. | tggtcatcttcatctgagctgtc |

TABLE 50-continued

Blocking Label Extender of HPV type 42

| SEQ ID NO | BLOCKING LABEL EXTENDER OF HPV TYPE 42 |
|---|---|
| 461. | ctgtgtacacacacacagtattctgtaa |
| 462. | cacaacgagtttaacagacttgtaaca |

In certain embodiments, the target polynucleotide is an E6 and/or E7 sequence from low risk-HPV type 43. In such embodiments, at least one Capture Extender probe (e.g., at least two, three, four, or five) comprises a target hybridizing sequence selected from Table 51 (underlined). At least one Capture Extender probe may comprise, consist essentially of, or consist of a sequence selected from SEQ ID NOS: 463 to 468 (Tables 51). In such embodiments, at least one Label Extender (e.g., at least two, three, four, or five) may comprise a target-hybridizing sequence shown in Table 52 (underlined). At least one Label Extender probe may comprise, consist essentially of, or consist of a sequence selected from SEQ ID NOS: 469 to 482 (Table. 52). The test may further employ a Blocking Label (BL), e.g., at least one, two, or three BLs each containing a sequence selected from SEQ ID NOS: 483 to 488 (Table 53).

TABLE 51

Capture Extender of HPV type 43

| SEQ ID NO | CAPTURE EXTENDER OF HPV TYPE 43 |
|---|---|
| 463. | agcatgcagcaaacggatatcTTTTTctcttggaaagaaagt |
| 464. | ccatgaaactgtagacaggccaTTTTTctcttggaaagaaagt |
| 465. | tcaaagtgcctatattgacttattttttTTTTTctcttggaaagaaagt |
| 466. | acagtatctgcatatgctgcgtagTTTTTctcttggaaagaaagt |
| 467. | atgcatgatttccagcaatgtagTTTTTctcttggaaagaaagt |
| 468. | ttaatatacccaacagcaggTTTTTctcttggaaagaaagt |

TABLE 52

Label Extender of HPV type 43

| SEQ ID NO | LABEL EXTENDER OF HPV TYPE 43 |
|---|---|
| 469. | catcacacaactcaaatatagtccgTTTTTgaagttaccgtttt |
| 470. | gcagagtaggcaaagttatgttacactTTTTTctgagtcaaagcat |
| 471. | acttccgtggtaagtaaccacttcTTTTTgaagttaccgtttt |
| 472. | tttaaatctctaaatgcaaacgataatTTTTTctgagtcaaagcat |
| 473. | aacactgtttgcttagtttcttcttctTTTTTgaagttaccgtttt |
| 474. | cttacagcatctaatgcacaaatcaTTTTTctgagtcaaagcat |
| 475. | tggtgataatggcttgtggcaTTTTTgaagttaccgtttt |
| 476. | gcacaatatgctgtacttttccacTTTTTctgagtcaaagcat |
| 477. | atgtattttaaagaattgtgcctttTTTTTgaagttaccgtttt |
| 478. | gcagtatcctttccacacgctTTTTTctgagtcaaagcat |

TABLE 52-continued

Label Extender of HPV type 43

| SEQ ID NO | LABEL EXTENDER OF HPV TYPE 43 |
|---|---|
| 479. | tggttgcatagttagcacatagtctTTTTTgaagttaccgtttt |
| 480. | cgttacaggttaagcttctaggttcTTTTTctgagtcaaagcat |
| 481. | attacacacagacaggatgtgcacTTTTTgaagttaccgtttt |
| 482. | agagcactgcacaacaagtcgaTTTTTctgagtcaaagcat |

TABLE 53

Blocking Label Extender of HPV type 43

| SEQ ID NO | BLOCKING LABEL EXTENDER OF HPV TYPE 43 |
|---|---|
| 483. | ctgatcgtcggcttttttcc |
| 484. | tctgagtctgagctgtctaattgct |

TABLE 53-continued

Blocking Label Extender of HPV type 43

| SEQ ID NO | BLOCKING LABEL EXTENDER OF HPV TYPE 43 |
|---|---|
| 485. | gggttgctcacgctcatcc |
| 486. | acttgctggtcctgttgcgt |
| 487. | tctgttacaactctgtaaacttgtagattc |
| 488. | tcttctagcttcttgatgtcactgtc |

In certain embodiments, the target polynucleotide is an E6 and/or E7 sequence from low risk-HPV type 44. In such embodiments, at least one Capture Extender probe (e.g., at least two, three, four, or five) comprises a target hybridizing sequence selected from Table 54 (underlined). At least one Capture Extender probe may comprise, consist essentially of, or consist of a sequence selected from SEQ ID NOS: 489 to 494 (Tables 54). In such embodiments, at least one Label Extender (e.g., at least two, three, four, or five) may comprise a target-hybridizing sequence shown in Table 55 (underlined). At least one Label Extender probe may comprise, consist essentially of, or consist of a sequence selected from SEQ ID NOS: 495 to 506 (Table 55). The test may further employ a Blocking Label (BL), e.g., at least one, two, or three BLs each containing a sequence selected from SEQ ID NOS: 507 to 510 (Table 56).

TABLE 54

Capture Extender of HPV type 44

| SEQ ID NO | CAPTURE EXTENDER OF HPV TYPE 44 |
|---|---|
| 489. | cctctgcagtacttaacgttttctgTTTTTctcttggaaagaaagt |
| 490. | gcacgtccagaattgacttatttgtTTTTTctcttggaaagaaagt |
| 491. | tttaatgaatcgcgccttgtcTTTTTctcttggaaagaaagt |
| 492. | cgacccttccaggtatcttgtaaTTTTTctcttggaaagaaagt |
| 493. | cctttaaggtagtatagtttccatgcaTTTTTctcttggaaagaaagt |
| 494. | gaggttccagctgtaaaacaatttTTTTTctcttggaaagaaagt |

TABLE 55

Label Extender of HPV type 44

| SEQ ID NO | LABEL EXTENDER OF HPV TYPE 44 |
|---|---|
| 495. | gcagacgtggaggcatttgcTTTTTgaagttaccgtttt |
| 496. | ccttgcacaactggtctatactttgtTTTTTctgagtcaaagcat |
| 497. | attgtgcataggaatgttgcactTTTTTgaagttaccgtttt |
| 498. | caaaacacgcataaaatttgcagTTTTTctgagtcaaagcat |
| 499. | acaaatggcacaggctgcaTTTTTgaagttaccgtttt |
| 500. | tgattgaccttaccttgtagttctaaTTTTTctgagtcaaagcat |
| 501. | ccgcgtagttaaaatgcctaaatTTTTTgaagttaccgtttt |
| 502. | ttcttcttccactgttactgcatatcTTTTTctgagtcaaagcat |
| 503. | ggcacaaatagcagcgtatcaTTTTTgaagttaccgtttt |
| 504. | cacgtggcacaatggtttgtTTTTTctgagtcaaagcat |

TABLE 55-continued

Label Extender of HPV type 44

| SEQ ID NO | LABEL EXTENDER OF HPV TYPE 44 |
|---|---|
| 505. | caatgtaggcctacagggtcagTTTTTgaagttaccgtttt |
| 506. | tctgagctgtctaattgctcattgTTTTTctgagtcaaagcat |

TABLE 56

Blocking Label Extender of HPV type 44

| SEQ ID NO | BLOCKING LABEL EXTENDER OF HPV TYPE 44 |
|---|---|
| 507. | ctacatataactgtttatatgcgaatgaataaa |
| 508. | aatggaaagtttcctcggtaca |
| 509. | caatatgtggcgcacctttc |
| 510. | tgatgtccaacaatggaagcag |

In other embodiments, the target polynucleotide is hepadnavirus polynucleotide, such as HBV. In such embodiments, the target polynucleotide is one or more polynucleotide sequences encoding the viral core protein, HBcAg; the proteolytic processing protein, HBeAg, and/or the viral surface antigen, HBsAg. In such embodiments, at least one Capture Extender probe (e.g., at least two, three, four, or five) may comprise a target-hybridizing sequence as selected from Table 57 (underlined). At least one Capture Extender probe may comprise, consist essentially of, or consist of a sequence selected from SEQ ID NOS: 511 to 519 (Tables 57). At least one Label Extender (e.g., at least two, three, four, or five) may comprise a target-hybridizing sequence selected from Table 58 (underlined). At least one Label Extender may comprise, consist essentially of, or consist of a sequence selected from SEQ ID NOS: 520 to 535 (Table 58). The test may optionally employ a Blocking Label (BL), e.g., at least one, two, or three BLs each containing a sequence selected from SEQ ID NOS: 536 to 553 (Table 59).

TABLE 57

Capture Extender of HBV

| SEQ ID NO | CAPTURE EXTENDER NUCLEOTIDE SEQUENCE OF HBV |
|---|---|
| 511. | ggggagWccgcgtaaagagattttctcttggaaagaaagt |
| 512. | tgcRacgtgcagaggtgaattttctcttggaaagaaagt |
| 513. | RagtccaagagtcctcttatgYaagactttttctcttggaaagaaagt |
| 514. | cagaggtgaaaaagttgcatgRttttctcttggaaagaaagt |
| 515. | aMggRtcaatgtccatgcctttttctcttggaaagaaagt |
| 516. | tcagaaggcaaaaaMgagagtaacttttttctcttggaaagaaagt |
| 517. | atDgcttgcctKagtgcHgtatgttttctcttggaaagaaagt |
| 518. | cggaagtgttgataagatagggtttttctcttggaaagaaagt |
| 519. | ctKcgtctgcgaggcgagttttctcttggaaagaaagt |

TABLE 58

Label Extender of HBV

| SEQ ID NO | LABEL EXTENDER NUCLEOTIDE SEQUENCE OF HBV |
|---|---|
| 520. | ggcagatgagaaggcacagactttttgaagttaccgtttt |
| 521. | gcgaagtgcacacggWccttttttctgagtcaaagcat |
| 522. | tcggtcgttgacattRcWgRtttttgaagttaccgtttt |
| 523. | cagtctttgaagtaKgcctcaaggttttttctgagtcaaagcat |
| 524. | gcctacagcctccYaRtacaaagactttttgaagttaccgtttt |
| 525. | tgMtggtgMRcaSaccaatttatttttctgagtcaaagcat |
| 526. | ggacatgWacaWgagatgatYaggtttttgaagttaccgtttt |
| 527. | cagcttggaggcttgaacagtRttttctgagtcaaagcat |
| 528. | agactctaaggcYtcYcgatactttttgaagttaccgtttt |
| 529. | RtgaggtgaRcaatgYtcMggttttctgagtcaaagcat |
| 530. | cctcKtcgtctaacaacagtagtYtctttttgaagttaccgtttt |
| 531. | cagcttggaggcttgaacagtRttttctgagtcaaagcat |
| 532. | cgacgcggcgattgagaYttttgaagttaccgtttt |
| 533. | attcccgagattgagatctYctgtttttctgagtcaaagcat |
| 534. | gWgtccaaggRatactaacattgagttttgaagttaccgtttt |
| 535. | cccMgtaaaRtttcccaccttatttttctgagtcaaagcat |

TABLE 59

Blocking Label Extender of HBV

| SEQ ID NO | BLOCKING LABEL EXTENDER NUCLEOTIDE SEQUENCE OF HBV |
|---|---|
| 536. | gcgttcacggtggtctcca |
| 537. | cttgggcaRgWHBYSDYgg |

TABLE 59-continued

Blocking Label Extender of HBV

| SEQ ID NO | BLOCKING LABEL EXTENDER NUCLEOTIDE SEQUENCE OF HBV |
|---|---|
| 538. | aRctcctcccaStcHKtaaaYaMa |
| 539. | ctttaaYctaRtctcctccccc |
| 540. | cYaaagccaYccaaggca |
| 541. | ccacagWagctccaaattctttat |
| 542. | gDagatcHcKDaYDgaaggaaagaag |
| 543. | agagcWgaggcKgtRtcDa |
| 544. | YatYaRBtcMccccaRcaVagR |
| 545. | ccacccaggtRgMYaRaKt |
| 546. | tgYWggRtcttccaaattaHYWc |
| 547. | cataRYtKactactaRDtccctRga |
| 548. | WYtttaRRcccatRttaRYRttRa |
| 549. | aWatRtgaaaccacaatagttgYctRa |
| 550. | gtYtctctYccaaaagtRagRcaRg |
| 551. | cRaaagaSaccaaataYtcWaKDacH |
| 552. | gWggagtgcgaatccacactc |
| 553. | cattWggtggtctRtaDgcDg |

The invention also provides a method for detecting a viral target polynucleotide from a RNA virus such as HIV or paramyxovirus (flu virus). The target polynucleotides for detecting a HIV infection can be HIV-A, -B or -F. In such embodiments, at least one Capture Extender probe (e.g., at least two, three, four, or five) may comprise a target-hybridizing sequence of Table 60 (underlined). At least one Capture Extender may comprise, consist essentially of, or consist of a sequence selected from SEQ ID NOS: 554 to 558 (Table 60). At least one Label Extender (e.g., at least two, three, four, or five) may comprise a target-hybridizing sequence selected from Table 61 (underlined). At least one Label Extender probe may comprise, consist essentially of, or consist of a sequence selected from SEQ ID NOS: 559 to 567 (Table 61). The test may optionally including a Blocking Label (BL), e.g., at least one, two, or three BLs each containing a sequence selected from SEQ ID NOS: 568 to 571 (Table 62).

TABLE 60

Capture Extender of HIV-A

| SEQ ID NO | CAPTURE EXTENDER NUCLEOTIDE SEQUENCE OF HIV-A |
|---|---|
| 554. | ttcatttcctccaatcccttatggTTTTTctcttggaaagaaagt |
| 555. | attgctgtgatatctttcatgttatcttgaTTTTTctcttggaaagaaagt |
| 556. | actgctaccagaattacttcccttctaaatgTTTTTctcttggaaagaaagt |
| 557. | cgctggtaaaattgctgccattgtctTTTTTctcttggaaagaaagt |
| 558. | ctccttgactttggggattgtagggaTTTTTctcttggaaagaaagt |

TABLE 61

Label Extender of HIV-A

| SEQ ID NO | LABEL EXTENDER NUCLEOTIDE SEQUENCE OF HIV-A |
|---|---|
| 559. | ctgattccagagctgactaatttatctacttgTTTTTctgagtcaaagcatgaagttac |
| 560. | gccttatctatcccatctaaaaatagtatcttcTTTTTctgagtcaaagcatgaagttac |
| 561. | agattaaaatcactagccattgctctccaTTTTTctgagtcaaagcatgaagttac |
| 562. | ggctactatttcctttgctactataggtggcTTTTTctgagtcaaagcatgaagttac |
| 563. | gactacagtctacctgtccatgcatggcTTTTTctgagtcaaagcatgaagttac |
| 564. | ctgcttctatatagccactggctacatggTTTTTctgagtcaaagcatgaagttac |
| 565. | cctgccctgtttctgctgggataacttTTTTTctgagtcaaagcatgaagttac |
| 566. | gtgtgtactacttttactggccatcctccTTTTTctgagtcaaagcatgaagttac |
| 567. | ccaccaacaggctgctttaaatgcagTTTTTctgagtcaaagcatgaagttac |

TABLE 62

Blocking Label Extender of HIV-A

| SEQ ID NO | BLOCKING LABEL EXTENDER NUCLEOTIDE SEQUENCE OF HIV-A |
|---|---|
| 568. | ttcccctttagttgacatttatcacagct |
| 569. | tgtgcaatctaattgccacatccctg |
| 570. | tgctaattttagcaaaaagtatgctgcct |
| 571. | atcccaaattcctgttggatgtttgc |

In another embodiment, the target polynucleotide is an HIV subtype B (HIV-B) polynucleotide. In such embodiments, at least one Capture Extender probe (e.g., at least two, three, four, or five) comprises a target-hybridizing sequence selected from Table 63 (underlined). At least one Capture Extender may comprise, consist essentially of, or consist of a sequence selected from SEQ ID NOS: 572 to 577 (Table 63). At least one Label Extender probe (e.g., at least two, three, four, or five) may comprise a target-hybridizing sequence selected from Table 64 (underlined). At least one Label Extender may comprise, consist essentially of, or consist of a sequence selected from SEQ ID NOS: 578 to 590 (Table 64). The test may optionally employ a Blocking Label (BL), e.g., at least one, two, or three BLs each containing a sequence selected from SEQ ID NOS: 591 to 595 (Table 65).

TABLE 63

Capture Extender of HIV-B

| SEQ ID NO | CAPTURE EXTENDER NUCLEOTIDE SEQUENCE OF HIV-B |
|---|---|
| 572. | tgcttctatatacccactggctacatgaactTTTTTctcttggaaagaaagt |
| 573. | caacaggcggccttgaccgcTTTTTctcttggaaagaaagt |
| 574. | tcctgcttgaccccgcccacTTTTTctcttggaaagaaagt |
| 575. | gcactatagtcccccaatcccccctcTTTTTctcttggaaagaaagt |
| 576. | ctttccagaggagctttgctggtccTTTTTctcttggaaagaaagt |
| 577. | actcttatcttgtattactactgccccttcacTTTTTctcttggaaagaaagt |

TABLE 64

Label Extender of HIV-B

| SEQ ID NO | LABEL EXTENDER NUCLEOTIDE SEQUENCE OF HIV-B |
|---|---|
| 578. | caatctagttgccatattcctggactacagtTTTTTctgagtcaaagcatgaagttac |
| 579. | gctaccaggataactatccttctaaatgtgtaTTTTTctgagtcaaagcatgaagttac |
| 580. | gccctgtctctgctgggatcacttcTTTTTctgagtcaaagcatgaagttac |
| 581. | tgtatgtattgtctttactggccatcttccTTTTTctgagtcaaagcatgaagttac |
| 582. | ttctttattcatagattctactactccttgactTTTTTctgagtcaaagcatgaagttac |
| 583. | gatctcttacctgtcctataattttctttaaTTTTTctgagtcaaagcatgaagttac |
| 584. | tttgtactgctgtcttaagatgttcagcctTTTTTctgagtcaaagcatgaagttac |
| 585. | ttcttttaaaattgtggatgaatactgccaTTTTTctgagtcaaagcatgaagttac |
| 586. | ctgttgctattatgtctattattctctcccctTTTTTctgagtcaaagcatgaagttac |
| 587. | aatttgttttgtaattctttggtttgtatgtTTTTTctgagtcaaagcatgaagttac |
| 588. | tgtaatagacccgaaaatttgaatttttgtTTTTTctgagtcaaagcatgaagttac |
| 589. | gccatctgttttccataatccctaatgatTTTTTctgagtcaaagcatgaagttac |
| 590. | cctgtctacttgccatacaatcatcacctTTTTTctgagtcaaagcatgaagttac |

TABLE 65

Blocking Label Extender of HIV-B

| SEQ ID NO | BLOCKING LABEL EXTENDER NUCLEOTIDE SEQUENCE OF HIV-B |
|---|---|
| 591. | tgctaattttaagagaaagtatgctgtttcct |
| 592. | actactggtgaagttgctgccattgtc |
| 593. | ttggggattgtagggaatgccaaat |
| 594. | tttccaaagtggatctctgctgtccc |
| 595. | ctttacttttcttcttggtactacttttatgtc |

In a further embodiment, the target polynucleotide may be an HIV subtype F (HIV-F) polynucleotide. In such embodiments, at least one Capture Extender (e.g., at least two, three, four, or five) may comprise a target-hybridizing sequence selected from Table 67 (underlined). At least one Capture Extender may comprise, consist essentially of, or consist of a sequence selected from SEQ ID NOS: 596 to 600 (Table 67). At least one Label Extender (e.g., at least one, two, three, four, or five) may comprise a target-hybridizing sequence selected from Table 68 (underlined). At least one Label Extender may comprise, consist essentially of, or consist of a sequence selected from SEQ ID NOS: 601 to 608 (Table 68). The test may optionally employ a Blocking Label (BL), e.g., containing the sequence of SEQ ID NO: 609 (Table 69).

TABLE 66

Capture Extender of HIV-F

| SEQ ID NO | CAPTURE EXTENDER NUCLEOTIDE SEQUENCE OF HIV-F |
|---|---|
| 596. | ttctttagctctttattcattgattctactactccTTTTTctcttggaaagaaagt |
| 597. | ttcccctgcactgtacccccaatcTTTTTctcttggaaagaaagt |
| 598. | gctgtccctgtaataaacccggaaattttTTTTTctcttggaaagaaagt |
| 599. | tgcccttcacctttccagagtagctTTTTTctcttggaaagaaagt |
| 600. | cgtcacctgccatctgttttccataatcTTTTTctcttggaaagaaagt |

TABLE 67

Label Extender of HIV-F

| SEQ ID NO | LABEL EXTENDER NUCLEOTIDE SEQUENCE OF HIV-F |
|---|---|
| 601. | ttcagcttgatctcttacctgtcctatgatcTTTTTctgagtcaaagcatgaagttac |
| 602. | atactgccatttgtactgctgtcttaagatgTTTTTctgagtcaaagcatgaagttac |
| 603. | ccccctttctctttaaaattgtggatgaTTTTTctgagtcaaagcatgaagttac |

TABLE 67-continued

Label Extender of HIV-F

| SEQ ID NO | LABEL EXTENDER NUCLEOTIDE SEQUENCE OF HIV-F |
|---|---|
| 604. | ttgtatgtctgttgctattatgtctattattctTTTTTctgagtcaaagcatgaagttac |
| 605. | gaatttttgtaacttgtttttgtaattctttagtTTTTTctgagtcaaagcatgaagtta |
| 606. | ttgctggtcctttccaaactgggtctctTTTTTctgagtcaaagcatgaagttac |
| 607. | ctactttatttcactattgtcttgtatgactacTTTTTctgagtcaaagcatgaagtta |
| 608. | tcatcctgtctacctgccacacaatTTTTTctgagtcaaagcatgaagttac |

TABLE 68

Blocking Label Extender of HIV-F

| SEQ ID NO | BLOCKING LABEL EXTENDER NUCLEOTIDE SEQUENCE OF HIV-F |
|---|---|
| 609. | cctaatgatctttgcttttcttcttggca |

The target polynucleotide may be a polynucleotide of a respiratory viruses, such as a influenza H1N1. For example, the target polynucleotide may be a sequence encoding a portion of hemaglutinin (HA), neuraminidase (NA), M protein, F protein, N protein, G protein, etc. In an exemplary embodiment, the target polynucleotide is an HA sequence. In such embodiments, at least one Capture Extender (e.g., at least two, three, four, or five) may comprise a target-hybridizing sequence selected from Table 69 (underlined). At least one Capture Extender may comprise, consist essentially of, or consist of a sequence selected from SEQ ID NOS: 610 to 629 (Tables 69). At least one Label Extender (e.g., at least two, three, four, or five) may comprise a target hybridizing sequence selected from Table 70 (underlined). At least one Label Extender may comprise, consist essentially of, or consist of a sequence selected from SEQ ID NOS: 630 to 689 (Table 70). The test may optionally employ a Blocking Label (BL), e.g., at least one, two, or three BLs each containing a sequence selected from SEQ ID NOS: 690 to 707 (Table 71).

TABLE 69

Capture Extender of Flu Virus, H1N1

| SEQ ID NO | CAPTURE EXTENDER NUCLEOTIDE SEQUENCE OF Flu Virus, H1N1 |
|---|---|
| 610. | ggttctattggaaaatgaaagaactttTTTTTctcttggaaagaaagt |
| 611. | caaaatgagcaggggtcaggTTTTTctcttggaaagaaagt |
| 612. | tgccggtttcattgaagggTTTTTctcttggaaagaaagt |
| 613. | ccagcctcccatttcagaatatacTTTTTctcttggaaagaaagt |
| 614. | acacccaagggtgctataaacaTTTTTctcttggaaagaaagt |

TABLE 69-continued

Capture Extender of Flu Virus, H1N1

| SEQ ID NO | CAPTURE EXTENDER NUCLEOTIDE SEQUENCE OF Flu Virus, H1N1 |
|---|---|
| 615. | caagccggaaatagcaataagaTTTTTctcttggaaagaaagt |
| 616. | aaaaggaaattcatacccaaagcTTTTTctcttggaaagaaagt |
| 617. | aaaggtgtaacggcagcatgtTTTTTctcttggaaagaaagt |
| 618. | ctcagtgtcatcatttgaaaggtttTTTTTctcttggaaagaaagt |
| 619. | gggtaaatgtaacattgctggctTTTTTctcttggaaagaaagt |
| 620. | ggttctattggaaaatgaaagaactttTTTTTctcttggaaagaaagt |
| 621. | caaaatgagcagggggtcaggTTTTTctcttggaaagaaagt |
| 622. | tgccggtttcattgaagggTTTTTctcttggaaagaaagt |
| 623. | ccagcctcccatttcagaatatacTTTTTctcttggaaagaaagt |
| 624. | acacccaagggtgctataaacaTTTTTctcttggaaagaaagt |
| 625. | caagccggaaatagcaataagaTTTTTctcttggaaagaaagt |
| 626. | aaaaggaaattcatacccaaagcTTTTTctcttggaaagaaagt |
| 627. | aaaggtgtaacggcagcatgtTTTTTctcttggaaagaaagt |
| 628. | ctcagtgtcatcatttgaaaggtttTTTTTctcttggaaagaaagt |
| 629. | ccagtaaactgattaactggttcttcaTTTTTctcttggaaagaaagt |

TABLE 70

Label Extender of Flu Virus, H1N1

| SEQ ID NO | LABEL EXTENDER NUCLEOTIDE SEQUENCE OF Flu Virus, H1N1 |
|---|---|
| 630. | tggacttacaatgccgaactgttTTTTTgaagttaccgttttt |
| 631. | tgatgatggtttcctggacattTTTTTctgagtcaaagcat |
| 632. | ggtaaagagttcaaccacctggaTTTTTgaagttaccgttttt |
| 633. | aagatgaatacacagttcacagcagtaTTTTTctgagtcaaagcat |
| 634. | cacacagaatgccattgacgagTTTTTgaagttaccgttttt |
| 635. | atatgcagccgacctgaagagTTTTTctgagtcaaagcat |
| 636. | tggatggtacggttatcaccatTTTTTctgagtcaaagcat |
| 637. | gggtggacagggatggtagaTTTTTctgagtcaaagcat |
| 638. | aggcctatttggggccatTTTTTgaagttaccgttttt |
| 639. | ggaatatcccgtctattcaatctagTTTTTctgagtcaaagcat |
| 640. | tgagactggccacaggattgaTTTTTgaagttaccgttttt |
| 641. | tccaaaatatgtaaaaagcacaaaatTTTTTctgagtcaaagcat |
| 642. | cacgattgcaatacaacttgtcaaTTTTTgaagttaccgttttt |

TABLE 70-continued

Label Extender of Flu Virus, H1N1

| SEQ ID NO | LABEL EXTENDER NUCLEOTIDE SEQUENCE OF Flu Virus, H1N1 |
|---|---|
| 643. | ggtattatcatttcagatacaccagtcTTTTTctgagtcaaagcat |
| 644. | gtggtaccgagatatgcattcgTTTTTgaagttaccgttttt |
| 645. | cattcgaagcaactggaaatctaTTTTTctgagtcaaagcat |
| 646. | agtagagccgggagacaaaataaTTTTTgaagttaccgttttt |
| 647. | gggagaatgaactattactggacactTTTTTctgagtcaaagcat |
| 648. | aatgcagatacatatgtttttgtggTTTTTgaagttaccgttttt |
| 649. | tgctgaccaacaaagtctctatcagTTTTTctgagtcaaagcat |
| 650. | ttctacaaaaatttaatatggctagttaaTTTTTgaagttaccgttttt |
| 651. | cctcatgctggagcaaaaagcTTTTTctgagtcaaagcat |
| 652. | ggcccaatcatgactcgaacTTTTTgaagttaccgttttt |
| 653. | gagatattccccaagacaagttcatTTTTTctgagtcaaagcat |
| 654. | tgaggagctaagagagcaattgagTTTTTgaagttaccgttttt |
| 655. | tacccaggagatttcatcgattaTTTTTctgagtcaaagcat |
| 656. | cctagttcagacaatggaacgtgtTTTTTgaagttaccgttttt |
| 657. | catggtcctacattgtggaaacaTTTTTctgagtcaaagcat |
| 658. | tgaatcactctccacagcaagctTTTTTgaagttaccgttttt |
| 659. | ggatcctgggaaatccagagtgTTTTTctgagtcaaagcat |
| 660. | tggacttacaatgccgaactgttTTTTTgaagttaccgttttt |
| 661. | tgatgatggtttcctggacattTTTTTctgagtcaaagcat |
| 662. | ggtaaagagttcaaccacctggaTTTTTgaagttaccgttttt |
| 663. | aagatgaatacacagttcacagcagtaTTTTTctgagtcaaagcat |
| 664. | cacacagaatgccattgacgagTTTTTgaagttaccgttttt |
| 665. | atatgcagccgacctgaagagTTTTTctgagtcaaagcat |
| 666. | tggatggtacggttatcaccatTTTTTgaagttaccgttttt |
| 667. | gggtggacagggatggtagaTTTTTctgagtcaaagcat |
| 668. | aggcctatttggggccatTTTTTgaagttaccgttttt |
| 669. | ggaatatcccgtctattcaatctagTTTTTctgagtcaaagcat |
| 670. | tgagactggccacaggattgaTTTTTgaagttaccgttttt |
| 671. | tccaaaatatgtaaaaagcacaaaatTTTTTctgagtcaaagcat |
| 672. | cacgattgcaatacaacttgtcaaTTTTTgaagttaccgttttt |
| 673. | ggtattatcatttcagatacaccagtcTTTTTctgagtcaaagcat |
| 674. | gtggtaccgagatatgcattcgTTTTTgaagttaccgttttt |
| 675. | cattcgaagcaactggaaatctaTTTTTctgagtcaaagcat |
| 676. | agtagagccgggagacaaaataaTTTTTgaagttaccgttttt |

TABLE 70-continued

| SEQ ID NO | Label Extender of Flu Virus, H1N1 — LABEL EXTENDER NUCLEOTIDE SEQUENCE OF Flu Virus, H1N1 |
|---|---|
| 677. | gggagaatgaactattactggacactTTTTTctgagtcaaagcat |
| 678. | aatgcagatacatatgtttttgtggTTTTTgaagttaccgtttt |
| 679. | tgctgaccaacaaagtctctatcagTTTTTctgagtcaaagcat |
| 680. | ttctacaaaaatttaatatggctagttaaTTTTTgaagttaccgtttt |
| 681. | cctcatgctggagcaaaaagcTTTTTctgagtcaaagcat |
| 682. | ggcccaatcatgactcgaacTTTTTgaagttaccgtttt |
| 683. | gagatattccccaagacaagttcatTTTTTctgagtcaaagcat |
| 684. | tgaggagctaagagagcaattgagTTTTTgaagttaccgtttt |
| 685. | tacccaggagatttcatcgattaTTTTTctgagtcaaagcat |
| 686. | cctagttcagacaatggaacgtgtTTTTTgaagttaccgtttt |
| 687. | catggtcctacattgtggaaacaTTTTTctgagtcaaagcat |
| 688. | tgaatcactctccacagcaagctTTTTTgaagttaccgtttt |
| 689. | ggatcctgggaaatccagagtgTTTTTctgagtcaaagcat |

TABLE 71

| SEQ ID NO | Blocking Label Extender of Flu Virus, H1N1 — BLOCKING LABEL EXTENDER NUCLEOTIDE SEQUENCE OF Flu Virus, H1N1 |
|---|---|
| 690. | aaaaagaatagagaatttaaataaaaaagt |
| 691. | attactaacaaagtaaattctgttattgaa |
| 692. | atccgatcacaattggaaaatg |
| 693. | caatggaaagaaatgctggatct |
| 694. | cccaaagtgagggatcaagaa |
| 695. | ggtcatcaagatacagcaagaagtt |
| 696. | gggcattcaccatccatctactag |
| 697. | gggaaagaagtcctcgtgctatg |
| 698. | tcagcaaatcctacattaatgataaa |
| 699. | aaaaagaatagagaatttaaataaaaaagt |
| 700. | attactaacaaagtaaattctgttattgaa |
| 701. | atccgatcacaattggaaaatg |
| 702. | caatggaaagaaatgctggatct |
| 703. | cccaaagtgagggatcaagaa |
| 704. | ggtcatcaagatacagcaagaagtt |
| 705. | gggcattcaccatccatctactag |

TABLE 71-continued

| SEQ ID NO | Blocking Label Extender of Flu Virus, H1N1 — BLOCKING LABEL EXTENDER NUCLEOTIDE SEQUENCE OF Flu Virus, H1N1 |
|---|---|
| 706. | gggaaagaagtcctcgtgctatg |
| 707. | tcagcaaatcctacattaatgataaa |

The present invention further provides a method for detecting viral target polynucleotides from a flavirus, for example, HCV. In such embodiments, at least one Capture Extender probe (e.g., at least two, three, four, or five) comprises a target-hybridizing sequence selected from Table 72 (underlined). At least one Capture Extender may comprise, consist essentially of, or consist of a sequence selected from SEQ ID NOS: 708 to 714 (Tables 72). At least one Label Extender (LE) (e.g., at least two, three, four, or five) may comprise a target-hybridizing sequence selected from Table 73 (underlined). At least one Label Extender may comprise, consist essentially of, or may consist of a sequence selected from SEQ ID NOS: 715 to 727 (Table 73). The test may optionally employ a Blocking Label (BL), e.g., at least one, two, or three BLs each containing a sequence selected from SEQ ID NOS: 728 to 732 (Table 74).

TABLE 72

| SEQ ID NO | Capture Extender of HCV — CAPTURE EXTENDER NUCLEOTIDE SEQUENCE OF HCV |
|---|---|
| 708. | taacgccatggctagacgctttctgcgtgaTTTTTctcttggaaagaaagt |
| 709. | gcgggttgatccaagaaaggacccggtcTTTTTctcttggaaagaaagt |
| 710. | ggcacgcccaaatctccaggcattgaTTTTTctcttggaaagaaagt |
| 711. | agacctcccggggcactcgcaaTTTTTctcttggaaagaaagt |
| 712. | cctaccctcgggctggcgagccTTTTTctcttggaaagaaagt |
| 713. | caccccaagccctcattgccatagagTTTTTctcttggaaagaaagt |
| 714. | cgagcggaatgtaccccatgagatcggTTTTTctcttggaaagaaagt |

TABLE 73

| SEQ ID NO | Label Extender of HCV — LABEL EXTENDER NUCLEOTIDE SEQUENCE OF HCV |
|---|---|
| 715. | ggtcctggaggctgcacgacactcatacTTTTTctgagtcaaagcatgaagttac |
| 716. | ccgcagaccactatggctctcccgTTTTTctgagtcaaagcatgaagttac |
| 717. | gtcctggcaattccggtgtactcaccgTTTTTctgagtcaaagcatgaagttac |
| 718. | caacactactcggctagcagtctcgcgggTTTTTctgagtcaaagcatgaagttac |

TABLE 73-continued

Label Extender of HCV

| SEQ ID NO | LABEL EXTENDER NUCLEOTIDE SEQUENCE OF HCV |
|---|---|
| 719. | caccctatcaggcagtaccacaaggcctt<u></u>TTTTTctgagtcaaagcatgaagttac |
| 720. | ttcgtgctcatggtgcacggtctacg<u></u>TTTTTctgagtcaaagcatgaagttac |
| 721. | ggtgttacgtttggttttttctttgaggtttag<u></u>TTTTTctgagtcaaagcatgaagttac |
| 722. | cccctgcgcggcaacaggtaaactccac<u></u>TTTTTctgagtcaaagcatgaagttac |
| 723. | gtcgcgcgcacacccaacctgg<u></u>TTTTTctgagtcaaagcatgaagttac |
| 724. | ttggggataggttgtcgccttccacga<u></u>TTTTTctgagtcaaagcatgaagttac |
| 725. | acggggtgacaggagccatcctgcc<u></u>TTTTTctgagtcaaagcatgaagttac |
| 726. | ccaaattgcgcgacctacgccgggg<u></u>TTTTTctgagtcaaagcatgaagttac |
| 727. | aagccgcacgtgagggtatcgatgaccttac<u></u>TTTTTctgagtcaaagcatgaagttac |

TABLE 74

Blocking Label Extender of HCV

| SEQ ID NO | BLOCKING LABEL EXTENDER NUCLEOTIDE SEQUENCE OF HCV |
|---|---|
| 728. | acttgacgtcctgtgggcggcgg |
| 729. | cgacgatctgaccaccgcccggga |
| 730. | ggttgcgaccgctcggaagtcttccta |
| 731. | ccaggggtacccgggctgagccca |
| 732. | tggggcccaactaggccgagagcc |

TABLE 75

Capture Extender of SARS Virus

| SEQ ID NO | CAPTURE EXTENDER NUCLEOTIDE SEQUENCE OF SARS Virus |
|---|---|
| 733. | ccagtaaactgattaactggttcttca<u></u>TTTTTctcttggaaagaaagt |
| 734. | gtgtatgttagcagcatttacaatca<u></u>TTTTTctcttggaaagaaagt |
| 735. | ccttttgcatggcaccattg<u></u>TTTTTctcttggaaagaaagt |
| 736. | gcaagattatgtccagaaagcaaa<u></u>TTTTTctcttggaaagaaagt |
| 737. | gctgccttaagaagctggatgt<u></u>TTTTTctcttggaaagaaagt |
| 738. | ggtttagcaccaaatatgcctg<u></u>TTTTTctcttggaaagaaagt |

TABLE 76

Label Extender of SARS Virus

| SEQ ID NO | LABEL EXTENDER NUCLEOTIDE SEQUENCE OF SARS Virus |
|---|---|
| 739. | caatctctgattgctcagtagtatcat<u></u>TTTTTgaagttaccgtttt |
| 740. | ggtgtaggttctggttgggct<u></u>TTTTTctgagtcaaagcat |
| 741. | ggcaacattgtcagtaagttttaaataa<u></u>TTTTTgaagttaccgtttt |
| 742. | tccttaacgatgtcaacacatttaat<u></u>TTTTTctgagtcaaagcat |
| 743. | gctacaccaccaccatgtttcag<u></u>TTTTTgaagttaccgtttt |
| 744. | gttgccttgttgagtgcacct<u></u>TTTTTctgagtcaaagcat |
| 745. | ccatttagcttaatgtaatcatcactct<u></u>TTTTTgaagttaccgtttt |
| 746. | caagaccctcctactgtaagaggg<u></u>TTTTTctgagtcaaagcat |
| 747. | ccaacaacatgcagacacttctta<u></u>TTTTTgaagttaccgtttt |
| 748. | cctcacctgcatttaggttaggt<u></u>TTTTTctgagtcaaagcat |
| 749. | tgtcctgtgaattgaattttcatat<u></u>TTTTTgaagttaccgtttt |
| 750. | ctgacaacaatggtgcaagtaaga<u></u>TTTTTctgagtcaaagcat |

TABLE 77

Blocking Label Extender of SARS Virus

| SEQ ID NO | BLOCKING LABEL EXTENDER NUCLEOTIDE SEQUENCE OF SARS Virus |
|---|---|
| 751. | ccataggattagcactttgtgcc |

The present invention further provides a method for detecting viral target polynucleotides from a coronavirus, for example, severe acute respiratory syndrome (SARS) virus. In such embodiments, at least one Capture Extender (e.g., at least two, three, four, or five) may comprise a target-hybridizing sequence selected from Table 75 (underlined). At least one Capture Extender may comprise, consist essentially of, or consist of a sequence selected from SEQ ID NOS: 733 to 738 (Table 75). At least one Label Extender (e.g., at least two, three, four, or five) may comprise a target-hybridizing sequence selected from Table 76 (underlined). At least one Label Extender may comprise, consist essentially of, or consist of a sequence selected from SEQ ID NOS: 739 to 750 (Table 76). The test may optionally employ a Blocking Label (BL), e.g., containing the sequence of SEQ ID NO: 751 (Table 77).

In one aspect of the invention, the method provides for detection of bacterial target polynucleotides. Non-limiting examples of bacteria are: *B. pertussis; Leptospira Pomona; S. paratyphi* A and B; *C. diphtheriae, C. tetani, C. botulinum, C. perfringens, C. feseri* and other gas gangrene bacteria; *B. anthracis; P. pestis; P. multocida; Neisseria* meningitides; *N. gonorrheae; Hemophilus influenzae; Actinomyces* (e.g., *Norcardia*); *Acinetobacter;* Bacillaceae (e.g., *Bacillus anthrasis*); *Bacteroides* (e.g., *Bacteroides fragilis*); *Blastomycosis; Bordetella* (*Bordetella pertusi*); *Borrelia* (e.g., *Borrelia burgdorferi*); *Brucella; Campylobacter; Chlamydia; Coccidioides; Corynebacterium* (e.g., *Corynebacterium diptheriae*); *E. coli* (e.g., Enterotoxigenic *E. coli* and Enterohemorrhagic *E. coli*); *Enterobacter* (e.g. *Enterobacter aerogenes*); Enterobacteriaceae (*Klebsiella, Salmonella* (e.g., *Salmonella typhi, Salmonella enteritidis, Serratia, Yersinia, Shigella*); *Erysipelothrix; Haemophilus* (e.g., *Haemophilus influenza* type B); *Helicobacter; Legionella* (e.g., *Legionella pneumophila*); *Leptospira; Listeria* (e.g., *Listeria monocytogenes*); *Mycoplasma; Mycobacterium* (e.g., *Mycobacterium leprae, Mycobacterium tuberculosis* and *Mycobacterium bovis*); *Vibrio* (e.g., *Vibrio cholerae*); Pasteurellacea (*Pasteurella haemolytica*); *Proteus; Pseudomonas* (e.g., *Pseudomonas aeruginosa*); Rickettsiaceae; *Spirochetes* (e.g., *Treponema* spp., *Leptospira* spp., *Borrelia* spp.); *Shigella* spp.; *Meningiococcus; Pneumococcus* and *Streptococcus* (e.g., *Streptococcus pneumoniae* and Groups A, B, and C Streptococci); *Ureaplasmas; Treponema pollidum;* and *Staphylococcus* (*Staphylococcus aureus* and *Staphylococcus epidermidis*).

The target polynucleotides from the bacteria can be a polynucleotide, DNA or a RNA (such as a ribosomal RNA) that is involved in the replication and transcription of the bacteria, housekeeping genes, repetitive sequences, terminal inverted repeat sequence (TIR), miniature inverted repeat transposable element (MITE), CpGs, and/or polynucleotide encoding other bacterial proteins that are expressed on the cell surface or as integral membrane proteins.

In one embodiment, the present invention provides a method for detecting *mycobacterium*. The target polynucleotide for detecting mycobacterium infection can be a 16S RNA sequence. At least one Capture Extender (e.g., at least two, three, four, or five) comprises a target-hybridizing sequence selected from Table 78 (underlined). At least one Capture Extender probe may comprise, consist essentially of, or consist of a sequence selected from SEQ ID NOS: 752 to 756 (Table 78). At least one Label Extender probe (e.g., at least two, three, four, or five) may comprise a target-hybridizing sequence selected from Table 79 (underlined). At least one Label Extender comprises, consists essentially of, or consists of a sequence selected from SEQ ID NOS: 757 to 770 (Table 79). The test may optionally employ a Blocking Label (BL), e.g., at least one, two, or three BLs each containing a sequence selected from SEQ ID NOS: 771 to 773 (Table 80).

TABLE 78

Capture Extender of *Mycobacterium tuberculosis*

| SEQ ID NO | CAPTURE EXTENDER NUCLEOTIDE SEQUENCE OF *Mycobacterium tuberculosis* |
|---|---|
| 752. | accgctaaagcgctttccaTTTTTctcttggaaagaaagt |
| 753. | ccgcgggctcatcccacTTTTTctcttggaaagaaagt |
| 754. | tggccggacaccctctcaTTTTTctcttggaaagaaagt |
| 755. | agttaagccgtgagatttcacgTTTTTctcttggaaagaaagt |
| 756. | tcgcccgcacgctcacTTTTTctcttggaaagaaagt |

TABLE 79

Label Extender of *Mycobacterium tuberculosis*

| SEQ ID NO | LABEL EXTENDER NUCLEOTIDE SEQUENCE OF *Mycobacterium tuberculosis* |
|---|---|
| 757. | cgccttggtaggccgtcaTTTTTgaagttaccgtttt |
| 758. | ggccggctacccgtcgtTTTTTctgagtcaaagcat |
| 759. | ggccgtatctcagtcccagtgTTTTTgaagttaccgtttt |
| 760. | gctgcctcccgtaggagtctgTTTTTctgagtcaaagcat |
| 761. | ccattgtgcaatattccccactTTTTTgaagttaccgtttt |
| 762. | gctgcatcaggcttgcgcTTTTTctgagtcaaagcat |
| 763. | tcccccacgcggcgtcTTTTTgaagttaccgtttt |
| 764. | tacaacccgaaggccgtcaTTTTTctgagtcaaagcat |
| 765. | tgcttcttctccacctaccgtcTTTTTgaagttaccgtttt |
| 766. | tggcacgtagttggccggTTTTTctgagtcaaagcat |
| 767. | ctacgtattaccgcggctgcTTTTTgaagttaccgtttt |
| 768. | ccggacaacgctcgcaccTTTTTctgagtcaaagcat |
| 769. | cgagctctttacgcccagtaattTTTTTgaagttaccgtttt |
| 770. | aacaacgcgacaaaccacctaTTTTTctgagtcaaagcat |

TABLE 80

Blocking Label Extender of *Mycobacterium tuberculosis*

| SEQ ID NO | BLOCKING LABEL EXTENDER NUCLEOTIDE SEQUENCE OF *Mycobacterium tuberculosis* |
|---|---|
| 771. | ccccaccaacaagctgatagg |
| 772. | ttcgtcgatggtgaaagaggtt |
| 773. | aatccgagagaacccggacc |

In another embodiment, the target polynucleotide is indicative of a spirochete bacterium, for example, *Treponema pallidum*, which causes syphilis, a sexually transmitted disease. In one embodiment, the target polynucleotide for detecting spirochete infection is a 16S RNA sequence. At least one Capture Extender probe (e.g., at least two, three, four, or five) comprises a target-hybridizing sequence selected from Table 81 (underlined). At least one Capture Extender comprises, consists essentially of, or consists of a sequence selected from SEQ ID NOS: 774 to 779 (Table 81). At least one Label Extender (LE) (e.g., at least two, three, four, or five) may comprise a target-hybridizing sequence selected from Table 82. At least one Label Extender may comprise, consist essentially of or consist of a sequence selected from SEQ ID NOS: 780 to 791 (Table 82). The test may optionally employ a Blocking Label (BL), e.g., containing the sequence of SEQ ID NO: 792 (Table 83).

TABLE 81

Capture Extender of Syphilis

| SEQ ID NO | CAPTURE EXTENDER NUCLEOTIDE SEQUENCE OF Syphilis |
|---|---|
| 774. | ccccttacgtgttaccgcgTTTTTctcttggaaagaaagt |
| 775. | ccaggcttaccagtccgccTTTTTctcttggaaagaaagt |
| 776. | cctccgtgattctagaccagcaTTTTTctcttggaaagaaagt |
| 777. | ttcgccaccggtgttcttcTTTTTctcttggaaagaaagt |
| 778. | cgcacctcagcgtcaatcatTTTTTctcttggaaagaaagt |
| 779. | taatgcgttcgcgtcggTTTTTctcttggaaagaaagt |

TABLE 82

Label Extender of Syphilis

| SEQ ID NO | LABEL EXTENDER NUCLEOTIDE SEQUENCE OF Syphilis |
|---|---|
| 780. | ggggcttattcgcacgactTTTTTgaagttaccgtttt |
| 781. | gctgctggcacgtaattagccTTTTTctgagtcaaagcat |
| 782. | aataattccgaacaacgctcgTTTTTgaagttaccgtttt |
| 783. | tgcatgcccttacgcccTTTTTctgagtcaaagcat |
| 784. | ttgagctcggggatttcacaTTTTTgaagttaccgtttt |
| 785. | gtacccagtgcagttcccaagTTTTTctgagtcaaagcat |
| 786. | cacttggaattccggtttccTTTTTgaagttaccgtttt |
| 787. | caaatatctacagattccacccctaTTTTTctgagtcaaagcat |
| 788. | tgttcgctccccacaccttTTTTTgaagttaccgtttt |
| 789. | tgtggactaccagggtatctaatccTTTTTctgagtcaaagcat |
| 790. | caacacctagtgtacatcgtttactgTTTTTgaagttaccgttt |
| 791. | cgccgagactcatgcccTTTTTctgagtcaaagcat |

TABLE 83

Blocking Label Extender of Syphilis

| SEQ ID NO | BLOCKING LABEL EXTENDER NUCLEOTIDE SEQUENCE OF Syphilis |
|---|---|
| 792. | cggccagaaacccgcc |

In another aspect of the present invention, the method also provides for detection of fungal target polynucleotide. Non-limiting examples of fungal infections include: aspergillosis (*Aspergillus fumigatus, Aspergillus flavus, Aspergillus terreus, Aspergillus nidulans,* and *Aspergillus niger*); blastomycosis (*Blastomyces dermatitidis*); coccidioidomycosis (*Coccidioides* species); cryptococcosis (*Cryptococcus neoformans, C. gattii*); histoplasmosis (*Histoplasma capsulatum*); mucormycosis or zygomycosis (*Mucorales* molds); paracoccidioidomycosis (*Paracoccidioides brasiliensis*); pneumocystis pneumonia (*Pneumocystis jiroveci*); sporotrichosis (*Sporothrix schenckii*); etc.

In one embodiment, the present invention provides a method for detecting fungal target polynucleotides from an *Aspergillus*, for example, *Aspergillus fumigatus*. *A. fumigatus* is a common, often lethal and difficult to diagnose cause of pathogenic disease in immuno-compromised subjects such as in organ transplant recipients, bone marrow transplant and subjects diagnosed with cancer and AIDS. In one embodiment, the target polynucleotide for detecting aspergillus infection is a 18S RNA or 28S RNA sequence. In such embodiments, at least one Capture Extender probe (e.g., at least two, three, four, or five) may comprise a target-hybridizing sequence selected from Table 84. At least one Capture Extender probe comprises, consists essentially of, or consists of a sequence selected from SEQ ID NOS: 793 to 798 (Table 84). At least one Label Extender (e.g., at least two, three, four, or five) may comprise a target-hybridizing sequence selected from Table 85. At least one Label Extender probe may comprise, consist essentially of, or consist of a sequence selected from SEQ ID NOS: 799 to 810 (Table 85). The test may optionally employ a Blocking Label (BL), e.g., at least one, two, or three BLs each containing a sequence selected from SEQ ID NOS: 811 to 813 (Table 86).

TABLE 84

Capture Extender of *Aspergillus fumigatus*

| SEQ ID NO | CAPTURE EXTENDER NUCLEOTIDE SEQUENCE OF *Aspergillus fumigatus* |
|---|---|
| 793. | actcgcggtgaggcggaTTTTTctcttggaaagaaagt |
| 794. | aaggtccagccggaccagtTTTTTctcttggaaagaaagt |
| 795. | catgaggttcccccagaaggaTTTTTctcttggaaagaaagt |
| 796. | cagctgaatactgacgccccTTTTTctcttggaaagaaagt |
| 797. | gaaaacatccttggcgaatgTTTTTctcttggaaagaaagt |
| 798. | cgagcgggtcatcatagaaacTTTTTctcttggaaagaaagt |

TABLE 85

Label Extender of *Aspergillus fumigatus*

| SEQ ID NO | LABEL EXTENDER NUCLEOTIDE SEQUENCE OF *Aspergillus fumigatus* |
|---|---|
| 799. | aggttcaactacgagcttttaactgTTTTTgaagttaccgtt |
| 800. | ccggccagccagacccaTTTTTctgagtcaaagcat |
| 801. | gcctgctttgaacactctaattttTTTTTgaagttaccgtttt |
| 802. | catgctaatgtattcgagcaaagTTTTTctgagtcaaagcat |
| 803. | cggtcctagaaaccaacaaaatagaTTTTTgaagttaccgtttt |
| 804. | cgactatccctattaatcattacggTTTTTctgagtcaaagcat |
| 805. | aaatccaagaatttcacctctgaTTTTTgaagttaccgtttt |
| 806. | ctttcgcagtagttcttcagcTTTTTctgagtcaaagcat |
| 807. | cctaactttcgttccctgattaatTTTTTgaagttaccgtttt |
| 808. | cggtatctgatcgtcttcgatccTTTTTctgagtcaaagcat |

TABLE 85-continued

Label Extender of *Aspergillus fumigatus*

| SEQ ID NO | LABEL EXTENDER NUCLEOTIDE SEQUENCE OF *Aspergillus fumigatus* |
|---|---|
| 809. | ggcatagtttatggttaagactacgaTTTTTgaagttaccgtt tt |
| 810. | accgcccgatccctagtcTTTTTctgagtcaaagcat |

TABLE 86

Blocking Label Extender of *Aspergillus fumigatus*

| SEQ ID NO | BLOCKING LABEL EXTENDER NUCLEOTIDE SEQUENCE OF *Aspergillus fumigatus* |
|---|---|
| 811. | ccccacagccagtgaaggc |
| 812. | ttcacagtaaaagtcctggttcc |
| 813. | accgcacgtcctattctattattc |

In another embodiment, the fungal target polynucleotides are from *Candida*, for example, *Candida albicans*, an opportunistic yeast which causes oral and genital infections in human, particularly in immuno-compromised subjects (e.g. organ and bone marrow transplantation recipients, cancer and AIDS patients). In one embodiment, the target polynucleotide for detecting *Candida* infection is a 18S or 28S RNA sequence. In such embodiments, at least one Capture Extender probe (e.g., at least two, three, four, or five) may comprise a target-hybridizing sequence selected from Table 87 (underlined). At least one Capture Extender probe may comprise, consist essentially of, or consist of a sequence selected from SEQ ID NOS: 814 to 819 (Table 87). At least one Label Extender probe (e.g., at least two, three, four, or five) may comprise a target-hybridizing sequence selected from Table 88 (underlined). At least one Label Extender probe may comprise, consist essentially of, or consist of a sequence selected from SEQ ID NOS: 820 to 831 (Table 88). The test may optionally employ a Blocking Label (BL), e.g., at least one or two BLs, such as the BLs of SEQ ID NOS: 832 to 833 (Table 89).

TABLE 87

Capture Extender of *Candida albicans*

| SEQ ID NO | CAPTURE EXTENDER NUCLEOTIDE SEQUENCE OF *Candida albicans* |
|---|---|
| 814. | aaaaagatggaccggccagTTTTTctcttggaaagaaagt |
| 815. | acccagaaggaaaggctcgTTTTTctcttggaaagaaagt |
| 816. | tggttcgccataaatggctTTTTTctcttggaaagaaagt |
| 817. | actgataccccgaccgtcTTTTTctcttggaaagaaagt |
| 818. | aaacgtccttggtaaatgctttcTTTTTctcttggaaagaaagt |
| 819. | gtgccgattgcgtcaataaaaTTTTTctcttggaaagaaagt |

TABLE 88

Label Extender of *Candida albicans*

| SEQ ID NO | LABEL EXTENDER NUCLEOTIDE SEQUENCE OF *Candida albicans* |
|---|---|
| 820. | gagcttttttaactgcaacaactttaataTTTTTgaagttaccgt ttt |
| 821. | ccaagcccaaggttcaactacTTTTTctgagtcaaagcat |
| 822. | gagcaaaggcctgctttgaaTTTTTgaagttaccgtttt |
| 823. | cctattctattattccatgctaatatattcTTTTTctgagtcaa agcat |
| 824. | aaccaacaaaatagaaccataacgtTTTTTgaagttaccgtttt |
| 825. | cctattaatcattacgatggtcctagaTTTTTctgagtcaaagc at |
| 826. | agaatttcacctctgacaactgaatTTTTTgaagttaccgtttt |
| 827. | gcagtagttagtcttcagtaaatccaTTTTTctgagtcaaagc at |
| 828. | cctaactttcgttcttgattaatgaTTTTTgaagttaccgtttt |
| 829. | cggtatctgatcatcttcgatccTTTTTctgagtcaaagcat |
| 830. | ggcatagtttatggttaagactacgaTTTTTgaagttaccgtt tt |
| 831. | gaacaacaaccgatccctagtcTTTTTctgagtcaaagcat |

TABLE 89

Blocking Label Extender of *Candida albicans*

| SEQ ID NO | BLOCKING LABEL EXTENDER NUCLEOTIDE SEQUENCE OF *Candida albicans* |
|---|---|
| 832. | gctgggtccagtacgcatc |
| 833. | cactctaattttttcaaagtaaaagtcc |

In another embodiment, the fungal target polynucleotides are from *Cryptococcus*. In particular, the target polynucleotides are from *Cryptococcus neoformans*, a medically important species of the *Crytococcus* best known for causing a severe form of meningitis and meningoencephalitis in subjects diagnosed with HIV-AIDS. The fungus is also known to infect and cause moderate to severe disease in patients undergoing cancer chemotherapy and metabolic immunosuppression etc. In one embodiment the target polynucleotide for detecting *Cryptococcus* infection is an 18S RNA sequence. In such embodiments, at least one Capture Extender (e.g., at least two, three, four, or five) comprises a target-hybridizing sequence selected from Table 90 (underlined). At least one Capture Extender probe may comprise, consist essentially of, or consist of a sequence selected from SEQ ID NOS: 834 to 839 (Table 90). At least one Label Extender (e.g., at least two, three, four, or five) may comprise a target-hybridizing sequence selected from Table 91 (underlined). At least one Label Extender may comprise, consist essentially of, or consist of a sequence selected from SEQ ID NOS: 840 to 851 (Table 91). The test may optionally employ a Blocking Label (BL), e.g., at least one, two, or three BLs each containing a sequence selected from SEQ ID NOS: 852 to 854 (Table 92).

TABLE 90

Capture Extender of Crytococcus neoformans

| SEQ ID NO | CAPTURE EXTENDER NUCLEOTIDE SEQUENCE OF Crytococcus neoformans |
|---|---|
| 834. | gcctcgccagacctgaagttTTTTTctcttggaaagaaagt |
| 835. | gcactccgtgaggaggaccTTTTTctcttggaaagaaagt |
| 836. | ggttccccctgcacacccagTTTTTctcttggaaagaaagt |
| 837. | gcgattgcctgctttgaacacTTTTTctcttggaaagaaagt |
| 838. | cggcatcgtttactgttaagactaTTTTTctcttggaaagaaagt |
| 839. | cgtgggccgatccctagtTTTTTctcttggaaagaaagt |

TABLE 91

Label Extender of Crytococcus neoformans

| SEQ ID NO | LABEL EXTENDER NUCLEOTIDE SEQUENCE OF Crytococcus neoformans |
|---|---|
| 840. | gaggtaaggtccagcaagacagtTTTTTgaagttaccgtttt |
| 841. | taaagagcatacaggaccaccagTTTTTctgagtcaaagcat |
| 842. | tattattccatgctaatgtattcggTTTTTgaagttaccgtttt |
| 843. | aaatagaaccgcacgtcctattcTTTTTctgagtcaaagcat |
| 844. | cggcgatcctagaaaccaacaTTTTTgaagttaccgtttt |
| 845. | ccgaccgtccctattaatcattaTTTTTctgagtcaaagcat |
| 846. | ccgtcaatctaagaatttcacctctaTTTTTgaagttaccgtttt |
| 847. | gctttcgcagttgttggtcttTTTTTctgagtcaaagcat |
| 848. | ccctaaccttcgttcttgatcaTTTTTgaagttaccgtttt |
| 849. | caacggtatctaatcgttttttgatcTTTTTctgagtcaaagcat |
| 850. | gccgacccagtcagagattgaTTTTTgaagttaccgtttt |
| 851. | caaagactttgatttctcgtaaggtTTTTTctgagtcaaagcat |

TABLE 92

Blocking Label Extender of Crytococcus neoformans

| SEQ ID NO | BLOCKING LABEL EXTENDER NUCLEOTIDE SEQUENCE OF Crytococcus neoformans |
|---|---|
| 852. | tctaattttttcaaggtaaaattcct |
| 853. | gcaacggaataccaatgccc |
| 854. | atgaaaacgtccttggcaaat |

The present invention provides methods for detection of target polynucleotides from uni- and/or multicellular parasites or protozoa. Non-limiting examples of parasites or protozoa include: leishmaniasis (*Leishmania fropica mexicana, Leishmania tropica, Leishmania major, Leishmania aethiopica, Leishmania braziliensis, Leishmania donovani, Leishmania infantum, Leishmania chagasi*); trypanosomiasis (*Trypanosoma brucei gambiense, Trypanosoma brucei rhodesiense*); toxoplasmosis (*Toxoplasma gondii*); schistosomiasis (*Schistosoma haematobium, Schistosoma japonicum, Schistosoma mansoni, Schistosoma mekongi, Schistosoma intercalatum*); malaria (*Plasmodium virax, Plasmodium falciparum, Plasmodium malariae* and *Plasmodium ovale*); Amebiasis (*Entamoeba histolytica*); Babesiosis (*Babesiosis microti*); Cryptosporidiosis (*Cryptosporidium parvum*); Dientamoebiasis (*Dientamoeba fragilis*); Giardiasis (*Giardia lamblia*); Helminthiasis and Trichomonas (*Trichomonas vaginalis*).

The method of the present invention described above may include detection of a housekeeping gene polynucleotide, where the level of the housekeeping gene polynucleotide is used for normalization (e.g., across samples) and/or calculation of the copy number of the target polynucleotide. In certain embodiments, the housekeeping gene polynucleotide is glyceraldehyde 3-phosphate dehydrogenase (GAPDH) polynucleotide. In such embodiments, at least one Capture Extender probe (e.g., at least two, three, four, or five) comprises a target hybridizing sequence selected from Table 93 (underlined). At least one Capture Extender probe may comprise, consist essentially of, or consist of a sequence selected from SEQ ID NOS: 855 to 858 (Tables 93). In such embodiments, at least one Label Extender (e.g., at least two, three, four, or five) may comprise a target-hybridizing sequence shown in Tables, 1, 2 or 94 (underlined). At least one Label Extender probe may comprise, consist essentially of, or consist of a sequence selected from SEQ ID NOS: 2 to 7 (Table 1), 8 to 13 (Table 2), or 859 to 870 (Table 94). The test may further employ a Blocking Label (BL), e.g., at least one, two, or three BLs each containing a sequence selected from SEQ ID NOS: 871 to 875 (Table 95).

TABLE 93

Capture Extender of GAPDH

| SEQ ID NO | CAPTURE EXTENDER NUCLEOTIDE SEQUENCE OF GAPDH |
|---|---|
| 855. | ggtcaatgaaggggtcattgatTTTTTctcttggaaagaaagt |
| 856. | ccttgacggtgccatggaatTTTTTctcttggaaagaaagt |
| 857. | cgccccacttgattttggaTTTTTctcttggaaagaaagt |
| 858. | gagatgatgacccttttggctcTTTTTctcttggaaagaaagt |

TABLE 94

Label Extender of GAPDH

| SEQ ID NO | LABEL EXTENDER NUCLEOTIDE SEQUENCE OF GAPDH |
|---|---|
| 859. | ggagcagagagcgaagcggTTTTTgaagttaccgtttt |
| 860. | cggctgactgtcgaacaggaTTTTTctgagtcaaagcat |
| 861. | gagcgatgtggctcggcTTTTTgaagttaccgtttt |
| 862. | tcaccttccccatggtgtctTTTTTctgagtcaaagcat |
| 863. | ccaggcgcccaatacgacTTTTTgaagttaccgtttt |
| 864. | agttaaaagcagccctggtgaTTTTTctgagtcaaagcat |
| 865. | tggaacatgtaaaccatgtagttgaTTTTTgaagttaccgtttt |

TABLE 94-continued

Label Extender of GAPDH

| SEQ ID NO | LABEL EXTENDER NUCLEOTIDE SEQUENCE OF GAPDH |
|---|---|
| 866. | ttgccatgggtggaatcatatTTTTTctgagtcaaagcat |
| 867. | tgacaagcttcccgttctcagTTTTTgaagttaccgtttt |
| 868. | tggtgatgggatttccattgaTTTTTctgagtcaaagcat |
| 869. | gacgtactcagcgccagcatTTTTTgaagttaccgtttt |
| 870. | aagacgccagtggactccacTTTTTctgagtcaaagcat |

TABLE 95

Blocking Label Extender of GAPDH

| SEQ ID NO | BLOCKING LABEL EXTENDER NUCLEOTIDE SEQUENCE OF GAPDH |
|---|---|
| 871. | caaatccgttgactccgacct |
| 872. | ggcaacaatatccactttaccag |
| 873. | gggatctcgctcctggaaga |
| 874. | cagccttctccatggtggtg |
| 875. | ccccctgcaaatgagccc |

According to another aspect, the present invention provides a kit for detecting target polynucleotides, for example, associated with a pathogenic organism. The kit comprises at least one Capture Extender probe and at least one Label Extender probe specific for a target polynucleotide from an infectious agent as described above. The kit may comprise a set of Capture Extender and/or Label extender probes illustrated or represented by the Tables provided herein. The kit may further comprise at least one Blocking Label probe specific for the target polynucleotide, or a set of Blocking Label probes illustrated or represented by the Tables provided herein. The kit may further comprise at least one or a series of signal-amplifying probes as described.

In some embodiments, the kit further comprises components for conducting a positive control. For example, the positive control may be a cell lysate derived from HeLa cells, a cell-line derived from cervical cancer cells, or any commercially available cell line having a particular characteristic of interest.

In some embodiments, the kit further comprises a probe pair or set as a normalization control, to normalize across samples and to calculate the target polynucleotide copy number. The normalization control probes may comprise at least one Capture Extender probe and at least one Label Extender probe specific for one or more housekeeping gene polynucleotides, such as but not limited to, GAPDH (GAPD). Exemplary pairs or sets of Capture Extender probes and Label Extender probes for GAPDH are disclosed in Tables 1, 2, 93, and 94 above. The kit may further comprise Blocking Label Extenders disclosed in Table 95 above.

In certain embodiments, the kit is configured such that the level of target polynucleotide and level of normlaization control are read simultaneously or sequentially from a patient sample in the same reaction. Such may be accomplished by employing different labels, such as alkaline phosphatases having different luminescent substrates, or combinations of different signal generating labels (e.g., alkaline phosphatase and horseradish peroxidase).

EXAMPLES

Example 1

Comparison of Currently Available HPV-Tests

TABLE 96 shows a comparison of the invention with currently available HPV-tests.

TABLE 96

| Company and Product | HPV test based on | Advantages/Disadvantages |
|---|---|---|
| Present invention | Use of primary probes hybridizing to the target sequence without amplification. Signal is intensified by additional probes which hybridize to the primary probes, creating a multi-layer probe. | No purification of RNA or DNA required from PAP smears. No need for RT-PCT. Amplifies signals, not target. |
| Access Genetics | Standard PCR technology | Sensitive. Contamination issues |
| Hologic (3$^{rd}$ wave) Invader ® HPV | 3 specifically designed oligonucleotides and a fluorescent signal detection technology | Poor specificity |
| Qiagen/ Diagene Hybrid Capture 2 ® (HC2) assay | Enzyme-linked antibody detection of RNA/DNA hybrid technology | Requires purification of RNA or DNA. RNA/DNA hybrid must be captured on solid phase. Poor specificity and sensitivity Expensive |
| Ventana's Inform ® HPV | In-situ hybridization technology | Requires intervention by eye Not sensitive |

Example 2

Protocol

The schematic in FIG. 1 illustrates the method of the invention. Briefly, the method involves capturing target polynucleotides from a sample by contacting with a Capture Extender and Label Extender under hybridizing conditions (e.g., about 55° C. for 120 minutes in 3×SSC, 10% dextransulfate, 0.2% casein, 10 μg/mL polyA and 100 μg/mL denatured salmon sperm DNA). Signal amplification is then carried out by sequentially hybridizing a pre-Amplifier, Amplifier Probe and Label Probe at 55° C., 55° C. and 50° C. respectively for 30 minutes each in 3×SSC, 10% dextransulfate, 0.2% casein, 10 μg/mL polyA and 100 μg/mL denatured salmon sperm DNA and with wash buffer: 20mmol/L Tris-HCL, 400 mmol/L lithium chloride, 1 mL/L Tween 20. The Label Probe may be directly conjugated with alkaline phosphatase, or biotinylated, labeled with fluorescein, or other light emitting dyes.

Example 3

Figure 2:
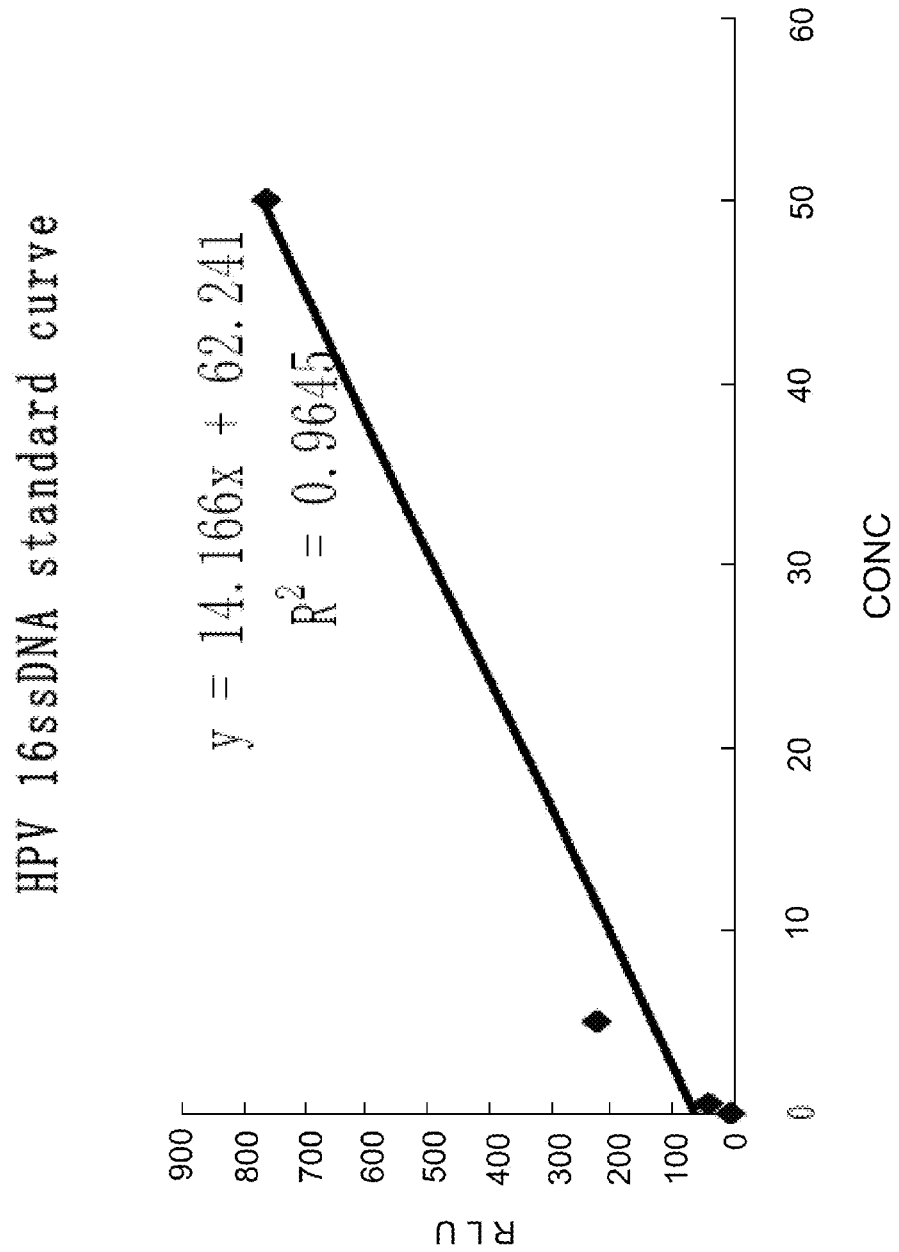
FIG. 2 shows a standard curve for detection of HPV type 16 ssDNA.

Correlation of Relative Light Units (RLU) with HPV Type 16 Sequence Concentration Samples containing various concentrations of HPV type 16 ss DNA sequences were incubated with Capture Probecoated plates together with HPV type 16-specific Capture Extender (CE), Label Extender (LE) and Blocking Label (BL) for 1, 2, 3, 4 h and overnight. Probe sets are identified in Tables 3 to 14. TABLE 97 and FIG. 2 below show the correlation of RLU with the concentration of viral DNA.

TABLE 97

|  | RLU1 | RLU2 | AVE | AVE-BK | std |
|---|---|---|---|---|---|
| 50 amol | 957.753 | 957.403 | 957.578 | 957.0605 | 0.25 |
| 5 amol | 862.611 | 662.097 | 762.354 | 761.8365 | 141.78 |
| 0.5 amol | 220.362 | 234.933 | 227.6475 | 227.13 | 10.30 |
| 0.05 amol | 42.555 | 45.472 | 44.0135 | 43.496 | 2.06 |
| 0.005 amol | 5.301 | 5.373 | 5.337 | 4.8195 | 0.05 |
| Background | 0.46 | 0.575 | 0.5175 | 0 | 0.08 |

The results show that the method of the invention using the probe set described for detecting HPV has a sensitivity of about 3000 copies, which, given the high specificity of the probe set, is sufficient for accurate HPV detection.

Example 4

Detection of HPV in Patient Samples at Various Stages of Infection

Figure 3:
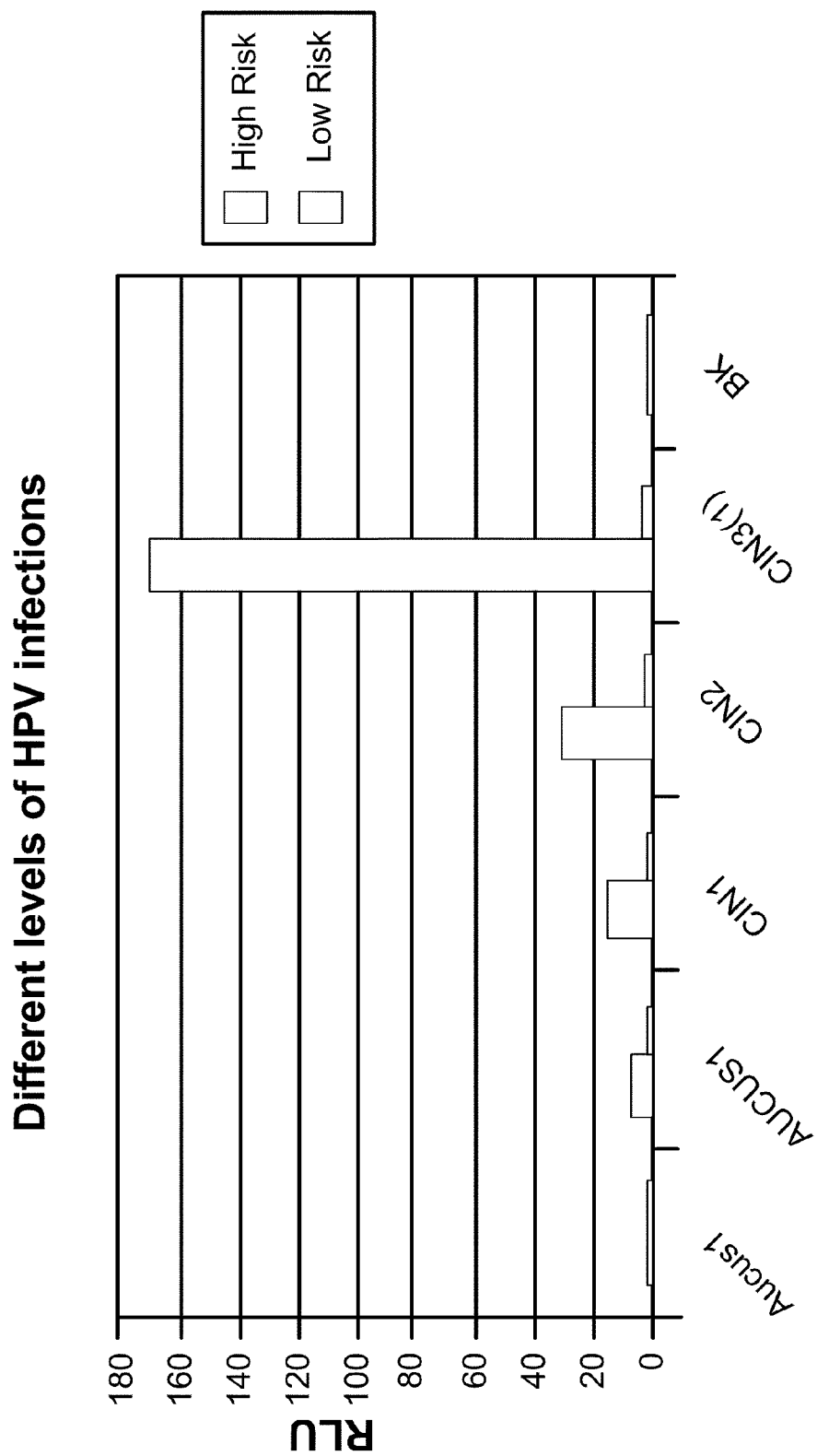
FIG. 3 shows the relative light units (RLU) emitted from Alkaline Phosphatase-labeled probe, for detecting HPV biomarkers in Pap smears of HPV patients during various disease states. AUCUS is atypical squamous cells of undetermined significance. CIN is cervical intraepithelial neoplasia. BK is background.

FIG. 3 shows the detection of HPV target polynucleotides using the method of the invention. HPV target polynucleotides in patient Pap smear samples at various stages of HPV infection, i.e. at the CIN (cervical intraepithelial neoplasia) stage 1, 2, or 3; or at the ASC-US (atypical squamous cells of undetermined significance) stage in high risk and low risk patients were detected using the probe sets identified in Tables 3 to 14.

The results in TABLE 98 and FIG. 3 show an increase in levels of HPV target polynucleotides in Pap smears of patients with CIN 3 infection.

TABLE 98

|  | ASCUS | ASCH | CIN1 | CIN2 | CIN3(1) | BK |
|---|---|---|---|---|---|---|
| High risk | 0.8965 | 6.3085 | 15.0365 | 29.804 | 168.932 | 0.8675 |
| Low risk | 1.1925 | 0.9135 | 0.655 | 2.724 | 2.8915 | 0.8225 |

ASC, which are abnormal cells of uncertain significance, and CIN1 usually recover spontaneously. The CIN1 have a few cells showing intraepithelial neoplasia which can be precancerous. CIN3 lesions represent severe neoplasia involving the full thickness of the mucosa and this class includes carcinoma in situ, a pre-invasive cancer. CIN3 lesions are less likely to recover spontaneously and commonly progress to invasive cancer. Background levels (BK) were very close to that of the lowest abnormal cell of uncertain significance grade.

Example 5

Detection Sensitivity for HIV

Figure 4:
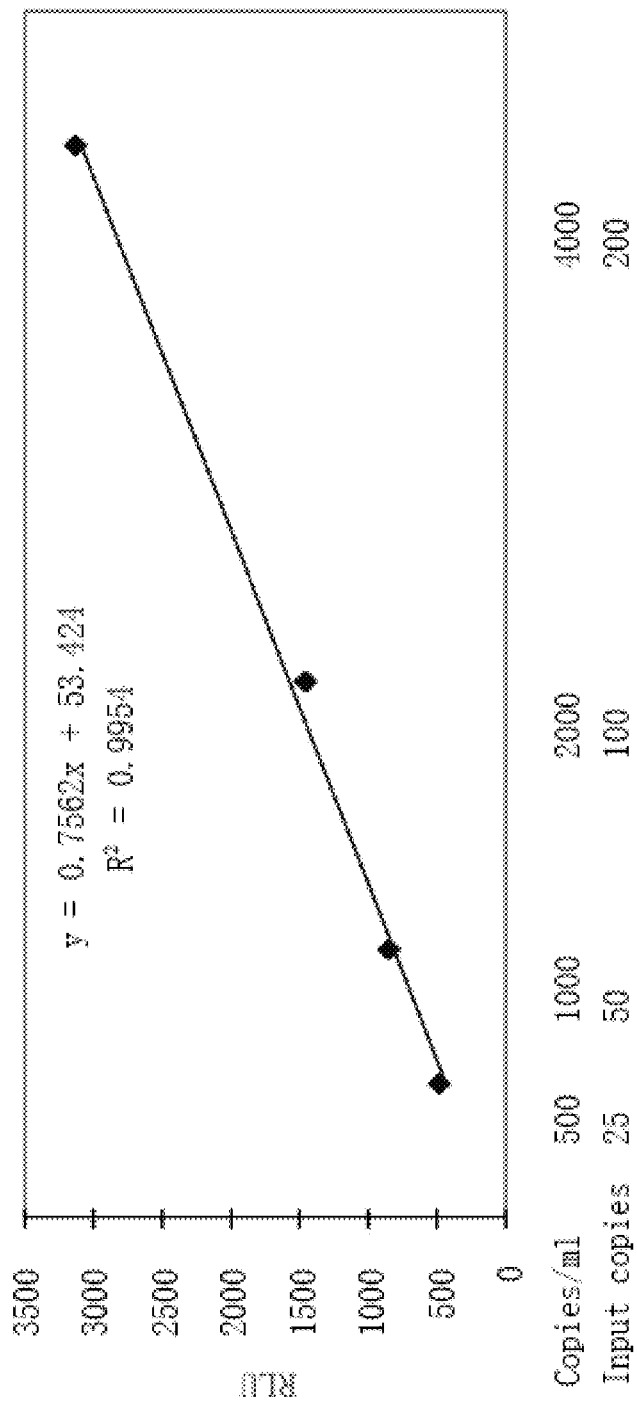
FIG. 4 shows detection of HIV target polynucleotides that are present in amounts as low as 25 copies.

FIG. 4 shows the detection sensitivity for HIV target polynucleotides (HIV-A, HIV-B, and HIV-F). HIV target polynucleotides were detected using the probe set identified in Tables 60 to 68 in serially diluted plasma samples, spiked with 25, 50, 100 and 200 copies of the HIV target polynucleotide.

The results show that this embodiment can detect as low as 25 copies. In addition, FIG. 4 shows that the assay is linear for samples that are serially diluted.

Example 6

Detection Sensitivity for HBV

Figure 5:
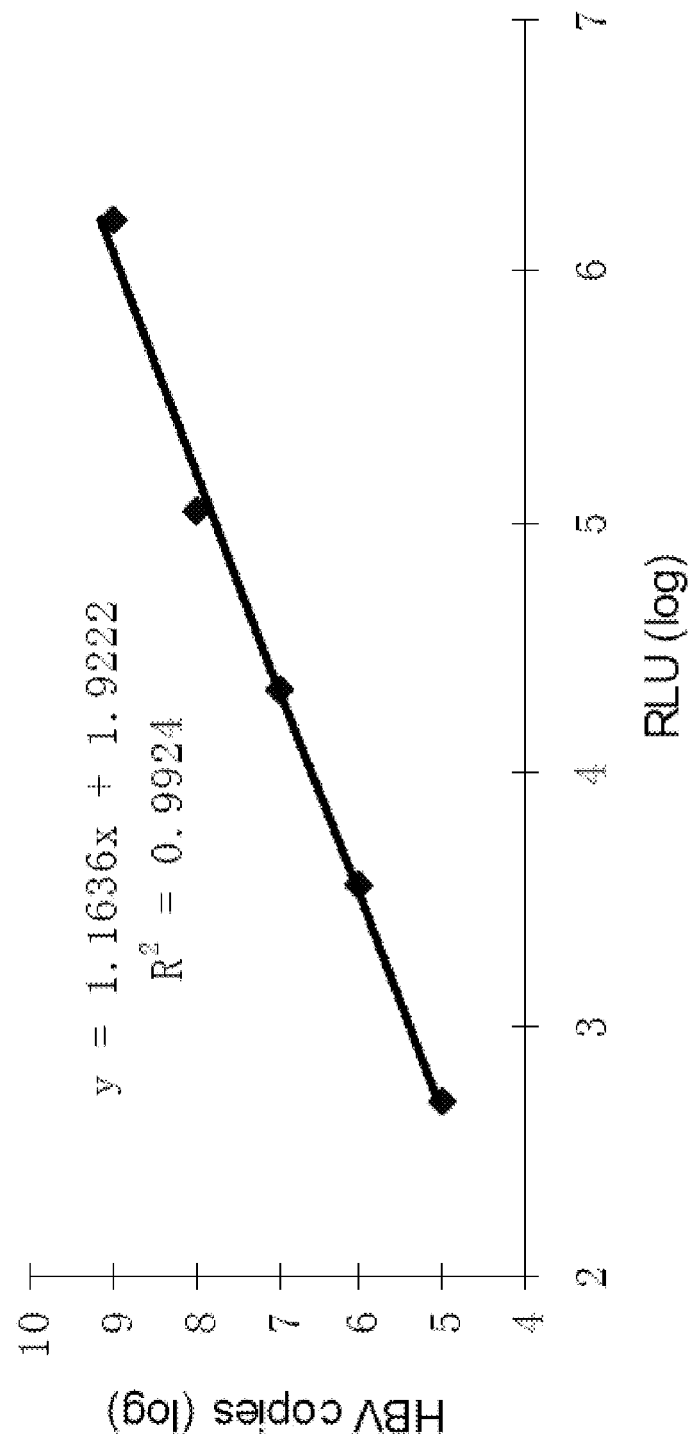
FIG. 5 shows a standard curve for the detection for HBV polynucleotides.

FIG. 5 shows the sensitivity of detection for HBV target polynucleotides. HBV target polynucleotides were detected using the probe set from Table 57, Table 58 and Table 59.

The results show that the method of detection in this embodiment, measured by log relative light units (RLU), is linearly correlated with the log number of copies of HBV.

Example 7

Detection Sensitivity for HCV

Figure 6:
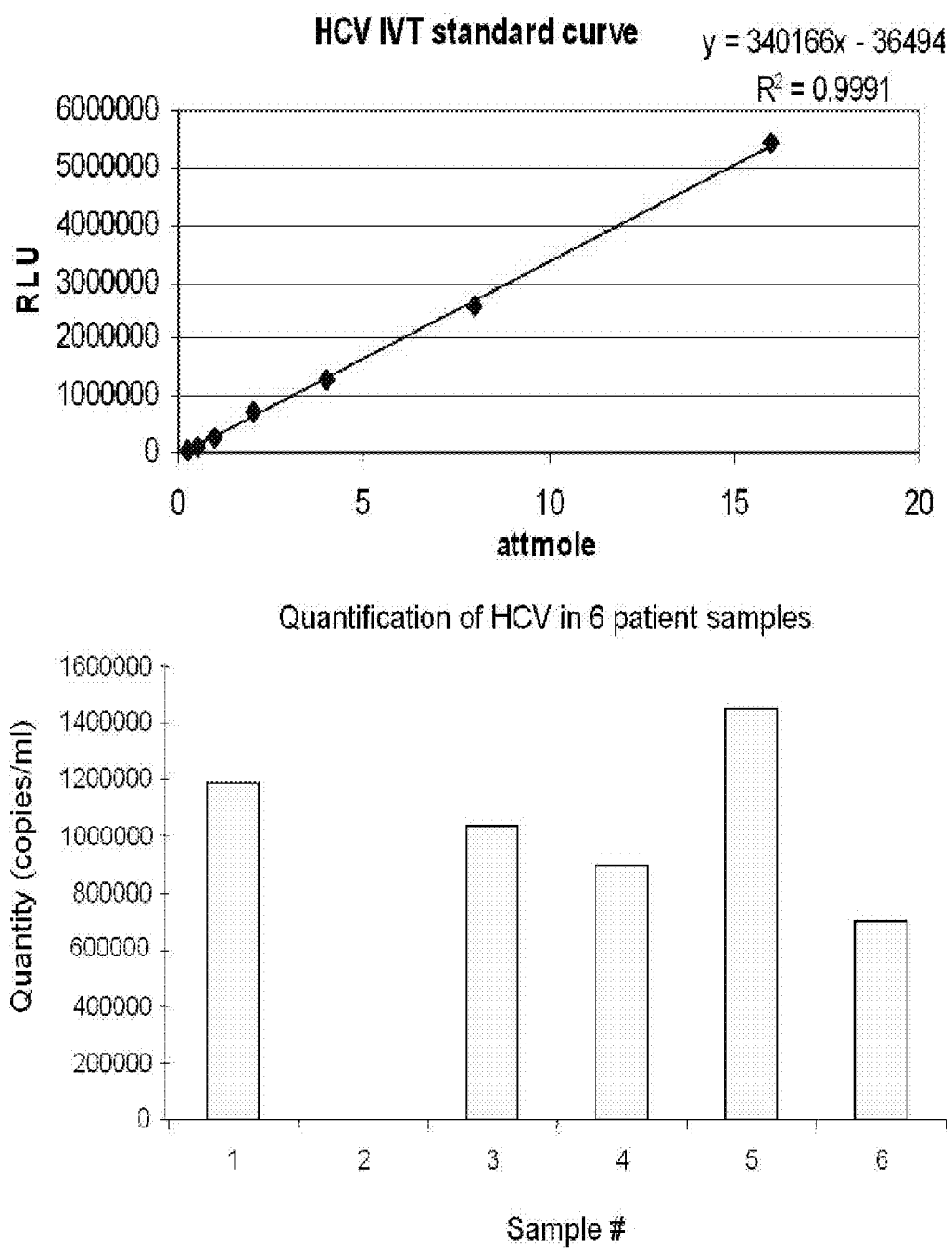
FIG. 6 shows a standard curve for the detection of HCV (top panel), and quantitation of HCV particles from sera of six patients (bottom panel).

FIGS. 6A and B show the sensitivity of detection for HCV target polynucleotides. HCV target polynucleotides were detected using the probe set from Table 72, Table 73 and Table 74.

FIG. 6A shows that, in this embodiment, log relative light units (RLU) is linearly correlated with the log number of copies of HCV.

FIG. 6B shows the quantitation of HCV in 6 patient samples.

Example 8

Detection Sensitivity for Coronavirus (SARS)

Figure 7:
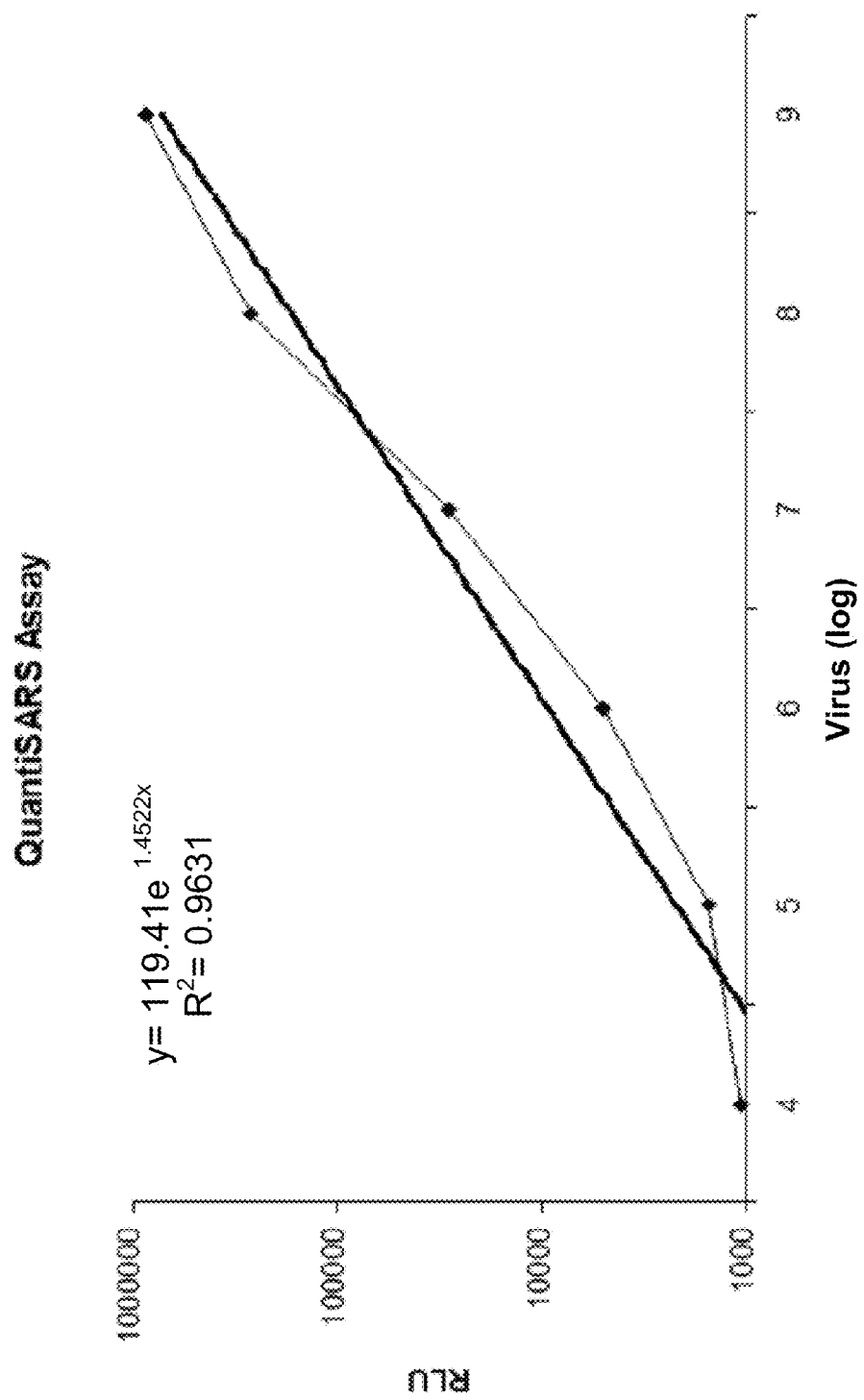
FIG. 7 shows a standard curve for the detection of SARS.

FIG. 7 shows the detection sensitivity for coronavirus (SARS) target polynucleotides. SARS target polynucleotides were detected using the probe sets from Table 75, Table 76 and Table 77.

Example: 9

Lack of Cross-Reactivity for H1N1 Assay

An assay for hemaglutinin-neuraminidase (H1N1) of Influenza virus was conducted. The H1N1 target polynucleotides were detected using the following probe sets from Table 69, Table 70 and Table 71.

TABLE 99 shows that the H1N1 assay does not cross-react with various strains of Influenza A, Influenza B or other respiratory virus.

TABLE 99

| Viruses Tested in Samples | Result |
|---|---|
| Influenza A: | |
| Brisbane/10/2007 H3N2 | negative |
| Brisbane/59/2007 H1N1 | negative |
| Hong Kong/29/2006 | negative |
| Netherlands/134/04 H1 | negative |
| New Caledonia/20/99 H1N1 | negative |
| Solomon Islands/03/2006 H1N1 | negative |
| Taiwan/42/2006 | negative |
| Victoria/3/75 H3 | negative |
| Wisconsin/67/05/H3N2 | negative |
| Singapore/63/04 | negative |
| Influenza B: | |
| Florida/04/2006 | negative |
| Florida/07/2004 | negative |

TABLE 99-continued

| Viruses Tested in Samples | Result |
|---|---|
| Malaysia/2506/2004 | negative |
| Panama/45/90 | negative |
| Yamanashi/166/98 | negative |
| Other Respiratory Viruses: | |
| Parainfluenza 1 | negative |
| Parainfluenza 2 | negative |
| Parainfluenza 3 | negative |
| Parainfluenza 4a | negative |
| Parainfluenza 4b | negative |
| Coronavirus 229E | negative |
| Coronavirus NL63 | negative |
| Coronavirus OC43 | negative |
| SARS (200300592) | negative |

Example: 10 ssDNA Complementary to 18S RNA or Fungal Cells as Standard Materials

Figure 8A:
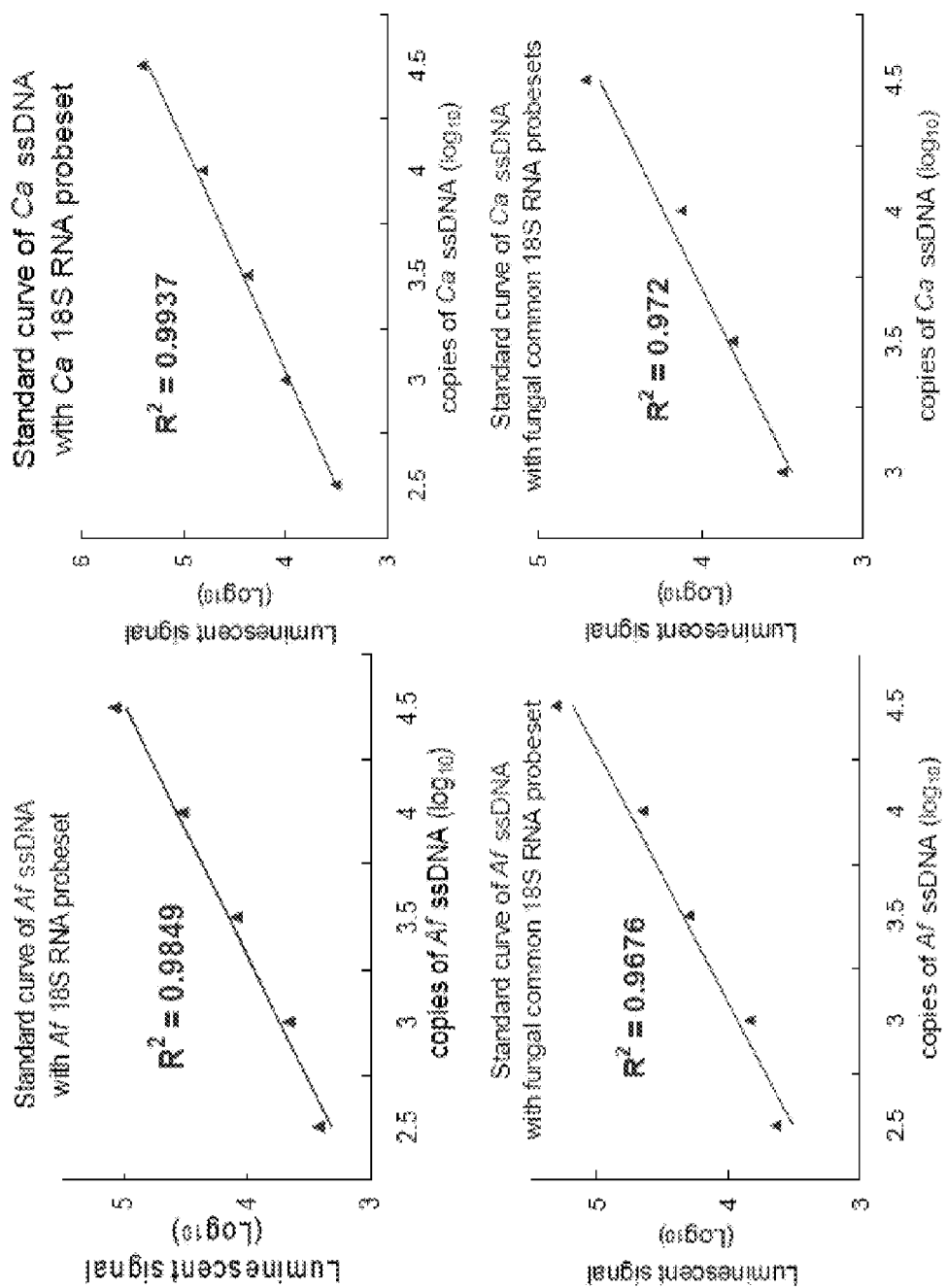
FIGS. 8A and B shows standard curves for the detection of ssDNA complementary to 18S RNA from fungal cells (*Candida albicans*).
Figure 8B:
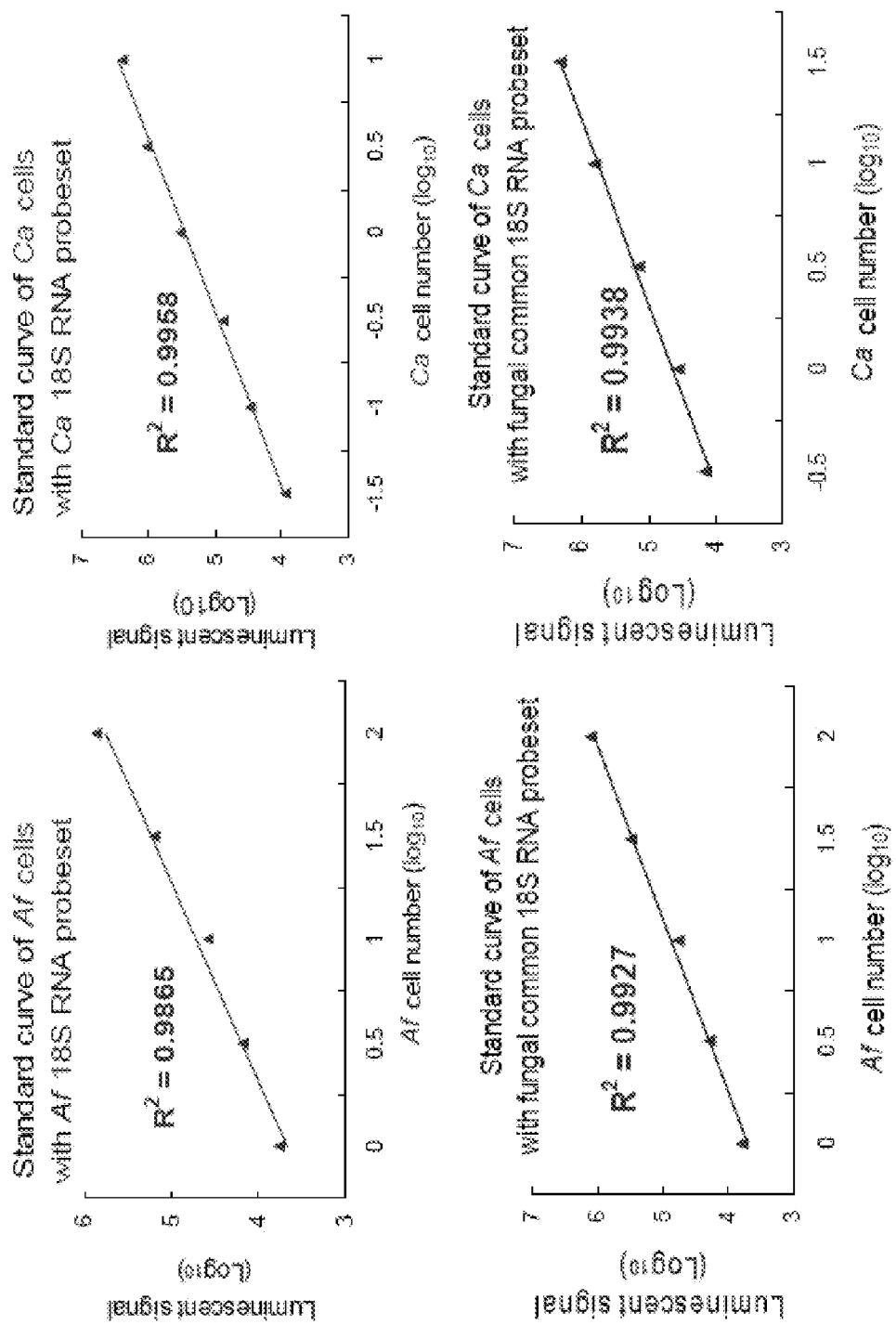

FIG. 8 shows the correlation between the numbers of fungal cells and 18S RNA copies using the probe sets described in Tables 84 to 89. Both fungal cells and ssDNA complementary to 18S RNA were tested for their usefulness as standard materials. The results show a correlation between the numbers of fungal cells and 18S RNA copies with the level of luminescence (R>0.95) detected.

Example: 11

Quantifying Different Species and Strains of *Aspergillus* and *Candida*

FIG. 9 shows the quantitation of different species and strains of *Aspergillus* and *Candida*. Various species of *Aspergillus* and *Candida* were detected using the 18S RNA probe set for *Aspergillus* (Table 84, Table 85, Table 86) and for *Candida* (Table 87, Table 88, and Table 89 respectively and the method described above.

The results show that the method of detection measured by log relative light units (RLU) can detect as few as 10 cells/well and there is no cross-reactivity between the 16S RNA probes from *Aspergillus* and *Candida*. The results show that the *Aspergillus* 16S RNA probe-set consistently detects various species of *Aspergillus* and not *Candida*, and the *Candida* 16S RNA probe-set detects only the *Candida* species and not *Aspergillus*. On the other hand, the common 18S RNA probe-set can detect either *Candida* or *Aspergillus* of various strains allowing for a single test that detects many potential fungal pathogens.

Example: 12

Quantification *Candida* in Clinical Blood Samples

Figure 10:
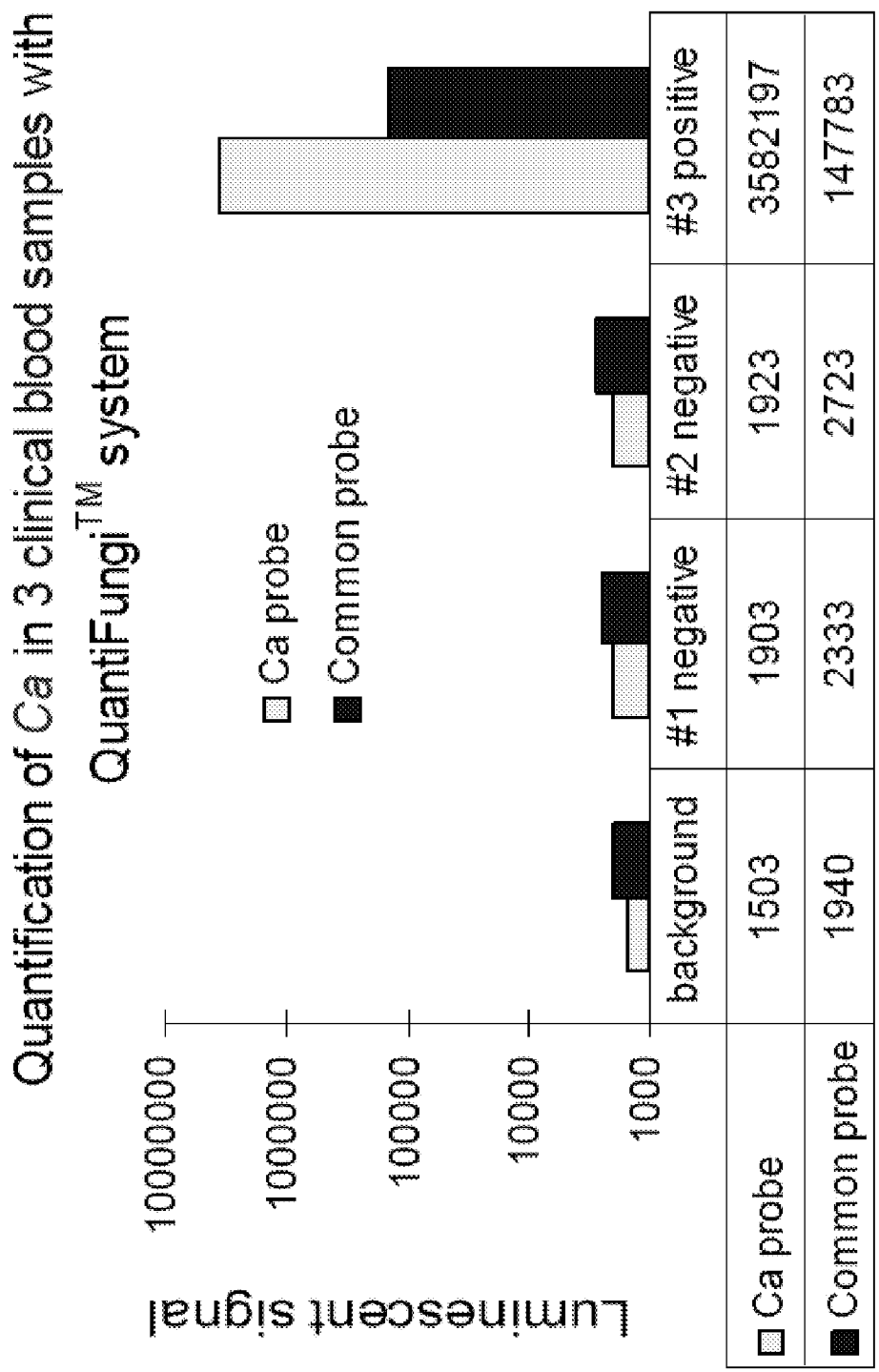
FIG. 10 shows quantifying *Candida* from three clinical blood samples.

FIG. 10 shows the quantification of *Candida*. Clinical blood samples from patients infected with *Candida* were assayed for the *Candida* target polynucleotides using the 18S RNA probe set *Candida* and a "common probe" from Table 84, Table 85, Table 86, Table 87, Table 88, and Table 89.

The results show detection measured by log relative light units (RLU). A 50 ul blood sample for an uninfected patient (negative) or infected patient blood sample (positive) was tested. The clinical culture within 24-48 hr showed that two of them were negative and one positive. The results (FIG. 10) of QuantiFungi™ assay, which took only 5 hours, were consistent with the results of clinical microbes culture.

All publications, patents and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

I claim:

1. A method for determining the presence, absence, or level of HPV type-16 in a sample, consisting of the following steps:
   (a) capturing a target polynucleotide, if present, from a sample by hybridization to a set of capture extender oligonucleotides probes consisting of SEQ ID NOs: 14 to 21 and wherein the target polynucleotide is indicative of the presence of said HPV type 16;
   (b) hybridizing said target polynucleotide with a set of blocking oligonucleotides probes consisting of SEQ ID NOs: 38 to 48; and
   (c) detecting the target polynucleotide by hybridization with a set of label extender oligonucleotides probes consisting of SEQ ID NOs: 22 to 37; and wherein said probes in steps (a), (b) and (c) for detecting HPV have a sensitivity of about 3000 copies.

2. The method of claim 1, wherein said sample is a biological sample.

3. The method of claim 2, wherein said biological sample is a pap smear.

4. The method of claim 1, wherein said capturing is done by hybridizing said sample with said set of capture extender oligonucleotides and a capture probe that hybridizes to said set of capture extender oligonucleotides and is attached to a solid support.

5. The method of claim 4, wherein said solid support is a bead.

6. The method of claim 4, wherein said solid support is a well of a plate.

7. The method of claim 1, wherein said detecting is done by hybridizing said set of extender oligonucleotides with an oligonucleotide probe that is directly or indirectly labeled.

8. The method of claim 7, wherein said oligonucleotide probe is directly or indirectly labeled with a label that is luminescent.

9. The method of claim 7, wherein said oligonucleotide probe is directly or indirectly labeled with a label that is chromogenic.

10. The method of claim 7, wherein said oligonucleotide probe is directly or indirectly labeled with a label that is fluorescent.

11. The method of claim 1, wherein, said capturing is done in the presence of oligonucleotides defined by SEQ ID NOS: 49-56; said hybridizing is done in the presence of oligonucleotides defined by SEQ ID NOS: 57-72; and said detecting is done in the presence of oligonucleotides defined by SEQ ID NOS: 73-75.

12. The method of claim 1, wherein, said capturing is done in the presence of further oligonucleotides that specifically detect HPV strains 31, 33, 35, 39, 45, 51, 52, 56, 58, 59 and 68.

* * * * *